US009011876B2

(12) United States Patent
Yagodich et al.

(10) Patent No.: US 9,011,876 B2
(45) Date of Patent: Apr. 21, 2015

(54) LIVE, ATTENUATED RESPIRATORY SYNCYTIAL VIRUS

(75) Inventors: Mary K. Yagodich, Bryn Mawr, PA (US); Michael P. Citron, Chester Springs, PA (US); Daniel J. Distefano, Harleysville, PA (US); Daniel L. Krah, Lansdale, PA (US); Xiaoping Liang, Collegeville, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 475 days.

(21) Appl. No.: 13/127,647

(22) PCT Filed: Nov. 3, 2009

(86) PCT No.: PCT/US2009/063024

§ 371 (c)(1), (2), (4) Date: May 4, 2011

(87) PCT Pub. No.: WO2010/053883

PCT Pub. Date: May 14, 2010

(65) Prior Publication Data

US 2011/0212130 A1 Sep. 1, 2011

Related U.S. Application Data

(60) Provisional application No. 61/198,327, filed on Nov. 5, 2008.

(51) Int. Cl.

| | |
|---|---|
| ***A61K 39/155*** | (2006.01) |
| ***C12N 7/00*** | (2006.01) |
| ***C12N 7/04*** | (2006.01) |
| ***C12N 15/45*** | (2006.01) |
| ***C12N 15/63*** | (2006.01) |
| ***C07K 14/005*** | (2006.01) |
| *A61K 39/00* | (2006.01) |

(52) U.S. Cl.

CPC ............. *C07K 14/005* (2013.01); *A61K 39/155* (2013.01); *A61K 2039/5254* (2013.01); *C12N 7/00* (2013.01); *C12N 2760/18522* (2013.01); *C12N 2760/18534* (2013.01); *C12N 2760/18564* (2013.01)

(58) Field of Classification Search

None

See application file for complete search history.

(56) References Cited

FOREIGN PATENT DOCUMENTS

| | | | |
|---|---|---|---|
| WO | 1997-38138 | A1 | 10/1997 |
| WO | WO9949017 | A2 | 9/1999 |
| WO | WO0104335 | A2 | 1/2001 |
| WO | WO2004028478 | A2 | 4/2004 |
| WO | 2004-087062 | A2 | 10/2004 |
| WO | WO 2004/087062 | * | 10/2004 |

OTHER PUBLICATIONS

Tang, et al., Virology, vol. 302, Issue 1, Oct. 10, 2002, pp. 207-216.*

Juhasz et al. 1999 Vaccine Vil 17, pp. 1416-1424.*

Anderson, L.J., et al., "Antigenic Characterization of Respiratory Syncytial Virus Strains with Monoclonal Antibodies", J. Infect. Dis., 1985, pp. 626-633, vol. 151.

Anderson, L.J., et al., "Multicenter Study of Strains of Respiratory Syncytial Virus", J. Infect. Dis., 1991, pp. 687-692, vol. 163.

Cane, P.A., et al, Respiratory Syncytial Virus Heterogeneity During an Epdiemic: Analysis by Limited Nucleotide Sequencing (SH gene) and Restriction Mapping (N gene), J. Gen. Vir., 1991, pp. 349-357, vol. 72.

Chin, J., et al, "Field Evaluation of a Respiratory Syncytial Virus Vaccine and a Trivalent Parainfluenza Virus Vaccine in a Pediatric Population", Am. J. Epidemiol., 1969, pp. 449-463, vol. 89.

Connors, et al., "a Cold Passage Attenuated Strain of Human Respiratory Syncytial Virus Contains Mutations in the F and L Genes", Virology, 1995, pp. 478-484, vol. 208.

Crowe, J.E., et al., "Acquisition of the ts Phenotype by a Chemically Mutagenized Cold-passaged Human Respiratory Syncytial Virus Vaccine Candidate Results From the Acquisition of a Single Mutation in the Polymerase (L) Gene, Virus Genes", 1996, pp. 269-273, vol. 13, No. 3.

Firestone, Cai-Yen, et al., "Nucleotide Sequence Analysis of the Respiratory Syncytial Virus Subgroup a Cold-Passaged (cp) Temperature Senstitive (ts) cpts-248/404 Live Attenuated Virus Vaccine Candidate", Virology, 1996, pp. 419-422, vol. 225.

Fulginiti, V.A., et al., "Respiratory Virus Immunization", Am. J. Epidemiol., 1969, pp. 435-448, vol. 89, No. 4.

Gharpure, M.A., et al., "Temperature-sensitive Mutants of Respiratory Syncytial Virus", J. Virol., 1969, pp. 414-421, vol. 3.

Huang, Y.T., et al., "The Genome of Respiratory Syncytial Virus Is a Negative-Stranded RNA That Codes for At Least Seven mRNA Species", Journal of Virology, 1982, pp. 150-157, vol. 43, No. 1.

Johnson, P.R., et al., "The G Glycoprotein of Human Respiratory Syncytial Viruses of Subgroups A and B: Extensive Sequence Divergence Between Antigenically Related Proteins", Proc. Natl. Acad. Sci. USA, 1987, pp. 5625-5629, vol. 84.

Juhasz, K., et al., "The Temperature-Senstitive (ts) Phenotype of a Cold-Passaged (cp) Live Attenuated Respiratory Syncytial Virus VAccine Candidate, Designed cpts530, Results From a Single Amino Acid Substitution in the L Protein", J. Virol., 1997, pp. 5814-5819, vol. 71, No. 8.

Juhasz, K., et al., "The Two Amino Acid Substitutions in the L Protein of cpts530/1009, a Live-Attenuated Respiratory Syncytial Virus Candidate Vaccine, Are Independent Temperature-Sensitive and Attenuation Mutations", Vaccine, 1999, pp. 1416-1424, vol. 17.

Kapikan et al., "An Epidemiologic Study of Altered Clinical Reactivity to Respiratory Syncytial (RS) Virus Infection in Children Previously Vaccinated With an Inactivated RS Virus Vaccine", American Journal of Epidemiology, 1968, pp. 405-421, vol. 89.

Kim, H.W., et al., "Respiratory Syncytial Virus Disease in Infants Despite Prior Administration of Antigenic Inactivated Vaccine", American Journal of Epidemiology, 1969, pp. 422-434, vol. 89.

(Continued)

*Primary Examiner* — Mary E Mosher

*Assistant Examiner* — Myron Hill

(74) *Attorney, Agent, or Firm* — Anna Cocuzzo; Henry P. Wu

(57) ABSTRACT

The present invention features live, attenuated respiratory syncytial viruses (RSV) useful as vaccines against RSV infection and/or the development of severe RSV-associated illnesses. The disclosed viruses are attenuated to the extent of being nonpathogenic when administered to a subject but substantially retain the antigenic and immunogenic properties of wild-type RSV.

11 Claims, 16 Drawing Sheets

(56) References Cited

OTHER PUBLICATIONS

Kim, H.W., et al., "Cell-Mediated Immunity to Respiratory Syncytial Virus Induced by Inactivated Vaccine or by Infection", Pediat. Res., 1976, pp. 75-78, vol. 10.

Lawson, N. D., et al., "Recombinant vesicular stomatitis viruses from DNA", Proc. Natl. Acad. Sci. USA 1995, pp. 4477-4481, vol. 92.

Mink, M.A., et al, "Nucleotide Sequences of the 3' Leader and 5' Trailer Regions of Human Respiratory syncytial Virus Genomic RNA", Virology, 1991, pp. 615-624, vol. 185.

Mufson, M.A., et al., "Two Distinct Subtypes of Human Respiratory Syncytial Virus", J. Gen Virol., 1985, pp. 2111-2124, vol. 66.

Murphy, B.R.., et al., "Formalin-Inactivated Respiratory Syncytial Virus Vaccine Induces Antibodies to the Fusion Glycoprotein That Are Deficient in Fusion-Inhibiting Activity", J. Clin. Microbiol., 1988, pp. 1595-1597, vol. 26, No. 8.

Palese, "Genetic engineering of infectious negative-strand RNA viruses", Trends in Microbiology, 1995, pp. 13-125, vol. 3.

Peret, T.C.T., et al., "Circulation Patterns of Genetically Distinct Group A and B Strains of Human Respiratory Syncytial Virus in a Community", J. Gen. Virol., 1998, pp. 2221-2229, vol. 79.

Prince, G.A., et al., "Enhancement of Respiratory Syncytial Virus Pulmonary Pathology in Cotton Rats by Prior Intramuscular Inoculation of Formalin-Inactivated Virus", J. Virol., 1986, pp. 721-728, vol. 57, No. 3.

Richardson et al., "Evaluation of five temperature-sensitive mutants of respiratory syncytial virus in primates: I. Viral shedding, immunologic response, and associated illness", J. Med. Virol., 1978, pp. 91-100, vol. 3.

Schnell et al., "Infectious rabies viruses from cloned cDNA", EMBO J, 1994, pp. 4195-4203, vol. 13.

Stec, D.S., et al., "Sequence Analysis of the Polymerase L Gene of Human Respiratory Syncytial Virus and Predicted Phylogeny of Nonsegmented Negative-Strand Viruses", Virology, 1991, pp. 273-287, vol. 183.

Sullender, W.M., et al., "Genetic Diversity of the Attachment Protein of Subgroup B Respiratory Syncytial Viruses", J. Virol., 1991, pp. 5425-5434, vol. 65, No. 10.

Tolley, K.P., et al., "Identification of Mutations Contributing to the Reduced Virulence of a Modified Strain of Respiratory Syncytial Virus", Vaccine, 1996, pp. 1637-1646, vol. 14, No. 17/18.

Whitehead, S.S., et al., "Recombinant Respiratory Syncytial Virus (RSV) Bearing a Set of Mutations From Cold-Passaged RSV Is Attenuated in Chimpanzees", J. Virol., 1988, pp. 4467-4471, vol. 72.

GenBank Accession No. U39662.

Whitehead, S.S., et al—Virology, 1998, vol. 247, pp. 232-239, Article No. VY989248.

* cited by examiner

```
                     1                                      40
      S2_NS2   (1)  MDTTHNDTTPQRLMITDMRPLSLETIIISLTRDIITHRFI
 MRK_287_NS2   (1)  MDTTHNDTTPQRLMITDMRPLSLETIITSLTRDIITHKFI
     P17_NS2   (1)  MDTTHNDTTPQRLMITDMRPLSLETIITSLTRDIITHKFI

                     41                                     80
      S2_NS2  (41)  YLINHECIVRKLDERQATFTFLVNYEMKLLHKVGSTKYKK
 MRK_287_NS2  (41)  YLINHECIVRKLDERQATFTFLVNYEMKLLHKVGSTKYKK
     P17_NS2  (41)  YLINHECIVRKLDERQATFTFLVNYEMKLLHKVGSTKYKK

                     81                                    120
      S2_NS2  (81)  YTEYNTKYGTFPMPIFINHDGFLECIGIKPTKHTPIIYKY
 MRK_287_NS2  (81)  YTEYNTKYGTFPMPIFINHDGFLECIGIKPTKHTPIIYKY
     P17_NS2  (81)  YTEYNTKYGTFPMPIFINHDGFLECIGIKPTKHTPIIYKY

                     121
      S2_NS2 (121)  DLNP- (SEQ ID NO: 2)
 MRK_287_NS2 (121)  DLNP- (SEQ ID NO: 4)
     P17_NS2 (121)  DLNP- (SEQ ID NO: 6)
```

FIG. 1

```
                   1                                       40
      S2_G    (1)  MSKNKDQRTAKTLEKTWDTLNHLLFISSCLYKLNLKSIAQ
 MRK_287_G    (1)  MSKNKDQRTAKTLERTWDTLNHLLFISSCLYKLNLKSVAQ
     P17_G    (1)  MSKNKDQRTAKTLERTWDTLNHLLFISSCLYKLNLKSVAQ

                   41                                      80
      S2_G   (41)  ITLSILAMIISTSLIIAAIIFIASANHKVTLTTAIIQDAT
 MRK_287_G   (41)  ITLSILAMIISTSLIIAAIIFIASANHKVTSTTTIIQDAT
     P17_G   (41)  ITLSILAMIISTSLIIAAIIFIASANHKVTSTTTIIQDAT

                   81                                     120
      S2_G   (81)  SQIKNTTPTYLTQNPQLGISFSNLSETTSQTTTILASTTP
 MRK_287_G   (81)  SQIKNTTPTYLTQSPQLGISPSNPSEITSQITTILASTTP
     P17_G   (81)  SQIKNTTPTYLTQSPQLGISPSNPSEITSQITTILASTTP

                   121                                    160
      S2_G  (121)  SVKSTLQSTTVKTKNTTTTKIQPSKPTTKQRQNKPPNKPN
 MRK_287_G  (121)  GVKSTLQSTTVGTKNTTTTQAQPSKPTTKQRQNKPPSKPN
     P17_G  (121)  GVKSTLQSTTVGTKNTTTTQAQPSKPTTKQRQNKPPSKPN

                   161                                    200
      S2_G  (161)  NDFHFEVFNFVPCSICSNNPTCWAICKRIPNKKPGKKTTT
 MRK_287_G  (161)  NDFHFEVFNFVPCSICSNNPTCWAICKRIPNKKPGKKTTT
     P17_G  (161)  NDFHFEVFNFVPCSICSNNPTCWAICKRIPNKKPGKKTTT

                   201                                    240
      S2_G  (201)  KPTKKPTIKTTKKDLKPQTTKPKEVPTTKPTEKPTINTTK
 MRK_287_G  (201)  KPTKKPTFKTTKKDPKPQTTKSKEVPTTKPTEEPTINTTK
     P17_G  (201)  KPTEEPTFKTAKEDPKPQTTGSGEVPTTKPTGEPTINTTK

                   241                                    280
      S2_G  (241)  TNIRTTLLTNNTTGNPEHTSQKGTLHSTSSDGNPSPSQVY
 MRK_287_G  (241)  TNITTTLLTSNTTRNPELTSQMETFHSTSSEGNPSPSQVS
     P17_G  (241)  TNITTTLLTSNTTRNPELTSQMETFHSTSSEGNPSPSQVS

                   281                 299
      S2_G  (281)  TTSEYLSQPPSPSNTTNQ- (SEQ ID NO: 8)
 MRK_287_G  (281)  ITSEYLSQPSSPPNTPR-  (SEQ ID NO: 10)
     P17_G  (281)  ITSEYLSQPSSPPNTPR-- (SEQ ID NO: 12)
```

FIG.2

```
                 1                                      40
     S2_F    (1) MELPILKTNAITAILAAVTLCFASSQNITEEFYQSTCSAV
MRK_287_F    (1) MELPILKANAITTILTAVTFCFASSQNITEEFYQSTCSAV
    P17_F    (1) MELPILKANAITTILTAVTFCFASSQNITEEFYQSTCSAV

                 41                                     80
     S2_F   (41) SKGYLSALRTGWYTSVITIELSNIKENKCNGTDAKVKLIK
MRK_287_F   (41) SKGYLSALRTGWYTSVITIELSNIKENKCNGTDAKVKLIK
    P17_F   (41) SKGYLSALRTGWYTSVITIELSNIKENKCNGTDAKVKLIK

                 81                                    120
     S2_F   (81) QELDKYKSAVTELQLLMQSTPATNNRARRELPRFMNYTLN
MRK_287_F   (81) QELDKYKNAVTELQLLMQSTPAANNRARRELPRFMNYTLN
    P17_F   (81) QELDKYKNAVTELQLLMQSTPAANNRARRELPRFMNYTLN

                 121                                   160
     S2_F  (121) NTKNTNVTLSKKRKRRFLGFLLGVGSAIASGIAVSKVLHL
MRK_287_F  (121) NAKKTNVTLSKKRKRRFLGFLLGVGSAIASGIAVSKVLHL
    P17_F  (121) NAKKTNVTLSKKRKRRFLGFLLGVGSAIASGIAVSKVLHL

                 161                                   200
     S2_F  (161) EGEVNKIKSALLSTNKAVVSLSNGVSVLTSKVLDLKNYID
MRK_287_F  (161) EGEVNKIKSALLSTNKAVVSLSNGVSVLTSKVLDLKNYID
    P17_F  (161) EGEVNKIKSALLSTNKAVVSLSNGVSVLTSKVLDLKNYID

                 201                                   240
     S2_F  (201) KQLLPIVNKQSCSISNIETVIEFQQKNNRLLEITREFSVN
MRK_287_F  (201) KQLLPIVNKQSCSISNIETVIEFQQKNNRLLEITREFSVN
    P17_F  (201) KQLLPIVNKQSCSISNIETVIEFQQKNNRLLEITREFSVN

                 241                                   280
     S2_F  (241) AGVTTPVSTYMLTNSELLSLINDMPITNDQKKLMSNNVQI
MRK_287_F  (241) AGVTTPVSTYMLTNSELLSLINDMPITNDQKKLMSNNVQI
    P17_F  (241) AGVTTPVSTYMLTNSELLSLINDMPITNDQKKLMSNNVQI

                 281                                   320
     S2_F  (281) VRQQSYSIMSIIKEEVLAYVVQLPLYGVIDTPCWKLHTSP
MRK_287_F  (281) VRQQSYSIMSIIKEEVLAYVVQLPLYGVIDTPCWKLHTSP
    P17_F  (281) VRQQSYSIMSIIKXEVLAYVVQLPLYGVIDTPCWKLHTSP
```

FIG. 3A

```
                 321                                     360
      S2_F (321) LCTTNTKEGSNICLTRTDRGWYCDNAGSVSFFPLAETCKV
 MRK_287_F (321) LCTTNTKEGSNICLTRTDRGWYCDNAGSVSFFPQAETCKV
     P17_F (321) LCTTNTKEGSNICLTRTDRGWYCDNAGSVSFFPQAETCKV

                 361                                     400
      S2_F (361) QSNRVFCDTMNSLTLPSEVNLCNIDIFNPKYDCKIMTSKT
 MRK_287_F (361) QSNRVFCDTMNSLTLPSEVNLCNVDIFNPKYDCKIMTSKT
     P17_F (361) QSNRVFCDTMNSLTLPSEVNLCNVDIFNPKYDCKIMTSKT

                 401                                     440
      S2_F (401) DVSSSVITSLGAIVSCYGKTKCTASNKNRGIIKTFSNGCD
 MRK_287_F (401) DVSSSVITSLGAIVSCYGKTKCTASNKNRGIIKTFSNGCD
     P17_F (401) DVSSSVITSLGAIVSCYGKTKCTASNKNRGIIKTFSNGCD

                 441                                     480
      S2_F (441) YVSNKGVDTVSVGNTLYYVNKQEGKSLYVKGEPIINFYDP
 MRK_287_F (441) YVSNKGVDTVSVGNTLYYVNKQEGKSLYVKGEPIINFYDP
     P17_F (441) YVSNKGVDTVSVGNTLYYVNKQEGKSLYVKGEPIINFYDP

                 481                                     520
      S2_F (481) LVFPSDEFDASISQVNEKINQSLAFIRKSDELLHNVNAGK
 MRK_287_F (481) LVFPSDEFDASISQVNEKINQSLAFIRKSDELLHNVNAGK
     P17_F (481) LVFPSXEFDASISQVNEKINQSLAFIRKSDELLHNVNAGK

                 521                                     560
      S2_F (521) STTNIMITTIIIVIIVILLSLIAVGLLLYCKARSTPVTLS
 MRK_287_F (521) STTNIMITAIIIVIVVILLSLIAVGLLLYCKARSTPVTLS
     P17_F (521) STTNIMITAIIIVIVVILLSLIAVGLLLYCKARSTPVTLS

                 561           575
      S2_F (561) KDQLSGINNIAFSN- (SEQ ID NO: 14)
 MRK_287_F (561) KDQLSGINNIAFSN- (SEQ ID NO: 16)
     P17_F (561) KDQLSGINNIAFSN- (SEQ ID NO: 18)
```

FIG.3B

```
                 1                                      40
     S2_L    (1) MDPIINGNSANVYLTDSYLKGVISFSECNALGSYIFNGPY
MRK_287_L    (1) MDPIINGNSANVYLTDSYLKGVISFSECNALGSYIFNGPY
    P17_L    (1) MDPIINGNSANVYLTDSYLKGVISFSECNALGSYIFNGPY

                 41                                     80
     S2_L   (41) LKNDYTNLISRQNPLIEHINLKKLNITQSLISKYHKGEIK
MRK_287_L   (41) LKNDYTNLISRQNPLIEHMNLKKLNITQSLISKYHKGEIK
    P17_L   (41) LKNDYTNLISRQNPLIEHMNLKKLNITQSLISKYHKGEIK

                 81                                    120
     S2_L   (81) IEEPTYFQSLLMTYKSMTSLEQITTTNLLKKIIRRAIEIS
MRK_287_L   (81) LEEPTYFQSLLMTYKSMTSSEQIATTNLLKKIIRRAIEIS
    P17_L   (81) LEEPTYFQSLLMTYKSMTSSEQIATTNLLKKIIRRAIEIS

                 121                                   160
     S2_L  (121) DVKVYAILNKLGLKEKDKIKSNNGQDEDNSVITTIIKDDI
MRK_287_L  (121) DVKVYAILNKLGLKEKDKIKSNNGQDEDNSVITTIIKDDI
    P17_L  (121) DVKVYAILNKLGLKEKDKIKSNNGQDEXNSVITTIIKDDI

                 161                                   200
     S2_L  (161) LLAVKDNQSHLKAVKNHSTKQKDTIKTTLLKKLMCSMQHP
MRK_287_L  (161) LSAVKDNQSHLKAGKNHSTKQKDTIKTTLLKKLMCSMQHP
    P17_L  (161) LSAVKDNQSHLKAGKNHSTKQKDTIKTTLLKKLMCSMQHP

                 201                                   240
     S2_L  (201) PSWLIHWFNLYTKLNNILTQYRSSEVKNHGFILIDNHTLN
MRK_287_L  (201) PSWLIHWFNLYTKLNNILTQYRSNEVKNHGFTLIDNQTLS
    P17_L  (201) PSWLIHWFNLYTKLNNILTQYRSNEVKNHGFTLIDNQTLS

                 241                                   280
     S2_L  (241) GFQFILNQYGCIVYHKELKRITVTTYNQFLTWKDISLSRL
MRK_287_L  (241) GFQFILNQYGCIVYNKELKRITVTTYNQFLTWKDISLSRL
    P17_L  (241) GFQFILNQYGCIVYNKELKRITVTTYNQFLTWKDISLSRL

                 281                                   320
     S2_L  (281) NVCLITWISNCLNTLNKSLGLRCGFNNVILTQLFLYGDCI
MRK_287_L  (281) NVCLITWISNCLNTLNKSLGLRCGFNNVILTQLFLYGDCI
    P17_L  (281) NVCLITWISNCLNTLNKSLGLRCGFNNVILTQLFLYGDCI
```

FIG.4A

```
                   321                                    360
       S2_L (321)  LKLFHNEGFYIIKEVEGFIMSLILNITEEDQFRKRFYNSM
  MRK_287_L (321)  LKLFHNEGFYIIKEVEGFIMSLILNITEEDQFRKRFYNSM
      P17_L (321)  LKLFHNEGFYIIKEVEGFIMSLILNITEEDQFRKRFYNSM

                   361                                    400
       S2_L (361)  LNNITDAANKAQKSLLSRVCHTLLDKTVSDNIINGRWIIL
  MRK_287_L (361)  LNNITDAANKAQKNLLSRVCHTLLDKTVSDNIINGRWIIL
      P17_L (361)  LNNITDAANKAQKNLLSRVCHTLLDKTVSDNIINGRWIIL

                   401                                    440
       S2_L (401)  LSKFLKLIKLAGDNNLNNLSELYFLFRIFGHPMVDERQAM
  MRK_287_L (401)  LSKFLKLIKLAGDNNLNNLSELYFLFRIFGHPMVDERQAM
      P17_L (401)  LSKFLKLIKLAGDNNLNNLSELYFLFRIFGHPMVDERQAM

                   441                                    480
       S2_L (441)  DAVKVNCNETKFYLLSSLSMLRGAFIYRIIKGFVNNYNRW
  MRK_287_L (441)  DAVKINCNETKFYLLSSLSMLRGAFIYRIIKGFVNNYNRW
      P17_L (441)  DAVKINCNETKFYLLSSLSMLRGAFIYRIIKGFVNNYNRW

                   481                                    520
       S2_L (481)  PTLRNAIVLPLRWLTYYKLNTYPSLLELTERDLIVLSGLR
  MRK_287_L (481)  PTLRNAIVLPLRWLTYYKLNTYPSLLELTERDLIVLSGLR
      P17_L (481)  PTLRNAIVLPLRWLTYYKLNTYPSLLELTERDLIVLSGLR

                   521                                    560
       S2_L (521)  FYREFRLPKKVDLEMIINDKAISPPKNLIWTSFPRNYMPS
  MRK_287_L (521)  FYREFRLPKKVDLEMIINDKAISPPKNLIWTSFPRNYMPS
      P17_L (521)  FYREFRLPKKVDLEMIINDKAISPPKNLIWTSFPRNYMPS

                   561                                    600
       S2_L (561)  HIQNYIEHEKLKFSESDKSRRVLEYYLRDNKFNECDLYNC
  MRK_287_L (561)  HIQNYIEHEKLKFSESDKSRRVLEYYLRDNKFNECDLYNC
      P17_L (561)  HIQNYIEHEKLKFSESDKSRRVLEYYLRDNKFNECDLYNC

                   601                                    640
       S2_L (601)  VVNQSYLNNPNHVVSLTGKERELSVGRMFAMQPGMFRQVQ
  MRK_287_L (601)  VVDQSYLNNPNHVVSLTGKERELSVGRMFAMQPGMFRQVQ
      P17_L (601)  VVDQSYLNNPNHVVSLTGKERELSVGRMFAMQPGMFRQVQ
```

FIG.4B

```
                  641                                      680
     S2_L (641)  ILAEKMIAENILQFFPESLTRYGDLELQKILELKAGISNK
MRK_287_L (641)  ILAEKMIAENILQFFPESLTRYGDLELQKILELKAGISNK
    P17_L (641)  ILAEKMIAENILQFFPESLTRYGDLELQKILELKAGISNK

                  681                                      720
     S2_L (681)  SNRYNDNYNNYISKCSIITDLSKFNQAFRYETSCICSDVL
MRK_287_L (681)  SNRYNDNYNNYISKCSIITDLSKFNQAFRYETSCICSDVL
    P17_L (681)  SNRYNDNYNNYISKCSIITDLSKFNQAFRYETSCICSDVL

                  721                                      760
     S2_L (721)  DELHGVQSLFSWLHLTIPHVTIICTYRHAPPYIRDHIVDL
MRK_287_L (721)  DELHGVQSLFSWLHLTIPHVTIICTYRHAPPYIGDHIVDL
    P17_L (721)  DELHGVQSLFSWLHLTIPHVTIICTYRHAPPYIGDHIVDL

                  761                                      800
     S2_L (761)  NNVDEQSGLYRYHMGGIEGWCQKLWTIEAISLLDLISLKG
MRK_287_L (761)  NNVDEQSGLYRYHMGGIEGWCQKLWTIEAISLLDLISLKG
    P17_L (761)  NNVDEQSGLYRYHMGGIEGWCQKLWTIEAISLLDLISLKG

                  801                                      840
     S2_L (801)  KFSITALINGDNQSIDISKPVRLMEGQTHAQADYLLALNS
MRK_287_L (801)  KFSITALINGDNQSIDISKPIRLMEGQTHAQADYLLALNS
    P17_L (801)  KFSITALINGDNQSIDISKPIRLMEGQTHAQADYLLALNS

                  841                                      880
     S2_L (841)  LKLLYKEYAGIGHKLKGTETYISRDMQFMSKTIQHNGVYY
MRK_287_L (841)  LKLLYKEYAGIGHKLKGTETYISRDMQFMSKTIQHNGVYY
    P17_L (841)  LKLLYKEYAGIGHKLKGTETYISRDMQFMSKTIQHNGVYY

                  881                                      920
     S2_L (881)  PASIKKVLRVGPWINTILDDFKVSLESIGSLTQELEYRGE
MRK_287_L (881)  PASIKKVLRVGPWINTILDDFKVSLESIGSLTQELEYRGE
    P17_L (881)  PASIKKVLRVGPWINTILDDFKVSLESIGSLTQELEYRGE

                  921                                      960
     S2_L (921)  SLLCSLIFRNVWLYNQIALQLKNHALCNNKLYLDILKVLK
MRK_287_L (921)  SLLCSLIFRNVWLYNQIALQLKNHALCNNKLYLDILKVLK
    P17_L (921)  SLLCSLIFRNVWLYNQIALQLKNHALCNNKLYLDILKVLK
```

FIG.4C

```
                   961                                     1000
     S2_L   (961)  HLKTFFNLDNIDTALTLYMNLPMLFGGGDPNLLYRSFYRR
MRK_287_L   (961)  HLKTFFNLDNIDTALTLYMNLPMLFGGGDPNLLYRSFYRR
    P17_L   (961)  HLKTFFNLDNIDTALTLYMNLPMLFGGGDPNLLYRSFYRR

                   1001                                    1040
     S2_L  (1001)  TPDFLTEAIVHSVFILSYYTNHDLKDKLQDLSDDRLNKFL
MRK_287_L  (1001)  TPDFLTEAIVHSVFILSYYTNHDLKDKLQDLSDDRLNKFL
    P17_L  (1001)  TPDFLTEAIVHSVFILSYYTNHDLKDKLQDLSDDRLNKFL

                   1041                                    1080
     S2_L  (1041)  TCIITFDKNPNAEFVTLMRDPQALGSERQAKITSEINRLA
MRK_287_L  (1041)  TCIITFDKNPNAEFVTLMRDPQALGSERQAKITSEINRLA
    P17_L  (1041)  TCIITFDKNPNAEFVTLMRDPQALGSERQAKITSEINRLA

                   1081                                    1120
     S2_L  (1081)  VTEVLSTAPNKIFSKSAQHYTTTEIDLNDIMQNIEPTYPH
MRK_287_L  (1081)  VTEVLSTAPNKIFSKSAQHYTTTEIDLNDIMQNIEPTYPH
    P17_L  (1081)  VTEVLSTAPNKIFSKSAQHYTTTEIDLNDIMQNIEPTYPH

                   1121                                    1160
     S2_L  (1121)  GLRVVYESLPFYKAEKIVNLISGTKSITNILEKTSAIDLT
MRK_287_L  (1121)  GLRVVYESLPFYKAEKIVNLISGTKSITNILEKTSAIDLT
    P17_L  (1121)  GLRVVYESLPFYKAEKIVNLISGTKSITNILEKTSAIDLT

                   1161                                    1200
     S2_L  (1161)  DIDRATEMMRKNITLLIRIFPLDCNRDKREILSMENLSIT
MRK_287_L  (1161)  DIDRATEMMRKNITLLIRILPLDCNRDKREILSMENLSIT
    P17_L  (1161)  DIDRATEMMRKNITLLIRILPLDCNRDKREILSMENLSIT

                   1201                                    1240
     S2_L  (1201)  ELSKYVRERSWSLSNIVGVTSPSIMYTMDIKYTTSTIASG
MRK_287_L  (1201)  ELSKYVRERSWSLFNIVGVTSPSIMYTMDIKYTTSTIASG
    P17_L  (1201)  ELSKYVRERSWSLFNIVGVTSPSIMYTMDIKYTTSTIASG

                   1241                                    1280
     S2_L  (1241)  IIIEKYNVNSLTRGERGPTKPWVGSSTQEKKTMPVYNRQV
MRK_287_L  (1241)  IIIEKYNVNSLTRGERGPTKPWVGSSTQEKKTMPVYNRQV
    P17_L  (1241)  IIIEKYNVNSLTRGERGPTKPWVGSSTQEKKTMPVYNRQV
```

FIG.4D

```
                  1281                                    1320
      S2_L (1281) LTKKQRDQIDLLAKLDWVYASIDNKDEFMEELSIGTLGLT
 MRK_287_L (1281) LTKKQRDQIDLLAKLDWVYASIDNKDEFMEELSIGTLGLT
     P17_L (1281) LTKKQRDQIDLLAKLDWVYASIDNKDEFMEELSIGTLGLT

                  1321                                    1360
      S2_L (1321) YEKAKKLFPQYLSVNYLHRLTVSSRPCEFPASIPAYRTTN
 MRK_287_L (1321) YEKAKKLFPQYLSVNYLHRLTVSSRPCEFPASIPAYRTTN
     P17_L (1321) YEKAKKLFPQYLSVNYLHRLTVSSRPCEFPASIPAYRTTN

                  1361                                    1400
      S2_L (1361) YHFDTSPINRILTEKYGDEDIDIVFQNCISFGLSLMSVVE
 MRK_287_L (1361) YHFDTSPINRILTEKYGDEDIDIVFQNCISFGLSLMSVVE
     P17_L (1361) YHFDTSPINRILTEKYGDEDIDIVFQNCISFGLSLMSVVE

                  1401                                    1440
      S2_L (1401) QFTNVCPNRIILIPKLNEIHLMKPPIFTGDVDIHKLKQVI
 MRK_287_L (1401) QFTNVCPNRIILIPKLNEIHLMKPPIFTGDVDIHKLKQVI
     P17_L (1401) QFTNVCPNRIILIPKLNEIHLMKPPIFTGDVDIHKLKQVI

                  1441                                    1480
      S2_L (1441) QKQHMFLPDKISLTQYVELFLSNKTLKSGSHVNSNLILAH
 MRK_287_L (1441) QKQHMFLPDKISLTQYVELFLSNKTLKSGSHVNSNLILAH
     P17_L (1441) QKQHMFLPDKISLTQYVELFLSNKTLKSGSHVNSNLILAH

                  1481                                    1520
      S2_L (1481) KISDYFHNTYILSTNLAGHWILIIQLMKDSKGIFEKDWGE
 MRK_287_L (1481) KISDYFHNTYILSTNLAGHWILIIQLMKDSKGIFEKDWGE
     P17_L (1481) KISDYFHNTYILSTNLAGHWILIIQLMKDSKGIFEKDWGE

                  1521                                    1560
      S2_L (1521) GYITDHMFINLKVFFNAYKTYLLCFHKGYGRAKLECDMNT
 MRK_287_L (1521) GYITDHMFINLKVFFNAYKTYLLCFHKGYGKAKLECDMNT
     P17_L (1521) GYITDHMFINLKVFFNAYKTYLLCFHKGYGKAKLECDMNT

                  1561                                    1600
      S2_L (1561) SDLLCVLELIDSSYWKSMSKVFLEQKVIKYILSQDASLHR
 MRK_287_L (1561) SDLLCVLELIDSSYWKSMSKVFLEQKVIKYILSQDASLHR
     P17_L (1561) SDLLCVLELIDSSYWKSMSKVFLEQKVIKYILSQDASLHR
```

FIG.4E

```
                     1601                                   1640
     S2_L (1601) VKGCHSFKLWFLKRLNVAEFTVCPWVVNIDYHPTHMKAIL
MRK_287_L (1601) VKGCHSFKLWFLKRLNVAEFTVCPWVVNIDYHPTHMKAIL
    P17_L (1601) VKGCHSFKLWFLKRLNVAEFTVCPWVVNIDYHPTHMKAIL

                     1641                                   1680
     S2_L (1641) TYIDLVRMGLINIDKIYIKNKHKFNDEFYTSNLFYINYNF
MRK_287_L (1641) TYIDLVRMGLINIDRIHIKNKHKFNDEFYTSNLFYINYNF
    P17_L (1641) TYIDLVRMGLINIDRIHIKNKHKFNDEFYTSNLFYINYNF

                     1681                                   1720
     S2_L (1681) SDNTHLLTKHIRIANSELENNYNKLYHPTPETLENILTNP
MRK_287_L (1681) SDNTHLLTKHIRIANSELENNYNKLYHPTPETLENILANP
    P17_L (1681) SDNTHLLTKHIRIANSELENNYNKLYHPTPETLENILANP

                     1721                                   1760
     S2_L (1721) VKCNDKKTLNDYCIGKNVDSIMLPLLSNKKLIKSSTMIRT
MRK_287_L (1721) IKSNDKKTLNEYCIGKNVDSIMLPLLSNKKLIKSSAMIRT
    P17_L (1721) IKSNDKKTLNEYCIGKNVDSIMLPLLSNKKLIKSSAMIRT

                     1761                                   1800
     S2_L (1761) NYSKQDLYNLFPTVVIDKIIDHSGNTAKSNQLYTTTSHQI
MRK_287_L (1761) NYSKQDLYNLFPMVVIDRIIDHSGNTAKSNQLYTTTSHQI
    P17_L (1761) NYSKQDLYNLFPMVVIDRIIDHSGNTAKSNQLYTTTSHQI

                     1801                                   1840
     S2_L (1801) PLVHNSTSLYCMLPWHHINRFNFVFSSTGCKISIEYILKD
MRK_287_L (1801) SLVHNSTSLYCMLPWHHINRFNFVFSSTGCKISIEYILKD
    P17_L (1801) SLVHNSTSLYCMLPWHHINRFNFVFSSTGCKISIEYILKD

                     1841                                   1880
     S2_L (1841) LKIKDPNCIAFIGEGAGNLLLRTVVELHPDIRYIYRSLKD
MRK_287_L (1841) LKIKDPNCIAFIGEGAGNLLLRTVVELHPDIRYIYRSLKD
    P17_L (1841) LKIKDPNCIAFIGEGAGNLLLRTVVELHPDIRYIYRSLKD

                     1881                                   1920
     S2_L (1881) CNDHSLPIEFLRLYNGHINIDYGENLTIPATDATNNIHWS
MRK_287_L (1881) CNDHSLPIEFLRLYNGHINIDYGENLTIPATDATNNIHWS
    P17_L (1881) CNDHSLPIEFLRLYNGHINIDYGENLTIPATDATNNIHWS
```

FIG.4F

```
                   1921                                    1960
      S2_L (1921)  YLHIKFAEPISLFVCDAELPVTVNWSKIIIEWSKHVRKCK
MRK_287_L (1921)  YLHIKFAEPISLFVCDAELPVTVNWSKIIIEWSKHVRKCK
     P17_L (1921)  YLHIKFAEPISLFVCDAELPVTVNWSKIIIEWSKHVRKCK

                   1961                                    2000
      S2_L (1961)  YCSSVNKCTLIVKYHAQDDIDFKLDNITILKTYVCLGSKL
MRK_287_L (1961)  YCSSVNKCMLIVKYHAQDDIDFKLDNITILKTYVCLGSKL
     P17_L (1961)  YCSSVNKCMLIVKYHAQDDIDFKLDNITILKTYVCLGSKL

                   2001                                    2040
      S2_L (2001)  KGSEVYLVLTIGPANVFPVFNVVQNAKLILSRTKNFIMPK
MRK_287_L (2001)  KGSEVYLVITIGPANIFPAFNVVQNAKLILSRTKNFIMPK
     P17_L (2001)  KGSEVYLVITIGPANIFPAFNVVQNAKLILSRTKNFIMPK

                   2041                                    2080
      S2_L (2041)  KADKESIDANIKSLIPFLCYPITKKGINTALSKLKSVVSG
MRK_287_L (2041)  KADKESIDANIKSLIPFLCYPITKKGINTALSKLKSVVSG
     P17_L (2041)  KADKESIDANIKSXIPFLCYPITKKGINTALSKLKSVVSG

                   2081                                    2120
      S2_L (2081)  DILSYSIAGRNEVFSNKLINHKHMNILKWFNHVLNFRSTE
MRK_287_L (2081)  DILSYSIAGRNEVFSNKLINHKHMNILKWFNHVLNFRSTE
     P17_L (2081)  DILSYSIAGRNEVFSNKLINHKHMNILKWFNHVLNFRSTE

                   2121                                    2160
      S2_L (2121)  LNYNHLYMVESTYPYLSELLNSLTTNELKKLIKITGSLLY
MRK_287_L (2121)  LNYNHLYMVESTYPYLSELLNSLTTNELKKLIKITGSLLY
     P17_L (2121)  LNYNHLYMVESTYPYLSELLNSLTTNELKKLIKITGSLLY

                   2161
      S2_L (2161)  NFHNE--- (SEQ ID NO: 20)
MRK_287_L (2161)  NFHNE--I (SEQ ID NO: 22)
     P17_L (2161)  NFHNE--I (SEQ ID NO: 24)
```

FIG.4G

LIVE, ATTENUATED RESPIRATORY SYNCYTIAL VIRUS

CROSS-REFERENCE TO RELATED APPLICATIONS

The present application claims the benefit of U.S. Provisional Application No. 61/198,327, filed Nov. 5, 2008, hereby incorporated by reference herein.

REFERENCE TO SEQUENCE LISTING SUBMITTED ELECTRONICALLY

The sequence listing of the present application is submitted electronically via EFS-Web as an ASCII formatted sequence listing with a file name "MRLIFD22569USPCT -SEQTXT-04MAY2011.TXT", creation date of May 4, 2011, and a size of 160 KB. This sequence listing submitted via EFS-Web is part of the specification and is herein incorporated by reference in its entirety.

BACKGROUND OF THE INVENTION

Human respiratory syncytial virus (RSV) is a negative-sense, single-stranded RNA virus and a member of the genus *Pneumovirus*, family Paramyxoviradae. RSV is the leading cause of viral pneumonia and bronchiolitis in infants under one and is a major cause of hospitalization and fatal respiratory tract disease in these infants. Serious disease can also develop in children with certain underlying illnesses (e.g., immunodeficiencies, congenital heart disease, and bronchopulmonary dysplasia). Virtually all children are infected by age two, and re-infection is common in older children and adults. (Chanock et al., in Viral Infections of Humans, 3rd ed., A. S. Evans, ed., Plenum Press, N.Y. (1989)) In healthy adults, most infections are asymptomatic and are generally confined to mild, upper respiratory tract disease; however, elderly patients and immunocompromised individuals are more likely to have severe and possibly life-threatening infections.

Two major, antigenic subgroups of RSV have been identified, A and B, as well as several different genotypes within each subgroup (Anderson et al., 1985, J. Infect. Dis. 151:626-633; Mufson et al., 1985, *J. Gen. Virol.* 66:2111-2124). The two antigenic subgroups are approximately 25% antigenically related by reciprocal cross-neutralization analysis. Multiple variants of each subgroup have been found to co-circulate in epidemics which occur annually during late fall, winter, and spring months in temperate climates (Anderson et al., 1991, *J. Infect. Dis.* 163:687-692). There is evidence that children infected with one of the two major RSV subgroups may be protected against re-infection by the homologous subgroup (Mufson et al., 1987, *J. Clin. Microbiol.* 26:1595-1597). This, along with evidence that protective immunity will accumulate following repeated infections, suggests that it is feasible to develop an RSV vaccination regiment for infants and young children which would provide sufficient immunity to protect against serious disease and death.

A native RSV genome typically comprises a negative-sense polynucleotide molecule which, through complementary viral mRNAs, encodes eleven species of viral proteins, i.e., the nonstructural species NS1 and NS2, N, P, matrix (M), small hydrophobic (SH), glycoprotein (O), fusion (F), M2(ORF1), M2(ORF2), and L, substantially as described in Mink et al., 1991, *Virology* 185:615-624; Stec et al., 1991, *Virology* 183:273-287; and Connors et al., 1995, *Virology.* 208:478-484.

While an immune prophylaxis, Synagis®, is currently marketed for prevention of RSV-associated diseases in premature birth, high-risk infants, despite decades of research, there is no safe and effective vaccine to combat RSV infection and the associated clinical diseases. Secretory antibodies appear to be most important in protecting the upper respiratory tract, whereas high levels of serum antibodies are thought to have a major role in resistance to RSV infection in the lower respiratory tract. However, purified human immunoglobulin (Ig) preparations suffer from the possibility of transmitting blood-borne viruses, while recombinant Ig preparations are expensive to manufacture.

Early attempts (1966) to vaccinate young children used a parenterally-administered, formalin-inactivated RSV vaccine. Unfortunately, administration of this vaccine in several field trials was shown to be specifically associated with the development of a significantly exacerbated illness following subsequent natural infection with RSV (Kapikian et al, 1968, *Am. J Epidemiol.* 89:405-421; Kim et al, 1969, *Am. J Epidemiol.* 89:422-434; Fulginiti et al, 1969, *Am. J Epidemiol.* 89:435-448; Chin et al; 1969, *Am. J Epidemiol.* 89:449-463). The reasons why this vaccine enhanced RSV disease are not clear. It has been suggested that this exposure to RSV antigens elicited an abnormal or unbalanced immune response which led to an immunopathological potentiation of natural disease (Kim et al, 1976, *Pediatr. Res.* 10:75-78; Prince et al, 1986, *J. Virol.* 57:721-728).

The use of a live-attenuated or live-vectored virus vaccine has several advantages over subunit or inactivated virus vaccines. Live, attenuated virus vaccines can mimic natural viral infection, efficiently triggering the host's immune system, and are more likely than a subunit or inactivated vaccine to give a robust immunity comprising both humoral and cellular components.

SUMMARY OF THE INVENTION

The present application discloses live strains of respiratory syncytial virus (RSV) suitable for immunization of a subject, including humans, against wild-type RSV infection. The provided strains are properly attenuated to effectively elicit production of an immune response in a vaccinated subject that protects against serious respiratory illnesses associated with RSV infection without causing respiratory disease upon immunization therewith. The attenuated strains were developed by passaging a phenotypically wild-type human RSV strain of subgroup A in Vero cells at a fixed multiplicity. Sequence analysis shows that mutations were induced through the passage process, resulting in a genetically-stable, immunogenic and protective, and avirulent RSV strain.

Different aspects of the present invention are directed to a live, attenuated RSV comprising: (1) one or more nucleotide and/or amino acid mutations identified herein; (2) a viral genome which comprises one or more of the nucleotide mutations and/or encodes one or more of the amino acid mutations identified in the attenuated RSV disclosed herein; and/or (3) a nucleic acid comprising a nucleotide sequence either having one or more of the nucleotide mutations described herein or encoding one or more amino acid mutations described herein.

Reference to "mutation" refers to the presence of a different amino acid or nucleotide at a specified amino acid or nucleotide position within a protein sequence or a gene and/or genomic sequence, respectively, than provided in a reference or wild-type sequence. The resulting mutation can be directly introduced into the reference or wild-type sequence or can be provided by a sequence other than the reference or wild-type sequence, as long as the end result provides for the indicated mutation.

A live, attenuated RSV of the present invention is immunogenic and protective against either RSV infection or the development of severe respiratory illness associated with RSV infection. In a preferred embodiment, a live, attenuated RSV is a human RSV suitable for immunization against wild-type RSV infection of subgroup A and/or B. Also disclosed herein are pharmaceutical compositions comprising said live, attenuated RSV and methods of treating a subject, preferably a human, against RSV infection by administering said compositions.

Examples of nucleic acids comprising a sequence either encoding one or more amino acid mutations as described herein or having one or more nucleotide mutations as described herein include: (1) full-length RSV genomic sequences based on a particular full-length RSV reference sequence; (2) different RSV nucleic acid regions based on particular RSV nucleic acid sequences described herein; (3) partial genomic sequences comprising one or more particular RSV nucleic acid sequences described herein; and, (4) full-length genomic sequences containing one or more particular RSV nucleic acid sequences described herein. Reference to a particular RSV nucleic acid sequence includes a specified sequence and/or the indicated identity to a specified sequence.

The term "treating" or "treatment" refers to both therapeutic and/or prophylactic treatment, including prevention or reduction of infection or reinfection, or the reduction or elimination of symptoms, diseases, or conditions associated with RSV infection. Those in need of treatment include the general population and/or patients infected with RSV. Examples of those in need include those already with an RSV-associated disorder(s), those prone to develop such a disorder, and/or those in which such a disorder is to be prevented.

A "disorder" is any condition resulting in whole or in part from RSV infection, including but not limited to pneumonia and bronchiolitis. Encompassed by the term "disorder" are chronic and acute disorders or diseases including those pathological conditions which predispose the mammal to the disorder in question.

The term "protect" or "protection," when used in the context of an attenuated virus or treatment method of the present invention, means reducing the likelihood of RSV infection, reinfection, a disorder(s) resulting from RSV infection, as well as reducing the severity of the infection, reinfection and/or a disorder(s) resulting from such infection.

The term "effective amount" means sufficient amount that, when introduced to a vertebrate host, preferably a human host, results in a protective immune response. One skilled in the art recognizes that this level may vary.

The live, attenuated RSV described herein can be derived from any RSV subgroup (A or B) or strain (e.g., human, bovine, murine), preferably derived from human. To engender a protective immune response, the RSV strain may be one which is endogenous to the subject being immunized, such as human RSV being used to immunize humans.

The term "wild-type" or "wt," in reference to a RSV strain, refers both to viruses having a genomic sequence that is wild-type at known markers for attenuation and/or viruses that are phenotypically wild-type (i.e., not attenuated), as shown in either an in vivo (e.g., in a human or other suitable animal model) or in vitro model of attenuation. The term "wild-type," in reference to a RSV protein or nucleic acid (e.g., gene, genomic) sequence refers to a sequence that does not contain markers known to contribute to an attenuated phenotype.

"Live, attenuated virus," in reference to a RSV disclosed herein, means a virus that is both genotypically different from a wild-type RSV (i.e., comprising differences in the genomic sequence) and phenotypically different from said wild-type virus (i.e., as evidenced by an attenuated phenotype). An attenuated virus is phenotypically different by displaying reduced virulence whilst still viable (or "live"); thus, viruses can display different degrees of attenuation. Those live, attenuated RSV of the present invention are attenuated, making them nonpathogenic in a subject host. An incompletely-attenuated virus displays a reduction in pathogenesis but is still capable of generating a disease response in a subject host. A live, attenuated RSV of the present invention can be naturally derived (e.g., via passaging a wild-type or incompletely-attenuated strain) or recombinantly produced. If recombinantly produced, recombinant RSV encompasses a RSV or RSV-like viral or subviral particle derived directly or indirectly from a recombinant expression system or propagated from virus or subviral particles produced there from. The live, attenuated RSV disclosed herein is in an isolated and typically purified form.

"Substantially similar" means that a given nucleic acid or amino acid sequence shares at least 80%, preferably at least 85%, more preferably at least 90%, and even more preferably at least 95% or at least 99% identity with a reference sequence, as dictated by the context of the text. Sequence identity to a reference sequence is determined by aligning a sequence with the reference sequence and determining the number of identical nucleotides or amino acids in the corresponding regions. This number is divided by the total number of amino acids in the reference sequence, multiplied by 100, and then rounded to the nearest whole number. Sequence identity can be determined by a number of art-recognized sequence comparison algorithms or by visual inspection (see generally Ausubel, F M, et al., Current Protocols in Molecular Biology, 4, John Wiley & Sons, Inc., Brooklyn, N.Y., A.1E.1-A.1F.11, 1996-2004). A substantially similar nucleic acid or amino acid sequence of the present invention, if it encodes or consists of the NS2, G, L or F protein, will maintain one or more of the nucleotide or amino acid mutations identified within p17, described in detail infra.

Reference to "isolated" indicates a different form than found in nature or in other than the native environment of wild-type virus, such as the nasopharynx of an infected individual. Thus, an isolated virus can be a heterologous component of a cell culture or other system. The different form can be, for example, a different purity than found in nature and/or a structure that is not found in nature.

Reference to open-ended terms such as "comprises" allows for additional elements or steps. Occasionally, phrases such as "one or more" are used with or without open-ended terms to highlight the possibility of additional elements or steps.

Unless explicitly stated, reference to terms such as "a," "an," and "the" is not limited to one and include the plural reference unless the context clearly dictates otherwise. For example, "a cell" does not exclude "cells." Occasionally, phrases such as one or more are used to highlight the possible presence of a plurality.

The term "mammalian" refers to any mammal, including a human.

The abbreviation "Kb" refers to kilobases.

The abbreviation "pfu" refers to plaque forming units.

The abbreviation "ORF" refers to the open reading frame of a gene.

Other features and advantages of the present invention are apparent from the additional descriptions provided herein including the different examples. The provided examples illustrate different components and methodology useful in practicing the present invention. The examples do not limit the claimed invention. Based on the present disclosure the skilled artisan can identify and employ other components and methodology useful for practicing the present invention.

BRIEF DESCRIPTION OF THE DRAWINGS

FIG. 1 shows an alignment of the amino acid sequences of the NS2 protein from a wild-type RSV strain, hRSV S2 (SEQ ID NO: 2; see NCBI GenBank Accession no. U39662; Tolley et al., 1996, *Vaccine* 14:1637-1646), Merck strain 287 (SEQ ID NO: 4) and p17 (SEQ ID NO: 6). The single-underlined amino acids indicate differences in the NS2 protein between the hRSV S2 strain and both the Merck 287 and p17 strains. The NS1 amino acid sequence of Merck strain p17_pp is the same as for p17 (SEQ ID NO: 6).

FIG. 2 shows an alignment of the amino acid sequences of the G protein from hRSV S2 (SEQ ID NO: 8), Merck strain 287 (SEQ ID NO: 10) and p17 (SEQ ID NO: 12). The single-underlined amino acids indicate differences in the G protein between the hRSV S2 strain and both the Merck 287 and p17 strains. The double-underlined amino acids indicate differences between the p17 strain and both the hRSV S2 and Merck 287 strains. The G amino acid sequence of Merck strain p17_pp is the same as for p17 (SEQ ID NO: 12).

FIGS. 3A and B show an alignment of the amino acid sequences of the F protein from hRSV S2 (SEQ ID NO: 14), Merck strain 287 (SEQ ID NO: 16) and p17 (SEQ ID NO: 18). The single-underlined amino acids indicate differences in the F protein between the hRSV S2 strain and both the Merck 287 and p17 strains. The double-underlined amino acids indicate differences between the p17 strain and both the hRSV S2 and Merck 287 strains. Amino acid position 294 of SEQ ID NO: 18 is designated as an "X," representing either a Glu or Lys residue. Amino acid position 486 of SEQ ID NO: 18 is also designated as an "X," representing either an Asp or Gly residue.

FIGS. 4A-G show an alignment of the amino acid sequences of the L protein from hRSV S2 (SEQ ID NO: 20), Merck strain 287 (SEQ ID NO: 22) and p17 (SEQ ID NO: 24). The single-underlined amino acids indicate differences in the L protein between the hRSV S2 strain and both the Merck 287 and p17 strains. The double-underlined amino acids indicate differences between the p17 strain and both the hRSV S2 and Merck 287 strains. Amino acid position 148 of SEQ ID NO: 24 is designated as an "X," representing either an Asp or Ala residue. Amino acid position 2054 is also designated as an "X," representing either a Leu or Phe residue.

DETAILED DESCRIPTION OF THE INVENTION

Figure 5:
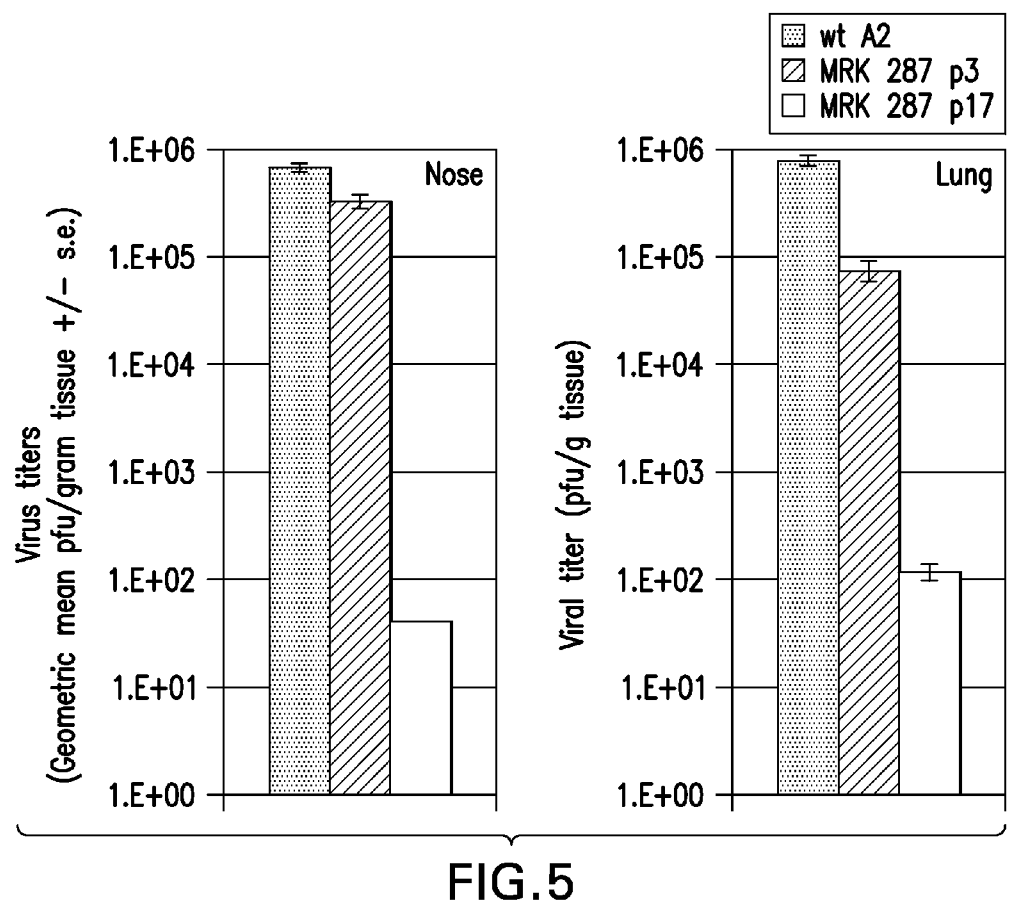
FIG. 5 compares viral titers (pfu/gram of tissue) of the wild-type hRSV A2 strain (Huang and Wetz, 1982, *J. Virol.* 43:150), passage 3 of Merck strain 287 ("p3"), and passage 17 of Merck strain 287 ("p17") in both nose and lung samples from cotton rats intranasally inoculated with said viruses.

The present invention relates to a live, attenuated respiratory syncytial virus (RSV) for use as a vaccine against RSV infection and/or the development of RSV-associated illnesses. The virus disclosed herein is attenuated such that it is nonpathogenic when administered to a subject, preferably a human, but substantially retains the antigenic and immunogenic properties of wild-type RSV. As such, the attenuated viruses disclosed herein are useful for stimulating a protective immune response in an inoculated mammal without producing the respiratory symptoms caused by wild-type virus.

I. Live, Attenuated RSV

The live, attenuated RSV viruses described herein were identified by serial passaging a hRSV A type strain, hereinafter called "Merck strain 287," "strain 287," or "p0." Merck strain 287 was derived from a RSV strain that was initially amplified two times in GMK cells. After this initial amplification, the virus underwent five additional passages in the human diploid cell line, WI-38. This passage 5 material, renamed Merck strain 287, was sequenced and shown to be both genetically wild-type at genetic markers known for attenuation and phenotypically wild-type (see Examples, infra).

Merck strain 287 was passaged in VERO CCL-81 monkey kidney cells at a fixed multiplicity. Virus titers remained constant over passaging, and the cytopathic effect of the virus in culture was also consistent. Attenuation of the passaged viruses was monitored by measuring a reduction in viral shedding in in vivo rodent and primate models. A marked attenuation was seen between passage 3 (p3) and passage 17 (p17) in both the cotton rat model and African green monkeys, showing a 2-4 log reduction in viral load. Sequence comparison of the genomic DNA isolated from the p17 virus population with the original Merck strain 287 identified nucleotide mutations within the p17 genome, the majority of which are located within the genes encoding the G, F, and L proteins (hereinafter referred to as the G, F and L genes, respectively). P17 contains a total of 21 nucleotide differences and 11 amino acid differences when compared with Merck strain 287. A plaque-purified virus derived from p17 (p17 pp) contains an additional nucleotide mutation when compared with Merck strain 287. Further sequence analysis was performed on passage 5 (p5), passage 10 (p10) and passage 15 (p15) to monitor the genetic changes over the passaging process, as well as on passage 18 (p18) and passage 22 (p22) to measure the genetic stability of the induced mutations. Immunogenicity and protection studies were also performed. These studies show that the p17 strain disclosed herein is genetically-stable, immunogenic and protective, and avirulent. Thus, a live, attenuated RSV of the present invention can be used as a vaccine to protect against disease caused by infection with RSV.

A detailed summary of the sequence comparison between Merck strain 287 (passage 0 or "p0") and various passaged strains thereof can be found in Examples 2 and 4, infra. Briefly, the full-length viral genome for p0, p17, and p17_pp (a plaque purified virus derived from p17) were sequenced and compared, as well as targeted sequences of passages 5, 10, 15, and 18. The genomic sequence of Merck strain 287 is set forth herein as SEQ ID NO: 25. The genomic sequences of p17 and the p17_pp strain are set forth herein as SEQ ID NO: 26 and SEQ ID NO: 91, respectively. The location of the 21 nucleotide differences between the viral genomes of Merck strain 287 and p17, as well as the specific nucleotide mutations, are listed in Table 5 (infra) (e.g., an alanine (A) to guanine (O) mutation at position 5295). The genomic sequence of the p17_pp strain is set forth herein as SEQ ID NO: 91. The genomic sequence of p17_pp is the same as that of p17 with the exception of an additional, silent nucleotide mutation within the gene encoding the NS1 protein (at nucleotide position 162 of the NS1 gene). Table 8 (infra) compares the nucleotide differences between Merck strain 287, p17 and p17_pp. Tables 6 and/or 9 (infra) also lists the location of the nucleotide mutations within the p17 and p17_pp genomic sequences, as well as the corresponding location of each mutation within a RSV gene open reading frame (ORF). For example, the mutation at position 5295 of the p17 viral genome corresponds to a mutation at nucleotide position 610 of the G gene ORF. Tables 6 and 9 additionally list whether or not a particular point mutation, or combination of point mutations, generates an amino substitution, as well as the amino acid position of said substitution. For example, the mutation at nucleotide position 5295 of the p17 viral genome leads to an amino acid substitution from lysine (LYS) to glutamic acid (GLU) at amino acid residue position 204 of the G protein. Of the 21 nucleotide differences between p17 and Merck strain 287 (and the 22 nucleotide differences between p17_pp and Merck strain 287), one nucleotide difference is located within an untranslated region of the viral genome (i.e., nucleotide 15046 within the 5' untranslated region).

Of the 21 nucleotide differences identified in the p17 viral genome, compared to the parental p0 strain (Merck strain 287), four of the nucleotide differences may represent polymorphisms within the virus population comprised within passage 17, located at nucleotide positions 6538, 7115, 8937 and 14656 of the RSV viral genome (see Example 2, infra). These positions are designated with an "n" in SEQ ID NO: 26. The "n" at position 6538 can be either a G or A; the "n" at position 7115 can be either an A or G; the "n" at position 8937 can be either an A or C; and, the "n" at position 14656 can be either a G or T. These nucleotide polymorphisms are also marked with an "n" in the gene sequences corresponding to the F and L genes (SEQ ID NOs: 17 and 23, respectively) and with an "x" in the protein sequences corresponding to the F and L proteins (SEQ ID NOs: 18 and 24, respectively). Polymorphisms represent the existence of two (or more) forms of a gene within a population, wherein each form is too common to be due merely to a new, minor mutation. Two of these potential polymorphisms are located within the coding region for the F protein, and two are located within the L protein coding region. These polymorphisms are evident on sequencing chromatograms, represented by double peaks corresponding to at least two nucleotides. The polymorphisms indicate that the population of viruses within the p17 pool of viruses from which DNA was extracted for sequence analysis is not a homogenous population of viruses. Each of these four nucleotide polymorphisms induces an amino acid substitution (see Example 2, infra).

The p17 RSV strain was plaque purified to a clonal population, p17_pp virus, and sequenced (see Example 4, infra). In addition to identifying a silent mutation at nucleotide 162 of the gene encoding the NS1 protein within the p17_pp genome, the polymorphisms identified within the genes encoding the L and F proteins of p17 were resolved (see Tables 8 and 9, infra). Thus, the genes encoding the F and L proteins of the p17_pp virus are set forth herein as SEQ ID NO: 92 and SEQ ID NO: 94, respectively, and the encoded proteins are SEQ ID NO: 93 and SEQ ID NO: 95.

Table 7 (within Example 2, infra) shows the progression of mutations induced over the passaging of Merck strain 287 described herein. For example, only one nucleotide mutation is seen in passage 5 (p5), located at nucleotide position 954 of the RSV genome. The number of nucleotide mutations increases over the passage process, and by p15, at least 20 of the 21 nucleotide mutations within p17 are present. While the twenty-first nucleotide difference seen in p17, located at nucleotide 15046 of the viral genome within the 5' untranslated region, may be present in p15, the gene segment that contains that portion of the p15 viral genome was not sequenced.

Figure 7:
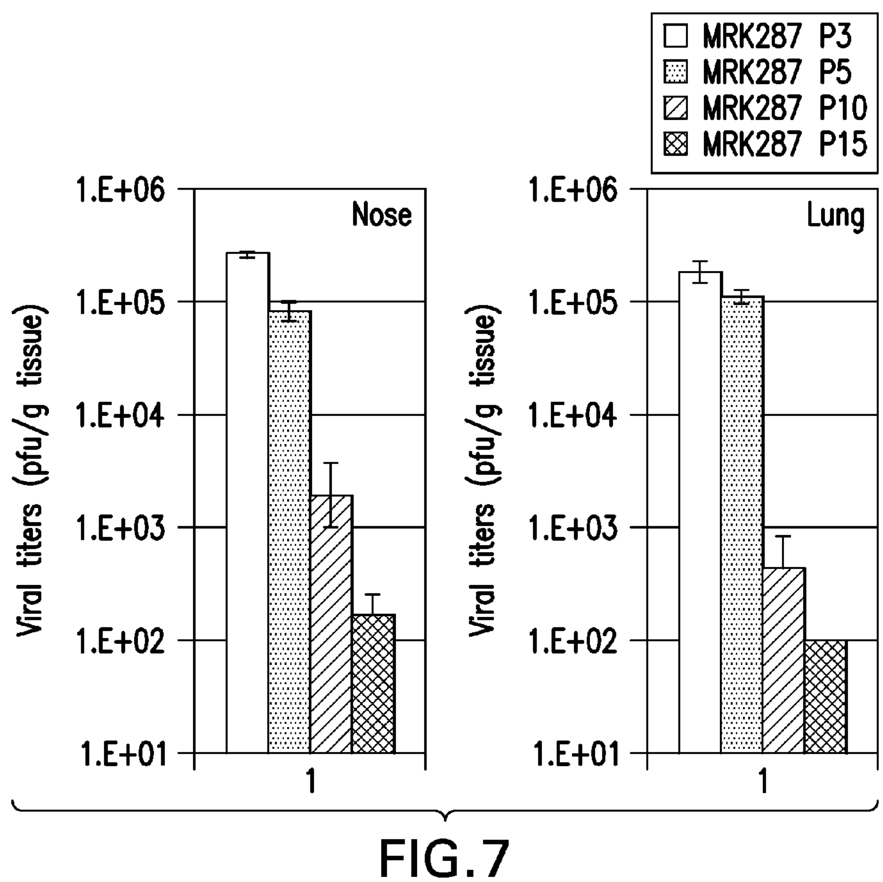
FIG. 7 compares viral titers (pfu/gram of tissue) of passages 3 ("p3"), 5 ("p5"), 10 ("p10") and 15 ("p15") of Merck strain 287 in both nose and lung samples from cotton rats intranasally inoculated with said viruses.

The results in FIG. 7 highlight the relationship between viral passage and the degree of attenuation, comparing the in vivo replication of p3, p5, p10, and p15 (see also Example 3, infra). Passage 5 (p5) already begins to show reduced replication compared to p3. Passages 10 (p10) and 15 (p15) display an even further reduction in replication, with a marked decrease in replication between p10 and p15. The p15 virus appears to be as attenuated as the p17 virus described above (see FIG. 5). When comparing the array of mutations present within p10 and p15, p15 has only two additional nucleotide differences, located within the F and L protein coding regions. Thus, and without being bound by any particular theory, it is possible that the mutations within the F and/or L protein coding regions are particularly important for attenuating RSV. A study of the attenuation of the plaque purified derivative of p17, p17_pp, shows that the virus is as attenuated as the parent p17 strain (see Example 4, infra).

Table 1 provides a summary of the Sequence Identification Numbers (SEQ ID NOs) for the NS1, NS2, G, F, and L gene open reading frames and encoded proteins for Merck strain 287 (MRK287), p17, p17_pp, and a published wild-type strain, hRSV S2 (disclosed in NCBI GenBank Accession no. U39662; Tolley et al., 1996, *Vaccine* 14:1637-1646).

TABLE 1

| RSV | NS1 SEQ ID NO: | | NS2 SEQ ID NO: | | G SEQ ID NO: | | F SEQ ID NO: | | L SEQ ID NO: | |
|---|---|---|---|---|---|---|---|---|---|---|
| strain | gene | prot. | gene | prot. | gene | prot. | gene | prot. | gene | prot. |
| Merck 287 (SEQ ID NO: 25) | 89 | 88 | 3 | 4 | 9 | 10 | 15 | 16 | 21 | 22 |

TABLE 1-continued

| RSV | NS1 SEQ ID NO: | | NS2 SEQ ID NO: | | G SEQ ID NO: | | F SEQ ID NO: | | L SEQ ID NO: | |
|---|---|---|---|---|---|---|---|---|---|---|
| strain | gene | prot. | gene | prot. | gene | prot. | gene | prot. | gene | prot. |
| p17 (SEQ ID NO: 26) | 89 | 88 | 5 | 6 | 11 | 12 | 17 | 18 | 23 | 24 |
| p17_pp (SEQ ID NO: 91) | 90 | 88 | 5 | 6 | 11 | 12 | 92 | 93 | 94 | 95 |
| S2 | 87 | 88 | 1 | 2 | 7 | 8 | 13 | 14 | 19 | 20 |

RSV is a negative-sense, nonsegmented, single-stranded RNA genome. As such, reassortment of genomic segments does not occur. However, a dependence on RNA polymerase lacking RNA proofreading and editing ability results in the RSV genome being quite mutable. Sequence studies of various RSV genes have confirmed the division of human RSV into two major groups (A and B), while also identifying many variants or lineages within each group (see, e.g., Peret et al., 1998, *J. Gen. Virol.* 79:2221-2229). Between the two antigenic subgroups of human RSV, amino acid sequence identity ranges from 96% (for the N protein) to 53% (for the G protein) (Johnson et al., 1987, *Proc. Natl. Acad. Sci. USA* 84:5625-5629). Within group A and group B strains, the G protein shows up to 20% and 9% amino acid diversity, respectively (Cane et al., 1991, *J. Gen. Virol.* 72:649-357; Sullender et al., 1991, *J. Virol.* 65:5425-5434).

As examples of this genetic heterogeneity, alignments of the NS2, G, F, and L proteins from Merck strain 287, p17, and hRSV S2 can be found in FIGS. 1, 2, 3 and 4, respectively. As shown in the alignment of the NS2 proteins in FIG. 1, while there are no amino acid differences between Merck strain 287 and the p17 passaged strain described herein, there are two amino acid differences between the wild-type hRSV S2 strain and both Merck strain 287 and p17 (underlined in FIG. 1). It is important to note, however, that both Merck strain 287 and hRSV S2 are phenotypically wild-type; and, thus, these amino acid differences between hRSV S2 and both Merck strain 287 and p17 neither induces nor contributes to the attenuation of p17 or p17_pp.

Similarly, there are amino acid differences between the wild-type hRSV S2 strain and both Merck strain 287 and p17 in the G, F, and L protein sequences (see the single-underlined amino acids in FIGS. 2, 3, and 4, respectively). However, there are also amino acid differences between the G, F, and L protein sequences of Merck strain 287 and p17 (see the double-underlined amino acids in FIGS. 2, 3, and 4, respectively). It is likely that one or more of these double-underlined amino acid differences contributes to the attenuated phenotype demonstrated for p17 and p17_pp.

As such, the present invention relates to live, attenuated RSV having a modified viral genome comprising one or more of the nucleotide mutations as described in p17 and/or p17_pp and/or encoding one or more of the amino acid mutations as described in p17 herein, as compared to Merck strain 287. In one embodiment, the viral genome of said attenuated RSV may contain, for example, additional nucleotide differences and/or encode additional amino acid differences, as compared to the Merck strain 287 genomic sequence as set forth in SEQ ID NO: 25 or another phenotypically wild-type RSV strain (e.g., hRSV S2), wherein said additional nucleotide and/or amino acid mutations do not substantially contribute to the attenuation phenotype.

In another embodiment, a live, attenuated RSV of the present invention may comprise one or more of the nucleotide and/or amino acid mutations as described in p17 and/or p17_pp in addition to further mutations at genetic markers known for attenuation (see, e.g., Conners et al., 1995, *Virology,* 208:478-484; Crowe et al., 1996, *Virus Genes* 13:269-273; Firestone et al., 1996, *Virology* 225:419-422; Whitehead et al., 1998, *J. Virol.* 72:4467-4471).

II. Examples of Different Embodiments

In a first embodiment, the present invention relates to a live, attenuated respiratory syncytial virus (RSV) comprising a viral genome, wherein the viral genome encodes proteins comprising one or more amino acids selected from the group consisting of: a glutamic acid at position 204 of the protein encoded by the G gene; a glutamic acid at position 205 of the protein encoded by the G gene; an alanine at position 211 of the protein encoded by the G gene; a glutamic acid at position 213 of the protein encoded by the G gene; a glycine at position 221 of the protein encoded by the G gene; a glycine at position 223 of the protein encoded by the G gene; a glycine at position 232 of the protein encoded by the G gene; a lysine at position 294 of the protein encoded by the F gene; a glycine at position 486 of the protein encoded by the F gene; an alanine at position 148 of the protein encoded by the L gene; and, a phenylalanine at position 2054 of the protein encoded by the L gene. Thus, in this embodiment, a live, attenuated RSV of the present invention comprises one, all or a subset of the amino acid residues referenced in this paragraph. The location of the recited amino acid residues are referenced as per their position within a particular amino acid sequence encoded by a gene within the viral genome. The G, F and L proteins are encoded by the G, F and L genes, respectively.

In a further embodiment, a live, attenuated RSV of the present invention comprises a viral genome comprising one or more nucleotides selected from the group consisting of: an adenine at nucleotide position 162 of the NS1 gene; an adenine at nucleotide position 327 of the NS2 gene; a guanine at nucleotide position 610 of the G gene; a guanine at nucleotide position 613 of the G gene; a guanine at nucleotide position 630 of the G gene; a guanine at nucleotide position 631 of the G gene; a guanine at nucleotide position 637 of the G gene; a guanine at nucleotide position 639 of the G gene; a guanine at nucleotide position 654 of the G gene; a guanine at nucleotide position 661 of the G gene; a guanine at nucleotide position 662 of the G gene; a guanine at nucleotide position 666 of the G gene; a guanine at nucleotide position 667 of the G gene; a guanine at nucleotide position 668 of the G gene; a guanine at nucleotide position 675 of the G gene; a guanine at nucleotide position 695 of the G gene; a guanine at nucleotide position 696 of the G gene; an adenine at nucleotide position 880 of the F gene; a guanine at nucleotide position 1457 of the F gene; a cytosine at nucleotide position 443 of the L gene; and, a thymine at nucleotide position 6162 of the L gene. The viral genome may comprise one, all or a subset of the specified nucleotides.

One, all or a subset of the specified amino acid residues and/or nucleotides can be comprised with a live, attenuated RSV of the present invention. The amino acid residues and nucleotides recited above correspond to the location of specific amino acid residues and nucleotides present in p17 and p17_pp described herein (see Tables 5, 6, 8 and 9, infra), For example, a live, attenuated RSV within this embodiment may comprise a lysine at position 294 of the protein encoded by the F gene, a glycine at position 486 of the protein encoded by the F gene, an alanine at position 148 of the protein encoded by the L gene, and a phenylalanine at position 2054 of the protein encoded by the L gene. As described supra, the results presented herein suggest that recited amino acid residues within the F and L proteins substantially contribute to the attenuated phenotype of p17 and p17_pp.

In a second embodiment, the present invention relates to a live, attenuated RSV comprising a viral genome which comprises one or more nucleotide mutations compared to a non-attenuated RSV viral genome, wherein one or more of the nucleotide mutations result in one or more amino acid mutations, and wherein the one or more amino acid mutations are located at amino acid positions selected from the group consisting of: positions 204, 205, 211, 213, 221, 223, and 232, each of the protein encoded by the G gene; positions 294 and 486, each of the protein encoded by the F gene; and, positions 148 and 2054, each of the protein encoded by the L gene. The non-attenuated RSV strain can be a genetically and/or phenotypically wild-type RSV and provides reference sequences. The location of the amino acid mutations are referenced as per their position within a particular amino acid sequence encoded by a gene within the viral genome. The G, F and L proteins are encoded by the G, F and L genes, respectively. The amino acid mutations recited above correspond to the location of amino acid substitutions present in p17 and p17_pp described herein when compared to a genetically wild-type (RSV S2 strain) and a phenotypically wild-type (Merck strain 287) RSV strain (see Tables 6 and 9, infra).

In a further embodiment, an amino acid mutation at position 204 of the protein encoded by the G gene is to a glutamic acid, an amino acid mutation at position 205 of the protein encoded by the G gene is to a glutamic acid, an amino acid mutation at position 211 of the protein encoded by the G gene is to an alanine, an amino acid mutation at position 213 of the protein encoded by the G gene is to a glutamic acid, an amino acid mutation at position 221 of the protein encoded by the G gene is to a glycine, an amino acid mutation at position 223 of the protein encoded by the G gene is to a glycine, an amino acid mutation at position 232 of the protein encoded by the G gene is to a glycine, an amino acid mutation at position 294 of the protein encoded by the F gene is to a lysine, an amino acid mutation at position 486 of the protein encoded by the F gene is to a glycine, an amino acid mutation at position 148 of the protein encoded by the L gene is to an alanine, and an amino acid mutation at position 2054 of the protein encoded by the L gene is to a phenylalanine.

In a still further embodiment, an amino mutation at position 204 of the protein encoded by the G gene is Lys204Glu, an amino acid mutation at position 205 of the protein encoded by the G gene is Lys205Glu, an amino acid mutation at position 211 of the protein encoded by the G gene is Thr211Ala, an amino acid mutation at position 213 of the protein encoded by the G gene is Lys213Glu, an amino acid mutation at position 221 of the protein encoded by the G gene is Lys221Gly, an amino acid mutation at position 223 of the protein encoded by the G gene is Lys223Gly, an amino acid mutation at position 232 of the protein encoded by the G gene is Glu232Gly, an amino acid mutation at position 294 of the protein encoded by the F gene is Glu294Lys, an amino acid mutation at position 486 of the protein encoded by the F gene is Asp486Gly, an amino acid mutation at position 148 of the protein encoded by the L gene Asp148Ala, and an amino acid mutation at position 2054 of the protein encoded by the L gene is Leu2054Phe. As an example, the term "Lys204Glu," used in reference to the G protein, indicates that the lysine (Lys) amino acid residue at amino acid position 204 of the G protein is substituted with a glutamic acid (Glu) amino acid residue. The amino acid residue abbreviations are recited infra. The amino acid mutations recited above correspond to the amino acid substitutions present in p17 and p17_pp described herein (see Table 6 and Table 9, infra).

In another embodiment, the viral genome comprises nucleotide mutations that result in either all or a subset of the recited amino acid mutations. For example, the viral genome of an attenuated RSV within this embodiment may comprise nucleotide mutations resulting in amino acid mutations at one or all of the recited amino acid positions within the proteins encoded by the F and L genes. As described supra, the results presented herein suggest that mutations within the F and L proteins substantially contribute to the attenuated phenotype of p17 and p17_pp.

In a further embodiment, the one or more nucleotide mutations within the viral genome of the attenuated RSV that result in the one or more amino acid mutations recited above are located at a nucleotide position selected from the group consisting of: positions 610, 613, 631, 637, 639, 661, 662, 667, 668, 695 and 696 of the G gene; positions 880 and 1457 of the gene; and, positions 443 and 6162 of the L gene. In this embodiment, two nucleotide positions may need to be mutated to generate an amino acid substitution. The location of the nucleotide mutations are referenced as per their position within a particular ORF contained within the viral genome. In an alternative, the location of nucleotide mutations can be reference as per their position within the viral genome itself. For example, nucleotide position 610 of the G gene corresponds to nucleotide position 5295 of the RSV genome. The relationship between a mutation at a specific position within an ORF described herein and its corresponding position within the RSV genome can be found in Table 6 and Table 9, infra.

In a still further embodiment, the viral genome further comprises one or more silent nucleotide mutations located at nucleotide positions selected from the group consisting of position 327 of the NS2 gene, position 630 of the G gene, position 654 of the G gene, position 666 of the G gene, and position 675 of the G gene. The viral genome may further comprise a silent mutation at nucleotide position 162 of the NS1 gene. The viral genome may comprise all or a subset of these silent nucleotide mutations. In another embodiment, the viral genome comprises all of the nucleotide mutations (silent and non-silent) recited above.

In another embodiment, the viral genome comprises one or more nucleotide mutations as compared to the viral genome of either a non-attenuated or an incompletely-attenuated RSV strain, wherein said one or more mutations are located at nucleotide positions selected from the group consisting of position 162 of the NS1 gene, position 327 of the NS2 gene, positions 610, 613, 630, 631, 637, 639, 654, 661, 662, 666, 667, 668, 675, 695, and 696 of the G gene, positions 880 and 1457 of the F gene, and, positions 443 and 6162 of the L gene. Said non-attenuated strain can be a genetically and/or phenotypically wild-type RSV. In a further embodiment, said viral genome comprises mutations at all of the recited nucleotide positions.

In a further embodiment, a nucleotide mutation at nucleotide position 162 of the NS1 gene is T260A, a nucleotide mutation at nucleotide position 327 of the NS2 gene is G327A, a nucleotide mutation at nucleotide position 610 of the G gene is A6100, a nucleotide mutation at nucleotide position 613 of the G gene is A613G, a nucleotide mutation at nucleotide position 630 of the G gene is A630G, a nucleotide mutation at nucleotide position 631 of the G gene is A6310, a nucleotide mutation at nucleotide position 637 of the G gene is A637G, a nucleotide mutation at nucleotide position 639 of the G gene is A639G, a nucleotide mutation at nucleotide position 654 of the G gene is A654G, a nucleotide mutation at nucleotide position 661 of the G gene is A6610, a nucleotide mutation at nucleotide position 662 of the G gene is A662G, a nucleotide mutation at nucleotide position 666 of the G gene is A666G, a nucleotide mutation at nucleotide position 667 of the G gene is A667G, a nucleotide mutation at nucleotide position 668 of the G gene is A668G, a nucleotide mutation at nucleotide position 675 of the G gene is A675G, a nucleotide mutation at nucleotide position 695 of the G gene is A695G, a nucleotide mutation at nucleotide position 696 of the G gene is A696G, a nucleotide mutation at nucleotide position 880 of the F gene is G880A, a nucleotide mutation at nucleotide position 1457 of the F gene is A14570, a nucleotide mutation at nucleotide position 443 of the L gene is A443C, and a nucleotide mutation at nucleotide position 6162 of the L gene is G61621. As an example the term "G327A," when used in reference to the NS2 gene of an attenuated RSV of this embodiment, indicates that the guanine nucleotide at this position is mutated to an adenine (A) nucleotide. The nucleotide abbreviations for thymine and cytosine are "T" and "C," respectively. The viral genome may comprise nucleotides mutations at all or a subset of the recited nucleotide positions.

In a further embodiment, the present invention also relates to a live, attenuated respiratory syncytial virus (RSV) comprising a viral genome which comprises one or more nucleotide mutations as compared to the viral genome of either a non-attenuated or an incompletely-attenuated RSV strain, wherein said one or more mutations are located at nucleotide positions selected from the group consisting of position 260, 954, 5295, 5298, 5315, 5316, 5322, 5324, 5339, 5346, 5347, 5351, 5352, 5353, 5360, 5380, 5381, 6538, 7115, 8937 and 14656 of the RSV genome. Each of the nucleotide mutations recited above is present within the RSV p17 and/or p17_pp strain described herein. In a further embodiment, said modified viral genome comprises mutations at all of the recited nucleotide positions.

When referencing a particular location within either an open reading frame encoding a RSV protein, the entire RSV genomic sequence, or an amino acid sequence of a RSV protein, it is appreciated that precise locations may vary slightly between RSV strains within and/or between antigenic subgroups (A versus B) and viral species (e.g., human versus bovine). As such, comparative nucleotide and/or amino acid analysis, whereby multiple reference sequences are aligned, can be used to identify the exact nucleotide and/or amino acid position that corresponds to a specifically-recited position described herein. Thus, encompassed within the prior embodiments, and those embodiments hereafter which recite specific amino acid or nucleotide positions, are live, attenuated RSV comprising a viral genome comprising one or more of the nucleotide and/or amino acid residues and/or one or more of the nucleotide mutations and/or amino acid mutations at positions that correspond to those specifically-recited positions as determined by sequence alignment and analysis of and with reference sequences.

In a third embodiment the viral genome of a live, attenuated RSV of the present invention comprises a nucleotide sequence encoding a NS1, NS2, G, F and/or L protein that is related to a wild-type NS1, NS2, G, F and/or L protein (e.g., SEQ ID NO: 88, 2, 8, 14 and 20, respectively, which correspond to the RSV S2 NS1, NS2, G, F and/or L protein sequences), wherein the NS1, NS2, G, F and/or L protein sequence contains one or a combination of the amino acids, or amino acid mutations, identified herein to differ between p17 and/or p17_pp and wild-type amino acid sequences of the specific viral protein, and wherein said related sequence has at least 95%, preferably 99%, sequence identity to said wild-type RSV protein sequence in the region outside of the one or combination of differing amino acids or amino acid mutations.

In a further embodiment the viral genome of a live, attenuated RSV of the present invention comprises a nucleotide sequence of a NS1, NS2, G, F and/or L gene that is related to a wild-type NS1, NS2, G, F and/or L gene sequence (e.g., SEQ ID NO: 87, 1, 7, 13 and 19, respectively, which correspond to the RSV S2 NS1, NS2, G, F and/or L gene sequences), wherein the NS1, NS2, G, F and/or L gene sequence contains one or a combination of the nucleotides, or nucleotide mutations, identified herein to differ between p17 and/or p17_pp and wild-type nucleotide sequences of the specific genes, and wherein said related sequence has at least 95%, preferably 99%, sequence identity to said wild-type RSV gene sequence in the region outside of the one or combination of differing nucleotides or nucleotide mutations.

In a fourth embodiment, the viral genome of a live, attenuated RSV encompassed by the present invention comprises an open reading frame encoding a G, F and/or L protein, wherein said protein(s) consist of the amino acid sequences as set forth in SEQ ID NO: 12, SEQ ID NO: 18 or SEQ ID NO: 93, and SEQ ID NO: 24 or SEQ ID NO: 95, respectively. SEQ ID NOs: 12, 18 and 24 represent the amino acid sequences of the G, F and L proteins within p17 described herein (see also FIGS. 2, 3 and 4, respectively). The polymorphisms within the F and L proteins are indicated in the corresponding recited sequences (SEQ ID NOs: 18 and 24). Thus, in a further embodiment, position 294 of the F protein of p17 (SEQ ID NO: 18) is a Lys residue, and/or position 486 of the F protein of p17 is a Gly residue. In a still further embodiment, position 148 of the L protein of p17 (SEQ ID NO: 24) is an Ala residue, and/or position 2054 of the L protein of p17 is a Phe residue. SEQ ID NO: 93 and SEQ ID NO: 95 represent the amino acid sequences of the F and L proteins within the plaque purified derivative of p17, p17_pp. The polymorphisms within these sequences have been resolved in the plaque purified virus and are reflected in SEQ ID NOs: 93 and 95.

In a further embodiment, the viral genome of a live, attenuated RSV comprises an open reading frame encoding a G, F and/or L protein, wherein the protein(s) consist of an amino acid sequence that is at least 80%, at least 85%, at least 90%, at least 95%, or at least 99% identical to the amino acid sequences set forth in SEQ ID NO: 12, SEQ ID NO: 18 or SEQ ID NO: 93, and SEQ ID NO: 24 or SEQ ID NO: 95, respectively, and wherein one or a combination of the specific amino acids within said G, F and/or L proteins identified herein to differ between p17 and/or p17_pp and wild-type amino acid sequences of the specific viral proteins are present.

In a fifth embodiment, the viral genome of a live, attenuated RSV described herein comprises an open reading frame encoding an NS1, NS2, G, F and/or L protein, wherein one or more of said open reading frames consist of the nucleotide sequences as set forth in SEQ ID NO: 89 or SEQ ID NO: 90, SEQ ID NO: 5, SEQ ID NO: 11, SEQ ID NO: 17 or SEQ ID NO: 92, and/or SEQ ID NO: 23 or SEQ ID NO: 94, respectively. SEQ ID NOs: 89, 5, 11, 17 and 23 represent the nucleotide sequences encoding the NS1, NS2, G, F and L proteins, respectively, within p17 described herein. The nucleotide sequences encoding the F and L proteins of p17 contain the nucleotide polymorphism described supra. Thus, in a further embodiment, position 880 of the F gene of p17 (SEQ ID NO: 17) is an adenine nucleotide, and/or position 1457 of the F gene of p17 is a guanine nucleotide. In a still further embodiment, position 443 of the L gene of p17 (SEQ ID NO: 23) is a cytosine nucleotide, and/or position 6162 of the L gene of p17 is a thymine nucleotide. SEQ ID NOs: 90, 5, 11, 92 and 94 represent the nucleotide sequences encoding the NS1, NS2, G, F and L proteins, respectively within p17_pp. The polymorphisms within the nucleotide sequences encoding the F and L proteins of p17 have been resolved in the plaque purified virus and are reflected in SEQ ID NOs: 92 and 94.

In a further embodiment, the viral genome of a live, attenuated RSV comprises open reading frame corresponding to an NS1, NS2, G, F and/or L gene that is at least 80%, at least 85%, at least 90%, at least 95%, or at least 99% identical to a nucleotide sequence set forth in SEQ ID NO: 90, SEQ ID NO: 5, SEQ ID NO: 11, SEQ ID NO: 17 or SEQ ID NO: 92, and/or SEQ ID NO: 23 or SEQ ID NO: 94, respectively, wherein one or a combination of the specific nucleotides within said NS1, NS2, G, F and/or L genes identified herein to differ between p17 and/or p17_pp and wild-type nucleotide sequences of the specific viral genes are present.

In a sixth embodiment, the viral genome of a live, attenuated RSV described in the prior embodiments further contains either a cytosine at position 15046, a mutation at position 15046, a mutation at position 15046 to a cytosine, or a mutation of A15046C, within the viral genome. Nucleotide position 15046 is located within the 5' untranslated region of the RSV genome.

In a seventh embodiment, the viral genome of a live, attenuated RSV described in the prior embodiments contains either further nucleotide and/or amino acid mutations at genetic markers known for attenuation of RSV or further nucleotides and/or amino acids known to confer an attenuated phenotype to RSV, preferably human RSV. This embodiment encompasses all of the live, attenuated RSV described in the prior embodiments, including strains derived there from that are further attenuated by, for example, chemical mutagenesis, cold adaptation, or genetic recombination (e.g. site-directed mutagenesis). Thus, incompletely-attenuated RSV mutants known in the art may be further attenuated (e.g., more completely attenuated) by introduction of the nucleotides and/or amino acids described herein to contribute to the attenuation of p17 and/or p17_pp.

In an eighth embodiment, a live, attenuated RSV described in the prior embodiments belong to either antigenic subgroup A or B of RSV. In a further embodiment, the live, attenuated RSV is a human RSV.

In a ninth embodiment, the viral genome of a live, attenuated RSV of the present invention comprises the nucleotide sequence as set forth in SEQ ID NO: 26 or SEQ ID NO: 91. SEQ ID NO: 26 represents the nucleotide sequence of the viral genome of p17 described herein. Nucleotide positions 6538, 7115, 8937 and 14656 of SEQ ID NO: 26 contain possible polymorphisms. Thus, the nucleotides at those positions within SEQ ID NO: 26 represent either G or A (for position 6538), A or G (for position 7115), A or C (for position 8937), and G or T (for position 14656). In a further embodiment, position 6538 is an adenine nucleotide; position 7115 is a guanine nucleotide; position 8937 is a cytosine nucleotide; and/or position 14656 is a thymine nucleotide. SEQ ID NO: 91 represents the nucleotide sequence of the viral genome of p17_pp described herein. In a further embodiment, a live, attenuated RSV comprises a nucleotide sequence that is at least 80%, at least 85%, at least 90%, at least 95%, or at least 99% identical, across the genome, to the nucleotide sequence set forth in SEQ ID NO: 26 or SEQ ID NO: 91, wherein one or a combination of the specific nucleotides identified herein to differ between p17 and/or p17_pp and wild-type nucleotide sequences of the specific viral genes are present.

In a tenth embodiment, a live, attenuated RSV of the present invention comprises a variant protein and/or nucleic acid sequence that is substantially similar to those sequences comprised within the attenuated RSV described in the prior embodiments corresponding to said attenuated RSV, having both physical/structural and functional properties that are substantially the same. In one embodiment, said live, attenuated RSV comprises a substantially similar protein encoded by a nucleic acid molecule that hybridizes under stringent conditions to the complement of a nucleic acid molecule encoding one or more of the modified proteins within the p17 or p17_pp virus. In a further embodiment, said live, attenuated RSV comprises nucleic acid molecules that hybridize to one or more of the modified nucleic acid molecules, or regions thereof (either coding or non-coding), within the p17 or p17_pp virus under stringent conditions.

In an eleventh embodiment, a live, attenuated RSV described in the prior embodiments is comprised within a population of live, attenuated RSV. A population of attenuated RSV means that said population of viruses is not necessarily homogenous for a single virus. For example, as described herein, polymorphisms have been found in the later passages of the RSV strains disclosed herein. There are four polymorphic sites within the p17 genome described herein. As such, a population of viruses, as represented by p17, may consist of different attenuated viruses having a genome comprising the fixed nucleotide mutations (i.e., non-polymorphic) described herein, as well as one of two possible nucleotides at the four polymorphic positions, 6538, 7115, 8937 and 14656. A RSV population can be generated by serially passaging either a non-attenuated or an incompletely-attenuated RSV strain in cell culture as described herein (see Example 1, infra), including but not limited to serially passaging Merck strain 287 having a viral genome as set forth in SEQ ID NO: 25. Virus populations can be purified to homogeneity or substantial homogeneity by passaging on suitable cell types or by performing a series of one or more cloning steps.

A further embodiment of the present invention encompasses a live, attenuated RSV, or population thereof, as described in the previous embodiments, wherein said virus is produced by a process comprising incorporating, by recombinant methods, one or more of the nucleotides and/or amino acids identified herein to differ between p17 or p17_pp and wild-type sequences of the specific viral proteins or genes (described in detail supra and infra) into either a non-attenuated or incompletely-attenuated RSV strain. In a further embodiment of the present invention, a live, attenuated RSV, or population thereof, as described in the prior embodiments is produced by a process comprising serially passaging Merck strain 287 (having the genomic sequence as set forth in SEQ ID NO: 25) as per the method described in Example 1, infra. Thus, said embodiment encompasses passaging a non-attenuated RSV strain comprising a viral genome as set forth in SEQ ID NO: 25 in a cell line (including, but not limited to African Green Monkey kidney cell line, Vero CCL-81) at a fixed multiplicity of infection (MOI) (e.g., between 1:100 and 1:1000).

A further embodiment of the present invention encompasses a method of attenuating a RSV comprising incorporating, by recombinant methods, one or more of the nucleotides and/or amino acids identified herein to differ between p17 or p17_pp and wild-type nucleotide or amino acid sequences of the specific viral genes or proteins (described in detail supra and infra) into either a non-attenuated or incompletely-attenuated RSV strain. A further embodiment of the present invention encompasses a method of attenuating a RSV comprising serially passaging Merck strain 287 (having the genomic sequence as set forth in SEQ ID NO: 25) as per the method described in Example 1, infra.

The present invention also includes one or more of the live, attenuated RSV described in the prior embodiments, a population thereof, or a vaccine comprising said attenuated viruses (i) for use in, (ii) for use as a medicament for, or (iii) for use in the preparation of a medicament for: (a) therapy (e.g., of the human body); (b) medicine; (c) inhibition of RSV replication; (d) treatment or prophylaxis of infection by RSV; or, (e) treatment, prophylaxis of, or delay in the onset or progression of RSV-associated disease(s). In these uses, the attenuated virus and/or vaccine can optionally be employed in combination with one or more anti-viral agents.

III. Pharmaceutical Compositions

A pharmaceutical composition comprising a live, attenuated RSV, or a virus population comprising said live, attenuated RSV, as described herein, and a pharmaceutically acceptable carrier is also provided by this invention.

Thus, a live, attenuated RSV described herein can be formulated with pharmaceutically acceptable carriers to help retain biological activity while also promoting increased stability during storage within an acceptable temperature range. As used herein, the term "pharmaceutically acceptable carrier" encompasses any suitable pharmaceutical carriers well known in the art and described in a variety of texts, such as Remington's Pharmaceutical Sciences. Potential carriers include, but are not limited to, physiologically balanced culture medium, phosphate buffer saline solution, water, emulsions (e.g., oil/water or water/oil emulsions), various types of wetting agents, cryoprotective additives or stabilizers such as proteins, peptides or hydrolysates (e.g., albumin, gelatin), sugars (e.g., sucrose, lactose, sorbitol), amino acids (e.g., sodium glutamate), or other protective agents. The resulting aqueous solutions may be packaged for use as is or lyophilized. Lyophilized preparations are combined with a sterile solution prior to administration for either single or multiple dosing. Formulated compositions, especially liquid formulations, may contain a bacteriostat to prevent or minimize degradation during storage, including but not limited to effective concentrations (usually ≤1% w/v) of benzyl alcohol, phenol, m-cresol, chlorobutanol, methylparaben, and/or propylparaben. A bacteriostat may be contraindicated for some patients; therefore, a lyophilized formulation may be reconstituted in a solution either containing or not containing such a component.

The pharmaceutical composition may optionally include an adjuvant to enhance the immune response of the host. Suitable adjuvants are, for example, toll-like receptor agonists, alum, AlPO4, alhydrogel, Lipid-A and derivatives or variants thereof, oil-emulsions, saponins, neutral liposomes, liposomes containing the vaccine and cytokines, non-ionic block copolymers, and chemokines. Non-ionic block polymers containing polyoxyethylene (POE) and polyxylpropylene (POP), such as POE-POP-POE block copolymers may be used as an adjuvant (Newman et al., 1998, *Critical Reviews in Therapeutic Drug Carrier Systems* 15:89-142). These adjuvants have the advantage in that they help to stimulate the immune system in a non-specific way, thus enhancing the immune response to a pharmaceutical product.

A live, attenuated RSV described herein, derived from one particular RSV subgroup or strain, can be combined with other attenuated RSV derived from a different subgroup or strain. The different viruses can be in an admixture and administered simultaneously, or administered separately. Due to the phenomenon of cross-protection among certain strains of RSV, immunization with one strain may protect against several different strains of the same or different subgroup. Thus, an isolated, attenuated RSV described herein may be combined with other non-naturally occurring RSV or exist within a population of attenuated RSV.

In some instances it may be desirable to combine a live, attenuated RSV described herein, or a composition thereof, with other pharmaceutical products (e.g., vaccines) which induce protective responses to other agents, particularly those causing other childhood illnesses. For example, an attenuated RSV composition described herein can be administered simultaneously (typically separately) or sequentially with other vaccines recommended by the Advisory Committee on Immunization Practices (ACIP; http://www.cdc.gov/vaccines/recs/ACIP/default.htm) for the targeted age group (e.g., infants from approximately one to six months of age). These additional vaccines include, but are not limited to, other parenterally-administered vaccines. As such, a live, attenuated RSV composition described herein may be administered simultaneously or sequentially with vaccines against, for example, hepatitis B (HepB), diphtheria, tetanus and pertussis (DTaP), pneumococcal bacteria (PCV), *Haemophilus influenzae* type b (Hib), polio, influenza and rotavirus.

IV. Methods of Use

Pharmaceutical compositions comprising a live, attenuated RSV, or a virus population comprising said live, attenuated RSV, are useful to vaccinate a subject to treat RSV infection and illnesses associated therewith. The scope of this invention is meant to include maternal immunization.

Thus, the present invention further provides a method of vaccinating a subject against RSV infection by administering to the subject an effective amount of a pharmaceutical composition described hereinabove. This subject may be an animal, for example, a mammal, such as a chimp or a human. Pharmaceutical compositions containing a live, attenuated RSV described herein are administered to a subject susceptible to or otherwise at risk of RSV infection or the development of severe illnesses associated with RSV infection (including re-infection), enhancing the subject's own immune response capabilities. In particular, due to the potentially serious consequences of RSV infection in neonates, seronegative and seropositive infants and young children, and the elderly, these individuals will benefit from immunization with the disclosed live, attenuated RSV compositions. Thus, particularly suitable candidates for immunization with the described pharmaceutical products are infants, children, the elderly, and adult candidates for immunosuppressive therapies. Seronegative individuals are those who exhibit no immunologic evidence of previous infection with a subgroup A or B RSV. Seropositive individuals are those who have acquired detectable RSV antibodies, either passively from the mother or as a result of past RSV infection.

Pharmaceutical compositions comprising the live, attenuated RSV described herein elicit the production of an immune response that is protective against serious lower respiratory tract disease, such as pneumonia and bronchiolitis, when the subject is subsequently infected or re-infected with a wild-type RSV. While the naturally circulating virus is still capable of causing infection, particularly in the upper respiratory tract, there is a much reduced possibility of rhinitis as a result of the vaccination and a possible boosting of resistance by subsequent infection by wild-type virus. Following vaccination, there are detectable levels of host engendered serum and secretory antibodies which are capable of neutralizing homologous (of the same subgroup) wild-type virus in vitro and in vivo. In many instances the host antibodies will also neutralize wild-type virus of a different, non-vaccine subgroup. To achieve higher levels of cross-protection, for example, against heterologous strains of another subgroup, subjects can be vaccinated with a live, attenuated RSV described herein from at least one predominant strain of both subgroups A and B. As such, a live, attenuated RSV described herein can belong to either antigenic subgroup A or B, and virus from both subgroups may be combined in vaccine formulations for more comprehensive coverage against prevalent RSV infections.

The live, attenuated RSV described herein, and pharmaceutical compositions thereof, are provided in an effective amount to induce or enhance an effective immune response against RSV in a subject, preferably a human. An effective amount will allow some growth and proliferation of the virus, in order to produce the desired immune response, but will not produce RSV-associated symptoms or illnesses. Based on the guidance provided herein, persons skilled in the art will readily be able to determine the proper amount of virus to use in the live vaccine. The precise amounts will depend on several factors, for example, the subject's state of health and weight, the mode of administration, the degree of attenuation of the virus, the nature of the formulation, and whether the immune system of the subject is compromised. In one embodiment, a general range of virus administration is about $10^3$ to about $10^7$ plaque forming units (PFU) or more of virus per human subject, including about $10^4$ to about $10^5$ PFU virus per human subject.

Administration may be in a form found to be effective at stimulating a protective immune response, choices which may include parenterally, intravenously, orally, or topically applied to a mucosal surface. In most instances, the live, attenuated RSV described herein is administered parenterally.

Single or multiple administrations of the live, attenuated RSV described herein, and pharmaceutical compositions thereof, can be carried out. In neonates and infants, multiple administration may be required to elicit sufficient levels of immunity. Administration may begin within the first months of life and continue at intervals throughout childhood, as necessary to maintain sufficient levels of protection against native (wild-type) RSV infection. For example, one possible vaccine schedule may consist of an initial administration at one month, and subsequent administrations at two months, six months, one year and/or two years. Vaccination frequency may be modified to be consistent with current guidelines for other concomitant use vaccines. Levels of induced immunity can be monitored by measuring amounts of neutralizing secretory and serum antibodies, and dosages adjusted or vaccinations repeated as necessary to maintain desired levels of protection.

In any event, the vaccine formulations, effective amounts thereof for administration, and specific mode of administration should provide a quantity of a live, attenuated RSV described herein sufficient to effectively stimulate, induce or boost an anti-RSV immune response, e.g., as can be determined by complement fixation, plaque neutralization, and/or enzyme-linked immunosorbent assay, among other methods (e.g., correlating responses with monitoring subjects for protection from signs and symptoms of upper and lower respiratory illness).

V. Generation of Live, Attenuated RSV

The live, attenuated RSV described herein may be biologically derived or recombinantly generated. A "biologically-derived RSV" means any RSV not produced by recombinant means (e.g., through passaging). A "recombinantly-generated RSV" means any RSV generated via viral cloning techniques (e.g., reverse genetics). The live, attenuated RSV comprise genomic variations compared to a reference RSV sequence, wherein said reference RSV sequence may be derived from a wild-type or an incompletely-attenuated RSV.

Accordingly, the RSV genome into which the specific nucleotides and/or amino acid residues described herein are introduced can be from a genetically and/or phenotypically wild-type virus or a derivative of wild-type virus, such as a virus already partially attenuated, in which ease the newly incorporated nucleotides and/or amino acid residues act to further attenuate the strain (e.g., to a desired level of restricted replication in a mammalian host while retaining sufficient immunogenicity to confer protection in a vaccinated subject). Either a biologically-derived or a recombinantly-generated subgroup A or B RSV can be partially attenuated by, for example, cold-passaging, chemical mutagenesis, or site-directed mutagenesis. Attenuating a virus by cold-passaging involves subjecting the virus to passage in cell culture at progressively lower temperatures. For example, whereas wild-type virus is typically cultivated at about 34-37° C., a partially-attenuated virus can be produced by passage in cell cultures (e.g., primary bovine kidney cells) at sub-optimal temperatures, e.g., 20-26° C. Attenuating a virus by chemical mutagenesis involves, for example, replication of the virus in the presence of a mutagen such as 5-fluorouridine or 5-fluorouracil at a concentration of about $10^{-3}$ to $10^{-5}$ M, preferably about $10^{-4}$ M, or exposure of the virus to nitrosoguanidine at a concentration of about 100 μg/ml, according to general procedures described in, e.g., Gharpure et al., 1969, *J. Virol.* 3:414-421 and Richardson et al., 1978, *J. Med. Virol.* 3:91-100. Other chemical mutagens can also be used. Partially-attenuated RSV can also be generated recombinantly by incorporating attenuating mutations (albeit, incomplete attenuating mutations) into the genome of the wild-type RSV. Various selection techniques may be combined to produce partially-attenuated mutants from non-attenuated subgroup A or B strains which are useful for further derivatization as described herein.

The live, attenuated RSV described herein can be produced by recombinant methods, e.g., from cDNA. Nucleotide and/or amino acid changes, either alone or in combination, can be incorporated into the genome of a wild-type or partially-attenuated RSV. These changes will specify the desired, phenotypic characteristics of the biologically-derived, attenuated RSV described in the Examples, infra. Infectious RSV can be produced by the intracellular co-expression in mammalian cells of a cDNA that encodes the genome or antigenome RNA of the live, attenuated RSV, together with those viral proteins necessary to generate a transcribing, replicating nucleocapsid containing associated proteins and genomic RNA (see, e.g., Palese, 1995, *Trends in Microbiology,* 3:123-125; Lawson et al., 1995, *Proc. Natl. Acad. Sci. USA* 92:4477-4481; Schnell et al, 1994, *EMBO J.* 13:4195-4203). An RSV antigenome means an isolated, positive-sense polynucleotide molecule which serves as the template for the synthesis of a progeny, negative-sense RSV genome. Thus, methods for producing a live, attenuated RSV having one or more of the nucleotide and/or amino acid described herein from one or more isolated polynucleotides, e.g., one or more cDNAs, are also encompassed by the present invention.

Introduction of the foregoing, defined nucleotides/amino acid residues (alone or in combination) into an infectious RSV clone can be achieved by a variety of well known methods. By "infectious clone" is meant cDNA or its product, synthetic or otherwise, which can be transcribed into genomic or antigenomic RNA capable of serving as template to produce the genome of an infectious virus or subviral particle. Defined mutations can be introduced by conventional techniques (e.g., site-directed mutagenesis) into a cDNA copy of a RSV genome or antigenome. The use of antigenomic or genomic cDNA subfragments to assemble a complete antigenomic or genomic cDNA has the advantage that each region can be manipulated separately (smaller cDNAs are easier to manipulate than large ones) and then readily assembled into a complete cDNA. A mutated subfragment, for example, can then be substituted for its counterpart subfragment from a genomic or antigenomic sequence from either a wild-type or incompletely attenuated RSV. Counterpart subfragments share substantial sequence identity with the selected, mutated subfragment. Thus, the complete antigenomic or genomic cDNA, or any subfragment thereof, can be used as template for oligonucleotide-directed mutagenesis. This can be through the intermediate of a single-stranded phagemid form, such as using the Muta-gene® kit of Bio-Rad Laboratories (Richmond, Calif.), a method using the double-stranded plasmid directly as template such as the Chameleon mutagenesis kit of Stratagene (La Jolla, Calif.), or by polymerase chain reaction employing either an oligonucleotide primer or template which contains the mutation(s) of interest. The RSV genome or antigenome may also be constructed by, e.g., assembling the cloned cDNA segments, representing in aggregate a complete antigenome, by polymerase chain reaction (PCR Protocols: A Guide to Methods and Applications, Innis et al., eds., Academic Press, San Diego (1990), incorporated herein by reference) of reverse-transcribed copies of RSV mRNA or genomic RNA. Alternatively, antigenomic or genomic RNA can be synthesized in vitro.

To produce infectious RSV from a cDNA-expressed genome or antigenome, the genome or antigenome is co-expressed with those RSV accessory proteins necessary to (i) produce a nucleocapsid capable of RNA replication, and (ii) render progeny nucleocapsids competent for both RNA replication and transcription. Transcription by the genome nucleocapsid provides the other RSV proteins and initiates a productive infection. Alternatively, additional RSV proteins needed for a productive infection can be supplied by co-expression.

For example, the infectious RSV clone of the live, attenuated virus genome described herein can be first incorporated into a plasmid vector. Plasmid vectors suitable for subsequent transfections and expression in a mammalian host cell are commercially available. The plasmid vector containing a cDNA copy can then be transfected into a host cell that expresses bacteriophage T7 RNA polymerase. Additional plasmid vectors that express the RSV major nucleocapsid (N) protein, nucleocapsid phosphoprotein (P), large (L) polymerase protein, and, optionally, the transcriptional elongation factor M2 ORF1 protein, can be co-transfected into the host cell. The cDNA is transcribed to produce full-length, negative-sense (genomic) RNA. Expression of the N, L and P proteins, and optionally the M2(ORF1) protein, facilitates synthesis of progeny virus. The virions are then isolated. For this method, it is preferable that a cDNA is constructed which is a positive-sense version of the RSV genome, corresponding to the replicative intermediate RNA, or antigenome, so as to minimize the possibility of hybridizing with positive-sense transcripts of the complementing sequences that encode the proteins necessary to generate a transcribing, replicating nucleocapsid (e.g., sequences that encode the N, P, L and M2(ORF1) proteins). When using a RSV minigenome system, the genome and antigenome are equally active in rescue, whether complemented by RSV or by plasmids, indicating that either genome or antigenome can be used depending on methodologic or other grounds.

The N, P, L and, optionally, M2(ORF1) proteins can be encoded by one or more expression vectors which can be the same or separate from that which encodes the genome or antigenome, and various combinations thereof. Additional proteins may be included as desired, encoded by separate vectors or by a vector encoding a N, P, L, or M2(ORF1) protein or the complete genome or antigenome. Expression of the genome or antigenome and proteins from transfected plasmids can be achieved, for example, by each cDNA being under the control of a promoter for T7 RNA polymerase, which in turn is supplied by infection, transfection or transduction with an expression system for the T7 RNA polymerase, e.g., a vaccinia virus MVA strain recombinant which expresses the T7 RNA polymerase (Wyatt et al., 1995, Virology, 210:202-205).

Isolated polynucleotides (e.g., cDNA) encoding the genome or antigenome and, separately, the N, P, L and, optionally, M2(ORF1) proteins, can be inserted by transfection, electroporation, mechanical insertion, transduction or the like, into cells which are capable of supporting a productive RSV infection, e.g., HEp-2, FRhL-DBS2, MRC, and Vero cells. Transfection of isolated polynucleotide sequences may be introduced into cultured cells by, for example, calcium phosphate-mediated transfection (Wigler et al., 1978, *Cell* 14:725; Corsaro & Pearson, 1981, *Somatic Cell Genetics* 7:603; Graham & Van der Eb, 1973, *Virology* 52:456), electroporation (Neumann et al., 1982, *EMBO J.* 1:841-845), DEAE-dextran mediated transfection (Ausubel et al., (ed.) Current Protocols in Molecular Biology, John Wiley and Sons, Inc., NY (1987)), cationic lipid-mediated transfection (Hawley-Nelson et al., 1993, *Focus* 15:73-79) or a commercially available transfection regent, e.g., LipofectACE® (Life Technologies). The viral proteins, and/or T7 RNA polymerase, can also be provided from transformed mammalian cells, or by transfection of preformed mRNA or protein.

Once a live, attenuated RSV of the present invention has been generated (e.g., as per the cloning and rescue experiments described above), the attenuated virus may be propagated in a number of cell lines which allow for RSV growth. RSV grows in a variety of human and animal cells. Examples of cell lines for propagation of the live, attenuated RSV include DBS-FRhL-2, MRC-5, and Vero cells. Highest virus yields are usually achieved with epithelial cell lines such as Vero cells. Cells are typically inoculated with virus at a multiplicity of infection ranging from about 0.001 to about 1.0 or more, and are cultivated under conditions permissive for replication of the virus, e.g., at about 30-37° C., and for about 3-5 days, or as long as necessary for virus to reach an adequate titer. Virus is removed from cell culture and separated from cellular components, typically by well known clarification procedures, e.g., centrifugation, and may be further purified as desired using procedures well known to those skilled in the art.

RSV which has been attenuated as described herein can be tested in in vivo and/or in vitro models to confirm adequate attenuation, genetic stability, and immunogenicity. The level of attenuation of a genetically-modified RSV may be determined by, for example, quantifying the amount of virus present in the respiratory tract of an infected subject and comparing the amount to that produced by a phenotypically wild-type RSV (e.g., RSV A2, Merck strain 287). Attenuated viruses can be tested a variety of animal models of RSV infection, described and summarized in Meignier et al., eds., Animal Models of Respiratory Syncytial Virus Infection, Merieux Foundation Publication, (1991). For example, the cotton rat model of RSV infection has been long held to be predictive of attenuation and efficacy in humans (U.S. Pat. No. 4,800,078; Prince et al., 1985, *Virus Res.* 3:193-206; Prince et al., 1987, *J. Virol.* 61:1851-1854). Other rodents, including mice, could also be similarly useful as these animals are permissive for RSV replication and have a core temperature more like that of humans (Wight et al., 1970, *J. Infect. Dis.* 122:501-512; Byrd and Prince, 1997, *Clin. Infect. Dis.* 25:1363-1368). In particular, primate models are genetically and immunologically relevant host systems in which to study RSV infection (McArthur-Vaughan and Gershwin, 2002, *J. Med. Primatol.* 31:61-73). For example, a primate model of RSV infection using the chimpanzee is predictive of attenuation and efficacy in humans (see, e.g., Richardson et al., 1978, *J. Med. Virol.* 3:91-100; Wright et al., 1982, *Infect. Immun.* 37:397-400; Crowe et al., 1993, *Vaccine* 11:1395-1404. African green monkeys have also been used as a model of RSV infection (Cheng et al., 2001, *Virology* 283:59-68; Kakuk et al., 1993, *J. Infect. Dis.* 167:553-61; Weiss et al., 2003, *J. Med. Primatol.* 32:82-88). Additionally, in vitro analysis of attenuation may include assessing growth of the virus in human airway epithelial cells (Wright et al., 2005, *J. Virol.* 79:8651-8654).

The live, attenuated RSV described herein will have a greater degree of restricted replication in both the upper and lower respiratory tracts of highly susceptible hosts, such as a monkeys and cotton rat, compared to the levels of replication of wild-type virus, e.g., over 1000-fold less. Methods for determining levels of RSV in the nasopharynx of an infected host are well known in the literature. Briefly, specimens can be obtained by aspiration or washing out of nasopharyngeal secretions and virus quantified in tissue culture or by other laboratory procedure. See, for example, Belshe et al., 1977, *J. Med. Virology* 1:157-162; Friedewald et al., 1968, *J. Amer. Med. Assoc.* 204:690-694; Gharpure et al., 1969, *J. Virol.* 3:414-421; and, Wright et al., 1973, *Arch. Ges. Virusforsch.* 41:238-247.

In addition to the criteria of viability, attenuation and immunogenicity, the properties of the live, attenuated RSV described herein must also be as stable as possible so that the desired attributes are maintained. Ideally, a virus which is useful as part of a pharmaceutical product (e.g., vaccine) must maintain its viability, its property of attenuation, its ability to replicate in the immunized host (albeit at lower levels), and its ability to effectively elicit the production of an immune response in a vaccinated subject that is sufficient to confer protection against serious disease caused by subsequent infection by wild-type virus.

VI. Recombinant Nucleic Acids

Nucleic acid molecules comprising either a full-length or partial attenuated RSV genome or antigenome described herein, a nucleotide sequence that encodes a modified viral protein described herein or a portion thereof, or a nucleotide sequence of a modified viral gene described herein or a portion thereof (see, e.g., the description of nucleic acids comprised within live, attenuated RSV of the present invention within Section II, supra), are also within the scope of the present invention. These nucleic acids may be deoxyribonucleic acid (DNA) molecules, complementary DNA molecules (cDNA), or ribonucleic acid (RNA) molecules.

A "triplet" codon of four possible nucleotide bases can exist in over 60 variant forms. Because these codons provide the message for only 20 different amino acids (as well as transcription initiation and termination), some amino acids can be coded for by more than one codon, a phenomenon known as codon redundancy. Thus, due to this degeneracy of the genetic code, a large number of different encoding nucleic acid sequences can be used to code for a particular protein. Amino acids are encoded by the following RNA codons:

```
A = Ala = Alanine:
codons GCA, GCC, GCG, GCU

C = Cys = Cysteine:
codons UGC, UGU

D = Asp = Aspartic acid:
codons GAC, GAU

E = Glu = Glutamic acid:
codons GAA, GAG

F = Phe = Phenylalanine:
codons UUC, UUU

G = Gly = Glycine:
codons GGA, GGC, GGG, GGU

H = His = Histidine:
codons CAC, CAU

I = Ile = Isoleucine:
codons AUA, AUC, AUU

K = Lys = Lysine:
codons AAA, AAG

L = Leu = Leucine:
codons UUA, UUG, CUA, CUC, CUG, CUU

M = Met = Methionine:
codon AUG

N = Asn = Asparagine:
codons AAC, AAU

P = Pro = Proline:
codons CCA, CCC, CCG, CCU

Q = Gln = Glutamine:
codons CAA, CAG

R = Arg = Arginine:
codons AGA, AGG, CGA, CGC, CGG, CGU

S = Ser = Serine:
codons AGC, AGU, UCA, UCC, UCG, UCU

T = Thr = Threonine:
codons ACA, ACC, ACG, ACU

V = Val = Valine:
codons GUA, GUC, GUG, GUU

W = Trp = Tryptophan:
codon UGG

Y = Tyr = Tyrosine:
codons UAC, UAU
```

Thus, the present invention includes nucleic acids that differ from the disclosed nucleic acid molecules but which encode the same protein sequence.

Also encompassed by the present invention are nucleic acid molecules comprising non-coding sequences (i.e., untranslated sequences) of the RSV of the present invention.

These non-coding regions include 5' non-coding regions, 3' non-coding regions, intergenic sequences, and other non-coding regions of the viral genome, including but not limited to, transcriptional, translational, and other regulatory regions. These nucleic acid molecules also may be DNA molecules, cDNA molecules or RNA molecules.

The present invention further includes substantially similar nucleic acid molecules to those nucleic acid molecules which encode one or more proteins of the live, attenuated RSV of the present invention, including but not limited to the NS1, NS2, G, F and/or L genes of the live, attenuated RSV described herein. When incorporated into a RSV viral genome, said NS1, NS2, G, F and/or L genes will produce the same attenuated, phenotypic effect. The present invention also encompasses substantially similar nucleic acid molecules characterized by changes in non-coding regions that do not alter the phenotype of the resulting virus produced there from.

Accordingly, included within the scope of this invention are nucleic acid molecules comprising either nucleotide sequences that encode variants of the proteins comprised within the live, attenuated RSV described herein, or nucleic acid molecules comprising variants of the non-coding nucleotide sequences comprised within the live, attenuated RSV described herein.

Included within the scope of the present invention are nucleic acid molecules containing one or more of the indicated nucleotides that hybridize to the complement of the nucleic acid molecules of the subject invention under stringent conditions. By way of example, and not limitation, a procedure using conditions of high stringency is described. Prehybridization of filters containing DNA is carried out for about 2 hours to overnight at about 65° C. in buffer composed of 6×SSC, 5×Denhardt's solution, and 100 g/ml denatured salmon sperm DNA. Filters are hybridized for about 12 to 48 hrs at 65° C. in prehybridization mixture containing 100 μg/ml denatured salmon sperm DNA and 5-20×$10^6$ cpm of $^{32}$P-labeled probe. Washing of filters is done at 37° C. for about 1 hour in a solution containing 2×SSC, 0.1% SDS. This is followed by a wash in 0.1×SSC, 0.1% SDS at 50° C. for 45 minutes before autoradiography. Other procedures using conditions of high stringency would include either a hybridization step carried out in 5×SSC, 5×Denhardt's solution, 50% formamide at about 42° C. for about 12 to 48 hours or a washing step carried out in 0.2×SSPE, 0.2% SDS at about 65° C. for about 30 to 60 minutes. Reagents mentioned in the foregoing procedures for carrying out high stringency hybridization are well known in the art. Details of the composition of these reagents can be found in Sambrook et al., Molecular Cloning: A Laboratory Manual 2$^{nd}$ Edition; Cold Spring Harbor Laboratory Press, Cold Spring Harbor, N.Y., (1989) or Sambrook and Russell, Molecular Cloning: A Laboratory Manual, 3rd Edition. Cold Spring Harbor Laboratory Press, Plainview, N.Y. (2001). In addition to the foregoing, other conditions of high stringency which may be used are also well known in the art.

Nucleic acid molecules of this invention may be operatively linked to a promoter of RNA transcription, as well as other regulatory sequences. As used herein, the term "operatively linked" means positioned in such a manner that the promoter will direct the transcription of RNA off of the nucleic acid molecule. An example of a promoter is the T7 promoter. Vectors which contain both a promoter and a cloning site to which an inserted piece of nucleic acid is operatively linked to the promoter, are well known in the art. These vectors may be capable of transcribing nucleic acid in vitro and in vivo. Examples of such vectors include those comprising nucleic acids derived from viral genomes of other RSV types (including both other attenuated subtypes and wild-type strains) that have been modified by substituting the nucleic acid regions encoding the polypeptides and/or the non-coding regions of the live, attenuated RSV described herein for the nucleic acids of said other RSV types. Further provided are recombinant virus encoded by the nucleic acid molecules of this invention.

Examples are provided below further illustrating different features of the present invention. The examples also illustrate useful methodology for practicing the invention. These examples do not limit the claimed invention.

EXAMPLE 1

Passaging of MRK RSV Strain 287

Cells and virus—African Green Monkey kidney cell line Vero CCL-81 was utilized both for virus growth studies and plaque assay to monitor viral output. Parent virus utilized was Merck 287 strain hRSV which was stored lyophilized at −20 C. The parent Merck 287 virus had undergone two passages in GMK cells, then five additional passages in WI-38 cells (Bunyak et al., 1978, *Proc. Soc. Exp. Biol. Med.* 157:636-642; Bunyak et al., 1979, *Proc. Soc. Exp. Biol. Med.* 160:272-277; Belshe et al., 1982, *J. Infect. Dis.* 145:311-319). By sequence analysis, it was confirmed to retain a wild-type genotype at all known positions associated with attenuation.

Virus passaging and virus stock preparation—Parent virus was used to infect week-old confluent Vero monolayers at a 1:100 or 1:1000 MOI with a 1 hr attachment at 32° C.; overlay post attachment with maintenance medium comprised of WM's Medium E (Gibco), 1.6% recombinant human albumin (Delta biotechnologies), 2 mM L-glutamine (Gibco), and 50 μg/ml Neomycin (Sigma). Cultures were observed for maximal cytopathic effect (CPE) >90%, and harvested and re-fed for additional harvests at 24 hr intervals until CPE was too advanced for optimal viral output.

Plaque assay—Harvested virus samples were titered at serial tenfold dilutions via plaque assay and used to inoculate confluent (48-72 hr) VERO monolayers in 12-well assay format (Costar), 100 μl/well, in triplicate per dilution of serial tenfold dilutions, four dilutions per plate total. Plates incubate at 35° C.±1° C. plus 5.0% $CO_2$ for one hour, overlay with maintenance medium comprised of WM's Medium E (Gibco), 1.6% recombinant human albumin (Delta biotechnologies), 2 mM L-glutamine (Gibco), and 50 mg/ml Neomycin (Sigma), and 0.5% final concentration of SeaPlaque® agarose. Plaques develop for 6-8 days at 35° C.±1° C. plus 5.0% $CO_2$. Plaques were visualized by adding 250 μl/well of 5 mg/mL MTT; Thialzolyl Blue Tetrazolium Bromide (Sigma-Aldrich®) in PBS and waiting 2-6 hours for cells to metabolize the stain. Titers were obtained on all harvests between passages not only to monitor viral yield, but to accurately measure titers for calculating the appropriate dilution for the MOI for the subsequent passage of virus.

Results—Merck HRSV strain 287 is derived from an isolated hRSV strain that was first amplified twice in GMK cells. After the initial amplification, the virus underwent five additional passages in the human diploid cell line WI-38. This passage 5 material was utilized in human clinical trials for vaccine use via a parenteral administration route. Merck strain 287, hRSV A type, showed a wild-type (WT) phenotype both in sequence analysis and in vivo in animal shedding experiments (see infra). Merck strain 287 was serially passaged 22 times (passage 1 (p1)-passage 22 (p22)) at a fixed multiplicity in VERO-CCL-81 monolayers. Virus titers remained constant over passaging and the cytopathic effect of the virus in culture also remained consistent. Virus yields were in the range of $10^6$-$10^7$ pfu/ml.

EXAMPLE 2

Sequencing of MRK RSV Strain 287 and Passaged Virus Stocks

RSV samples—Materials were supplied in 500-1000 μl aliquots of harvested viral supernatants from infected VERO cells. Full-length sequences were generated for: 1) MRK RSV Strain 287; 2) MRK RSV Strain 287, passage 17 ("p17"); and, 3) MRK RSV Strain 287, passage 22 ("p22"). Partial (targeted) sequences were generated for: 1) MRK RSV Strain 287, passage 5 ("p5"); 2) MRK RSV Strain 287, passage 10 ("p10"); 3) MRK RSV Strain 287, passage 15 ("p15"); and, 4) MRK RSV Strain 287, passage 18 ("p18").

RNA extraction—RNA was extracted from virus culture supernatants using the QiaAMP Viral RNA Extraction Kit (Qiagen, cat. no. 52904) as per the manufacturer's protocol. In short, 140 μl of virus culture supernatants were added to lysis buffer, loaded onto a binding filter, washed and eluted in 60 μl of RNase-free water. Extracted RNA samples were stored at minus 20° C. Extracted RNA samples were used as templates for amplification of genome into double-stranded DNA fragments by reverse-transcriptase polymerase chain reaction (RT-PCR). Multiple extractions of each sample were performed to obtain sufficient materials for the RT-PCR amplifications.

Amplification of RSV genome by RT-PCR—The RSV genome of samples was amplified into double-stranded DNA using the Qiagen OneStep RT-PCR kit (Qiagen, cat. no. 210212). For full-length sequencing (MRK RSV 287 and passages P17 and P22), thirty (30) amplifications of 1000 base pair (bp) fragments were conducted, with each fragment overlapping adjacent fragments by approximately 500 bp. Amplification reactions were numbered 1 to 30 (for the primer pair) and carried out as listed below. For partial-length sequencing (MRK RSV 287 passages P5, P10, P15 and P18) seven (7) amplifications of 1000 base pair (bp) fragments were conducted, using primer pairs 2, 10, 11, 13, 14, 18, and 29. Amplification reactions were numbered accordingly (for the primer pair) and carried out as listed below.

Master Mix (per reaction): 10 μl 5× QIAGEN OneStep RT-PCR buffer; 2 μl dNTP mix; 3 μl primer A (forward primer)—10 μM stock, 600 nM final; 3 μl primer B (reverse primer)-19 μM stock, 600 nM final; 2 μl QIAGEN OneStep RT-PCR Enzyme Mix; 5 μl RNA template; 25 μl molecular biology grade water.

Amplification reactions were carried out in a Biometra thermocycler with the following conditions: 30 minutes, 50° C.—reverse transcription step; 15 min 95° C.—initial PCR activation step (DNA polymerase activation) 3-step cycling (repeat for 40 cycles total); 1 min, 94° C.—denaturation; 1 minute, 55° C.—annealing; 1 minute, 72° C.—extension; 10 min 72° C.—final extension.

Primers used for the RT-PCR amplifications are listed in Tables 2 and 3.

TABLE 2

RT-PCR amplification (sequencing) primers, pairs 1-15

| Primer Pair | Primer | Primer Sequence (5' → 3') | SEQ ID NO | 5' binding position | Product Length |
|---|---|---|---|---|---|
| 1 | FWD | ACGGGAAAAAATGCGTACAACAAAC | 27 | 1 | 1056 |
| | REV | GTGTAGTCATGCATAGAGTTGTTGTTTTAGATTGTGTGAA | 28 | 1056 | |
| 2 | FWD | TATCAACTAGCTAATCAATGTCACTAACACC | 29 | 530 | 1043 |
| | REV | CCTCTCCCATTTCTTTTAGCATTTT | 30 | 1572 | |
| 3 | FWD | TTCACACAATCTAAAACAACAACTCTATGCATGACTACAC | 31 | 1017 | 1000 |
| | REV | TTTGGGCATATTCATAAACCTCAAC | 32 | 2016 | |
| 4 | FWD | AATCCCACAAAAAAATGCTAAAAGAAATGGGAGAGGTAGC | 33 | 1537 | 1018 |
| | REV | CTGTCTCATTTGTTGGGTTGATAATAGTTGA | 34 | 2554 | |
| 5 | FWD | TATGAATATGCCCAAAAATTGGGTGGTGAAGCA | 35 | 2001 | 1194 |
| | REV | TGGCTGGTTGTTTTGTTGGCTGCTT | 36 | 3194 | |
| 6 | FWD | GCCCTATAACATCAAATTCAACTATTATCAACCC | 37 | 2507 | 1028 |
| | REV | CGCTTATGGTAAATTTGCTGGGCAT | 38 | 3534 | |
| 7 | FWD | ACATCAGAGAAATTGAACAACCTGT | 39 | 3001 | 1002 |
| | REV | TTGTAGCTGTGTGCTTCCAATTTGT | 40 | 4002 | |
| 8 | FWD | CTAGCACAAATGCCCAGCAAATTTACCATAAGCG | 41 | 3501 | 1097 |
| | REV | GTGGTTTGCATGGTGGGACGTTGAT | 42 | 4597 | |
| 9 | FWD | AGATTTGCAATCAAACCTATGGAAG | 43 | 4002 | 1002 |
| | REV | TTCAGACGGATTAGAGGGACTGATT | 44 | 5003 | |
| 10 | FWD | CATCAATCCAACAGCTCAAAACAGT | 45 | 4501 | 1002 |
| | REV | TACCTTCGGAGGAAGTTGAGTGGAA | 46 | 5502 | |

TABLE 2-continued

RT-PCR amplification (sequencing) primers, pairs 1-15

| Primer Pair | Primer | Primer Sequence (5' → 3') | SEQ ID NO | 5' binding position | Product Length |
|---|---|---|---|---|---|
| 11 | FWD | GAAATTACATCAACAAATCACCACC A | 47 | 5001 | 1000 |
| | REV | AAACCTTGGTAGTTCTCTTCTGGCT | 48 | 6000 | |
| 12 | FWD | TAATCCAAGCCCTTCTCAAGTCTCC | 49 | 5501 | 1114 |
| | REV | GATGTGTGTAATTTCCAACAAGGTG | 50 | 6614 | |
| 13 | FWD | CACTCAACAATGCCAAAAAAACCAA TGTAAC | 51 | 6011 | 1117 |
| | REV | GCATCAAATTCACCAGAGGGGAATA | 52 | 7127 | |
| 14 | FWD | TAGACAGCAAAGTTACTCTATCATG | 53 | 6501 | 1001 |
| | REV | GATGGTTTATAGATGAGAGTTTCGA | 54 | 7501 | |
| 15 | FWD | ACACTGTGTCTGTAGGCAACACATTA TATTATG | 55 | 7001 | 1067 |
| | REV | GTCTGCTGGCAATCTTTTTAACAGAT GGATAGTTTGTTTA | 56 | 8067 | |

TABLE 3

RT-PCR amplification (sequencing) primers, pairs 16-30

| Primer Pair | Primer | Primer Sequence (5'→ 3') | SEQ ID NO | 5' binding position | Product Length |
|---|---|---|---|---|---|
| 16 | FWD | TGCCAGATTAACTTACTATCTGAAAA ATGAAAACTGGGG | 57 | 7558 | 1020 |
| | REV | CACTCTGAGAAAGAGATAACACCTTT TAAATAACTATCGG | 58 | 8577 | |
| 17 | FWD | TAAACAAACTATCCATCTGTTAAAAA GATTGCCAGCAGAC | 59 | 8028 | 1000 |
| | REV | GAGTGATTTTTGCCTGCTTTAAGAT | 60 | 9027 | |
| 18 | FWD | GGAAATTCTGCTAATGTTTATCTAAC CG | 61 | 8513 | 1046 |
| | REV | CGTTTTCTGAATTGATCTTCTTCTG | 62 | 9558 | |
| 19 | FWD | TCATCTTAAAGCAGGCAAAAATCACT CTACA | 63 | 9001 | 1053 |
| | REV | CGTAGTCCTGATAACACAATCAAATC TCTTTCTGTAAGTT | 64 | 10053 | |
| 20 | FWD | CAGAAGAAGATCAATTCAGAAAACG | 65 | 9534 | 1010 |
| | REV | GCGATTTGATTTGTTACTTATTC- CTGC | 66 | 10543 | |
| 21 | FWD | CCTTCTTTGTTGGAACTTACAGAAA | 67 | 10001 | 1000 |
| | REV | GCAAATAATCTGCTTGAGCATGAGT | 68 | 11000 | |
| 22 | FWD | GAAAGCAGGAATAAGTAACAAATCA AATCGC | 69 | 10513 | 1136 |
| | REV | CGTTAGGGTTTTTGTCAAACGTGATT ATGCATGTTAAGAA | 70 | 11648 | |
| 23 | FWD | ATAGCCTTAAATTACTGTATAAAGAG TATGCAGGCATAGG | 71 | 11010 | 1000 |
| | REV | TTTTTCCTCATCATCTCAGTGGCTC | 72 | 12009 | |
| 24 | FWD | GACTTCCTCACAGAGGCTATAGTTC | 73 | 11501 | 1016 |
| | REV | GTAAGTCGATGCAAATAGTTGACAC | 74 | 12516 | |
| 25 | FWD | ACTTTGCTTATAAGGATACTTCCATT GG | 75 | 12014 | 1041 |
| | REV | CTCTCCCCAATCTTTTTCAAAAATAC CCTTAGAATCTTTC | 76 | 13054 | |
| 26 | FWD | ATTTGCATCGACTTACAGTCAGTAG | 77 | 12501 | 1131 |
| | REV | GGGTTTCTGGTGTAGGATGATATAAT T | 78 | 13631 | |

TABLE 3-continued

RT-PCR amplification (sequencing) primers, pairs 16-30

| Primer Pair | Primer | Primer Sequence (5'→3') | SEQ ID NO | 5' binding position | Product Length |
|---|---|---|---|---|---|
| 27 | FWD | GAAAGATTCTAAGGGTATTTTTGAAAAAGATTGGGGAGAG | 79 | 13015 | 1044 |
| | REV | CCTTCACCTATGAATGCATAACAATTGGGATCTTTA | 80 | 14058 | |
| 28 | FWD | TTACAACAAATTATATCATCCTACACCAGAAACCCTAGAG | 81 | 13597 | 1025 |
| | REV | CAGCTTTCTTAGGCATGATGAAATTTTTGGTTCTTGATAG | 82 | 14621 | |
| 29 | FWD | ATTAAAGATCCCAATTGTATAGCATTCATAGGTGAAGGAG | 83 | 14021 | 909 |
| | REV | GGTTGTCAAGCTGTTTAACAATTCA | 84 | 14929 | |
| 30 | FWD | TCGGAGGTTTACTTAGTCATCACAA | 85 | 14501 | 537 |
| | REV | GGTAGTGTATAGCTATGGGAATCTTTAT | 86 | 15037 | |

Amplified RT-PCR products were purified using the QIAGEN QIAquick PCR Purification kit (QIAGEN, cat. no. 28104), as per the manufactures protocol. Purified RT-PCR products were numbered 1 to 30 (based on primer pair), stored at −20° C. and shipped for sequencing to GeneWiz (South Plainfield, N.J.).

Sequencing of amplified RT-PCR products—Purified RT-PCR products were submitted to GeneWiz (South Plainfield, N.J.) for dye-termination sequencing. Sequencing was conducted using the RT-PCR amplification primers, which were submitted together with the RT-PCR products. For each RT-PCR products two (2) sequences were generated, one using the forward primer and one using the reverse primer.

RT-PCR product sequence analysis and RSV genome assembly—Generated RT-PCR fragment sequences were imported into Sequencher™ sequence analysis software (GeneCodes, Ann Arbor, Mich.) and sequences were assembled by performing "contig" assemblies. This consists of the importation of all 60 RT-PCR product sequences (2 sequences for each of 30 products) and the assembly of a full-length sequence using the 500 bp overlap regions as scaffolds. Sequences were edited for extraneous and missed peaks using commonly accepted practices. Finalized sequences were exported as fasta-formatted files and imported into VectorNTI™ for comparisons and sequences analyses. For targeted sequencing of p5, p10, p15, and p18, individual fragment assemblies were made (i.e., fragments 2, 10, 11, etc.) rather than a full-length genome assembly. Final sequences were imported into VectorNTI™ and sequence comparisons and analyses were performed.

Results—Full-length genomic sequences were generated for the original source material (MRK 287), as well as passage 17 (p17) and passage 22 (p22). Targeted sequences of additional passage levels were obtained for passages 5 (p5), 10 (p10), 15 (p15) and 18 (p18). Viral RNA was extracted from culture supernatant samples; double-stranded DNA fragments of the genome were generated from the RNA by reverse-transcriptase polymerase chain reaction (RT-PCR); RT-PCR products were purified and sequenced; and, generated sequences were assembled into a full-length viral genome.

The following comparisons and analyses were conducted:

1) Homology "blast" analysis of MRK RSV 287 strain sequence was conducted against known sequencing in common databases (Genbank, EMBL) to determine sequence-relatedness of MRK RSV 287 against other RSV sequences.

2) Sequence alignment of MRK RSV 287 strain against MRK RSV p17 to determine sequence differences between original MRK RSV strain 287 and p17.

3) Amino acid analyses of any sequence differences between original MRK RSV strain 287 and p17 to determine amino acid sequence differences, if any, associated with nucleic acid sequence differences between the 2 samples.

4) Sequence alignment of MRK RSV 287 strain p17 against MRK RSV p22 to determine sequence differences between MRK RSV strain 287 p17 and p22, in order to determine whether additional point mutations are acquired elsewhere in the viral genome.

5) Comparison of gene segments 2, 10, 11, 13, 14, 18 and 29 from MRK RSV strain 287 and p5, p10, p15, p17, p18, and p22 to determine sequence differences between original MRK RSV strain 287 and associated passaged materials, in order to understand the acquisition of point mutations with increasing passage level and the possible markers of attenuation.

The results of sequence analyses are summarized below:

1) MRK RSV Strain 287 sequence analysis—Comparisons of MRK RSV strain 287 with known wild-type and vaccine strains of RSV (listed in Table 4) indicate that MRK RSV 287 does not contain point mutations previously identified as attenuation markers (data not shown). MRK RSV strain 287 yielded a sequence of 15,205 nucleotides. Passages 17 and 22 yielded 15,000 nucleotides, with the extreme 5' end missing. MRK RSV Strain 287 was similar to known RSV subgroup A strains, with greater than 95% homology scores.

TABLE 4

Genbank accession information on selected RSV sequences

| Genbank Accession Number | Sequence Description |
|---|---|
| U50362.1 | Human RSV, mutant cp-RSV, complete genome |
| U50363.1 | Human RSV, mutant cpts-248, complete genome |
| U63644.1 | Human RSV, mutant cpts-248/404, complete genome |
| AF035006.1 | Human RSV, recombinant mutant rA2cp, complete genome |

2) Comparison of MRK RSV Strain 287 and Passage 17 sequences—Comparisons of genomic sequences from MRK RSV strain 287 and p17 indicates that there are 21 sequence differences (point mutations) between the 2 sequences. A summary of sequence differences is listed in Table 5.

TABLE 5

Sequence differences between MRK RSV Strain 287 and p17

| Nucleotide Position | MRK RSV Strain 287 | p17 |
|---|---|---|
| 954 | G | A |
| 5295 | A | G |
| 5298 | A | G |
| 5315 | A | G |
| 5316 | A | G |
| 5322 | A | G |
| 5324 | A | G |
| 5339 | A | G |
| 5346 | A | G |
| 5347 | A | G |
| 5351 | A | G |
| 5352 | A | G |
| 5353 | A | G |
| 5360 | A | G |
| 5380 | A | G |
| 5381 | A | G |
| 6538 | G | A (R?) * |
| 7115 | A | G (R?) * |
| 8937 | A | C (M?) * |
| 14656 | G | T (K?) * |
| 15046 | A | C |

TABLE 5-continued

* possible polymorphisms; R, M and K represent IUPAC codes for polymorphisms: R = A or G; K = G or T; M = A or C 3) Comparison of MRK RSV Strain 287 and Passage 17 Amino Acid Sequences—The gene location of each identified point mutation in p17 compared to the original MRK RSV Strain 287 sequence was mapped and an amino acid sequence was generated for each gene containing point mutations. Of the 21 point mutations, 1 is in the 5' untranslated region (3' to the viral L gene) and 20 are within open-reading frames (viral genes). Of the 20 open-reading frame (ORF) mutations, five (5) are silent and the remaining fifteen (15) affect eleven (11) amino acids in three (3) genes. The 3 affected ORFs encode the G (Glycoprotein), F (Fusion protein) and L (Large protein, RNA dependent RNA polymerase) proteins. One silent mutation occurs with the NS2 gene ORF, and four (4) silent mutations with the G gene ORF. A summary of sequence differences is listed in Table 6.

TABLE 6

Amino acid sequence comparison between MRK RSV 287 and Passage 17

| Nucleotide (nt) Position | RSV gene - nt position | Gene amino acid position | Note | MRK RSV 287 amino acid | MRK RSV p17 amino acid |
|---|---|---|---|---|---|
| 954 | NS2-327 | 109 | Silent mutation | LYS | LYS |
| 5295 | G-610 | 204 | | LYS | GLU |
| 5298 | G-613 | 205 | | LYS | GLU |
| 5315 | G-630 | 210 | Silent mutation | THR | THR |
| 5316 | G-631 | 211 | | THR | ALA |
| 5322 | G-637 | 213 | | LYS | GLU |
| 5324 | G-639 | | | | |
| 5339 | G-654 | 219 | Silent mutation | GLN | GLN |
| 5346 | G-661 | 221 | | LYS | GLY |
| 5347 | G-662 | | | | |
| 5351 | G-666 | 222 | Silent mutation | SER | SER |
| 5352 | G-667 | 223 | | LYS | GLY |
| 5353 | G-668 | | | | |
| 5360 | G-675 | 226 | Silent mutation | VAL | VAL |
| 5380 | G-695 | 232 | | GLU | GLY |
| 5381 | G-696 | | | | |
| 6538 | F-880 | 294 | | GLU | LYS*[1] |
| 7115 | F-1457 | 486 | | ASP | GLY*[2] |

TABLE 6-continued

Amino acid sequence comparison between MRK RSV 287 and Passage 17

| Nucleotide (nt) Position | RSV gene - nt position | Gene amino acid position | Note | MRK RSV 287 amino acid | MRK RSV p17 amino acid |
|---|---|---|---|---|---|
| 8937 | L-443 | 148 | | ASP | ALA*[3] |
| 14656 | L-6162 | 2054 | | LEU | PHE*[4] |
| 15046 | NTR | NA | 5' untranslated region | NA | NA |

*possible polymorphisms:
[1]= GLU/LYS,
[2]= ASP/GLY,
[3]= ASP/ALA,
[4]= LEU/PHE

4) Sequence alignment of MRK RSV p17 against MRK RSV p22—Sequence comparisons between p17 and p22 found the two sequences to be identical. There was a possible difference in the polymorphism level at nucleotide position number 14656, but this was not been quantified.

5) Comparison of gene segments 2, 10, 11, 13, 14, 18, and 29 from MRK RSV strain 287 and passages 5, 10, 15, 17, 18 and 22—Sequences were generated from selected gene segments of MRK RSV strain 287 passages p5, p10, p15 and p18. These sequences were compared to MRK RSV strain 287, as well as to MRK RSV Strain passage 17 and passage 22. Table 7 is a comparison of the sequences at the previously identified sites of the RSV p17 point mutations. It is evident from the data presented that the silent NS2 mutation was acquired by the 5$^{th}$ passage, while the G gene mutations were present by the 10$^{th}$ passage. Mutations in the F and L genes were beginning to appear by passage 10, and evidence of all point mutations is present at passage 17. The polymorphism at position 14656 is still evident, while the presence of other polymorphisms is in question. Table 7 summarizes the comparisons of the various passage levels analyzed.

TABLE 7

| Nueleotide Position | Strain 287 | p5 | p10 | p15 | p17 | p18 | p22 |
|---|---|---|---|---|---|---|---|
| 954 | G | A | A | A | A | A | A |
| 5295 | A | A | G | G | G | G | G |
| 5298 | A | A | G | G | G | G | G |
| 5315 | A | A | G | G | G | G | G |
| 5316 | A | A | G | G | G | G | G |
| 5322 | A | A | G | G | G | G | G |
| 5324 | A | A | G | G | G | G | G |
| 5339 | A | A | G | G | G | G | G |
| 5346 | A | A | G | G | G | G | G |
| 5347 | A | A | G | G | G | G | G |
| 5351 | A | A | G | G | G | G | G |
| 5352 | A | A | G | G | G | G | G |
| 5353 | A | A | G | G | G | G | G |
| 5360 | A | A | G | G | G | G | G |
| 5380 | A | A | G | G | G | G | G |
| 5381 | A | A | G | G | G | G | G |
| 6538 | G | G | G | A (R?)* | A (R?)* | A (R?)* | A (R?)* |
| 7115 | A | A | G (R?)* | G (R?)* | G (R?)* | G (R?)* | G (R?)* |
| 8937 | A | A | C (M?)* | C (M?)* | C (M?)* | C (M?)* | C (M?)* |
| 14656 | G | G | G | T (K?)* | T (K?)* | T (K?)* | T (K?)* |
| 15046 | A | no data | no data | no data | C | no data | C |

*possible polymorphisms; R, M and K represent IUPAC codes for polymorphisms: R = A or G; K = G or T; M = A or C

EXAMPLE 3

Attenuation of MRK RSV 287 Passaged Strains

African Green monkey challenge study—All animals were prescreened for seroneutralizing antibody titers. Only those with titers ≤4 were used in the current studies. The monkeys were anesthetized using 10 mg/kg ketamine, intramuscularly, and challenged with two doses each of $10^{5.5}$ pfu of virus. The virus was administered by combined intranasal and intratracheal inoculation, 1 ml at each site per dose. Following challenge, nasopharyngeal swabs were collected daily from each monkey for 12 consecutive days, and bronchoalveolar lavage were collected at days 4, 5, 7, and 10. The nasopharyngeal samples were collected by gently rubbing 2-3 areas of the oropharynx region using a Darcon swab and placing the tips in a solution containing Hanks balanced salt solution (HBSS) containing 0.2 M Sucrose, 3.8 mM $KH_2PO_4$, 7.2 mM $K_2PO_4$ and 4.4 mM monosodium glutamate (SPG), and 0.1% gelatin. For bronchoalveolar lavage, approximately 5-7 ml HBSS was infused directly into the lung and aspirated via a sterile French catheter and syringe. Recovered samples were supplemented with 1/10 volume of 10×SPG and 1/10 volume of 1% gelatin, aliquoted and immediately stored frozen at −70° C.

Cotton rat challenge study—Four to 8-week old, female, cotton rats (*Sigmodon hispidus*) were inoculated intranasally with $10^{5.5}$ pfu of virus in 0.1 ml volume at day 0. Lung (left lobes) and nasal turbinates were removed four days post inoculation, homogenized in 10 volumes of Hanks Balanced Salt Solution (Walkersville, Md.) containing SPG on ice. Samples were clarified by centrifugation at 2000 rpm for 10 minutes, aliquoted and immediately stored frozen at −70° C.

Viral titration—Virus titers were determined on Hep-2 cells. Briefly, test sample were made with serial dilutions. 0.1 ml of the sample was added to a well of 24-well plates containing confluent Hep-2 cells. Cells were incubated at 37° C. for 1 hour. After incubation, the cells were washed once with PBS and overlaid with 0.5 ml of 1% agarose in MEM per well and incubated at the 37° C. for 4 days. After incubation, the agarose overlays were removed and cells were stained with crystal violet and viral plaques were counted. Viral titers were expressed as the plaque forming units (pfu) per gram tissue.

Viral neutralization assay—For viral neutralization assay, all sera were heat-inactivated at 56° C. for 30 minutes. Test sera were prepared in serial 2-fold dilutions in Eagle's Minimum Essential Medium (EMEM) and incubated. Wild-type A2 virus was as the target virus and was diluted in EMEM to the final titer of $10^3$ pfu/ml. Equal volume of serum and the virus were mixed and incubated at 37° C. for 1 hour. After incubation, 0.1 ml of the virus was transferred to a well of 24-well plates, which was followed by the viral plaque assay as described above. The neutralizing titers were defined as the highest dilution which induced >50% reduction of the viral plaques.

Results—

1) MRK 287 p17 is highly attenuated in cotton rats and African green monkeys—To evaluate in vivo replication properties, we compared p17 virus with its parental p3 virus and wt A2 strain in cotton rat and African green challenge models. The data from cotton rats and the non-human primate studies collectively suggest that p17 virus is highly attenuated.

In the cotton rat study, 6 animals per group were inoculated intranasally with $10^{5.5}$ pfu of a test virus; 4 days after challenge, nose and lung samples were collected and used for virus titration (FIG. 5). The parental p3 virus was found to be fully replication competent, which yielded approximately 5 logs of the virus in both nose and lung tissues. The titers in the nose were comparable to that of wt A2 strain, while that in the lungs were approximately 1 log lower. In contrast, the replication of p17 virus was restricted. No virus was recovered in the nose based on the lower assay detection limit, 40 pfu per gram tissue, and lung virus was detected only in one out of the four animals. The viral titer of this animal was also low, i.e., 200 pfu per gram tissue. Compared with the parental p3 virus, the p17 had at least 4- and 2.5-log lower titers in the nose and lungs, respectively.

Figure 6:
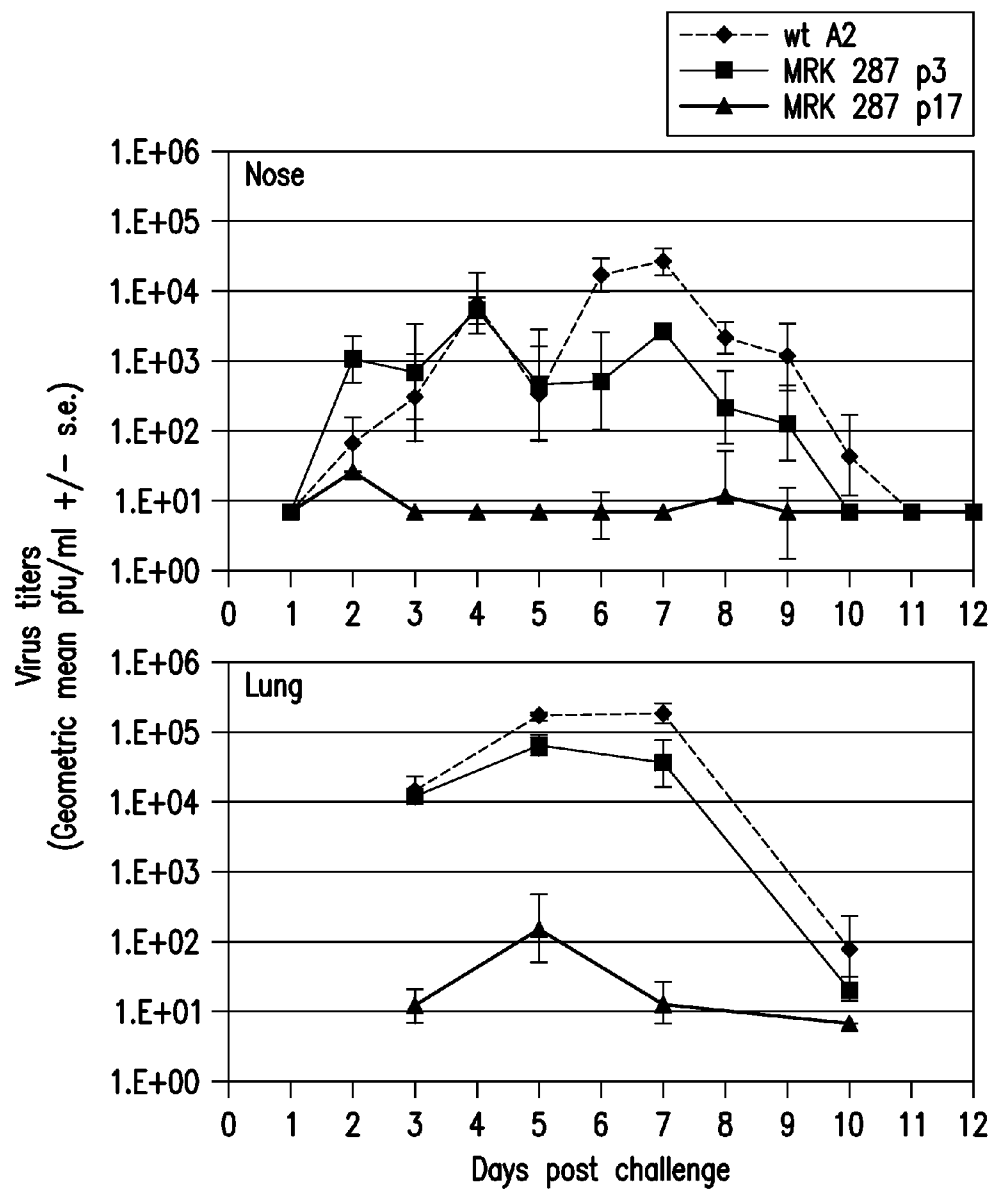
FIG. 6 compares viral titers (pfu/gram of tissue) of the wild-type hRSV A2 strain, passage 3 of Merck strain 287 ("p3"), and passage 17 of Merck strain 287 ("p17") in both nose and lung samples from African green monkeys inoculated with said viruses by combined intranasal or intratracheal routes.

In the African green monkey study, four animals per group were inoculated with a total of $2\times10^{5.5}$ pfu of virus, of which half was administered by intranasal inoculation and the other half by intratracheal inoculation. At various time points post challenge, nasopharyngeal swabs and lung lavage were collected and used for virus titration. The results are shown in FIG. 6. Consistent with that in cotton rats, the parental p3 virus showed significant viral replication both in the nose and lungs, where the peak titers were around $10^4$ and $10^5$ pfu/ml in nose and lungs, respectively. In addition, its overall viral shedding profiles were rather similar to that of wt A2 virus, in that the titers peaked between days 4 and 7 and lasted around 10 days. In contrast, the p17 virus was only detected sporadically and with low titers. For example, nose virus was detected only in two monkeys on day 2 and in one monkey on day 8, and lung virus was detected in 1, 3 and 1 monkeys on days 2, 3 and 7, respectively. Among all the positive samples, the highest titer, which was from one of the day 2 nose samples, was 400 pfu per gram tissue.

To better understand the relationship between viral passage and in vivo replication, we also tested MRK 287 viruses at passages preceding p17 in the cotton rat model. Six animals per group were challenged with $10^5$ pfu of virus and samples were harvested on day 4 post challenge. As shown in FIG. 7, the virus at passage 5 (p5) already begins to show reduced replication, and those in passages 10 (p10) and 15 (p15) show further reduction in replication. The p15 virus seems to be as attenuated as the p17 virus described above (FIG. 5). No p17 virus was recovered in the lungs and while it was detected in the nasal samples, the titers were >3 logs lower than that of the parental p3 virus.

2) Single intramuscular immunization with MRK287 p17 vaccine virus induces strong seroneutralizing (SN) antibody responses and confers significant protection against wt virus challenge in cotton rats and African green monkeys—Immunogenicity and protection studies were conducted in both cotton rats and African green monkeys. The data demonstrates that single systemic immunization with the attenuated vaccine strain MRK287 p17 is able to induce significant SN titers and confer protection against wt virus challenge in the animal models.

Figure 8:
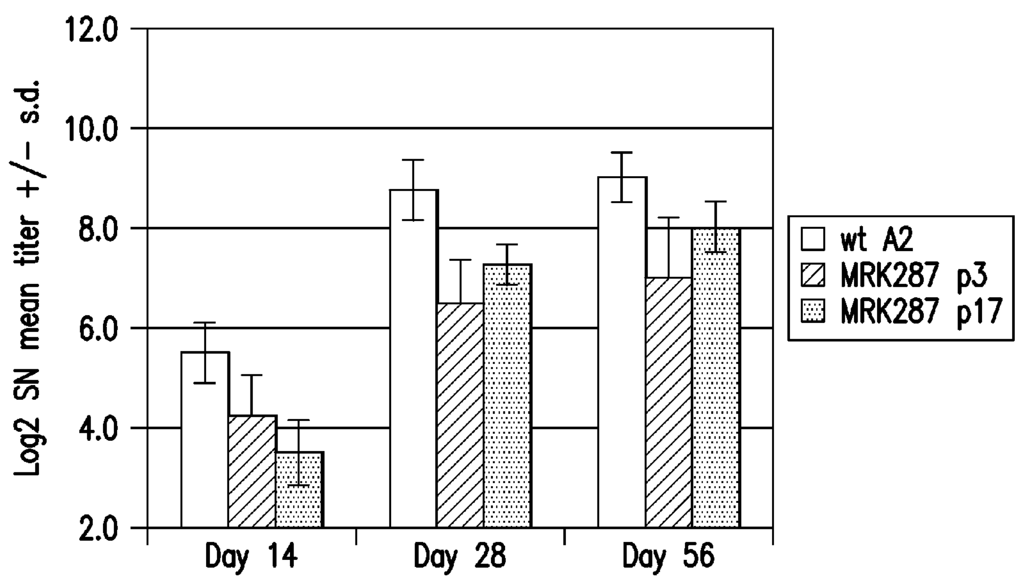
FIG. 8 compares the seroneutralizing (SN) antibody titers against wild-type hRSV A2 following immunization with wt hRSV A2, passage 3 of Merck strain 287 ("p3") or passage 17 of Merck strain 287 ("p17") at days 14, 28 and 56 post immunization in cotton rats. The rats were immunized intramuscularly with the viruses.
Figure 9:
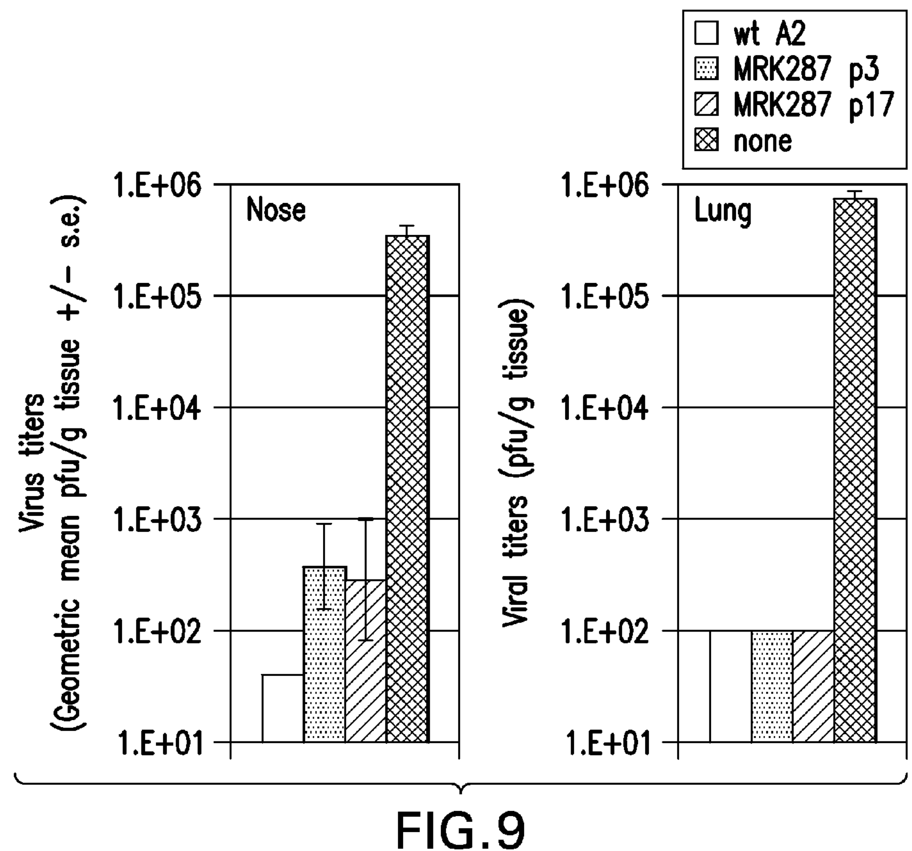
FIG. 9 compares the viral titers (pfu/gram of tissue) in nose and lung samples of cotton rats first immunized intramuscularly with either wild-type hRSV A2, Merck strain 287 p3 or Merck strain 287 p17, or no virus, and then challenged intranasally with $10^{5.5}$ pfu of wt A2 virus.

For the cotton rat study, animals of 4 per group were immunized intramuscularly with $10^{4.5}$ pfu of wt A2, MRK287 p3, or MRK287 p17 virus. Blood samples were collected at days 14, 28, and 56 and used for seroneutralizing (SN) antibody determination against wt A2 virus. At day 56, both the immunized animals and a group of naïve animals were challenged intranasally with $10^{5.5}$ pfu of wt A2 virus, and nose and lung tissues were collected at 4 days post challenge. Single intramuscular immunization with all three viruses induced significant SN titers, which reached peak level around day 28 and persisted till day 56 when the animals were challenged (FIG. 8). The animals receiving the A2 virus exhibited higher SN titers than those receiving MRK 287 viruses. This could be due to the fact the SN was determined against A2 strain. The SN titers of the animals receiving the parent MRK287 p3 virus and those receiving p17 virus were comparable, although there was trend that the latter induced higher SN titers at days 28 and 56. Following challenge, there was no detectable virus from the lung tissues of all three immunized groups (FIG. 9), indicating the vaccination provided a complete protection in the lower respiratory tract. With regard to nasal samples, animals receiving wt A2 had no detectable virus, and animals receiving either MRK287 p3 or p17 had very low titers, approximately 3 logs lower than that of the naïve animals.

Figure 10:
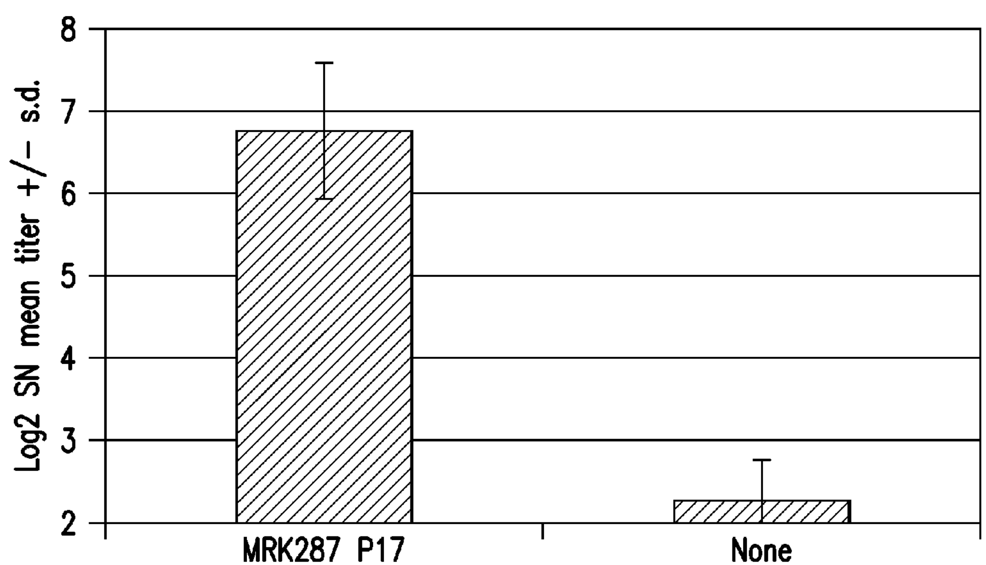
FIG. 10 compares the seroneutralizing (SN) antibody titers against wild-type hRSV A2 in African green monkeys twenty-eight days after immunization with passage 17 of Merck strain 287 ("p17") or no virus ("none") in the nose and lung. The monkeys were immunized intramuscularly.
Figure 11:
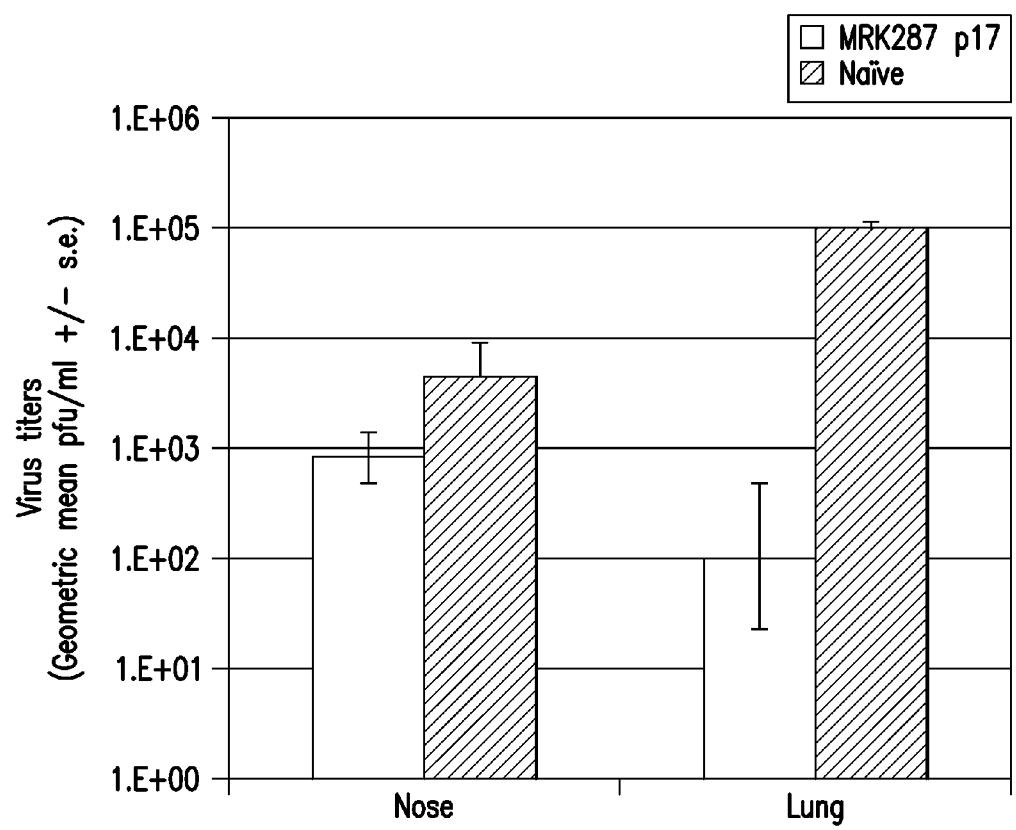
FIG. 11 compares the mean viral titers (pfu/ml) in nose and lung samples of African green monkeys first immunized intramuscularly with either Merck strain 287 p17 or no virus, and then challenged by intranasal and intratracheal inoculation with $10^{5.5}$ pfu of wt A2 virus.

The African green monkey study involved two groups, one experimental group and one naïve control group, with 4 animals each. For the experimental group, animals were immunized intramuscularly with $10^{5.5}$ pfu of MRK287 p17 virus at day 0. Both groups were challenged with $2\times10^{5.5}$ pfu of wt A2 virus by intranasal and intratracheal inoculation at day 28. Nasal swabs and lung lavage were collected at day 7 post challenge for virus titration. FIG. 10 shows the SN titers at day 28. The animals receiving the vaccine developed approximately mean SN titers of 1:128 (7 log 2). Following challenge, native animals had approximately 3.5- and 5-log pfu/ml virus at day 7 in the nasal and lung samples, respectively (FIG. 11). The animals that received the vaccine had about 1 log lower viral titers in the nose and 3 logs lower titers in the lungs than that in the naïve animals.

EXAMPLE 4

Plaque Purified p17

Plaque purification—The p17 virus passage was titrated for the purpose of isolating and harvesting individual plaques with the intent of identifying single (clonal), genetic populations of the passage 17 virus. The virus was titrated to target ≤10 plaques per well. The starting titer of the virus stock was $1.7 \times 10^6$ pfu/mL, and the range of final dilutions run for assay were 1:10,000, 1:20,000, and 1:40,000. On day 7 post inoculation, plates were visualized both macroscopically and microscopically for singular plaques on the monolayer. Passage 17 virus produced two, distinct plaque morphologies, large (approximately 2 mM in diameter) and small (≤1 mM in diameter). For the initial isolation, ten small morphology (#1-10), and ten large morphology plaques (#11-20) were isolated. Isolation was performed by placing a 1 mL sterile serological pipet through the agarose and circling the perimeter of the plaque to be isolated. By drawing up the area with suction, the material was then transferred to 1 mL of RSV maintenance medium, dispersed and aliquotted 5×200 uL. Plaque #1 and #11 were chosen for titration and immediate amplification in Vero tissue culture plates. The remainder of aliquots were frozen via liquid nitrogen and stored at −70° C. Secondary amplification consisted of titering plaques at 1:20, 1:200, and 1:2000 in Vero plates. Some plates received agarose overlay for creating a secondary population of plaques from the parent plaque, while others received liquid RSV maintenance medium overlay to create stocks of parent plaques #1 and #11 for subsequent sequence analysis. Out of secondary plaque assay of plaques #1 and #11, two plaques were isolated. These plaques were chosen due to their segregation from other plaques on the plate (thus reducing the likelihood of obtaining a mixed population) and their plaque morphology being similar to the parent. Two plaques each were isolated from parent plaque and labeled #1-1 and #1-2 (e.g., plaques isolated from plaque #11 received nomenclature of #11-1 and #11-2). Plaque #1-2 was chosen to titrate and amplify in a third round of plaque purification: 1×200 ul of plaque #1-2 was titrated simultaneously for plaque purification and amplification to create additional stocks of #1-2 parent. Plaques isolated from #1-2 were labeled #1-2.1, #1-2.2, #1-2.3, #1-2.4, #1.2-5, and #1-2.6. Sequence analysis performed on isolates halted after analysis of #1-2.1 showed a clonal population.

Amplification of plaque #1-2.1 for virus stocks—Growth of virus stocks followed standard procedure, outlined previously. 200 ul of original plaque was amplified in Vero cell, 12-well cultures. Stock from first amplification (pp1) were used to inoculate Vero T150 cultures; harvested material (pp 2) was amplified one additional time to create a large volume (about 1 L) of material for experimental use. Aliquots of #1-2.1 taken from each scale up were provided for sequence analysis. PP3 material was utilized for use in cotton rat studies.

Cotton rat challenge study—Four, 4-8 week old, female, cotton rats (*Sigmodon hispidus*) were inoculated intranasally, under isoflurane anesthesia with $10^5$ pfu of virus in 0.1 ml volume at day 0. Lung (left lobes) and nasal turbinates were removed four days post inoculation, homogenized in 10 volumes of Hanks Balanced Salt Solution (Walkersville, Md.) containing SPG on ice. Samples were clarified by centrifugation at 2000 rpm for 10 minutes, aliquoted and immediately stored frozen at −70° C. The viruses include: (1) MRK287 p22, (2) MRK287 p17, (3) MRK287 p17 plaque purified, (4) MRK287 p15, (5) MRK287 p10, (6) MRK287 p5, (7) MRK287 p3, and (8) RSV A2 wild-type. Nose and lung homogenates were titrated in Vero cells and were expressed as plaque forming units (pfu) per gram tissue.

Results—MRK287 passage 17 (p17) was plaque purified to a clonal population ("p17_pp") and sequenced as described in Example 2. One additional nucleotide mutation was seen in the plaque purified virus, located at nucleotide position 260 within the RSV genome, corresponding to nucleotide position 162 within the gene coding for the NS1 protein. This is a silent mutation (i.e., does not result in an amino acid mutation). SEQ ID NO: 87 corresponds to the wild-type gene sequence encoding NS1 (e.g., S2 strain). SEQ ID NO: 89 corresponds to the nucleotide sequence encoding NS1 within MRK287 and p17. SEQ ID NO: 90 corresponds to the nucleotide sequence encoding NS1 within p17_pp. Tables 8 and 9 compare the mutations in MRK287 p17 and the plaque purified version (p17_pp). SEQ ID NO: 88 corresponds to the amino acid sequence of NS1 (which is the same for the wt S2 virus, MRK287, MRK287 p17 and MRK287 p17_pp).

TABLE 8

Sequence differences between MRK RSV Strain 287, p17 and p17_pp

| Nucleotide Position | MRK RSV 287 | p17 | p17_pp |
|---|---|---|---|
| 260 | T | T | A |
| 954 | G | A | A |
| 5295 | A | G | G |
| 5298 | A | G | G |
| 5315 | A | G | G |
| 5316 | A | G | G |
| 5322 | A | G | G |
| 5324 | A | G | G |
| 5339 | A | G | G |
| 5346 | A | G | G |
| 5347 | A | G | G |
| 5351 | A | G | G |
| 5352 | A | G | G |
| 5353 | A | G | G |
| 5360 | A | G | G |
| 5380 | A | G | G |
| 5381 | A | G | G |
| 6538 | G | A (R?) * | A |
| 7115 | A | G (R?) * | G |
| 8937 | A | C (M?) * | C |
| 14656 | G | T (K?) * | T |
| 15046 | A | C | TBD |

* possible polymorphisms; R, M and K represent IUPAC codes for polymorphisms: R = A or G; K = G or T; M = A or C

TABLE 9

Amino acid sequence comparison between MRK RSV 287, p17 and p17_pp

| Nucleotide (nt) Position | RSV gene - nt position | Gene amino acid position | Note | MRK RSV 287 amino acid | p17 amino acid | p17_app amino acid |
|---|---|---|---|---|---|---|
| 260 | NS1-162 | 54 | Silent mutation | ILE | ILE | ILE |
| 954 | NS2-327 | 109 | Silent mutation | LYS | LYS | LYS |

TABLE 9-continued

Amino acid sequence comparison between MRK RSV 287, p17 and p17_pp

| Nucleotide (nt) Position | RSV gene - nt position | Gene amino acid position | Note | MRK RSV 287 amino acid | p17 amino acid | p17_app amino acid |
|---|---|---|---|---|---|---|
| 5295 | G-610 | 204 | | LYS | GLU | GLU |
| 5298 | G-613 | 205 | | LYS | GLU | GLU |
| 5315 | G-630 | 210 | Silent mutation | THR | THR | THR |
| 5316 | G-631 | 211 | | THR | ALA | ALA |
| 5322 | G-637 | 213 | | LYS | GLU | GLU |
| 5324 | G-639 | | | | | |
| 5339 | G-654 | 219 | Silent mutation | GLN | GLN | GLN |
| 5346 | G-661 | 221 | | LYS | GLY | GLY |
| 5347 | G-662 | | | | | |
| 5351 | G-666 | 222 | Silent mutation | SER | SER | SER |
| 5352 | G-667 | 223 | | LYS | GLY | GLY |
| 5353 | G-668 | | | | | |
| 5360 | G-675 | 226 | Silent mutation | VAL | VAL | VAL |
| 5380 | G-695 | 232 | | GLU | GLY | GLY |
| 5381 | G-696 | | | | | |
| 6538 | F-880 | 294 | | GLU | LYS*[1] | LYS |
| 7115 | F-1457 | 486 | | ASP | GLY*[2] | GLY |
| 8937 | L-443 | 148 | | ASP | ALA*[3] | ALA |
| 14656 | L-6162 | 2054 | | LEU | PHE*[4] | PHE |
| 15046 | NTR | NA | 5' untranslated region | NA | NA | NA |

*possible polymorphisms:
[1]= GLU/LYS,
[2]= ASP/GLY,
[3]= ASP/ALA,
[4]= LEU/PHE

The mean titers of the 4 individual animals in the cotton rat challenge study, and the lower and upper confidence intervals (CI), for each animal inoculated with (1) MRK287 p22, (2) MRK287 p17, (3) MRK287 p17 plaque purified, (4) MRK287 p15, (5) MRK287 p10, (6) MRK287 p5, (7) MRK287 p3, or (8) RSV A2 wild-type are shown in Table 10. The virus titers of RSV A2 wild-type and MRK287 p3 have above 4 log pfu/g tissue. MRK287 p5 lung samples still have approximately 4 logs virus pfu/g. In contrast, the virus at and after passage 10, including the plaque purified MRK287 p17, show a reduction by more than 2 logs from the wild-type strains, in both lung and nose samples. Furthermore, these data confirm that plaque purified MRK287 p17 is as attenuated as MRK287 p17.

TABLE 10

Viral titers (log pfu/gram tissue)

| Virus | Nose* | | | Lung* | | |
|---|---|---|---|---|---|---|
| | Mean | Lower 95% CI | Upper 95% CI | Mean | Lower 95% CI | Upper 95% CI |
| RSV A2 wt | 4.77 | 4.72 | 4.82 | 4.65 | 4.45 | 4.84 |
| MRK287 P3 | 4.09 | 3.52 | 4.66 | 4.19 | 3.64 | 4.73 |
| MRK287 P5 | nd | — | — | 4.08 | 3.90 | 4.26 |
| MRK287 P10 | 2.51 | 2.07 | 2.94 | 2.19 | 1.65 | 2.73 |
| MRK287 P15 | 1.60 | 1.60 | 1.60 | 2.00 | 2.00 | 2.00 |
| MRK287 P17 | 1.60 | 1.60 | 1.60 | 2.08 | 1.87 | 2.28 |

TABLE 10-continued

| Viral titers (log pfu/gram tissue) | | | | | | |
|---|---|---|---|---|---|---|
| | Nose* | | | Lung* | | |
| Virus | Mean | Lower 95% CI | Upper 95% CI | Mean | Lower 95% CI | Upper 95% CI |
| MRK287 P17 plaque purified | 2.11 | 1.56 | 2.66 | 2.32 | 1.43 | 3.21 |
| MRK287 P22 | 1.90 | 1.31 | 2.49 | 2.91 | 2.01 | 3.81 |

*Detection limit was 1.6 pfu/g for nose and 2.0 pfu/g for lung samples

What is claimed is:

1. A live, attenuated respiratory syncytial virus (RSV) comprising a viral genome, wherein the viral genome encodes proteins that comprise a glutamic acid at position 204 of the protein encoded by the G gene; a glutamic acid at position 205 of the protein encoded by the G gene; an alanine at position 211 of the protein encoded by the G gene; a glutamic acid at position 213 of the protein encoded by the G gene; a glycine at position 221 of the protein encoded by the G gene; a glycine at position 223 of the protein encoded by the G gene; a glycine at position 232 of the protein encoded by the G gene; a glycine at position 486 of the protein encoded by the F gene; and an alanine at position 148 of the protein encoded by the L gene.

2. The attenuated RSV of claim 1, wherein the viral genome encodes proteins that further comprise a lysine at position 294 of the protein encoded by the F gene, and a phenylalanine at position 2054 of the protein encoded by the L gene.

3. The attenuated RSV of claim 2, wherein the proteins encoded by the G, F and L genes comprise amino acid sequences that are at least 95% identical to the amino acid sequences as set forth in SEQ ID NO: 12, SEQ ID NO: 18 and SEQ ID NO: 24, respectively.

4. The attenuated RSV of claim 3, wherein the proteins encoded by the G, F, and L genes consist of the amino acid sequences as set forth in SEQ ID NO: 12, SEQ ID NO: 18 and SEQ ID NO: 24, respectively.

5. The attenuated RSV of claim 1, wherein the viral genome further comprises one or more nucleotides selected from the group consisting an adenine at nucleotide position 162 of the NS1gene, an adenine at nucleotide position 327 of the NS2gene, a guanine at nucleotide position 630 of the G gene, a guanine at nucleotide position 654 of the G gene, a guanine at nucleotide position 666 of the G gene, and a guanine at nucleotide position 675 of the G gene.

6. The attenuated RSV of claim 5, wherein the viral genome comprises an adenine at nucleotide position 162 of the NS1gene, an adenine at nucleotide position 327 of the NS2 gene, a guanine at nucleotide position 630 of the G gene, a guanine at nucleotide position 654 of the G gene, a guanine at nucleotide position 666 of the G gene, and a guanine at nucleotide position 675 of the G gene.

7. The attenuated RSV of claim 6, wherein the viral genome comprises NS1, NS2, G, F and L genes that are at least 95% identical to the nucleotide sequences as set forth in SEQ ID NO: 90, SEQ ID NO: 5, SEQ ID NO: 11, SEQ ID NO: 17, and SEQ ID NO: 23, respectively.

8. The attenuated RSV of claim 7, wherein the viral genome comprises NS1, NS2, G, F, and L genes consisting of the nucleotide sequences as set forth in SEQ ID NO: 90, SEQ ID NO: 5, SEQ ID NO: 11, SEQ ID NO: 17, and SEQ ID NO: 23, respectively.

9. An immunogenic composition comprising the live, attenuated RSV of claim 1 and a pharmaceutically acceptable carrier.

10. A nucleic acid molecule comprising a genomic or antigenomic sequence encoding the live, attenuated RSV of claim 1.

11. The nucleic acid molecule of claim 10, wherein said nucleic acid molecule is an expression vector.

* * * * *

SEQUENCE LISTING

```
<160> NUMBER OF SEQ ID NOS: 95

<210> SEQ ID NO 1
<211> LENGTH: 375
<212> TYPE: DNA
<213> ORGANISM: Respiratory syncytial virus, S2

<400> SEQUENCE: 1

atggacacaa cacacaatga caccacacca caaagactga tgatcacaga catgagacca      60

ttgtcacttg agactataat aatatcacta accagagaca tcataacaca cagatttata     120

tacttgataa atcatgaatg tatagtgaga aaacttgatg aaagacaggc cacatttaca     180

ttcctggtca actatgaaat gaaactattg cacaaagtgg gaagcactaa atacaaaaaa     240

tatactgaat acaacacaaa atatggcact tttcctatgc caatatttat caatcatgat     300

gggttcttag aatgcattgg cattaagcct acaaagcaca ctcccataat atacaagtat     360

gatctcaatc catga                                                      375


<210> SEQ ID NO 2
<211> LENGTH: 124
<212> TYPE: PRT
<213> ORGANISM: Respiratory syncytial virus, S2 strain

<400> SEQUENCE: 2

Met Asp Thr Thr His Asn Asp Thr Thr Pro Gln Arg Leu Met Ile Thr
1               5                   10                  15

Asp Met Arg Pro Leu Ser Leu Glu Thr Ile Ile Ile Ser Leu Thr Arg
            20                  25                  30

Asp Ile Ile Thr His Arg Phe Ile Tyr Leu Ile Asn His Glu Cys Ile
        35                  40                  45

Val Arg Lys Leu Asp Glu Arg Gln Ala Thr Phe Thr Phe Leu Val Asn
    50                  55                  60

Tyr Glu Met Lys Leu Leu His Lys Val Gly Ser Thr Lys Tyr Lys Lys
65                  70                  75                  80

Tyr Thr Glu Tyr Asn Thr Lys Tyr Gly Thr Phe Pro Met Pro Ile Phe
                85                  90                  95

Ile Asn His Asp Gly Phe Leu Glu Cys Ile Gly Ile Lys Pro Thr Lys
            100                 105                 110

His Thr Pro Ile Ile Tyr Lys Tyr Asp Leu Asn Pro
        115                 120


<210> SEQ ID NO 3
<211> LENGTH: 375
<212> TYPE: DNA
<213> ORGANISM: Respiratory syncytial virus, Merck strain 287

<400> SEQUENCE: 3
```

```
atggacacga ctcacaatga taccacacca caaagactga tgatcacaga tatgagacca     60

ttgtcacttg agaccataat aacatcacta accagagaca tcataacaca caaatttata    120

tacttgataa atcatgaatg catagtgaga aaacttgatg aaagacaagc cacatttaca    180

ttcctggtca actatgaaat gaaactattg cacaaagtag gaagcactaa atataaaaaa    240

tatactgaat acaacacaaa atatggcact ttccctatgc cgatattcat caatcatgat    300

gggttcttag aatgcattgg cattaagcct acaaagcata ctcccataat atacaagtat    360

gatctcaatc cataa                                                     375


<210> SEQ ID NO 4
<211> LENGTH: 124
<212> TYPE: PRT
<213> ORGANISM: Respiratory syncytial virus, Merck strain 287

<400> SEQUENCE: 4

Met Asp Thr Thr His Asn Asp Thr Thr Pro Gln Arg Leu Met Ile Thr
1               5                   10                  15

Asp Met Arg Pro Leu Ser Leu Glu Thr Ile Ile Thr Ser Leu Thr Arg
            20                  25                  30

Asp Ile Ile Thr His Lys Phe Ile Tyr Leu Ile Asn His Glu Cys Ile
        35                  40                  45

Val Arg Lys Leu Asp Glu Arg Gln Ala Thr Phe Thr Phe Leu Val Asn
    50                  55                  60

Tyr Glu Met Lys Leu Leu His Lys Val Gly Ser Thr Lys Tyr Lys Lys
65                  70                  75                  80

Tyr Thr Glu Tyr Asn Thr Lys Tyr Gly Thr Phe Pro Met Pro Ile Phe
                85                  90                  95

Ile Asn His Asp Gly Phe Leu Glu Cys Ile Gly Ile Lys Pro Thr Lys
            100                 105                 110

His Thr Pro Ile Ile Tyr Lys Tyr Asp Leu Asn Pro
        115                 120


<210> SEQ ID NO 5
<211> LENGTH: 375
<212> TYPE: DNA
<213> ORGANISM: Respiratory syncytial virus, Merck strain p17

<400> SEQUENCE: 5

atggacacga ctcacaatga taccacacca caaagactga tgatcacaga tatgagacca     60

ttgtcacttg agaccataat aacatcacta accagagaca tcataacaca caaatttata    120

tacttgataa atcatgaatg catagtgaga aaacttgatg aaagacaagc cacatttaca    180

ttcctggtca actatgaaat gaaactattg cacaaagtag gaagcactaa atataaaaaa    240

tatactgaat acaacacaaa atatggcact ttccctatgc cgatattcat caatcatgat    300

gggttcttag aatgcattgg cattaaacct acaaagcata ctcccataat atacaagtat    360

gatctcaatc cataa                                                     375


<210> SEQ ID NO 6
<211> LENGTH: 124
<212> TYPE: PRT
<213> ORGANISM: Respiratory syncytial virus, Merck strain p17

<400> SEQUENCE: 6

Met Asp Thr Thr His Asn Asp Thr Thr Pro Gln Arg Leu Met Ile Thr
1               5                   10                  15
```

```
Asp Met Arg Pro Leu Ser Leu Glu Thr Ile Ile Thr Ser Leu Thr Arg
            20                  25                  30

Asp Ile Ile Thr His Lys Phe Ile Tyr Leu Ile Asn His Glu Cys Ile
        35                  40                  45

Val Arg Lys Leu Asp Glu Arg Gln Ala Thr Phe Thr Phe Leu Val Asn
    50                  55                  60

Tyr Glu Met Lys Leu Leu His Lys Val Gly Ser Thr Lys Tyr Lys Lys
65                  70                  75                  80

Tyr Thr Glu Tyr Asn Thr Lys Tyr Gly Thr Phe Pro Met Pro Ile Phe
                85                  90                  95

Ile Asn His Asp Gly Phe Leu Glu Cys Ile Gly Ile Lys Pro Thr Lys
            100                 105                 110

His Thr Pro Ile Ile Tyr Lys Tyr Asp Leu Asn Pro
        115                 120


<210> SEQ ID NO 7
<211> LENGTH: 897
<212> TYPE: DNA
<213> ORGANISM: Respiratory syncytial virus, S2

<400> SEQUENCE: 7

atgtccaaaa acaaggacca acgcaccgcc aagacactag aaaagacctg ggacactctc      60

aatcatctat tattcatatc atcgtgctta tacaagttaa atcttaaatc tatagcacaa     120

atcacattat ccattctggc aatgataatc tcaacttcac ttataattgc agccatcata     180

ttcatagcct cggcaaacca caaagtcaca ctaacaactg caatcataca agatgcaaca     240

agccagatca agaacacaac cccaacatac ctcacccaga atccccagct tggaatcagc     300

ttctccaatc tgtctgaaac tacatcacaa accaccacca tactagcttc aacaacacca     360

agtgtcaagt caaccctgca atccacaaca gtcaagacca aaaacacaac aacaaccaaa     420

atacaaccca gcaagcccac cacaaaacaa cgccaaaaca aaccaccaaa caaacccaat     480

aatgattttc actttgaagt gttcaacttt gtaccttgca gcatatgcag caacaatcca     540

acctgctggg ctatctgtaa aagaatacca aacaaaaaac ctggaaagaa aaccaccacc     600

aagcccacaa aaaaaccaac catcaagaca accaaaaaag atctcaaacc tcaaaccaca     660

aaaccaaagg aagtacctac caccaagccc acagaaaagc caaccatcaa caccaccaaa     720

acaaacatca gaactacact gctcaccaac aataccacag gaaatccaga acacacaagt     780

caaaagggaa ccctccactc aacctcctcc gatggcaatc caagcccttc acaagtctat     840

acaacatccg agtacctatc acaacctcca tctccatcca acacaacaaa ccagtag        897


<210> SEQ ID NO 8
<211> LENGTH: 298
<212> TYPE: PRT
<213> ORGANISM: Respiratory syncytial virus, S2

<400> SEQUENCE: 8

Met Ser Lys Asn Lys Asp Gln Arg Thr Ala Lys Thr Leu Glu Lys Thr
 1               5                  10                  15

Trp Asp Thr Leu Asn His Leu Leu Phe Ile Ser Ser Cys Leu Tyr Lys
            20                  25                  30

Leu Asn Leu Lys Ser Ile Ala Gln Ile Thr Leu Ser Ile Leu Ala Met
        35                  40                  45

Ile Ile Ser Thr Ser Leu Ile Ile Ala Ala Ile Ile Phe Ile Ala Ser
    50                  55                  60
```

```
Ala Asn His Lys Val Thr Leu Thr Thr Ala Ile Ile Gln Asp Ala Thr
65                  70                  75                  80

Ser Gln Ile Lys Asn Thr Thr Pro Thr Tyr Leu Thr Gln Asn Pro Gln
                85                  90                  95

Leu Gly Ile Ser Phe Ser Asn Leu Ser Glu Thr Thr Ser Gln Thr Thr
            100                 105                 110

Thr Ile Leu Ala Ser Thr Thr Pro Ser Val Lys Ser Thr Leu Gln Ser
        115                 120                 125

Thr Thr Val Lys Thr Lys Asn Thr Thr Thr Thr Lys Ile Gln Pro Ser
    130                 135                 140

Lys Pro Thr Thr Lys Gln Arg Gln Asn Lys Pro Pro Asn Lys Pro Asn
145                 150                 155                 160

Asn Asp Phe His Phe Glu Val Phe Asn Phe Val Pro Cys Ser Ile Cys
                165                 170                 175

Ser Asn Asn Pro Thr Cys Trp Ala Ile Cys Lys Arg Ile Pro Asn Lys
            180                 185                 190

Lys Pro Gly Lys Lys Thr Thr Thr Lys Pro Thr Lys Lys Pro Thr Ile
        195                 200                 205

Lys Thr Thr Lys Lys Asp Leu Lys Pro Gln Thr Thr Lys Pro Lys Glu
    210                 215                 220

Val Pro Thr Thr Lys Pro Thr Glu Lys Pro Thr Ile Asn Thr Thr Lys
225                 230                 235                 240

Thr Asn Ile Arg Thr Thr Leu Leu Thr Asn Asn Thr Thr Gly Asn Pro
                245                 250                 255

Glu His Thr Ser Gln Lys Gly Thr Leu His Ser Thr Ser Ser Asp Gly
            260                 265                 270

Asn Pro Ser Pro Ser Gln Val Tyr Thr Thr Ser Glu Tyr Leu Ser Gln
        275                 280                 285

Pro Pro Ser Pro Ser Asn Thr Thr Asn Gln
    290                 295
```

<210> SEQ ID NO 9
<211> LENGTH: 900
<212> TYPE: DNA
<213> ORGANISM: Respiratory syncytial virus, Merck strain 287

<400> SEQUENCE: 9

```
atgtccaaaa acaaagacca acgcactgct aagacactag aaaggacctg ggacactctc     60

aatcatttat tattcatatc atcgtgctta tataagttaa atcttaaatc tgtagcacaa    120

atcacattat ccattttggc aatgataatc tcaacttcac ttataattgc agccatcata    180

ttcattgcct cggcaaacca caaagtcaca tcaacaacta caatcataca agatgcaaca    240

agccagatca agaacacaac cccaacatac ctcacccaga gtcctcagct tggaatcagt    300

ccctctaatc cgtctgaaat tacatcacaa atcaccacca tactagcttc aacaacacca    360

ggagtcaagt caaccctgca atccacaaca gtcgggacca agaatacaac aacaactcaa    420

gcacaaccca gcaagcccac cacaaaacaa cgccaaaaca aaccaccaag caaacccaac    480

aatgattttc actttgaagt gttcaacttt gtaccctgca gcatatgcag caacaatcca    540

acctgctggg ccatctgcaa aagaataccc aacaaaaaac caggaaagaa aaccaccacc    600

aagcccacaa aaaaaccaac cttcaagaca accaaaaaag atcccaaacc tcaaaccact    660

aaatcaaagg aggtacccac caccaagccc acagaagagc caactatcaa caccaccaaa    720

acaaacatca caactacact actcacctcc aacaccacga gaaatccaga actcacaagt    780
```

```
caaatggaaa ccttccactc aacttcctcc gaaggtaatc caagcccttc tcaagtctcc     840

ataacatccg agtacctatc acaaccttca tctccaccca acacaccacg ctagtagtta     900


<210> SEQ ID NO 10
<211> LENGTH: 297
<212> TYPE: PRT
<213> ORGANISM: Respiratory syncytial virus, Merck strain 287

<400> SEQUENCE: 10

Met Ser Lys Asn Lys Asp Gln Arg Thr Ala Lys Thr Leu Glu Arg Thr
 1               5                  10                  15

Trp Asp Thr Leu Asn His Leu Leu Phe Ile Ser Ser Cys Leu Tyr Lys
            20                  25                  30

Leu Asn Leu Lys Ser Val Ala Gln Ile Thr Leu Ser Ile Leu Ala Met
        35                  40                  45

Ile Ile Ser Thr Ser Leu Ile Ile Ala Ala Ile Ile Phe Ile Ala Ser
    50                  55                  60

Ala Asn His Lys Val Thr Ser Thr Thr Thr Ile Ile Gln Asp Ala Thr
65                  70                  75                  80

Ser Gln Ile Lys Asn Thr Thr Pro Thr Tyr Leu Thr Gln Ser Pro Gln
                85                  90                  95

Leu Gly Ile Ser Pro Ser Asn Pro Ser Glu Ile Thr Ser Gln Ile Thr
            100                 105                 110

Thr Ile Leu Ala Ser Thr Thr Pro Gly Val Lys Ser Thr Leu Gln Ser
        115                 120                 125

Thr Thr Val Gly Thr Lys Asn Thr Thr Thr Thr Gln Ala Gln Pro Ser
    130                 135                 140

Lys Pro Thr Thr Lys Gln Arg Gln Asn Lys Pro Pro Ser Lys Pro Asn
145                 150                 155                 160

Asn Asp Phe His Phe Glu Val Phe Asn Phe Val Pro Cys Ser Ile Cys
                165                 170                 175

Ser Asn Asn Pro Thr Cys Trp Ala Ile Cys Lys Arg Ile Pro Asn Lys
            180                 185                 190

Lys Pro Gly Lys Lys Thr Thr Thr Lys Pro Thr Lys Lys Pro Thr Phe
        195                 200                 205

Lys Thr Thr Lys Lys Asp Pro Lys Pro Gln Thr Thr Lys Ser Lys Glu
    210                 215                 220

Val Pro Thr Thr Lys Pro Thr Glu Glu Pro Thr Ile Asn Thr Thr Lys
225                 230                 235                 240

Thr Asn Ile Thr Thr Thr Leu Leu Thr Ser Asn Thr Thr Arg Asn Pro
                245                 250                 255

Glu Leu Thr Ser Gln Met Glu Thr Phe His Ser Thr Ser Ser Glu Gly
            260                 265                 270

Asn Pro Ser Pro Ser Gln Val Ser Ile Thr Ser Glu Tyr Leu Ser Gln
        275                 280                 285

Pro Ser Ser Pro Pro Asn Thr Pro Arg
    290                 295


<210> SEQ ID NO 11
<211> LENGTH: 900
<212> TYPE: DNA
<213> ORGANISM: Respiratory syncytial virus, Merck strain p17

<400> SEQUENCE: 11

atgtccaaaa acaaagacca acgcactgct aagacactag aaaggacctg ggacactctc      60
```

```
aatcatttat tattcatatc atcgtgctta tataagttaa atcttaaatc tgtagcacaa    120

atcacattat ccattttggc aatgataatc tcaacttcac ttataattgc agccatcata    180

ttcattgcct cggcaaacca caaagtcaca tcaacaacta caatcataca agatgcaaca    240

agccagatca agaacacaac cccaacatac ctcacccaga gtcctcagct tggaatcagt    300

ccctctaatc cgtctgaaat tacatcacaa atcaccacca tactagcttc aacaacacca    360

ggagtcaagt caaccctgca atccacaaca gtcgggacca agaatacaac aacaactcaa    420

gcacaaccca gcaagcccac cacaaaacaa cgccaaaaca aaccaccaag caaacccaac    480

aatgatttc actttgaagt gttcaacttt gtaccctgca gcatatgcag caacaatcca    540

acctgctggg ccatctgcaa aagaataccc aacaaaaaac caggaaagaa aaccaccacc    600

aagcccacag aagaaccaac cttcaagacg gccaaagagg atcccaaacc tcagaccact    660

ggatcggggg aggtgcccac caccaagccc acaggggagc caactatcaa caccaccaaa    720

acaaacatca caactacact actcacctcc aacaccacga gaaatccaga actcacaagt    780

caaatggaaa ccttccactc aacttcctcc gaaggtaatc caagcccttc tcaagtctcc    840

ataacatccg agtacctatc acaaccttca tctccaccca acacaccacg ctagtagtta    900
```

<210> SEQ ID NO 12
<211> LENGTH: 297
<212> TYPE: PRT
<213> ORGANISM: Respiratory syncytial virus, Merck strain p17

<400> SEQUENCE: 12

```
Met Ser Lys Asn Lys Asp Gln Arg Thr Ala Lys Thr Leu Glu Arg Thr
 1               5                  10                  15

Trp Asp Thr Leu Asn His Leu Leu Phe Ile Ser Ser Cys Leu Tyr Lys
            20                  25                  30

Leu Asn Leu Lys Ser Val Ala Gln Ile Thr Leu Ser Ile Leu Ala Met
        35                  40                  45

Ile Ile Ser Thr Ser Leu Ile Ile Ala Ala Ile Ile Phe Ile Ala Ser
    50                  55                  60

Ala Asn His Lys Val Thr Ser Thr Thr Thr Ile Ile Gln Asp Ala Thr
65                  70                  75                  80

Ser Gln Ile Lys Asn Thr Thr Pro Thr Tyr Leu Thr Gln Ser Pro Gln
                85                  90                  95

Leu Gly Ile Ser Pro Ser Asn Pro Ser Glu Ile Thr Ser Gln Ile Thr
            100                 105                 110

Thr Ile Leu Ala Ser Thr Thr Pro Gly Val Lys Ser Thr Leu Gln Ser
        115                 120                 125

Thr Thr Val Gly Thr Lys Asn Thr Thr Thr Thr Gln Ala Gln Pro Ser
    130                 135                 140

Lys Pro Thr Thr Lys Gln Arg Gln Asn Lys Pro Pro Ser Lys Pro Asn
145                 150                 155                 160

Asn Asp Phe His Phe Glu Val Phe Asn Phe Val Pro Cys Ser Ile Cys
                165                 170                 175

Ser Asn Asn Pro Thr Cys Trp Ala Ile Cys Lys Arg Ile Pro Asn Lys
            180                 185                 190

Lys Pro Gly Lys Lys Thr Thr Thr Lys Pro Thr Glu Glu Pro Thr Phe
        195                 200                 205

Lys Thr Ala Lys Glu Asp Pro Lys Pro Gln Thr Thr Gly Ser Gly Glu
    210                 215                 220

Val Pro Thr Thr Lys Pro Thr Gly Glu Pro Thr Ile Asn Thr Thr Lys
```

```
225                 230                 235                 240

Thr Asn Ile Thr Thr Thr Leu Leu Thr Ser Asn Thr Thr Arg Asn Pro
                245                 250                 255

Glu Leu Thr Ser Gln Met Glu Thr Phe His Ser Thr Ser Ser Glu Gly
            260                 265                 270

Asn Pro Ser Pro Ser Gln Val Ser Ile Thr Ser Glu Tyr Leu Ser Gln
        275                 280                 285

Pro Ser Ser Pro Pro Asn Thr Pro Arg
    290                 295


<210> SEQ ID NO 13
<211> LENGTH: 1725
<212> TYPE: DNA
<213> ORGANISM: Respiratory syncytial virus, S2

<400> SEQUENCE: 13

atggagttgc caatcctcaa aacaaatgca attaccgcaa tccttgctgc agtcacactc      60

tgttttgctt ccagtcaaaa catcactgaa gaattttatc aatcaacatg cagtgcagtc     120

agcaaaggct atcttagtgc tctaagaact ggttggtata ctagtgttat aactatagaa     180

ttaagtaata tcaaggaaaa taagtgtaat ggaacagatg ctaaggtaaa attgataaaa     240

caagaattag ataaatataa aagtgctgta acagaattgc agttgctcat gcaaagcaca     300

ccggcaacca acaatcgagc cagaagagaa ctaccaaggt ttatgaatta tacactcaac     360

aataccaaaa ataccaatgt aacattaagc aagaaaagga aaagaagatt tcttggcttt     420

ttgttaggtg ttggatctgc aatcgccagt ggcattgctg tatctaaggt cctgcaccta     480

gaaggggaag tgaacaagat caaaagtgct ctactatcca caaacaaggc tgtagtcagc     540

ttatcaaatg gagttagtgt cttaaccagc aaagtgttag acctcaaaaa ctatatagat     600

aaacagttgt tacctattgt gaacaagcaa agctgtagca tatcaaacat tgaaactgtg     660

atagagttcc aacaaaagaa caacagacta ctagagatta ccagggaatt tagtgttaat     720

gcaggtgtaa ctacacctgt aagcacttat atgttaacaa atagtgaatt attatcatta     780

atcaatgata tgcctataac aaatgatcag aaaaagttaa tgtccaacaa tgttcaaata     840

gttagacagc aaagttactc tatcatgtcc ataataaagg aggaagtctt agcatatgta     900

gtacaattac cactatatgg tgtaatagat acaccttgtt ggaaactaca cacatcccct     960

ctatgtacaa ccaacacaaa ggaagggtcc aacatctgtt taacaagaac cgacagagga    1020

tggtactgtg acaatgcagg atcagtatct ttcttcccac tagctgaaac atgtaaagtt    1080

caatcgaatc gagtattttg tgacacaatg aacagtttaa cattaccaag tgaagtaaat    1140

ctctgcaaca ttgacatatt caaccccaaa tatgattgca aaattatgac ttcaaaaaca    1200

gatgtaagca gctccgttat cacatctcta ggagccattg tgtcatgcta tggcaaaact    1260

aaatgtacag catccaataa aaatcgtgga atcataaaga cattttctaa cgggtgcgat    1320

tatgtatcaa ataagggggt ggacactgtg tctgtaggta atacattata ttatgtaaat    1380

aagcaagaag gcaaaagtct ctatgtaaaa ggtgaaccaa taataaattt ctatgaccca    1440

ttagtgttcc cctctgatga atttgatgca tcaatatctc aagtcaatga gaagattaac    1500

cagagcctag catttattcg taaatccgat gaattattac ataatgtaaa tgctggtaaa    1560

tccaccacaa atatcatgat aactactata attatagtga ttatagtaat attgttatca    1620

ttaattgccg ttggactgct cctatactgc aaggccagaa gcacaccagt cacactaagc    1680

aaggatcaac tgagtggtat aaataatatt gcatttagta actaa                     1725
```

<210> SEQ ID NO 14
<211> LENGTH: 574
<212> TYPE: PRT
<213> ORGANISM: Respiratory syncytial virus, S2

<400> SEQUENCE: 14

```
Met Glu Leu Pro Ile Leu Lys Thr Asn Ala Ile Thr Ala Ile Leu Ala
 1               5                  10                  15

Ala Val Thr Leu Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Ser Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Thr Lys Asn Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Leu Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Ile
```

```
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Ile Ile Ile Val Ile Ile Val Ile Leu Leu Ser Leu Ile Ala Val
    530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570


<210> SEQ ID NO 15
<211> LENGTH: 1725
<212> TYPE: DNA
<213> ORGANISM: Respiratory syncytial virus, Merck strain 287

<400> SEQUENCE: 15

atggagttgc caatcctcaa agcgaatgca attaccacaa tcctcactgc agtcacattt      60

tgttttgctt ctagtcaaaa catcactgaa gaattttatc aatcaacatg cagtgcagtt     120

agcaaaggct atcttagtgc tctaagaact ggttggtata ccagtgttat aactatagaa     180

ttaagtaata tcaaggaaaa taagtgtaat ggaacagatg ctaaggtaaa attgataaaa     240

caagaattag ataaatataa aaatgctgta acagaattgc agttgctaat gcaaagcaca     300

ccagcagcaa acaatcgagc cagaagagaa ctaccaaggt ttatgaatta tacactcaac     360

aatgccaaaa aaaccaatgt aacattaagc aaaaaaagga aaagaagatt tcttggtttt     420

ttgttaggag ttggatctgc aatcgccagt ggcattgctg tatctaaggt cctacaccta     480

gaaggggaag tgaacaagat caaaagtgct ctactatcca caaacaaggc tgtagtcagc     540

ttatcaaatg gagttagtgt cttaaccagc aaagtgttag acctcaaaaa ttatatagat     600

aaacaattgt tacctattgt gaacaagcaa agctgcagca tatcaaatat agaaactgtg     660

atagagttcc aacaaaagaa caacagacta ctagagatta ccagggaatt tagtgttaat     720

gcaggtgtaa ctacacctgt aagcacttac atgttgacta atagtgaatt attgtcatta     780

atcaatgata tgcctataac aaatgatcag aagaagttaa tgtccaacaa tgttcaaata     840

gttagacagc aaagttactc tatcatgtcc ataataaaag aggaagtctt agcatatgta     900

gtacaattac cactatatgg tgttatagat acaccttgtt ggaaattaca cacatcccct     960

ctatgtacaa ccaacacaaa agaagggtcc aacatctgtt taacaagaac tgacagagga    1020
```

```
tggtactgtg acaatgcagg atcagtctct ttcttcccac aagctgaaac atgtaaagtt   1080

caatcgaatc gagtattttg tgacacaatg aacagtttaa cattaccaag tgaagtaaat   1140

ctctgcaatg ttgacatatt caatcccaaa tatgattgta aaattatgac ttcaaaaaca   1200

gatgtaagca gctctgttat cacatctcta ggagccattg tgtcatgcta tggcaaaact   1260

aaatgtacag catccaataa aaatcgtgga atcataaaga cattttctaa cgggtgcgat   1320

tatgtatcaa ataaaggggt ggacactgtg tctgtaggca acacattata ttatgtaaat   1380

aagcaagaag gcaaaagtct ctatgtaaaa ggtgaaccaa taataaattt ctatgaccca   1440

ttagtattcc cctctgatga atttgatgca tcaatatctc aagtcaacga gaagattaac   1500

cagagcctgg catttattcg taaatccgat gaattattac ataatgtaaa tgctggtaaa   1560

tccaccacaa acatcatgat aactgctata attatagtga ttgtagtaat attattatca   1620

ttaattgctg taggactgct cctatactgt aaggccagaa gcacaccagt cacactaagc   1680

aaagatcaac tgagtggtat aaataatatt gcatttagta actaa                    1725
```

<210> SEQ ID NO 16
<211> LENGTH: 574
<212> TYPE: PRT
<213> ORGANISM: Respiratory syncytial virus, Merck strain 287

<400> SEQUENCE: 16

```
Met Glu Leu Pro Ile Leu Lys Ala Asn Ala Ile Thr Thr Ile Leu Thr
1               5                   10                  15

Ala Val Thr Phe Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Ala Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
```

```
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Ala Ile Ile Ile Val Ile Val Val Ile Leu Leu Ser Leu Ile Ala Val
    530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570
```

<210> SEQ ID NO 17
<211> LENGTH: 1725
<212> TYPE: DNA
<213> ORGANISM: Respiratory syncytial virus, Merck strain p17
<220> FEATURE:
<221> NAME/KEY: variation
<222> LOCATION: (880)...(880)
<223> OTHER INFORMATION: n = g or a
<221> NAME/KEY: variation
<222> LOCATION: (1457)...(1457)
<223> OTHER INFORMATION: n = g or a

<400> SEQUENCE: 17

```
atggagttgc caatcctcaa agcgaatgca attaccacaa tcctcactgc agtcacattt      60
```

```
tgttttgctt ctagtcaaaa catcactgaa gaattttatc aatcaacatg cagtgcagtt    120

agcaaaggct atcttagtgc tctaagaact ggttggtata ccagtgttat aactatagaa    180

ttaagtaata tcaaggaaaa taagtgtaat ggaacagatg ctaaggtaaa attgataaaa    240

caagaattag ataaatataa aaatgctgta acagaattgc agttgctaat gcaaagcaca    300

ccagcagcaa acaatcgagc cagaagagaa ctaccaaggt ttatgaatta tacactcaac    360

aatgccaaaa aaaccaatgt aacattaagc aaaaaaagga aaagaagatt tcttggtttt    420

ttgttaggag ttggatctgc aatcgccagt ggcattgctg tatctaaggt cctacaccta    480

gaaggggaag tgaacaagat caaaagtgct ctactatcca caaacaaggc tgtagtcagc    540

ttatcaaatg gagttagtgt cttaaccagc aaagtgttag acctcaaaaa ttatatagat    600

aaacaattgt tacctattgt gaacaagcaa agctgcagca tatcaaatat agaaactgtg    660

atagagttcc aacaaaagaa caacagacta ctagagatta ccagggaatt tagtgttaat    720

gcaggtgtaa ctacacctgt aagcacttac atgttgacta atagtgaatt attgtcatta    780

atcaatgata tgcctataac aaatgatcag aagaagttaa tgtccaacaa tgttcaaata    840

gttagacagc aaagttactc tatcatgtcc ataataaaan aggaagtctt agcatatgta    900

gtacaattac cactatatgg tgttatagat acaccttgtt ggaaattaca cacatcccct    960

ctatgtacaa ccaacacaaa agaagggtcc aacatctgtt taacaagaac tgacagagga   1020

tggtactgtg acaatgcagg atcagtctct ttcttcccac aagctgaaac atgtaaagtt   1080

caatcgaatc gagtattttg tgacacaatg aacagtttaa cattaccaag tgaagtaaat   1140

ctctgcaatg ttgacatatt caatcccaaa tatgattgta aaattatgac ttcaaaaaca   1200

gatgtaagca gctctgttat cacatctcta ggagccattg tgtcatgcta tggcaaaact   1260

aaatgtacag catccaataa aaatcgtgga atcataaaga cattttctaa cgggtgcgat   1320

tatgtatcaa ataaaggggt ggacactgtg tctgtaggca acacattata ttatgtaaat   1380

aagcaagaag gcaaaagtct ctatgtaaaa ggtgaaccaa taataaattt ctatgaccca   1440

ttagtattcc cctctgntga atttgatgca tcaatatctc aagtcaacga gaagattaac   1500

cagagcctgg catttattcg taaatccgat gaattattac ataatgtaaa tgctggtaaa   1560

tccaccacaa acatcatgat aactgctata attatagtga ttgtagtaat attattatca   1620

ttaattgctg taggactgct cctatactgt aaggccagaa gcacaccagt cacactaagc   1680

aaagatcaac tgagtggtat aaataatatt gcatttagta actaa                   1725
```

<210> SEQ ID NO 18
<211> LENGTH: 574
<212> TYPE: PRT
<213> ORGANISM: Respiratory syncytial virus, Merck strain p17
<220> FEATURE:
<221> NAME/KEY: SITE
<222> LOCATION: (294)...(294)
<223> OTHER INFORMATION: Xaa = Glu or Lys
<221> NAME/KEY: SITE
<222> LOCATION: (486)...(486)
<223> OTHER INFORMATION: Xaa = Asp or Gly

<400> SEQUENCE: 18

```
Met Glu Leu Pro Ile Leu Lys Ala Asn Ala Ile Thr Thr Ile Leu Thr
 1               5                  10                  15

Ala Val Thr Phe Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45
```

```
Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Ala Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Xaa Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460
```

-continued

```
Lys Ser Leu Tyr Val Lys Gly Glu Pro Ile Ile Asn Phe Tyr Asp Pro
465                 470                 475                 480

Leu Val Phe Pro Ser Xaa Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Ala Ile Ile Ile Val Ile Val Val Ile Leu Leu Ser Leu Ile Ala Val
    530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570


<210> SEQ ID NO 19
<211> LENGTH: 6498
<212> TYPE: DNA
<213> ORGANISM: Respiratory syncytial virus, S2

<400> SEQUENCE: 19

atggatccca ttattaatgg aaattctgct aatgtgtatc taaccgatag ttatttaaaa      60

ggtgttattt ctttctcaga atgtaatgct ttaggaagtt acatattcaa tggtccttat     120

ctcaaaaatg attataccaa cttaattagt agacaaaatc cattaataga acacataaat     180

ctaaagaaac taaatataac acagtcctta atatctaagt atcataaagg tgaaataaaa     240

atagaagaac ctacttattt tcagtcatta cttatgacat acaagagtat gacctcgtta     300

gaacagatta ctaccactaa tttacttaaa aagataataa gaagagctat agaaattagt     360

gatgtcaaag tctatgctat attgaataaa ctggggctta aagaaaaaga caagattaaa     420

tccaacaatg gacaagatga agacaactca gttattacaa ccataatcaa agatgatata     480

cttttagctg ttaaggataa tcaatctcat cttaaagcag tcaaaaatca ctctacaaaa     540

caaaaagata caatcaaaac aacactcttg aagaaattaa tgtgttcaat gcaacatcct     600

ccatcatggt taatacattg gtttaattta tacacaaaat taaacaacat attaacacag     660

tatcgatcaa gtgaggtaaa aaaccatggt tttatattga tagacaatca tactctcaat     720

ggattccaat ttattttgaa tcaatatggt tgtatagttt atcataagga actcaaaaga     780

attactgtga caacctataa tcaattcttg acatggaaag atattagcct tagtagatta     840

aatgtttgtt taattacatg gattagtaac tgtttgaaca cattaaataa aagcttaggc     900

ttaagatgcg gattcaataa tgttatcttg acacaactat tcctctatgg agattgtata     960

ctaaaactat tccacaatga ggggttctac ataataaaag aggtagaggg atttattatg    1020

tctctaattt taaatataac agaagaagat caattcagaa aacggtttta taatagtatg    1080

ctcaacaaca tcacagatgc tgctaataaa gctcagaaaa gtctgctatc aagagtatgt    1140

catacattat tagataagac agtatccgat aatataataa atggcagatg gataattcta    1200

ttaagtaagt tccttaaatt aattaagctt gcaggtgaca ataaccttaa caatctgagt    1260

gaattatatt ttttgttcag aatatttgga cacccaatgg tagatgaaag acaagccatg    1320

gatgctgtta aagttaattg caacgagacc aaattttact tgttaagcag tttgagtatg    1380

ttaagaggtg cctttatata tagaattata aaaggatttg taaataatta caacagatgg    1440

cctactttaa ggaatgctat tgttttaccc ttaagatggt taacttacta taaactaaac    1500
```

```
acttatcctt ccttgttgga acttacagaa agagatttga ttgttttatc aggactacgt   1560
ttctatcgtg agtttcggtt gcctaaaaaa gtggatcttg aaatgatcat aaatgataag   1620
gctatatcac ctcctaaaaa tttgatatgg actagtttcc ctagaaatta tatgccgtca   1680
cacatacaaa attatataga acatgaaaaa ttaaaatttt ccgagagtga taaatcaaga   1740
agagtattag agtactattt aagagataac aaattcaatg aatgtgattt atacaactgt   1800
gtagttaatc aaagttatct taacaaccct aatcatgtgg tatctttgac aggcaaagaa   1860
agagaactca gtgtaggtag aatgtttgca atgcaaccag gaatgttcag acaagttcaa   1920
atattagcag agaaaatgat agctgaaaac attttacaat tctttcctga aagtcttaca   1980
agatatggtg atctagaact acagaaaata ttagaattga aagcaggaat aagtaacaaa   2040
tcaaatcgtt acaatgataa ttacaacaat tacattagta agtgctctat catcacagat   2100
ctcagcaaat tcaatcaagc atttcgatat gaaacatcat gtatttgtag tgatgtactg   2160
gatgaactgc atggtgtaca atctctattt tcctggttac atttaactat tcctcatgtc   2220
acaataatat gcacatatag gcatgcaccc ccctatataa gagatcatat tgtagatctt   2280
aacaatgtag atgaacaaag tggattatat agatatcata tgggtggtat cgaagggtgg   2340
tgtcaaaaac tatggaccat agaagctata tcactattgg atctaatatc tctcaaaggg   2400
aaattctcaa ttactgcttt aattaatggt gacaatcaat caatagatat aagtaaacca   2460
gtcagactca tggaaggtca aactcatgct caagcagatt atttgctagc attaaatagt   2520
cttaaattac tgtataaaga gtatgcaggc ataggccaca aattaaaagg aactgagact   2580
tatatatcaa gagatatgca atttatgagt aaaacaattc aacataacgg tgtatattac   2640
ccagctagta taaagaaagt cctaagagtg ggaccgtgga taaacactat acttgatgat   2700
ttcaaagtga gtctagaatc tataggtagt ttgacacaag aattagaata tagaggagaa   2760
agtctattat gcagtttaat atttagaaat gtatggttat ataatcaaat tgctttacaa   2820
ctaaaaaatc atgcattatg taacaataaa ttatatttgg acatattaaa ggttctgaaa   2880
cacttaaaaa ccttttttaa tcttgataat attgatacag cattaacatt gtatatgaat   2940
ttgcccatgt tatttggtgg tggtgatccc aacttgttat atcgaagttt ctatagaaga   3000
actcctgatt tcctcacaga ggctatagtt cactctgtgt tcatacttag ttattataca   3060
aaccatgatt taaaagataa acttcaagat ctgtcagatg atagattgaa taagttctta   3120
acatgcataa tcacatttga caaaaaccct aatgctgaat tcgtaacatt gatgagagat   3180
cctcaagctt tagggtctga gagacaagct aaaattacta gcgaaatcaa tagactggca   3240
gttacagagg ttttgagcac agctccaaac aaaatattct ccaaaagtgc acaacactat   3300
accactacag agatagatct aaatgatatt atgcaaaata tagaacctac atatcctcac   3360
gggctaagag ttgtttatga aagtttaccc ttttataaag cagagaaaat agtaaatctt   3420
atatccggta caaaatctat aactaacata ctggaaaaga cttctgccat agacttaaca   3480
gatattgata gagccactga gatgatgagg aaaaacataa ctttgcttat aaggatattt   3540
ccattagatt gtaacagaga taaaagggaa atattgagta tggaaaacct aagtattact   3600
gaattaagca aatatgttag ggaaagatct tggtctttat ccaatatagt tggtgttaca   3660
tcacctagta tcatgtatac aatggacatc aaatatacaa caagcactat agctagtggc   3720
ataatcatag agaaatataa tgttaacagt ttaacacgtg gtgagagagg acccactaaa   3780
ccatgggttg gttcatctac acaagagaaa aaaacaatgc cagtttataa tagacaagtt   3840
ttaaccaaaa aacagagaga tcaaatagat ctattagcaa aattggattg ggtgtatgca   3900
```

```
tctatagata acaaggatga attcatggaa gaacttagca taggaactct tgggttaaca   3960
tatgagaaag ccaaaaaatt atttccacaa tatttaagtg ttaactattt gcatcgcctt   4020
acagtcagta gtagaccatg tgaattccct gcatcaatac cagcttatag aactacaaat   4080
tatcactttg atactagccc tattaatcgc atattaacag aaaagtatgg tgatgaagat   4140
attgatatag tattccaaaa ctgtataagc tttggcctta gcttaatgtc agtagtagaa   4200
caatttacta atgtatgtcc taacagaatt attcttatac ctaagcttaa tgagatacat   4260
ttaatgaaac ctcccatatt cacaggtgat gttgatattc acaagttaaa acaagtgata   4320
caaaaacagc atatgttttt accagacaaa ataagtttga ctcaatatgt ggaattattc   4380
ttaagtaata aaacactcaa atctggatct catgttaatt ctaatttaat attggcgcat   4440
aagatatctg actattttca taatacttac attttaagta ctaatttagc tggacattgg   4500
attctgatta tacaacttat gaaagattct aagggtattt ttgaaaaaga ttggggagag   4560
ggatatataa ctgatcatat gttcattaat ttgaaagttt tcttcaatgc ttataagacc   4620
tatctcttgt gttttcataa aggttacggc agagcaaagc tggagtgtga tatgaatact   4680
tcagatctcc tatgtgtatt ggaattaata gacagtagtt attggaagtc tatgtctaag   4740
gtatttttag aacaaaaagt tatcaaatac attcttagcc aggatgcaag tttacataga   4800
gtaaaaggat gtcatagctt caaactatgg tttcttaaac gtcttaatgt agcagaattc   4860
acagtttgcc cttgggttgt taacatagat tatcatccaa cacatatgaa agcaatatta   4920
acttatatag atcttgttag aatgggattg ataaatatag ataaaatata cattaaaaat   4980
aaacacaaat tcaatgatga attttatact tctaatctct tttacattaa ttataacttc   5040
tcagataata ctcatctatt aactaaacat ataaggattg ctaattctga attagaaaat   5100
aattacaaca aattatatca tcctacacca gaaaccctag aaaatatact aaccaatccg   5160
gttaaatgta atgacaaaaa gacactgaat gactattgta taggtaaaaa tgttgactca   5220
ataatgttac cattgttatc taataagaag cttattaaat cgtctacaat gattagaacc   5280
aattacagca aacaagattt gtataattta tttcctacgg ttgtgattga taaaattata   5340
gatcattcag gtaatacagc caaatctaac caactttaca ctactacttc tcatcaaata   5400
cctttagtgc acaatagcac atcactttat tgcatgcttc cttggcatca tattaataga   5460
ttcaattttg tatttagttc tacaggttgt aaaattagta tagagtatat tttaaaagac   5520
cttaaaatta aagatcctaa ttgtatagca ttcataggtg aaggagcagg gaatttatta   5580
ttgcgtacag tagtggaact tcatcctgat ataagatata tttacagaag tctgaaagat   5640
tgcaatgatc atagtttacc tattgagttt ttaaggctgt acaatggaca tatcaacatt   5700
gattatggtg aaaatttgac cattcctgct acagatgcaa ccaacaacat tcattggtct   5760
tatttacata taaagtttgc tgaacctatc agtctttttg tctgtgatgc tgaattgcct   5820
gtaacagtca actggagtaa aattataata gagtggagca agcatgtaag aaaatgcaag   5880
tactgttcct cagttaataa atgtacgtta atagtaaaat atcatgctca agatgatatc   5940
gatttcaaat tagacaatat aactatatta aaaacttatg tatgcttagg cagtaagtta   6000
aaggggtctg aagtttactt agtccttaca ataggtcctg caaatgtgtt cccagtattt   6060
aatgtagtac aaaatgctaa attgatacta tcaagaacca aaaatttcat catgcctaag   6120
aaggctgata aagagtctat tgatgcaaat attaaaagtt tgataccctt tctttgttac   6180
cctataacaa aaaaaggaat taatactgca ttgtcaaaac taaagagtgt tgttagtgga   6240
```

gatatactat catattctat agcaggacgt aatgaagttt tcagcaataa acttataaat 6300
cataagcata tgaacatctt aaaatggttc aatcatgttt taaatttcag atcaacagaa 6360
ctaaactata atcatttata tatggtagaa tctacatatc cttatctaag tgaattgtta 6420
aacagcttga caactaatga acttaaaaaa ctgattaaaa tcacaggtag tttgttatac 6480
aactttcata atgaataa 6498

<210> SEQ ID NO 20
<211> LENGTH: 2165
<212> TYPE: PRT
<213> ORGANISM: Respiratory syncytial virus, S2

<400> SEQUENCE: 20

Met Asp Pro Ile Ile Asn Gly Asn Ser Ala Asn Val Tyr Leu Thr Asp
1 5 10 15

Ser Tyr Leu Lys Gly Val Ile Ser Phe Ser Glu Cys Asn Ala Leu Gly
20 25 30

Ser Tyr Ile Phe Asn Gly Pro Tyr Leu Lys Asn Asp Tyr Thr Asn Leu
35 40 45

Ile Ser Arg Gln Asn Pro Leu Ile Glu His Ile Asn Leu Lys Lys Leu
50 55 60

Asn Ile Thr Gln Ser Leu Ile Ser Lys Tyr His Lys Gly Glu Ile Lys
65 70 75 80

Ile Glu Glu Pro Thr Tyr Phe Gln Ser Leu Leu Met Thr Tyr Lys Ser
85 90 95

Met Thr Ser Leu Glu Gln Ile Thr Thr Thr Asn Leu Leu Lys Lys Ile
100 105 110

Ile Arg Arg Ala Ile Glu Ile Ser Asp Val Lys Val Tyr Ala Ile Leu
115 120 125

Asn Lys Leu Gly Leu Lys Glu Lys Asp Lys Ile Lys Ser Asn Asn Gly
130 135 140

Gln Asp Glu Asp Asn Ser Val Ile Thr Thr Ile Ile Lys Asp Asp Ile
145 150 155 160

Leu Leu Ala Val Lys Asp Asn Gln Ser His Leu Lys Ala Val Lys Asn
165 170 175

His Ser Thr Lys Gln Lys Asp Thr Ile Lys Thr Thr Leu Leu Lys Lys
180 185 190

Leu Met Cys Ser Met Gln His Pro Pro Ser Trp Leu Ile His Trp Phe
195 200 205

Asn Leu Tyr Thr Lys Leu Asn Asn Ile Leu Thr Gln Tyr Arg Ser Ser
210 215 220

Glu Val Lys Asn His Gly Phe Ile Leu Ile Asp Asn His Thr Leu Asn
225 230 235 240

Gly Phe Gln Phe Ile Leu Asn Gln Tyr Gly Cys Ile Val Tyr His Lys
245 250 255

Glu Leu Lys Arg Ile Thr Val Thr Thr Tyr Asn Gln Phe Leu Thr Trp
260 265 270

Lys Asp Ile Ser Leu Ser Arg Leu Asn Val Cys Leu Ile Thr Trp Ile
275 280 285

Ser Asn Cys Leu Asn Thr Leu Asn Lys Ser Leu Gly Leu Arg Cys Gly
290 295 300

Phe Asn Asn Val Ile Leu Thr Gln Leu Phe Leu Tyr Gly Asp Cys Ile
305 310 315 320

Leu Lys Leu Phe His Asn Glu Gly Phe Tyr Ile Ile Lys Glu Val Glu

-continued

```
                325                 330                 335

Gly Phe Ile Met Ser Leu Ile Leu Asn Ile Thr Glu Glu Asp Gln Phe
            340                 345                 350

Arg Lys Arg Phe Tyr Asn Ser Met Leu Asn Asn Ile Thr Asp Ala Ala
        355                 360                 365

Asn Lys Ala Gln Lys Ser Leu Leu Ser Arg Val Cys His Thr Leu Leu
    370                 375                 380

Asp Lys Thr Val Ser Asp Asn Ile Ile Asn Gly Arg Trp Ile Ile Leu
385                 390                 395                 400

Leu Ser Lys Phe Leu Lys Leu Ile Lys Leu Ala Gly Asp Asn Asn Leu
                405                 410                 415

Asn Asn Leu Ser Glu Leu Tyr Phe Leu Phe Arg Ile Phe Gly His Pro
            420                 425                 430

Met Val Asp Glu Arg Gln Ala Met Asp Ala Val Lys Val Asn Cys Asn
        435                 440                 445

Glu Thr Lys Phe Tyr Leu Leu Ser Ser Leu Ser Met Leu Arg Gly Ala
    450                 455                 460

Phe Ile Tyr Arg Ile Ile Lys Gly Phe Val Asn Asn Tyr Asn Arg Trp
465                 470                 475                 480

Pro Thr Leu Arg Asn Ala Ile Val Leu Pro Leu Arg Trp Leu Thr Tyr
                485                 490                 495

Tyr Lys Leu Asn Thr Tyr Pro Ser Leu Leu Glu Leu Thr Glu Arg Asp
            500                 505                 510

Leu Ile Val Leu Ser Gly Leu Arg Phe Tyr Arg Glu Phe Arg Leu Pro
        515                 520                 525

Lys Lys Val Asp Leu Glu Met Ile Ile Asn Asp Lys Ala Ile Ser Pro
    530                 535                 540

Pro Lys Asn Leu Ile Trp Thr Ser Phe Pro Arg Asn Tyr Met Pro Ser
545                 550                 555                 560

His Ile Gln Asn Tyr Ile Glu His Glu Lys Leu Lys Phe Ser Glu Ser
                565                 570                 575

Asp Lys Ser Arg Arg Val Leu Glu Tyr Tyr Leu Arg Asp Asn Lys Phe
            580                 585                 590

Asn Glu Cys Asp Leu Tyr Asn Cys Val Val Asn Gln Ser Tyr Leu Asn
        595                 600                 605

Asn Pro Asn His Val Val Ser Leu Thr Gly Lys Glu Arg Glu Leu Ser
    610                 615                 620

Val Gly Arg Met Phe Ala Met Gln Pro Gly Met Phe Arg Gln Val Gln
625                 630                 635                 640

Ile Leu Ala Glu Lys Met Ile Ala Glu Asn Ile Leu Gln Phe Phe Pro
                645                 650                 655

Glu Ser Leu Thr Arg Tyr Gly Asp Leu Glu Leu Gln Lys Ile Leu Glu
            660                 665                 670

Leu Lys Ala Gly Ile Ser Asn Lys Ser Asn Arg Tyr Asn Asp Asn Tyr
        675                 680                 685

Asn Asn Tyr Ile Ser Lys Cys Ser Ile Ile Thr Asp Leu Ser Lys Phe
    690                 695                 700

Asn Gln Ala Phe Arg Tyr Glu Thr Ser Cys Ile Cys Ser Asp Val Leu
705                 710                 715                 720

Asp Glu Leu His Gly Val Gln Ser Leu Phe Ser Trp Leu His Leu Thr
                725                 730                 735

Ile Pro His Val Thr Ile Ile Cys Thr Tyr Arg His Ala Pro Pro Tyr
            740                 745                 750
```

```
Ile Arg Asp His Ile Val Asp Leu Asn Asn Val Asp Glu Gln Ser Gly
        755                 760                 765

Leu Tyr Arg Tyr His Met Gly Gly Ile Glu Gly Trp Cys Gln Lys Leu
    770                 775                 780

Trp Thr Ile Glu Ala Ile Ser Leu Leu Asp Leu Ile Ser Leu Lys Gly
785                 790                 795                 800

Lys Phe Ser Ile Thr Ala Leu Ile Asn Gly Asp Asn Gln Ser Ile Asp
                805                 810                 815

Ile Ser Lys Pro Val Arg Leu Met Glu Gly Gln Thr His Ala Gln Ala
            820                 825                 830

Asp Tyr Leu Leu Ala Leu Asn Ser Leu Lys Leu Leu Tyr Lys Glu Tyr
        835                 840                 845

Ala Gly Ile Gly His Lys Leu Lys Gly Thr Glu Thr Tyr Ile Ser Arg
    850                 855                 860

Asp Met Gln Phe Met Ser Lys Thr Ile Gln His Asn Gly Val Tyr Tyr
865                 870                 875                 880

Pro Ala Ser Ile Lys Lys Val Leu Arg Val Gly Pro Trp Ile Asn Thr
                885                 890                 895

Ile Leu Asp Asp Phe Lys Val Ser Leu Glu Ser Ile Gly Ser Leu Thr
            900                 905                 910

Gln Glu Leu Glu Tyr Arg Gly Glu Ser Leu Leu Cys Ser Leu Ile Phe
        915                 920                 925

Arg Asn Val Trp Leu Tyr Asn Gln Ile Ala Leu Gln Leu Lys Asn His
    930                 935                 940

Ala Leu Cys Asn Asn Lys Leu Tyr Leu Asp Ile Leu Lys Val Leu Lys
945                 950                 955                 960

His Leu Lys Thr Phe Phe Asn Leu Asp Asn Ile Asp Thr Ala Leu Thr
                965                 970                 975

Leu Tyr Met Asn Leu Pro Met Leu Phe Gly Gly Gly Asp Pro Asn Leu
            980                 985                 990

Leu Tyr Arg Ser Phe Tyr Arg Arg Thr Pro Asp Phe Leu Thr Glu Ala
        995                 1000                1005

Ile Val His Ser Val Phe Ile Leu Ser Tyr Tyr Thr Asn His Asp Leu
    1010                1015                1020

Lys Asp Lys Leu Gln Asp Leu Ser Asp Asp Arg Leu Asn Lys Phe Leu
1025                1030                1035                1040

Thr Cys Ile Ile Thr Phe Asp Lys Asn Pro Asn Ala Glu Phe Val Thr
                1045                1050                1055

Leu Met Arg Asp Pro Gln Ala Leu Gly Ser Glu Arg Gln Ala Lys Ile
            1060                1065                1070

Thr Ser Glu Ile Asn Arg Leu Ala Val Thr Glu Val Leu Ser Thr Ala
        1075                1080                1085

Pro Asn Lys Ile Phe Ser Lys Ser Ala Gln His Tyr Thr Thr Thr Glu
    1090                1095                1100

Ile Asp Leu Asn Asp Ile Met Gln Asn Ile Glu Pro Thr Tyr Pro His
1105                1110                1115                1120

Gly Leu Arg Val Val Tyr Glu Ser Leu Pro Phe Tyr Lys Ala Glu Lys
                1125                1130                1135

Ile Val Asn Leu Ile Ser Gly Thr Lys Ser Ile Thr Asn Ile Leu Glu
            1140                1145                1150

Lys Thr Ser Ala Ile Asp Leu Thr Asp Ile Asp Arg Ala Thr Glu Met
        1155                1160                1165
```

-continued

```
Met Arg Lys Asn Ile Thr Leu Leu Ile Arg Ile Phe Pro Leu Asp Cys
    1170                1175                1180

Asn Arg Asp Lys Arg Glu Ile Leu Ser Met Glu Asn Leu Ser Ile Thr
1185                1190                1195                1200

Glu Leu Ser Lys Tyr Val Arg Glu Arg Ser Trp Ser Leu Ser Asn Ile
                1205                1210                1215

Val Gly Val Thr Ser Pro Ser Ile Met Tyr Thr Met Asp Ile Lys Tyr
            1220                1225                1230

Thr Thr Ser Thr Ile Ala Ser Gly Ile Ile Ile Glu Lys Tyr Asn Val
        1235                1240                1245

Asn Ser Leu Thr Arg Gly Glu Arg Gly Pro Thr Lys Pro Trp Val Gly
    1250                1255                1260

Ser Ser Thr Gln Glu Lys Lys Thr Met Pro Val Tyr Asn Arg Gln Val
1265                1270                1275                1280

Leu Thr Lys Lys Gln Arg Asp Gln Ile Asp Leu Leu Ala Lys Leu Asp
                1285                1290                1295

Trp Val Tyr Ala Ser Ile Asp Asn Lys Asp Glu Phe Met Glu Glu Leu
            1300                1305                1310

Ser Ile Gly Thr Leu Gly Leu Thr Tyr Glu Lys Ala Lys Lys Leu Phe
        1315                1320                1325

Pro Gln Tyr Leu Ser Val Asn Tyr Leu His Arg Leu Thr Val Ser Ser
    1330                1335                1340

Arg Pro Cys Glu Phe Pro Ala Ser Ile Pro Ala Tyr Arg Thr Thr Asn
1345                1350                1355                1360

Tyr His Phe Asp Thr Ser Pro Ile Asn Arg Ile Leu Thr Glu Lys Tyr
                1365                1370                1375

Gly Asp Glu Asp Ile Asp Ile Val Phe Gln Asn Cys Ile Ser Phe Gly
            1380                1385                1390

Leu Ser Leu Met Ser Val Val Glu Gln Phe Thr Asn Val Cys Pro Asn
        1395                1400                1405

Arg Ile Ile Leu Ile Pro Lys Leu Asn Glu Ile His Leu Met Lys Pro
    1410                1415                1420

Pro Ile Phe Thr Gly Asp Val Asp Ile His Lys Leu Lys Gln Val Ile
1425                1430                1435                1440

Gln Lys Gln His Met Phe Leu Pro Asp Lys Ile Ser Leu Thr Gln Tyr
                1445                1450                1455

Val Glu Leu Phe Leu Ser Asn Lys Thr Leu Lys Ser Gly Ser His Val
            1460                1465                1470

Asn Ser Asn Leu Ile Leu Ala His Lys Ile Ser Asp Tyr Phe His Asn
        1475                1480                1485

Thr Tyr Ile Leu Ser Thr Asn Leu Ala Gly His Trp Ile Leu Ile Ile
    1490                1495                1500

Gln Leu Met Lys Asp Ser Lys Gly Ile Phe Glu Lys Asp Trp Gly Glu
1505                1510                1515                1520

Gly Tyr Ile Thr Asp His Met Phe Ile Asn Leu Lys Val Phe Phe Asn
                1525                1530                1535

Ala Tyr Lys Thr Tyr Leu Leu Cys Phe His Lys Gly Tyr Gly Arg Ala
            1540                1545                1550

Lys Leu Glu Cys Asp Met Asn Thr Ser Asp Leu Leu Cys Val Leu Glu
        1555                1560                1565

Leu Ile Asp Ser Ser Tyr Trp Lys Ser Met Ser Lys Val Phe Leu Glu
    1570                1575                1580

Gln Lys Val Ile Lys Tyr Ile Leu Ser Gln Asp Ala Ser Leu His Arg
```

```
1585                1590                1595                1600

Val Lys Gly Cys His Ser Phe Lys Leu Trp Phe Leu Lys Arg Leu Asn
                1605                1610                1615

Val Ala Glu Phe Thr Val Cys Pro Trp Val Val Asn Ile Asp Tyr His
            1620                1625                1630

Pro Thr His Met Lys Ala Ile Leu Thr Tyr Ile Asp Leu Val Arg Met
        1635                1640                1645

Gly Leu Ile Asn Ile Asp Lys Ile Tyr Ile Lys Asn Lys His Lys Phe
    1650                1655                1660

Asn Asp Glu Phe Tyr Thr Ser Asn Leu Phe Tyr Ile Asn Tyr Asn Phe
1665                1670                1675                1680

Ser Asp Asn Thr His Leu Leu Thr Lys His Ile Arg Ile Ala Asn Ser
                1685                1690                1695

Glu Leu Glu Asn Asn Tyr Asn Lys Leu Tyr His Pro Thr Pro Glu Thr
            1700                1705                1710

Leu Glu Asn Ile Leu Thr Asn Pro Val Lys Cys Asn Asp Lys Lys Thr
        1715                1720                1725

Leu Asn Asp Tyr Cys Ile Gly Lys Asn Val Asp Ser Ile Met Leu Pro
    1730                1735                1740

Leu Leu Ser Asn Lys Lys Leu Ile Lys Ser Ser Thr Met Ile Arg Thr
1745                1750                1755                1760

Asn Tyr Ser Lys Gln Asp Leu Tyr Asn Leu Phe Pro Thr Val Val Ile
                1765                1770                1775

Asp Lys Ile Ile Asp His Ser Gly Asn Thr Ala Lys Ser Asn Gln Leu
            1780                1785                1790

Tyr Thr Thr Thr Ser His Gln Ile Pro Leu Val His Asn Ser Thr Ser
        1795                1800                1805

Leu Tyr Cys Met Leu Pro Trp His His Ile Asn Arg Phe Asn Phe Val
    1810                1815                1820

Phe Ser Ser Thr Gly Cys Lys Ile Ser Ile Glu Tyr Ile Leu Lys Asp
1825                1830                1835                1840

Leu Lys Ile Lys Asp Pro Asn Cys Ile Ala Phe Ile Gly Glu Gly Ala
                1845                1850                1855

Gly Asn Leu Leu Leu Arg Thr Val Val Glu Leu His Pro Asp Ile Arg
            1860                1865                1870

Tyr Ile Tyr Arg Ser Leu Lys Asp Cys Asn Asp His Ser Leu Pro Ile
        1875                1880                1885

Glu Phe Leu Arg Leu Tyr Asn Gly His Ile Asn Ile Asp Tyr Gly Glu
    1890                1895                1900

Asn Leu Thr Ile Pro Ala Thr Asp Ala Thr Asn Asn Ile His Trp Ser
1905                1910                1915                1920

Tyr Leu His Ile Lys Phe Ala Glu Pro Ile Ser Leu Phe Val Cys Asp
                1925                1930                1935

Ala Glu Leu Pro Val Thr Val Asn Trp Ser Lys Ile Ile Ile Glu Trp
            1940                1945                1950

Ser Lys His Val Arg Lys Cys Lys Tyr Cys Ser Ser Val Asn Lys Cys
        1955                1960                1965

Thr Leu Ile Val Lys Tyr His Ala Gln Asp Asp Ile Asp Phe Lys Leu
    1970                1975                1980

Asp Asn Ile Thr Ile Leu Lys Thr Tyr Val Cys Leu Gly Ser Lys Leu
1985                1990                1995                2000

Lys Gly Ser Glu Val Tyr Leu Val Leu Thr Ile Gly Pro Ala Asn Val
                2005                2010                2015
```

```
Phe Pro Val Phe Asn Val Val Gln Asn Ala Lys Leu Ile Leu Ser Arg
            2020                2025                2030

Thr Lys Asn Phe Ile Met Pro Lys Lys Ala Asp Lys Glu Ser Ile Asp
        2035                2040                2045

Ala Asn Ile Lys Ser Leu Ile Pro Phe Leu Cys Tyr Pro Ile Thr Lys
    2050                2055                2060

Lys Gly Ile Asn Thr Ala Leu Ser Lys Leu Lys Ser Val Val Ser Gly
2065                2070                2075                2080

Asp Ile Leu Ser Tyr Ser Ile Ala Gly Arg Asn Glu Val Phe Ser Asn
                2085                2090                2095

Lys Leu Ile Asn His Lys His Met Asn Ile Leu Lys Trp Phe Asn His
            2100                2105                2110

Val Leu Asn Phe Arg Ser Thr Glu Leu Asn Tyr Asn His Leu Tyr Met
        2115                2120                2125

Val Glu Ser Thr Tyr Pro Tyr Leu Ser Glu Leu Leu Asn Ser Leu Thr
    2130                2135                2140

Thr Asn Glu Leu Lys Lys Leu Ile Lys Ile Thr Gly Ser Leu Leu Tyr
2145                2150                2155                2160

Asn Phe His Asn Glu
                2165
```

<210> SEQ ID NO 21
<211> LENGTH: 6505
<212> TYPE: DNA
<213> ORGANISM: Respiratory syncytial virus, Merck strain 287

<400> SEQUENCE: 21

```
atggatccca ttattaatgg aaattctgct aatgtttatc taaccgatag ttatttaaaa      60

ggtgttatct ctttctcaga gtgtaatgct ttaggaagct acatattcaa tggtccttat     120

ctcaaaaatg attataccaa cttaattagt agacaaaatc cattaataga acacatgaat     180

ctaaagaaac taaatataac acagtcctta atatctaagt atcataaagg tgaaataaaa     240

ttagaagaac cgacttattt tcagtcatta cttatgacat acaagagtat gacctcgtca     300

gaacagattg ctaccactaa tttacttaaa aagataataa gaagagctat agaaataagt     360

gatgtcaaag tctatgctat attgaataaa ctagggctta aagaaaagga caagattaaa     420

tccaacaatg gacaagatga agacaattca gttattacga ccataatcaa agatgatata     480

ctttcagctg ttaaagataa tcaatctcat cttaaagcag gcaaaaatca ctctacaaaa     540

caaaaagaca caatcaaaac aacactcctg aagaaattga tgtgttcaat gcaacatcct     600

ccatcatggt taatacattg gtttaactta tacacaaaat taaacaacat attaacacag     660

tatcgatcaa atgaggtaaa aaaccatggg tttacattga tagataatca aactcttagt     720

ggatttcaat ttattttgaa ccaatatggt tgtatagttt ataataagga actcaaaaga     780

attactgtga caacctataa tcaattcttg acatggaaag atattagcct tagtagatta     840

aatgtttgtt taattacatg gattagtaac tgcttgaaca cattaaataa aagcttaggc     900

ttaagatgcg gattcaataa tgttatctta acacaactat tcctttatgg agattgtata     960

ctaaaactat ttcacaatga ggggttctac ataataaaag aggtagaggg atttattatg    1020

tctctaattt taaatataac agaagaagat caattcagaa aacgatttta taatagtatg    1080

ctcaacaaca tcacagatgc tgctaataaa gctcagaaaa atctgctatc aagagtatgt    1140

catacattat tagataagac agtatccgat aatataataa atggcagatg gataattcta    1200
```

-continued

```
ttaagtaagt tccttaaatt aattaagctt gcgggtgaca ataaccttaa caatctgagt   1260
gaactatatt ttttgttcag aatatttgga cacccaatgg tagatgaaag acaagccatg   1320
gatgctgtta aaattaattg caatgagacc aaattttact tgctaagcag tctaagtatg   1380
ttaagaggtg cctttatata tagaattata aaagggtttg taaataatta caacagatgg   1440
cctactttaa gaaatgctat tgttttaccc ttaagatggt taacttacta taaactaaac   1500
acttatcctt ctttgttgga acttacagaa agagatttga ttgtgttatc aggactacgt   1560
ttctatcgtg agtttcggtt gcctaaaaaa gtggatcttg aaatgattat aaatgataaa   1620
gctatatcac ctcctaaaaa tttgatatgg actagtttcc ctagaaatta catgccatca   1680
cacatacaaa actatataga acatgaaaaa ttaaaatttt ccgagagtga taaatcaaga   1740
agagtattag agtattattt aagagataac aagttcaatg aatgtgattt atacaactgt   1800
gtagttgatc aaagttatct aaacaaccct aatcatgtgg tatcattgac aggcaaagaa   1860
agagaactca gtgtaggtag aatgtttgca atgcaaccgg gaatgttcag acaggttcaa   1920
atattagcag agaaaatgat agctgaaaac attttacaat tctttcctga aagtcttaca   1980
agatatggtg atctagaact acaaaaaata ttagaattga aagcaggaat aagtaacaaa   2040
tcaaatcgct acaatgacaa ttacaacaat tacattagta agtgctctat catcacagat   2100
ctcagcaaat tcaatcaagc atttcgatat gaaacgtcat gtatttgtag tgatgtgctt   2160
gatgaactgc atggtgtaca atctctattt tcctggttac atttaactat tcctcatgtt   2220
acaataatat gtacatatag gcatgcaccc ccctatatag gagatcatat tgtagatctt   2280
aacaatgtag atgaacaaag tggattatat agatatcaca tgggtggcat cgaagggtgg   2340
tgtcaaaaac tatggaccat agaagctata tcactattgg atctaatatc tctcaaaggg   2400
aaattctcaa ttactgcttt aattaatggt gacaatcaat caatagatat aagcaaacca   2460
attagactca tggaaggtca aactcatgct caagcagatt atttgctagc attaaatagc   2520
cttaaattac tgtataaaga gtatgcaggc ataggccaca aattaaaagg aactgagact   2580
tatatatcac gagatatgca atttatgagt aaaacaattc aacataacgg tgtgtattac   2640
ccagctagta taaagaaagt cctaagagtg ggaccgtgga taaacactat acttgatgat   2700
ttcaaagtga gtttagaatc tataggtagt ttgacacaag aattagaata tagaggtgaa   2760
agtctattat gcagtttaat atttagaaat gtatggttat ataatcagat tgctctacaa   2820
ttaaaaaatc atgcattatg taacaataaa ctatatttgg acatattaaa ggttctgaaa   2880
cacttaaaaa cctttttttaa tcttgataat attgatacag cattaacatt gtatatgaat   2940
ttacctatgt tatttggtgg tggtgatccc aacttgttat atcgaagttt ctatagaaga   3000
acccccgact tcctcacaga ggctatagtt cactctgtgt tcatacttag ttattataca   3060
aaccatgact taaaagataa acttcaagat ctgtcagatg atagattgaa taagttctta   3120
acatgcataa tcacgtttga caaaaaccct aacgctgaat tcgtaacatt gatgagagat   3180
cctcaagctt tagggtctga gagacaagct aaaattacta gcgaaatcaa taggctggca   3240
gttacagagg ttttgagtac agctccaaac aaaatattct ccaaaagtgc acaacattat   3300
accactacag agatagatct aaatgatatt atgcaaaata tagaacctac atatcctcat   3360
gggctaagag ttgtttatga aagtttaccc ttttataaag cagagaaaat agtaaatctt   3420
atatcaggta caaaatctat aactaacata ctggaaaaaa cttctgccat agacttaaca   3480
gatattgata gagccactga gatgatgagg aaaaacataa ctttgcttat aaggatactt   3540
ccattggatt gtaacagaga taaaagagag atattgagta tggaaaacct aagtattact   3600
```

```
gaattaagca aatatgttag ggaaagatct tggtctttat tcaatatagt tggtgttaca   3660
tcacccagta tcatgtatac aatggacatc aaatatacta caagcactat agctagtggc   3720
ataattatag agaaatataa tgttaacagt ttaacacgtg gtgagagagg acccactaaa   3780
ccatgggttg gttcatctac acaagagaaa aaaacaatgc cagtttataa tagacaagtc   3840
ttaaccaaaa aacagagaga tcaaatagat ctattagcaa aattggattg ggtgtatgca   3900
tctatagata acaaggatga attcatggaa gaactcagca taggaaccct tgggttaaca   3960
tatgaaaaag ccaagaaatt atttccacaa tatttaagtg tcaactattt gcatcgactt   4020
acagtcagta gtagaccatg tgaattccct gcatcaatac cagcttatag aacaacaaat   4080
tatcactttg acactagccc tattaatcgc atattaacag aaaagtatgg tgatgaagat   4140
attgacatag tattccaaaa ctgtataagc tttggcctta gcttaatgtc agtagtagaa   4200
caatttacta atgtatgtcc taacagaatt attctcatac ctaagcttaa tgagatacat   4260
ttgatgaaac ctcccatatt cacaggtgat gttgatattc acaagttaaa acaagtgata   4320
caaaaacagc atatgttttt accagacaaa ataagtttga ctcaatatgt agaattattc   4380
ttaagtaata aaacactcaa atctggatct catgttaatt ctaatttaat attggcacat   4440
aaaatatctg actattttca taatacttac attttaagta ctaatttagc tggacattgg   4500
attctgatta tacaacttat gaaagattct aagggtattt ttgaaaaaga ttggggagag   4560
ggatatataa ctgatcatat gtttattaat ttgaaagttt tcttcaatgc ctataagacc   4620
tatctcttgt gttttcataa aggttatggc aaagcaaagc tggagtgtga tatgaacacc   4680
tcagatctcc tatgtgtatt ggaattaata gacagtagtt attggaaatc tatgtctaag   4740
gtatttttag aacaaaaagt tatcaaatac attcttagcc aagatgcaag tttacataga   4800
gtaaaaggat gtcatagctt caaattatgg tttcttaaac gtcttaatgt agcagaattc   4860
acagtttgcc cttgggttgt taacatagat tatcatccaa cacatatgaa agcaatatta   4920
acttatatag atcttgttag aatgggattg ataaatatag atagaataca cattaaaaat   4980
aaacacaaat tcaatgatga attttatact tctaatctct tctacattaa ttataacttc   5040
tcagataata ctcatctatt aactaaacat ataaggattg ctaattctga attagaaaat   5100
aattacaaca aattatatca tcctacacca gaaaccctag agaatatact agccaatccg   5160
attaaaagta atgacaaaaa gacactgaat gaatattgta taggtaaaaa tgttgactca   5220
ataatgttac cattgttatc taataagaag cttattaaat cgtctgcaat gattagaacc   5280
aattacagca aacaagattt gtataattta ttccctatgg ttgtgattga tagaattata   5340
gatcattcag gcaatacagc caaatccaac caactttaca ctactacttc ccaccaaata   5400
tctttagtgc acaatagcac atcactttac tgcatgcttc cttggcatca tattaataga   5460
ttcaattttg tatttagttc tacaggttgt aaaattagta tagagtatat tttaaaagat   5520
cttaaaatta aagatcccaa ttgtatagca ttcataggtg aaggagcagg gaatttatta   5580
ttgcgtacag tagtggaact tcatcctgac ataagatata tttacagaag tctgaaagat   5640
tgcaatgatc atagtttacc tattgagttt ttaaggctgt acaatggaca tatcaacatt   5700
gattatggtg aaaatttgac cattcctgct acagatgcaa ccaacaacat tcattggtct   5760
tatttacata taaagtttgc tgaacctatc agtctttttg tctgtgatgc tgaattgcct   5820
gtaacagtca attggagtaa aattataata gaatggagca agcatgtaag aaagtgcaag   5880
tactgttcct cagttaataa atgtatgtta atagtaaaat atcatgctca agatgatatt   5940
```

```
gatttcaaat tagacaatat aactatatta aaaacttatg tatgcttagg cagtaagtta   6000

aagggatcgg aggtttactt agtcatcaca ataggtcctg caaatatatt cccagcattt   6060

aatgtagtac aaaatgctaa attgatacta tcaagaacca aaaatttcat catgcctaag   6120

aaagctgata aagagtctat tgatgcaaat attaaaagtt tgatacccct tctttgttac   6180

cctataacaa aaaaaggaat taatactgca ttgtcaaaac taaagagtgt tgttagtgga   6240

gatatactat catattctat agctggacgt aatgaagttt tcagcaataa acttataaat   6300

cataaacata tgaacatctt aaaatggttc aatcatgttt taaatttcag atcaacagaa   6360

ttaaactata accatttata tatggtagaa tctacatatc cttacctaag tgaattgtta   6420

aacagcttga caaccaatga acttaaaaaa ctgattaaaa tcacaggtag tctgttatac   6480

aactttcata atgaataatg aataa                                         6505
```

```
<210> SEQ ID NO 22
<211> LENGTH: 2166
<212> TYPE: PRT
<213> ORGANISM: Respiratory syncytial virus, Merck strain 287

<400> SEQUENCE: 22

Met Asp Pro Ile Ile Asn Gly Asn Ser Ala Asn Val Tyr Leu Thr Asp
 1               5                  10                  15

Ser Tyr Leu Lys Gly Val Ile Ser Phe Ser Glu Cys Asn Ala Leu Gly
            20                  25                  30

Ser Tyr Ile Phe Asn Gly Pro Tyr Leu Lys Asn Asp Tyr Thr Asn Leu
        35                  40                  45

Ile Ser Arg Gln Asn Pro Leu Ile Glu His Met Asn Leu Lys Lys Leu
    50                  55                  60

Asn Ile Thr Gln Ser Leu Ile Ser Lys Tyr His Lys Gly Glu Ile Lys
65                  70                  75                  80

Leu Glu Glu Pro Thr Tyr Phe Gln Ser Leu Leu Met Thr Tyr Lys Ser
                85                  90                  95

Met Thr Ser Ser Glu Gln Ile Ala Thr Thr Asn Leu Leu Lys Lys Ile
            100                 105                 110

Ile Arg Arg Ala Ile Glu Ile Ser Asp Val Lys Val Tyr Ala Ile Leu
        115                 120                 125

Asn Lys Leu Gly Leu Lys Glu Lys Asp Lys Ile Lys Ser Asn Asn Gly
    130                 135                 140

Gln Asp Glu Asp Asn Ser Val Ile Thr Thr Ile Ile Lys Asp Asp Ile
145                 150                 155                 160

Leu Ser Ala Val Lys Asp Asn Gln Ser His Leu Lys Ala Gly Lys Asn
                165                 170                 175

His Ser Thr Lys Gln Lys Asp Thr Ile Lys Thr Thr Leu Leu Lys Lys
            180                 185                 190

Leu Met Cys Ser Met Gln His Pro Pro Ser Trp Leu Ile His Trp Phe
        195                 200                 205

Asn Leu Tyr Thr Lys Leu Asn Asn Ile Leu Thr Gln Tyr Arg Ser Asn
    210                 215                 220

Glu Val Lys Asn His Gly Phe Thr Leu Ile Asp Asn Gln Thr Leu Ser
225                 230                 235                 240

Gly Phe Gln Phe Ile Leu Asn Gln Tyr Gly Cys Ile Val Tyr Asn Lys
                245                 250                 255

Glu Leu Lys Arg Ile Thr Val Thr Thr Tyr Asn Gln Phe Leu Thr Trp
            260                 265                 270
```

```
Lys Asp Ile Ser Leu Ser Arg Leu Asn Val Cys Leu Ile Thr Trp Ile
        275                 280                 285

Ser Asn Cys Leu Asn Thr Leu Asn Lys Ser Leu Gly Leu Arg Cys Gly
    290                 295                 300

Phe Asn Asn Val Ile Leu Thr Gln Leu Phe Leu Tyr Gly Asp Cys Ile
305                 310                 315                 320

Leu Lys Leu Phe His Asn Glu Gly Phe Tyr Ile Ile Lys Glu Val Glu
                325                 330                 335

Gly Phe Ile Met Ser Leu Ile Leu Asn Ile Thr Glu Glu Asp Gln Phe
            340                 345                 350

Arg Lys Arg Phe Tyr Asn Ser Met Leu Asn Asn Ile Thr Asp Ala Ala
        355                 360                 365

Asn Lys Ala Gln Lys Asn Leu Leu Ser Arg Val Cys His Thr Leu Leu
    370                 375                 380

Asp Lys Thr Val Ser Asp Asn Ile Ile Asn Gly Arg Trp Ile Ile Leu
385                 390                 395                 400

Leu Ser Lys Phe Leu Lys Leu Ile Lys Leu Ala Gly Asp Asn Asn Leu
                405                 410                 415

Asn Asn Leu Ser Glu Leu Tyr Phe Leu Phe Arg Ile Phe Gly His Pro
            420                 425                 430

Met Val Asp Glu Arg Gln Ala Met Asp Ala Val Lys Ile Asn Cys Asn
        435                 440                 445

Glu Thr Lys Phe Tyr Leu Leu Ser Ser Leu Ser Met Leu Arg Gly Ala
    450                 455                 460

Phe Ile Tyr Arg Ile Ile Lys Gly Phe Val Asn Asn Tyr Asn Arg Trp
465                 470                 475                 480

Pro Thr Leu Arg Asn Ala Ile Val Leu Pro Leu Arg Trp Leu Thr Tyr
                485                 490                 495

Tyr Lys Leu Asn Thr Tyr Pro Ser Leu Leu Glu Leu Thr Glu Arg Asp
            500                 505                 510

Leu Ile Val Leu Ser Gly Leu Arg Phe Tyr Arg Glu Phe Arg Leu Pro
        515                 520                 525

Lys Lys Val Asp Leu Glu Met Ile Ile Asn Asp Lys Ala Ile Ser Pro
    530                 535                 540

Pro Lys Asn Leu Ile Trp Thr Ser Phe Pro Arg Asn Tyr Met Pro Ser
545                 550                 555                 560

His Ile Gln Asn Tyr Ile Glu His Glu Lys Leu Lys Phe Ser Glu Ser
                565                 570                 575

Asp Lys Ser Arg Arg Val Leu Glu Tyr Tyr Leu Arg Asp Asn Lys Phe
            580                 585                 590

Asn Glu Cys Asp Leu Tyr Asn Cys Val Val Asp Gln Ser Tyr Leu Asn
        595                 600                 605

Asn Pro Asn His Val Val Ser Leu Thr Gly Lys Glu Arg Glu Leu Ser
    610                 615                 620

Val Gly Arg Met Phe Ala Met Gln Pro Gly Met Phe Arg Gln Val Gln
625                 630                 635                 640

Ile Leu Ala Glu Lys Met Ile Ala Glu Asn Ile Leu Gln Phe Phe Pro
                645                 650                 655

Glu Ser Leu Thr Arg Tyr Gly Asp Leu Glu Leu Gln Lys Ile Leu Glu
            660                 665                 670

Leu Lys Ala Gly Ile Ser Asn Lys Ser Asn Arg Tyr Asn Asp Asn Tyr
        675                 680                 685

Asn Asn Tyr Ile Ser Lys Cys Ser Ile Ile Thr Asp Leu Ser Lys Phe
```

```
    690                 695                 700

Asn Gln Ala Phe Arg Tyr Glu Thr Ser Cys Ile Cys Ser Asp Val Leu
705                 710                 715                 720

Asp Glu Leu His Gly Val Gln Ser Leu Phe Ser Trp Leu His Leu Thr
                725                 730                 735

Ile Pro His Val Thr Ile Ile Cys Thr Tyr Arg His Ala Pro Pro Tyr
            740                 745                 750

Ile Gly Asp His Ile Val Asp Leu Asn Asn Val Asp Glu Gln Ser Gly
        755                 760                 765

Leu Tyr Arg Tyr His Met Gly Gly Ile Glu Gly Trp Cys Gln Lys Leu
    770                 775                 780

Trp Thr Ile Glu Ala Ile Ser Leu Leu Asp Leu Ile Ser Leu Lys Gly
785                 790                 795                 800

Lys Phe Ser Ile Thr Ala Leu Ile Asn Gly Asp Asn Gln Ser Ile Asp
                805                 810                 815

Ile Ser Lys Pro Ile Arg Leu Met Glu Gly Gln Thr His Ala Gln Ala
            820                 825                 830

Asp Tyr Leu Leu Ala Leu Asn Ser Leu Lys Leu Leu Tyr Lys Glu Tyr
        835                 840                 845

Ala Gly Ile Gly His Lys Leu Lys Gly Thr Glu Thr Tyr Ile Ser Arg
    850                 855                 860

Asp Met Gln Phe Met Ser Lys Thr Ile Gln His Asn Gly Val Tyr Tyr
865                 870                 875                 880

Pro Ala Ser Ile Lys Lys Val Leu Arg Val Gly Pro Trp Ile Asn Thr
                885                 890                 895

Ile Leu Asp Asp Phe Lys Val Ser Leu Glu Ser Ile Gly Ser Leu Thr
            900                 905                 910

Gln Glu Leu Glu Tyr Arg Gly Glu Ser Leu Leu Cys Ser Leu Ile Phe
        915                 920                 925

Arg Asn Val Trp Leu Tyr Asn Gln Ile Ala Leu Gln Leu Lys Asn His
    930                 935                 940

Ala Leu Cys Asn Asn Lys Leu Tyr Leu Asp Ile Leu Lys Val Leu Lys
945                 950                 955                 960

His Leu Lys Thr Phe Phe Asn Leu Asp Asn Ile Asp Thr Ala Leu Thr
                965                 970                 975

Leu Tyr Met Asn Leu Pro Met Leu Phe Gly Gly Gly Asp Pro Asn Leu
            980                 985                 990

Leu Tyr Arg Ser Phe Tyr Arg Arg Thr Pro Asp Phe Leu Thr Glu Ala
        995                 1000                1005

Ile Val His Ser Val Phe Ile Leu Ser Tyr Tyr Thr Asn His Asp Leu
    1010                1015                1020

Lys Asp Lys Leu Gln Asp Leu Ser Asp Asp Arg Leu Asn Lys Phe Leu
1025                1030                1035                1040

Thr Cys Ile Ile Thr Phe Asp Lys Asn Pro Asn Ala Glu Phe Val Thr
                1045                1050                1055

Leu Met Arg Asp Pro Gln Ala Leu Gly Ser Glu Arg Gln Ala Lys Ile
            1060                1065                1070

Thr Ser Glu Ile Asn Arg Leu Ala Val Thr Glu Val Leu Ser Thr Ala
        1075                1080                1085

Pro Asn Lys Ile Phe Ser Lys Ser Ala Gln His Tyr Thr Thr Thr Glu
    1090                1095                1100

Ile Asp Leu Asn Asp Ile Met Gln Asn Ile Glu Pro Thr Tyr Pro His
1105                1110                1115                1120
```

```
Gly Leu Arg Val Val Tyr Glu Ser Leu Pro Phe Tyr Lys Ala Glu Lys
                1125                1130                1135

Ile Val Asn Leu Ile Ser Gly Thr Lys Ser Ile Thr Asn Ile Leu Glu
            1140                1145                1150

Lys Thr Ser Ala Ile Asp Leu Thr Asp Ile Asp Arg Ala Thr Glu Met
        1155                1160                1165

Met Arg Lys Asn Ile Thr Leu Leu Ile Arg Ile Leu Pro Leu Asp Cys
    1170                1175                1180

Asn Arg Asp Lys Arg Glu Ile Leu Ser Met Glu Asn Leu Ser Ile Thr
1185                1190                1195                1200

Glu Leu Ser Lys Tyr Val Arg Glu Arg Ser Trp Ser Leu Phe Asn Ile
                1205                1210                1215

Val Gly Val Thr Ser Pro Ser Ile Met Tyr Thr Met Asp Ile Lys Tyr
            1220                1225                1230

Thr Thr Ser Thr Ile Ala Ser Gly Ile Ile Ile Glu Lys Tyr Asn Val
        1235                1240                1245

Asn Ser Leu Thr Arg Gly Glu Arg Gly Pro Thr Lys Pro Trp Val Gly
    1250                1255                1260

Ser Ser Thr Gln Glu Lys Lys Thr Met Pro Val Tyr Asn Arg Gln Val
1265                1270                1275                1280

Leu Thr Lys Lys Gln Arg Asp Gln Ile Asp Leu Leu Ala Lys Leu Asp
                1285                1290                1295

Trp Val Tyr Ala Ser Ile Asp Asn Lys Asp Glu Phe Met Glu Glu Leu
            1300                1305                1310

Ser Ile Gly Thr Leu Gly Leu Thr Tyr Glu Lys Ala Lys Lys Leu Phe
        1315                1320                1325

Pro Gln Tyr Leu Ser Val Asn Tyr Leu His Arg Leu Thr Val Ser Ser
    1330                1335                1340

Arg Pro Cys Glu Phe Pro Ala Ser Ile Pro Ala Tyr Arg Thr Thr Asn
1345                1350                1355                1360

Tyr His Phe Asp Thr Ser Pro Ile Asn Arg Ile Leu Thr Glu Lys Tyr
                1365                1370                1375

Gly Asp Glu Asp Ile Asp Ile Val Phe Gln Asn Cys Ile Ser Phe Gly
            1380                1385                1390

Leu Ser Leu Met Ser Val Val Glu Gln Phe Thr Asn Val Cys Pro Asn
        1395                1400                1405

Arg Ile Ile Leu Ile Pro Lys Leu Asn Glu Ile His Leu Met Lys Pro
    1410                1415                1420

Pro Ile Phe Thr Gly Asp Val Asp Ile His Lys Leu Lys Gln Val Ile
1425                1430                1435                1440

Gln Lys Gln His Met Phe Leu Pro Asp Lys Ile Ser Leu Thr Gln Tyr
                1445                1450                1455

Val Glu Leu Phe Leu Ser Asn Lys Thr Leu Lys Ser Gly Ser His Val
            1460                1465                1470

Asn Ser Asn Leu Ile Leu Ala His Lys Ile Ser Asp Tyr Phe His Asn
        1475                1480                1485

Thr Tyr Ile Leu Ser Thr Asn Leu Ala Gly His Trp Ile Leu Ile Ile
    1490                1495                1500

Gln Leu Met Lys Asp Ser Lys Gly Ile Phe Glu Lys Asp Trp Gly Glu
1505                1510                1515                1520

Gly Tyr Ile Thr Asp His Met Phe Ile Asn Leu Lys Val Phe Phe Asn
                1525                1530                1535
```

```
Ala Tyr Lys Thr Tyr Leu Leu Cys Phe His Lys Gly Tyr Gly Lys Ala
            1540                1545                1550

Lys Leu Glu Cys Asp Met Asn Thr Ser Asp Leu Leu Cys Val Leu Glu
        1555                1560                1565

Leu Ile Asp Ser Ser Tyr Trp Lys Ser Met Ser Lys Val Phe Leu Glu
    1570                1575                1580

Gln Lys Val Ile Lys Tyr Ile Leu Ser Gln Asp Ala Ser Leu His Arg
1585                1590                1595                1600

Val Lys Gly Cys His Ser Phe Lys Leu Trp Phe Leu Lys Arg Leu Asn
                1605                1610                1615

Val Ala Glu Phe Thr Val Cys Pro Trp Val Val Asn Ile Asp Tyr His
            1620                1625                1630

Pro Thr His Met Lys Ala Ile Leu Thr Tyr Ile Asp Leu Val Arg Met
        1635                1640                1645

Gly Leu Ile Asn Ile Asp Arg Ile His Ile Lys Asn Lys His Lys Phe
    1650                1655                1660

Asn Asp Glu Phe Tyr Thr Ser Asn Leu Phe Tyr Ile Asn Tyr Asn Phe
1665                1670                1675                1680

Ser Asp Asn Thr His Leu Leu Thr Lys His Ile Arg Ile Ala Asn Ser
                1685                1690                1695

Glu Leu Glu Asn Asn Tyr Asn Lys Leu Tyr His Pro Thr Pro Glu Thr
            1700                1705                1710

Leu Glu Asn Ile Leu Ala Asn Pro Ile Lys Ser Asn Asp Lys Lys Thr
        1715                1720                1725

Leu Asn Glu Tyr Cys Ile Gly Lys Asn Val Asp Ser Ile Met Leu Pro
    1730                1735                1740

Leu Leu Ser Asn Lys Lys Leu Ile Lys Ser Ser Ala Met Ile Arg Thr
1745                1750                1755                1760

Asn Tyr Ser Lys Gln Asp Leu Tyr Asn Leu Phe Pro Met Val Val Ile
                1765                1770                1775

Asp Arg Ile Ile Asp His Ser Gly Asn Thr Ala Lys Ser Asn Gln Leu
            1780                1785                1790

Tyr Thr Thr Thr Ser His Gln Ile Ser Leu Val His Asn Ser Thr Ser
        1795                1800                1805

Leu Tyr Cys Met Leu Pro Trp His His Ile Asn Arg Phe Asn Phe Val
    1810                1815                1820

Phe Ser Ser Thr Gly Cys Lys Ile Ser Ile Glu Tyr Ile Leu Lys Asp
1825                1830                1835                1840

Leu Lys Ile Lys Asp Pro Asn Cys Ile Ala Phe Ile Gly Glu Gly Ala
                1845                1850                1855

Gly Asn Leu Leu Leu Arg Thr Val Val Glu Leu His Pro Asp Ile Arg
            1860                1865                1870

Tyr Ile Tyr Arg Ser Leu Lys Asp Cys Asn Asp His Ser Leu Pro Ile
        1875                1880                1885

Glu Phe Leu Arg Leu Tyr Asn Gly His Ile Asn Ile Asp Tyr Gly Glu
    1890                1895                1900

Asn Leu Thr Ile Pro Ala Thr Asp Ala Thr Asn Asn Ile His Trp Ser
1905                1910                1915                1920

Tyr Leu His Ile Lys Phe Ala Glu Pro Ile Ser Leu Phe Val Cys Asp
                1925                1930                1935

Ala Glu Leu Pro Val Thr Val Asn Trp Ser Lys Ile Ile Ile Glu Trp
            1940                1945                1950

Ser Lys His Val Arg Lys Cys Lys Tyr Cys Ser Ser Val Asn Lys Cys
```

```
        1955                1960                1965

Met Leu Ile Val Lys Tyr His Ala Gln Asp Asp Ile Asp Phe Lys Leu
    1970                1975                1980

Asp Asn Ile Thr Ile Leu Lys Thr Tyr Val Cys Leu Gly Ser Lys Leu
1985                1990                1995                2000

Lys Gly Ser Glu Val Tyr Leu Val Ile Thr Ile Gly Pro Ala Asn Ile
                2005                2010                2015

Phe Pro Ala Phe Asn Val Val Gln Asn Ala Lys Leu Ile Leu Ser Arg
            2020                2025                2030

Thr Lys Asn Phe Ile Met Pro Lys Lys Ala Asp Lys Glu Ser Ile Asp
        2035                2040                2045

Ala Asn Ile Lys Ser Leu Ile Pro Phe Leu Cys Tyr Pro Ile Thr Lys
    2050                2055                2060

Lys Gly Ile Asn Thr Ala Leu Ser Lys Leu Lys Ser Val Val Ser Gly
2065                2070                2075                2080

Asp Ile Leu Ser Tyr Ser Ile Ala Gly Arg Asn Glu Val Phe Ser Asn
                2085                2090                2095

Lys Leu Ile Asn His Lys His Met Asn Ile Leu Lys Trp Phe Asn His
            2100                2105                2110

Val Leu Asn Phe Arg Ser Thr Glu Leu Asn Tyr Asn His Leu Tyr Met
        2115                2120                2125

Val Glu Ser Thr Tyr Pro Tyr Leu Ser Glu Leu Leu Asn Ser Leu Thr
    2130                2135                2140

Thr Asn Glu Leu Lys Lys Leu Ile Lys Ile Thr Gly Ser Leu Leu Tyr
2145                2150                2155                2160

Asn Phe His Asn Glu Ile
                2165


<210> SEQ ID NO 23
<211> LENGTH: 6505
<212> TYPE: DNA
<213> ORGANISM: Respiratory syncytial virus, Merck strain p17
<220> FEATURE:
<221> NAME/KEY: variation
<222> LOCATION: (443)...(443)
<223> OTHER INFORMATION: n = a or c
<221> NAME/KEY: variation
<222> LOCATION: (6162)...(6162)
<223> OTHER INFORMATION: n = g or t

<400> SEQUENCE: 23

atggatccca ttattaatgg aaattctgct aatgtttatc taaccgatag ttatttaaaa     60

ggtgttatct ctttctcaga gtgtaatgct ttaggaagct acatattcaa tggtccttat    120

ctcaaaaatg attataccaa cttaattagt agacaaaatc cattaataga acacatgaat    180

ctaaagaaac taaatataac acagtcctta atatctaagt atcataaagg tgaaataaaa    240

ttagaagaac cgacttattt tcagtcatta cttatgacat acaagagtat gacctcgtca    300

gaacagattg ctaccactaa tttacttaaa aagataataa gaagagctat agaaataagt    360

gatgtcaaag tctatgctat attgaataaa ctagggctta aagaaaagga caagattaaa    420

tccaacaatg gacaagatga agncaattca gttattacga ccataatcaa agatgatata    480

ctttcagctg ttaaagataa tcaatctcat cttaaagcag gcaaaaatca ctctacaaaa    540

caaaaagaca caatcaaaac aacactcctg aagaaattga tgtgttcaat gcaacatcct    600

ccatcatggt taatacattg gtttaactta tacacaaaat taaacaacat attaacacag    660

tatcgatcaa atgaggtaaa aaaccatggg tttacattga tagataatca aactcttagt    720
```

```
ggatttcaat ttattttgaa ccaatatggt tgtatagttt ataataagga actcaaaaga    780
attactgtga caacctataa tcaattcttg acatggaaag atattagcct tagtagatta    840
aatgtttgtt taattacatg gattagtaac tgcttgaaca cattaaataa aagcttaggc    900
ttaagatgcg gattcaataa tgttatctta acacaactat tcctttatgg agattgtata    960
ctaaaactat ttcacaatga ggggttctac ataataaaag aggtagaggg atttattatg   1020
tctctaattt taaatataac agaagaagat caattcagaa aacgatttta taatagtatg   1080
ctcaacaaca tcacagatgc tgctaataaa gctcagaaaa atctgctatc aagagtatgt   1140
catacattat tagataagac agtatccgat aatataataa atggcagatg gataattcta   1200
ttaagtaagt tccttaaatt aattaagctt gcgggtgaca ataaccttaa caatctgagt   1260
gaactatatt ttttgttcag aatatttgga cacccaatgg tagatgaaag acaagccatg   1320
gatgctgtta aaattaattg caatgagacc aaattttact tgctaagcag tctaagtatg   1380
ttaagaggtg cctttatata tagaattata aaagggtttg taaataatta caacagatgg   1440
cctactttaa gaaatgctat tgttttaccc ttaagatggt taacttacta taaactaaac   1500
acttatcctt ctttgttgga acttacagaa agagatttga ttgtgttatc aggactacgt   1560
ttctatcgtg agtttcggtt gcctaaaaaa gtggatcttg aaatgattat aaatgataaa   1620
gctatatcac ctcctaaaaa tttgatatgg actagtttcc ctagaaatta catgccatca   1680
cacatacaaa actatataga acatgaaaaa ttaaaatttt ccgagagtga taaatcaaga   1740
agagtattag agtattattt aagagataac aagttcaatg aatgtgattt atacaactgt   1800
gtagttgatc aaagttatct aaacaaccct aatcatgtgg tatcattgac aggcaaagaa   1860
agagaactca gtgtaggtag aatgtttgca atgcaaccgg gaatgttcag acaggttcaa   1920
atattagcag agaaaatgat agctgaaaac attttacaat tctttcctga aagtcttaca   1980
agatatggtg atctagaact acaaaaaata ttagaattga aagcaggaat aagtaacaaa   2040
tcaaatcgct acaatgacaa ttacaacaat tacattagta agtgctctat catcacagat   2100
ctcagcaaat tcaatcaagc atttcgatat gaaacgtcat gtatttgtag tgatgtgctt   2160
gatgaactgc atggtgtaca atctctattt tcctggttac atttaactat tcctcatgtt   2220
acaataatat gtacatatag gcatgcaccc ccctatatag gagatcatat tgtagatctt   2280
aacaatgtag atgaacaaag tggattatat agatatcaca tgggtggcat cgaagggtgg   2340
tgtcaaaaac tatggaccat agaagctata tcactattgg atctaatatc tctcaaaggg   2400
aaattctcaa ttactgcttt aattaatggt gacaatcaat caatagatat aagcaaacca   2460
attagactca tggaaggtca aactcatgct caagcagatt atttgctagc attaaatagc   2520
cttaaattac tgtataaaga gtatgcaggc ataggccaca aattaaaagg aactgagact   2580
tatatatcac gagatatgca atttatgagt aaaacaattc aacataacgg tgtgtattac   2640
ccagctagta taaagaaagt cctaagagtg ggaccgtgga taaacactat acttgatgat   2700
ttcaaagtga gtttagaatc tataggtagt ttgacacaag aattagaata tagaggtgaa   2760
agtctattat gcagtttaat atttagaaat gtatggttat ataatcagat tgctctacaa   2820
ttaaaaaatc atgcattatg taacaataaa ctatatttgg acatattaaa ggttctgaaa   2880
cacttaaaaa cctttttaa tcttgataat attgatacag cattaacatt gtatatgaat   2940
ttacctatgt tatttggtgg tggtgatccc aacttgttat atcgaagttt ctatagaaga   3000
acccccgact tcctcacaga ggctatagtt cactctgtgt tcatacttag ttattataca   3060
```

```
aaccatgact taaaagataa acttcaagat ctgtcagatg atagattgaa taagttctta   3120
acatgcataa tcacgtttga caaaaaccct aacgctgaat tcgtaacatt gatgagagat   3180
cctcaagctt tagggtctga gagacaagct aaaattacta gcgaaatcaa taggctggca   3240
gttacagagg ttttgagtac agctccaaac aaaatattct ccaaaagtgc acaacattat   3300
accactacag agatagatct aaatgatatt atgcaaaata tagaacctac atatcctcat   3360
gggctaagag ttgtttatga aagtttaccc ttttataaag cagagaaaat agtaaatctt   3420
atatcaggta caaaatctat aactaacata ctggaaaaaa cttctgccat agacttaaca   3480
gatattgata gagccactga gatgatgagg aaaaacataa ctttgcttat aaggatactt   3540
ccattggatt gtaacagaga taaaagagag atattgagta tggaaaacct aagtattact   3600
gaattaagca aatatgttag ggaaagatct tggtctttat tcaatatagt tggtgttaca   3660
tcacccagta tcatgtatac aatggacatc aaatatacta caagcactat agctagtggc   3720
ataattatag agaaatataa tgttaacagt ttaacacgtg gtgagagagg acccactaaa   3780
ccatgggttg gttcatctac acaagagaaa aaaacaatgc cagtttataa tagacaagtc   3840
ttaaccaaaa aacagagaga tcaaatagat ctattagcaa aattggattg ggtgtatgca   3900
tctatagata acaaggatga attcatggaa gaactcagca taggaaccct tgggttaaca   3960
tatgaaaaag ccaagaaatt atttccacaa tatttaagtg tcaactattt gcatcgactt   4020
acagtcagta gtagaccatg tgaattccct gcatcaatac cagcttatag aacaacaaat   4080
tatcactttg acactagccc tattaatcgc atattaacag aaaagtatgg tgatgaagat   4140
attgacatag tattccaaaa ctgtataagc tttggcctta gcttaatgtc agtagtagaa   4200
caatttacta atgtatgtcc taacagaatt attctcatac ctaagcttaa tgagatacat   4260
ttgatgaaac ctcccatatt cacaggtgat gttgatattc acaagttaaa acaagtgata   4320
caaaaacagc atatgttttt accagacaaa ataagtttga ctcaatatgt agaattattc   4380
ttaagtaata aaacactcaa atctggatct catgttaatt ctaatttaat attggcacat   4440
aaaatatctg actattttca taatacttac attttaagta ctaatttagc tggacattgg   4500
attctgatta tacaacttat gaaagattct aagggtattt ttgaaaaaga ttggggagag   4560
ggatatataa ctgatcatat gtttattaat ttgaaagttt tcttcaatgc ctataagacc   4620
tatctcttgt gttttcataa aggttatggc aaagcaaagc tggagtgtga tatgaacacc   4680
tcagatctcc tatgtgtatt ggaattaata gacagtagtt attggaaatc tatgtctaag   4740
gtatttttag aacaaaaagt tatcaaatac attcttagcc aagatgcaag tttacataga   4800
gtaaaaggat gtcatagctt caaattatgg tttcttaaac gtcttaatgt agcagaattc   4860
acagtttgcc cttgggttgt taacatagat tatcatccaa cacatatgaa agcaatatta   4920
acttatatag atcttgttag aatgggattg ataaatatag atagaataca cattaaaaat   4980
aaacacaaat tcaatgatga attttatact tctaatctct tctacattaa ttataacttc   5040
tcagataata ctcatctatt aactaaacat ataaggattg ctaattctga attagaaaat   5100
aattacaaca aattatatca tcctacacca gaaaccctag agaatatact agccaatccg   5160
attaaaagta atgacaaaaa gacactgaat gaatattgta taggtaaaaa tgttgactca   5220
ataatgttac cattgttatc taataagaag cttattaaat cgtctgcaat gattagaacc   5280
aattacagca aacaagattt gtataattta ttccctatgg ttgtgattga tagaattata   5340
gatcattcag gcaatacagc caaatccaac caactttaca ctactacttc ccaccaaata   5400
tctttagtgc acaatagcac atcactttac tgcatgcttc cttggcatca tattaataga   5460
```

```
ttcaattttg tatttagttc tacaggttgt aaaattagta tagagtatat tttaaaagat   5520

cttaaaatta aagatcccaa ttgtatagca ttcataggtg aaggagcagg gaatttatta   5580

ttgcgtacag tagtggaact tcatcctgac ataagatata tttacagaag tctgaaagat   5640

tgcaatgatc atagtttacc tattgagttt ttaaggctgt acaatggaca tatcaacatt   5700

gattatggtg aaaatttgac cattcctgct acagatgcaa ccaacaacat tcattggtct   5760

tatttacata taaagtttgc tgaacctatc agtctttttg tctgtgatgc tgaattgcct   5820

gtaacagtca attggagtaa aattataata gaatggagca agcatgtaag aaagtgcaag   5880

tactgttcct cagttaataa atgtatgtta atagtaaaat atcatgctca agatgatatt   5940

gatttcaaat tagacaatat aactatatta aaaacttatg tatgcttagg cagtaagtta   6000

aagggatcgg aggtttactt agtcatcaca ataggtcctg caaatatatt cccagcattt   6060

aatgtagtac aaaatgctaa attgatacta tcaagaacca aaaatttcat catgcctaag   6120

aaagctgata aagagtctat tgatgcaaat attaaaagtt tnataccctt tctttgttac   6180

cctataacaa aaaaaggaat taatactgca ttgtcaaaac taaagagtgt tgttagtgga   6240

gatatactat catattctat agctggacgt aatgaagttt tcagcaataa acttataaat   6300

cataaacata tgaacatctt aaaatggttc aatcatgttt taaatttcag atcaacagaa   6360

ttaaactata accatttata tatggtagaa tctacatatc cttacctaag tgaattgtta   6420

aacagcttga caaccaatga acttaaaaaa ctgattaaaa tcacaggtag tctgttatac   6480

aactttcata atgaataatg aataa                                         6505
```

```
<210> SEQ ID NO 24
<211> LENGTH: 2166
<212> TYPE: PRT
<213> ORGANISM: Respiratory syncytial virus, Merck strain p17
<220> FEATURE:
<221> NAME/KEY: SITE
<222> LOCATION: (148)...(148)
<223> OTHER INFORMATION: Xaa = Asp or Ala
<221> NAME/KEY: SITE
<222> LOCATION: (2054)...(2054)
<223> OTHER INFORMATION: Xaa = Leu or Phe

<400> SEQUENCE: 24

Met Asp Pro Ile Ile Asn Gly Asn Ser Ala Asn Val Tyr Leu Thr Asp
1               5                   10                  15

Ser Tyr Leu Lys Gly Val Ile Ser Phe Ser Glu Cys Asn Ala Leu Gly
            20                  25                  30

Ser Tyr Ile Phe Asn Gly Pro Tyr Leu Lys Asn Asp Tyr Thr Asn Leu
        35                  40                  45

Ile Ser Arg Gln Asn Pro Leu Ile Glu His Met Asn Leu Lys Lys Leu
    50                  55                  60

Asn Ile Thr Gln Ser Leu Ile Ser Lys Tyr His Lys Gly Glu Ile Lys
65                  70                  75                  80

Leu Glu Glu Pro Thr Tyr Phe Gln Ser Leu Leu Met Thr Tyr Lys Ser
                85                  90                  95

Met Thr Ser Ser Glu Gln Ile Ala Thr Thr Asn Leu Leu Lys Lys Ile
            100                 105                 110

Ile Arg Arg Ala Ile Glu Ile Ser Asp Val Lys Val Tyr Ala Ile Leu
        115                 120                 125

Asn Lys Leu Gly Leu Lys Glu Lys Asp Lys Ile Lys Ser Asn Asn Gly
    130                 135                 140
```

```
Gln Asp Glu Xaa Asn Ser Val Ile Thr Thr Ile Ile Lys Asp Asp Ile
145                 150                 155                 160

Leu Ser Ala Val Lys Asp Asn Gln Ser His Leu Lys Ala Gly Lys Asn
                165                 170                 175

His Ser Thr Lys Gln Lys Asp Thr Ile Lys Thr Thr Leu Leu Lys Lys
            180                 185                 190

Leu Met Cys Ser Met Gln His Pro Pro Ser Trp Leu Ile His Trp Phe
        195                 200                 205

Asn Leu Tyr Thr Lys Leu Asn Asn Ile Leu Thr Gln Tyr Arg Ser Asn
    210                 215                 220

Glu Val Lys Asn His Gly Phe Thr Leu Ile Asp Asn Gln Thr Leu Ser
225                 230                 235                 240

Gly Phe Gln Phe Ile Leu Asn Gln Tyr Gly Cys Ile Val Tyr Asn Lys
                245                 250                 255

Glu Leu Lys Arg Ile Thr Val Thr Thr Tyr Asn Gln Phe Leu Thr Trp
            260                 265                 270

Lys Asp Ile Ser Leu Ser Arg Leu Asn Val Cys Leu Ile Thr Trp Ile
        275                 280                 285

Ser Asn Cys Leu Asn Thr Leu Asn Lys Ser Leu Gly Leu Arg Cys Gly
    290                 295                 300

Phe Asn Asn Val Ile Leu Thr Gln Leu Phe Leu Tyr Gly Asp Cys Ile
305                 310                 315                 320

Leu Lys Leu Phe His Asn Glu Gly Phe Tyr Ile Ile Lys Glu Val Glu
                325                 330                 335

Gly Phe Ile Met Ser Leu Ile Leu Asn Ile Thr Glu Glu Asp Gln Phe
            340                 345                 350

Arg Lys Arg Phe Tyr Asn Ser Met Leu Asn Asn Ile Thr Asp Ala Ala
        355                 360                 365

Asn Lys Ala Gln Lys Asn Leu Leu Ser Arg Val Cys His Thr Leu Leu
    370                 375                 380

Asp Lys Thr Val Ser Asp Asn Ile Ile Asn Gly Arg Trp Ile Ile Leu
385                 390                 395                 400

Leu Ser Lys Phe Leu Lys Leu Ile Lys Leu Ala Gly Asp Asn Asn Leu
                405                 410                 415

Asn Asn Leu Ser Glu Leu Tyr Phe Leu Phe Arg Ile Phe Gly His Pro
            420                 425                 430

Met Val Asp Glu Arg Gln Ala Met Asp Ala Val Lys Ile Asn Cys Asn
        435                 440                 445

Glu Thr Lys Phe Tyr Leu Leu Ser Ser Leu Ser Met Leu Arg Gly Ala
    450                 455                 460

Phe Ile Tyr Arg Ile Ile Lys Gly Phe Val Asn Asn Tyr Asn Arg Trp
465                 470                 475                 480

Pro Thr Leu Arg Asn Ala Ile Val Leu Pro Leu Arg Trp Leu Thr Tyr
                485                 490                 495

Tyr Lys Leu Asn Thr Tyr Pro Ser Leu Leu Glu Leu Thr Glu Arg Asp
            500                 505                 510

Leu Ile Val Leu Ser Gly Leu Arg Phe Tyr Arg Glu Phe Arg Leu Pro
        515                 520                 525

Lys Lys Val Asp Leu Glu Met Ile Ile Asn Asp Lys Ala Ile Ser Pro
    530                 535                 540

Pro Lys Asn Leu Ile Trp Thr Ser Phe Pro Arg Asn Tyr Met Pro Ser
545                 550                 555                 560

His Ile Gln Asn Tyr Ile Glu His Glu Lys Leu Lys Phe Ser Glu Ser
```

```
                565                 570                 575

Asp Lys Ser Arg Arg Val Leu Glu Tyr Tyr Leu Arg Asp Asn Lys Phe
            580                 585                 590

Asn Glu Cys Asp Leu Tyr Asn Cys Val Val Asp Gln Ser Tyr Leu Asn
        595                 600                 605

Asn Pro Asn His Val Val Ser Leu Thr Gly Lys Glu Arg Glu Leu Ser
    610                 615                 620

Val Gly Arg Met Phe Ala Met Gln Pro Gly Met Phe Arg Gln Val Gln
625                 630                 635                 640

Ile Leu Ala Glu Lys Met Ile Ala Glu Asn Ile Leu Gln Phe Phe Pro
                645                 650                 655

Glu Ser Leu Thr Arg Tyr Gly Asp Leu Glu Leu Gln Lys Ile Leu Glu
            660                 665                 670

Leu Lys Ala Gly Ile Ser Asn Lys Ser Asn Arg Tyr Asn Asp Asn Tyr
        675                 680                 685

Asn Asn Tyr Ile Ser Lys Cys Ser Ile Ile Thr Asp Leu Ser Lys Phe
    690                 695                 700

Asn Gln Ala Phe Arg Tyr Glu Thr Ser Cys Ile Cys Ser Asp Val Leu
705                 710                 715                 720

Asp Glu Leu His Gly Val Gln Ser Leu Phe Ser Trp Leu His Leu Thr
                725                 730                 735

Ile Pro His Val Thr Ile Ile Cys Thr Tyr Arg His Ala Pro Pro Tyr
            740                 745                 750

Ile Gly Asp His Ile Val Asp Leu Asn Asn Val Asp Glu Gln Ser Gly
        755                 760                 765

Leu Tyr Arg Tyr His Met Gly Gly Ile Glu Gly Trp Cys Gln Lys Leu
    770                 775                 780

Trp Thr Ile Glu Ala Ile Ser Leu Leu Asp Leu Ile Ser Leu Lys Gly
785                 790                 795                 800

Lys Phe Ser Ile Thr Ala Leu Ile Asn Gly Asp Asn Gln Ser Ile Asp
                805                 810                 815

Ile Ser Lys Pro Ile Arg Leu Met Glu Gly Gln Thr His Ala Gln Ala
            820                 825                 830

Asp Tyr Leu Leu Ala Leu Asn Ser Leu Lys Leu Leu Tyr Lys Glu Tyr
        835                 840                 845

Ala Gly Ile Gly His Lys Leu Lys Gly Thr Glu Thr Tyr Ile Ser Arg
    850                 855                 860

Asp Met Gln Phe Met Ser Lys Thr Ile Gln His Asn Gly Val Tyr Tyr
865                 870                 875                 880

Pro Ala Ser Ile Lys Lys Val Leu Arg Val Gly Pro Trp Ile Asn Thr
                885                 890                 895

Ile Leu Asp Asp Phe Lys Val Ser Leu Glu Ser Ile Gly Ser Leu Thr
            900                 905                 910

Gln Glu Leu Glu Tyr Arg Gly Glu Ser Leu Leu Cys Ser Leu Ile Phe
        915                 920                 925

Arg Asn Val Trp Leu Tyr Asn Gln Ile Ala Leu Gln Leu Lys Asn His
    930                 935                 940

Ala Leu Cys Asn Asn Lys Leu Tyr Leu Asp Ile Leu Lys Val Leu Lys
945                 950                 955                 960

His Leu Lys Thr Phe Phe Asn Leu Asp Asn Ile Asp Thr Ala Leu Thr
                965                 970                 975

Leu Tyr Met Asn Leu Pro Met Leu Phe Gly Gly Gly Asp Pro Asn Leu
            980                 985                 990
```

```
Leu Tyr Arg Ser Phe Tyr Arg Arg Thr Pro Asp Phe Leu Thr Glu Ala
        995                 1000                1005

Ile Val His Ser Val Phe Ile Leu Ser Tyr Tyr Thr Asn His Asp Leu
    1010                1015                1020

Lys Asp Lys Leu Gln Asp Leu Ser Asp Asp Arg Leu Asn Lys Phe Leu
1025                1030                1035                1040

Thr Cys Ile Ile Thr Phe Asp Lys Asn Pro Asn Ala Glu Phe Val Thr
                1045                1050                1055

Leu Met Arg Asp Pro Gln Ala Leu Gly Ser Glu Arg Gln Ala Lys Ile
            1060                1065                1070

Thr Ser Glu Ile Asn Arg Leu Ala Val Thr Glu Val Leu Ser Thr Ala
        1075                1080                1085

Pro Asn Lys Ile Phe Ser Lys Ser Ala Gln His Tyr Thr Thr Thr Glu
    1090                1095                1100

Ile Asp Leu Asn Asp Ile Met Gln Asn Ile Glu Pro Thr Tyr Pro His
1105                1110                1115                1120

Gly Leu Arg Val Val Tyr Glu Ser Leu Pro Phe Tyr Lys Ala Glu Lys
                1125                1130                1135

Ile Val Asn Leu Ile Ser Gly Thr Lys Ser Ile Thr Asn Ile Leu Glu
            1140                1145                1150

Lys Thr Ser Ala Ile Asp Leu Thr Asp Ile Asp Arg Ala Thr Glu Met
        1155                1160                1165

Met Arg Lys Asn Ile Thr Leu Leu Ile Arg Ile Leu Pro Leu Asp Cys
    1170                1175                1180

Asn Arg Asp Lys Arg Glu Ile Leu Ser Met Glu Asn Leu Ser Ile Thr
1185                1190                1195                1200

Glu Leu Ser Lys Tyr Val Arg Glu Arg Ser Trp Ser Leu Phe Asn Ile
                1205                1210                1215

Val Gly Val Thr Ser Pro Ser Ile Met Tyr Thr Met Asp Ile Lys Tyr
            1220                1225                1230

Thr Thr Ser Thr Ile Ala Ser Gly Ile Ile Ile Glu Lys Tyr Asn Val
        1235                1240                1245

Asn Ser Leu Thr Arg Gly Glu Arg Gly Pro Thr Lys Pro Trp Val Gly
    1250                1255                1260

Ser Ser Thr Gln Glu Lys Lys Thr Met Pro Val Tyr Asn Arg Gln Val
1265                1270                1275                1280

Leu Thr Lys Lys Gln Arg Asp Gln Ile Asp Leu Leu Ala Lys Leu Asp
                1285                1290                1295

Trp Val Tyr Ala Ser Ile Asp Asn Lys Asp Glu Phe Met Glu Glu Leu
            1300                1305                1310

Ser Ile Gly Thr Leu Gly Leu Thr Tyr Glu Lys Ala Lys Lys Leu Phe
        1315                1320                1325

Pro Gln Tyr Leu Ser Val Asn Tyr Leu His Arg Leu Thr Val Ser Ser
    1330                1335                1340

Arg Pro Cys Glu Phe Pro Ala Ser Ile Pro Ala Tyr Arg Thr Thr Asn
1345                1350                1355                1360

Tyr His Phe Asp Thr Ser Pro Ile Asn Arg Ile Leu Thr Glu Lys Tyr
                1365                1370                1375

Gly Asp Glu Asp Ile Asp Ile Val Phe Gln Asn Cys Ile Ser Phe Gly
            1380                1385                1390

Leu Ser Leu Met Ser Val Val Glu Gln Phe Thr Asn Val Cys Pro Asn
        1395                1400                1405
```

```
Arg Ile Ile Leu Ile Pro Lys Leu Asn Glu Ile His Leu Met Lys Pro
    1410                1415                1420

Pro Ile Phe Thr Gly Asp Val Asp Ile His Lys Leu Lys Gln Val Ile
1425                1430                1435                1440

Gln Lys Gln His Met Phe Leu Pro Asp Lys Ile Ser Leu Thr Gln Tyr
                1445                1450                1455

Val Glu Leu Phe Leu Ser Asn Lys Thr Leu Lys Ser Gly Ser His Val
            1460                1465                1470

Asn Ser Asn Leu Ile Leu Ala His Lys Ile Ser Asp Tyr Phe His Asn
        1475                1480                1485

Thr Tyr Ile Leu Ser Thr Asn Leu Ala Gly His Trp Ile Leu Ile Ile
    1490                1495                1500

Gln Leu Met Lys Asp Ser Lys Gly Ile Phe Glu Lys Asp Trp Gly Glu
1505                1510                1515                1520

Gly Tyr Ile Thr Asp His Met Phe Ile Asn Leu Lys Val Phe Phe Asn
                1525                1530                1535

Ala Tyr Lys Thr Tyr Leu Leu Cys Phe His Lys Gly Tyr Gly Lys Ala
            1540                1545                1550

Lys Leu Glu Cys Asp Met Asn Thr Ser Asp Leu Leu Cys Val Leu Glu
        1555                1560                1565

Leu Ile Asp Ser Ser Tyr Trp Lys Ser Met Ser Lys Val Phe Leu Glu
    1570                1575                1580

Gln Lys Val Ile Lys Tyr Ile Leu Ser Gln Asp Ala Ser Leu His Arg
1585                1590                1595                1600

Val Lys Gly Cys His Ser Phe Lys Leu Trp Phe Leu Lys Arg Leu Asn
                1605                1610                1615

Val Ala Glu Phe Thr Val Cys Pro Trp Val Val Asn Ile Asp Tyr His
            1620                1625                1630

Pro Thr His Met Lys Ala Ile Leu Thr Tyr Ile Asp Leu Val Arg Met
        1635                1640                1645

Gly Leu Ile Asn Ile Asp Arg Ile His Ile Lys Asn Lys His Lys Phe
    1650                1655                1660

Asn Asp Glu Phe Tyr Thr Ser Asn Leu Phe Tyr Ile Asn Tyr Asn Phe
1665                1670                1675                1680

Ser Asp Asn Thr His Leu Leu Thr Lys His Ile Arg Ile Ala Asn Ser
                1685                1690                1695

Glu Leu Glu Asn Asn Tyr Asn Lys Leu Tyr His Pro Thr Pro Glu Thr
            1700                1705                1710

Leu Glu Asn Ile Leu Ala Asn Pro Ile Lys Ser Asn Asp Lys Lys Thr
        1715                1720                1725

Leu Asn Glu Tyr Cys Ile Gly Lys Asn Val Asp Ser Ile Met Leu Pro
    1730                1735                1740

Leu Leu Ser Asn Lys Lys Leu Ile Lys Ser Ser Ala Met Ile Arg Thr
1745                1750                1755                1760

Asn Tyr Ser Lys Gln Asp Leu Tyr Asn Leu Phe Pro Met Val Val Ile
                1765                1770                1775

Asp Arg Ile Ile Asp His Ser Gly Asn Thr Ala Lys Ser Asn Gln Leu
            1780                1785                1790

Tyr Thr Thr Thr Ser His Gln Ile Ser Leu Val His Asn Ser Thr Ser
        1795                1800                1805

Leu Tyr Cys Met Leu Pro Trp His His Ile Asn Arg Phe Asn Phe Val
    1810                1815                1820

Phe Ser Ser Thr Gly Cys Lys Ile Ser Ile Glu Tyr Ile Leu Lys Asp
```

```
1825                1830                1835                1840

Leu Lys Ile Lys Asp Pro Asn Cys Ile Ala Phe Ile Gly Glu Gly Ala
                1845                1850                1855

Gly Asn Leu Leu Leu Arg Thr Val Val Glu Leu His Pro Asp Ile Arg
            1860                1865                1870

Tyr Ile Tyr Arg Ser Leu Lys Asp Cys Asn Asp His Ser Leu Pro Ile
        1875                1880                1885

Glu Phe Leu Arg Leu Tyr Asn Gly His Ile Asn Ile Asp Tyr Gly Glu
    1890                1895                1900

Asn Leu Thr Ile Pro Ala Thr Asp Ala Thr Asn Asn Ile His Trp Ser
1905                1910                1915                1920

Tyr Leu His Ile Lys Phe Ala Glu Pro Ile Ser Leu Phe Val Cys Asp
                1925                1930                1935

Ala Glu Leu Pro Val Thr Val Asn Trp Ser Lys Ile Ile Ile Glu Trp
            1940                1945                1950

Ser Lys His Val Arg Lys Cys Lys Tyr Cys Ser Ser Val Asn Lys Cys
        1955                1960                1965

Met Leu Ile Val Lys Tyr His Ala Gln Asp Asp Ile Asp Phe Lys Leu
    1970                1975                1980

Asp Asn Ile Thr Ile Leu Lys Thr Tyr Val Cys Leu Gly Ser Lys Leu
1985                1990                1995                2000

Lys Gly Ser Glu Val Tyr Leu Val Ile Thr Ile Gly Pro Ala Asn Ile
                2005                2010                2015

Phe Pro Ala Phe Asn Val Val Gln Asn Ala Lys Leu Ile Leu Ser Arg
            2020                2025                2030

Thr Lys Asn Phe Ile Met Pro Lys Lys Ala Asp Lys Glu Ser Ile Asp
        2035                2040                2045

Ala Asn Ile Lys Ser Xaa Ile Pro Phe Leu Cys Tyr Pro Ile Thr Lys
    2050                2055                2060

Lys Gly Ile Asn Thr Ala Leu Ser Lys Leu Lys Ser Val Val Ser Gly
2065                2070                2075                2080

Asp Ile Leu Ser Tyr Ser Ile Ala Gly Arg Asn Glu Val Phe Ser Asn
                2085                2090                2095

Lys Leu Ile Asn His Lys His Met Asn Ile Leu Lys Trp Phe Asn His
            2100                2105                2110

Val Leu Asn Phe Arg Ser Thr Glu Leu Asn Tyr Asn His Leu Tyr Met
        2115                2120                2125

Val Glu Ser Thr Tyr Pro Tyr Leu Ser Glu Leu Leu Asn Ser Leu Thr
    2130                2135                2140

Thr Asn Glu Leu Lys Lys Leu Ile Lys Ile Thr Gly Ser Leu Leu Tyr
2145                2150                2155                2160

Asn Phe His Asn Glu Ile
                2165


<210> SEQ ID NO 25
<211> LENGTH: 15205
<212> TYPE: DNA
<213> ORGANISM: Respiratory syncytial virus, Merck strain 287

<400> SEQUENCE: 25

acgggaaaaa atgcgtacaa caaacttgcg taaaccaaaa aaatggggca aataagagtt      60

tgataagtac cacttaaatt taactccctt agttagagat gggcagcaat tcattgagta     120

tgataaaagt tagattacaa aatttgtttg acaatgatga agtagcattg ttaaaaataa     180
```

```
catgctatac tgataaatta atacatttaa ctaatgcttt ggctaaggca gtgatacata    240
caataaaatt gaatggcatt gtgtttgtgc atgttattac aagtagtgat atttgcccta    300
ataataatat tgtagtaaaa tccaatttca caacaatgcc agtactacaa aatggaggct    360
atatatggga aatgatggaa ttaacacatt gctctcaacc taatggtcta ctagatgaca    420
attgtgaaat taaattctcc aaaaaactaa gtgattcaac aatgaccaat tatatgaatc    480
aattatctga attgcttgga tttgatctta atccataaat tataattaat atcaactagc    540
taatcaatgt cactaacacc attagttaat ataaaactta acagaagaca aaaatggggc    600
aaataaatca attcagccaa cccaaccatg gacacgactc acaatgatac cacaccacaa    660
agactgatga tcacagatat gagaccattg tcacttgaga ccataataac atcactaacc    720
agagacatca taacacacaa atttatatac ttgataaatc atgaatgcat agtgagaaaa    780
cttgatgaaa gacaagccac atttacattc ctggtcaact atgaaatgaa actattgcac    840
aaagtaggaa gcactaaata taaaaaatat actgaataca acacaaaata tggcactttc    900
cctatgccga tattcatcaa tcatgatggg ttcttagaat gcattggcat taagcctaca    960
aagcatactc ccataatata caagtatgat ctcaatccat aaacttcaac acaatattca   1020
cacaatctaa aacaacaact ctatgcatga ctacactcca tagtccaaat ggagcctgaa   1080
aattatagta atttaaaatt aaggagagat ataagataga agatggggca aatacaaaga   1140
tggctcttag caaagtcaag ttgaatgata cactcaacaa agatcaactt ctgtcatcta   1200
gcaaatacac catccaacgg agcacaggag atagtattga tactcctaat tatgatgtgc   1260
agaaacacat caataagtta tgtggcatgt tattaatcac agaagatgct aatcataaat   1320
tcactgggtt aataggtatg ttatatgcga tgtctaggtt aggaagagaa gacaccataa   1380
aaatactcag agatgcggga tatcatgtaa aagcaaatgg agtagatgta acaacacatc   1440
gtcaagacat taatgggaaa gaaatgaaat ttgaagtgtt aacattggca agcttaacaa   1500
ctgaaattca aatcaacatt gaaatagaat ctagaaaatc ctacaaaaaa atgctaaaag   1560
aaatgggaga ggtagctcca gaatacaggc atgactctcc tgattgtggg atgataatat   1620
tatgtatagc agcattagta ataaccaaat tggcagcagg ggatagatct ggtcttacag   1680
ctgtgattag gagagctaat aatgtcttaa aaaatgaaat gaaacgttat aaaggcttac   1740
tacccaagga catagccaac agcttctatg aggtgtttga aaaacatccc cactttatag   1800
atgtttttgt tcattttggt atagcacaat cttctaccag aggtggcagt agagtcgaag   1860
ggatttttgc aggattgttt atgaatgcct atggtgcagg gcaagtgatg ttacggtggg   1920
gagtcttagc aaaatcagtt aaaaatatta tgttaggaca tgctagtgtg caagcagaaa   1980
tggaacaagt tgttgaggtt tatgaatatg cccaaaaatt gggtggtgaa gcaggattct   2040
accatatatt gaacaaccca aaagcttcat tattatcctt gactcaattt cctcacttct   2100
ccagtgtagt attaggcaat gctgctggcc taggcataat gggagagtac agaggtacac   2160
cgaggaatca agatctatat gatgcagcaa aggcatatgc tgaacaactc aaagaaaatg   2220
gtgtgattaa ctacagtgta ctagacttga cagcagaaga actagaggct atcaaacatc   2280
agcttaatcc aaaagataat gatgtagagc tttgagttaa taaaaaaatg gggcaaataa   2340
atcatcatgg aaaagtttgc tcctgaattc catggagaag atgcaaacaa cagggctact   2400
aaatttctag agtcaataaa gggcaaattc gcatcaccta aagatcccaa gaaaaaagat   2460
agtatcatat ctgtcaactc aatagatata gaagtaacca aagaaagccc tataacatca   2520
aattcaacta ttatcaaccc aacaaatgag acagatgata ctgcagggaa caagcccaat   2580
```

```
tatcaaagaa aacctctagt aagtttcaaa gaagacccca caccaagtga taatcccttt   2640
tctaaactat acaaagaaac catagaaaca tttgataaca atgaagaaga atccagctat   2700
tcatatgagg aaataaatga tcagacaaac gacaatataa cggcaagatt agataggatt   2760
gatgaaaagt taagtgaaat actaggaatg cttcacacat tagtggtggc aagtgcagga   2820
cctacatctg ctcgggatgg tataagagat gccatggttg gtttaagaga agaaatgata   2880
gaaaaaatca gaactgaagc attaatgacc aatgacagat tagaagctat ggcaagactc   2940
aggaatgagg aaagtgaaaa gatggcaaaa gacacatcag atgaagtatc tctaaatcca   3000
acatcagaga aattgaacaa cctgttggaa gggaatgata gtgacaatga tctatcactt   3060
gaagatttct gattagttac caatcttaac atcaaaacac aacaccaaca gaagaccaac   3120
aaactaacca acccaatcat ccaaccaaac atccatctgc caatcagcta agcagccaac   3180
aaaacaacca gccaatccaa aactagccac ccggaaaaaa tcgacaatat agttacaaaa   3240
aaagaaaggg tggggcaaat atggaaacat acgtgaacaa gcttcacgaa ggctccacat   3300
acacagctgc tgttcaatac aatgtcctag aaaaagacga tgaccctgca tcacttacaa   3360
tatgggtgcc catgttccaa tcatctatgc cagcagattt actcataaaa gaactagcta   3420
atgtcaacat actagtgaaa caaatatcca cacccaaggg accttcacta agagtcatga   3480
taaactcaag aagtgcagtg ctagcacaaa tgcccagcaa atttaccata agcgctaatg   3540
tgtccttaga tgaaagaagc aaactagcat atgatgtaac cacaccctgt gaaatcaagg   3600
catgcagtct aacatgccta aaatcaaaaa atatgttaac tacagttaaa gatctcacta   3660
tgaagacact caaccctaca catgatatta ttgctttatg tgaatttgaa aacatagtaa   3720
catcaaaaaa agtcataata ccaacatacc taagatccat cagtgtcaga aataaggatc   3780
tgaacacact tgaaaatata acaaccactg aattcaaaaa tgctatcaca aatgcaaaaa   3840
tcatccctta ctcaggatta ctattagtca tcacagtgac tgacaacaaa ggagcattca   3900
aatacataaa gccacaaagt caattcatag tagatcttgg agcttaccta gaaaaagaaa   3960
gtatatatta tgtcaccaca aattggaagc acacagctac aagatttgca atcaaaccta   4020
tggaagatta accttcttca actacatcag tgtgttaatt catacaaact ttctacctac   4080
attcttcact tcaccatcac aatcacaaac acttcgtggt tcaaccaatc aaacaaaact   4140
tatctaaagt cccagatcat cccaagtcat tgtttatcag atctagtact caaataagtt   4200
aataaaaaca tacacatggg gcaaataatc atcggagaaa atccaactaa tcacaatatc   4260
tgttaacata gacaagtcaa cacaccatac agaatcaacc gatggaaaat acatccataa   4320
caatagaatt ctcaagcaaa ttctggccct actttacact aatacacatg atcacaacaa   4380
taatctcttt actaatcata atctccatca tgattgcaat actaaacaaa ctttgtgaat   4440
ataacgtatt ccataacaaa acctttgagt taccaagagc tcgagtcaac acatagcatt   4500
catcaatcca acagctcaaa acagtaacct tgtatttaaa agtgaacaac ccctgcctct   4560
ttacaacacc ttatcaacgt cccaccatgc aaaccaccat ccatactata tagtagttaa   4620
ttaaaatagt cataacaatg aactaggata tcaagactaa caataacatt ggggcaaatg   4680
caaacatgtc caaaaacaaa gaccaacgca ctgctaagac actagaaagg acctgggaca   4740
ctctcaatca tttattattc atatcatcgt gcttatataa gttaaatctt aaatctgtag   4800
cacaaatcac attatccatt ttggcaatga taatctcaac ttcacttata attgcagcca   4860
tcatattcat tgcctcggca aaccacaaag tcacatcaac aactacaatc atacaagatg   4920
```

```
caacaagcca gatcaagaac acaaccccaa catacctcac ccagagtcct cagcttggaa   4980
tcagtccctc taatccgtct gaaattacat cacaaatcac caccatacta gcttcaacaa   5040
caccaggagt caagtcaacc ctgcaatcca caacagtcgg gaccaagaat acaacaacaa   5100
ctcaagcaca acccagcaag cccaccacaa aacaacgcca aaacaaacca ccaagcaaac   5160
ccaacaatga ttttcacttt gaagtgttca actttgtacc ctgcagcata tgcagcaaca   5220
atccaacctg ctgggccatc tgcaaaagaa tacccaacaa aaaaccagga aagaaaacca   5280
ccaccaagcc cacaaaaaaa ccaaccttca agacaaccaa aaaagatccc aaacctcaaa   5340
ccactaaatc aaaggaggta cccaccacca agcccacaga agagccaact atcaacacca   5400
ccaaaacaaa catcacaact acactactca cctccaacac cacgagaaat ccagaactca   5460
caagtcaaat ggaaaccttc cactcaactt cctccgaagg taatccaagc ccttctcaag   5520
tctccataac atccgagtac ctatcacaac cttcatctcc acccaacaca ccacgctagt   5580
agttattaaa aaacatatta tcacagaaag ccatgaccaa ctcaaacaga atcaaaataa   5640
actctggggc aaataacaat ggagttgcca atcctcaaag cgaatgcaat taccacaatc   5700
ctcactgcag tcacattttg ttttgcttct agtcaaaaca tcactgaaga attttatcaa   5760
tcaacatgca gtgcagttag caaaggctat cttagtgctc taagaactgg ttggtatacc   5820
agtgttataa ctatagaatt aagtaatatc aaggaaaata agtgtaatgg aacagatgct   5880
aaggtaaaat tgataaaaca agaattagat aaatataaaa atgctgtaac agaattgcag   5940
ttgctaatgc aaagcacacc agcagcaaac aatcgagcca gaagagaact accaaggttt   6000
atgaattata cactcaacaa tgccaaaaaa accaatgtaa cattaagcaa aaaaaggaaa   6060
agaagatttc ttggtttttt gttaggagtt ggatctgcaa tcgccagtgg cattgctgta   6120
tctaaggtcc tacacctaga aggggaagtg aacaagatca aaagtgctct actatccaca   6180
aacaaggctg tagtcagctt atcaaatgga gttagtgtct taaccagcaa agtgttagac   6240
ctcaaaaatt atatagataa acaattgtta cctattgtga acaagcaaag ctgcagcata   6300
tcaaatatag aaactgtgat agagttccaa caaaagaaca acagactact agagattacc   6360
agggaattta gtgttaatgc aggtgtaact acacctgtaa gcacttacat gttgactaat   6420
agtgaattat tgtcattaat caatgatatg cctataacaa atgatcagaa gaagttaatg   6480
tccaacaatg ttcaaatagt tagacagcaa agttactcta tcatgtccat aataaaagag   6540
gaagtcttag catatgtagt acaattacca ctatatggtg ttatagatac accttgttgg   6600
aaattacaca catcccctct atgtacaacc aacacaaaag aagggtccaa catctgttta   6660
acaagaactg acagaggatg gtactgtgac aatgcaggat cagtctcttt cttcccacaa   6720
gctgaaacat gtaaagttca atcgaatcga gtattttgtg acacaatgaa cagtttaaca   6780
ttaccaagtg aagtaaatct ctgcaatgtt gacatattca atcccaaata tgattgtaaa   6840
attatgactt caaaaacaga tgtaagcagc tctgttatca catctctagg agccattgtg   6900
tcatgctatg gcaaaactaa atgtacagca tccaataaaa atcgtggaat cataaagaca   6960
ttttctaacg ggtgcgatta tgtatcaaat aaaggggtgg acactgtgtc tgtaggcaac   7020
acattatatt atgtaaataa gcaagaaggc aaaagtctct atgtaaaagg tgaaccaata   7080
ataaatttct atgacccatt agtattcccc tctgatgaat ttgatgcatc aatatctcaa   7140
gtcaacgaga agattaacca gagcctggca tttattcgta aatccgatga attattacat   7200
aatgtaaatg ctggtaaatc caccacaaac atcatgataa ctgctataat tatagtgatt   7260
gtagtaatat tattatcatt aattgctgta ggactgctcc tatactgtaa ggccagaagc   7320
```

```
acaccagtca cactaagcaa agatcaactg agtggtataa ataatattgc atttagtaac   7380
taaataaaat agcatctaat catgttctta cgatggttta ctatctactc atagacagcc   7440
catctgtcat tggattttcc taaaatctga acttcatcga aactctcatc tataaaccat   7500
ctcacttaca ctatttaagt agattcctag ttcatagtta tataaaacat aattgaatgc   7560
cagattaact tactatctga aaaaatgaaa actggggcaa atatgtcacg aaggaatcct   7620
tgcaaatttg aaattcgagg tcattgctta aatggtaaga ggtgtcattt tagtcataat   7680
tattttgaat ggccacccca tgcactgctt gtaagacaaa actttatgtt aaacagaata   7740
cttaagtcta tggataaaag tatagatacc ttatcagaaa taagtggagc tgcagagttg   7800
gacagaacag aagagtatgc tcttggtgta gttggagtgc tagagagtta tataggatca   7860
ataaacaata taactaaaca atcagcatgt gttgccatga gcaaactcct cactgaactc   7920
aatagtgatg atatcaaaaa gctgagggac aatgaagagc taaattcacc caagataaga   7980
gtgtacaata ctgtcatatc atatattgaa agcaacagga aaaacaataa acaaactatc   8040
catctgttaa aaagattgcc agcagacgtg ttgaagaaaa ccatcaaaaa cacattggat   8100
atccataaga gcataaccat caacaaccca aaagaattaa ctgttagtga tacaaatgac   8160
catgccaaaa ataatgatac tacctgacaa atatccttgt agtataactt ccatactaat   8220
tacaagtaga tgtagagtta ctatgtataa tcaaaagaac acactatatt tcaatcaaaa   8280
caatccaaat aaccatatgt actcactaaa tcaaacattc aatgaaatcc attggacctc   8340
tcaagatttg attgacacaa ttcaaaattt tctacaacat ctaggtatta ctgaggatat   8400
atatacaata tatatattag tgtcataaca ctcaattcta acacttacaa catcgttaca   8460
ttattaaatc aaacaattca agttgtggga caaaatggat cccattatta atggaaattc   8520
tgctaatgtt tatctaaccg atagttattt aaaaggtgtt atctctttct cagagtgtaa   8580
tgctttagga agctacatat tcaatggtcc ttatctcaaa aatgattata ccaacttaat   8640
tagtagacaa aatccattaa tagaacacat gaatctaaag aaactaaata taacacagtc   8700
cttaatatct aagtatcata aaggtgaaat aaaattagaa gaaccgactt attttcagtc   8760
attacttatg acatacaaga gtatgacctc gtcagaacag attgctacca ctaatttact   8820
taaaaagata ataagaagag ctatagaaat aagtgatgtc aaagtctatg ctatattgaa   8880
taaactaggg cttaaagaaa aggacaagat taaatccaac aatggacaag atgaagacaa   8940
ttcagttatt acgaccataa tcaaagatga tatactttca gctgttaaag ataatcaatc   9000
tcatcttaaa gcaggcaaaa atcactctac aaaacaaaaa gacacaatca aaacaacact   9060
cctgaagaaa ttgatgtgtt caatgcaaca tcctccatca tggttaatac attggtttaa   9120
cttatacaca aaattaaaca acatattaac acagtatcga tcaaatgagg taaaaaacca   9180
tgggtttaca ttgatagata atcaaactct tagtggattt caatttattt tgaaccaata   9240
tggttgtata gtttataata aggaactcaa aagaattact gtgacaacct ataatcaatt   9300
cttgacatgg aaagatatta gccttagtag attaaatgtt tgtttaatta catggattag   9360
taactgcttg aacacattaa ataaaagctt aggcttaaga tgcggattca ataatgttat   9420
cttaacacaa ctattccttt atggagattg tatactaaaa ctatttcaca atgaggggtt   9480
ctacataata aaagaggtag agggatttat tatgtctcta attttaaata taacagaaga   9540
agatcaattc agaaaacgat tttataatag tatgctcaac aacatcacag atgctgctaa   9600
taaagctcag aaaaatctgc tatcaagagt atgtcataca ttattagata agacagtatc   9660
```

```
cgataatata ataaatggca gatggataat tctattaagt aagttcctta aattaattaa   9720
gcttgcgggt gacaataacc ttaacaatct gagtgaacta tattttttgt tcagaatatt   9780
tggacaccca atggtagatg aaagacaagc catggatgct gttaaaatta attgcaatga   9840
gaccaaattt tacttgctaa gcagtctaag tatgttaaga ggtgccttta tatatagaat   9900
tataaaaggg tttgtaaata attacaacag atggcctact ttaagaaatg ctattgtttt   9960
acccttaaga tggttaactt actataaact aaacacttat ccttctttgt tggaacttac  10020
agaaagagat ttgattgtgt tatcaggact acgtttctat cgtgagtttc ggttgcctaa  10080
aaaagtggat cttgaaatga ttataaatga taaagctata tcacctccta aaaatttgat  10140
atggactagt ttccctagaa attacatgcc atcacacata caaaactata tagaacatga  10200
aaaattaaaa ttttccgaga gtgataaatc aagaagagta ttagagtatt atttaagaga  10260
taacaagttc aatgaatgtg atttatacaa ctgtgtagtt gatcaaagtt atctaaacaa  10320
ccctaatcat gtggtatcat tgacaggcaa agaaagagaa ctcagtgtag gtagaatgtt  10380
tgcaatgcaa ccgggaatgt tcagacaggt tcaaatatta gcagagaaaa tgatagctga  10440
aaacatttta caattctttc ctgaaagtct tacaagatat ggtgatctag aactacaaaa  10500
aatattagaa ttgaaagcag gaataagtaa caaatcaaat cgctacaatg acaattacaa  10560
caattacatt agtaagtgct ctatcatcac agatctcagc aaattcaatc aagcatttcg  10620
atatgaaacg tcatgtattt gtagtgatgt gcttgatgaa ctgcatggtg tacaatctct  10680
attttcctgg ttacatttaa ctattcctca tgttacaata atatgtacat ataggcatgc  10740
accccccctat ataggagatc atattgtaga tcttaacaat gtagatgaac aaagtggatt  10800
atatagatat cacatgggtg gcatcgaagg gtggtgtcaa aaactatgga ccatagaagc  10860
tatatcacta ttggatctaa tatctctcaa agggaaattc tcaattactg ctttaattaa  10920
tggtgacaat caatcaatag atataagcaa accaattaga ctcatggaag gtcaaactca  10980
tgctcaagca gattatttgc tagcattaaa tagccttaaa ttactgtata aagagtatgc  11040
aggcataggc cacaaattaa aaggaactga gacttatata tcacgagata tgcaatttat  11100
gagtaaaaca attcaacata acggtgtgta ttacccagct agtataaaga aagtcctaag  11160
agtgggaccg tggataaaca ctatacttga tgatttcaaa gtgagtttag aatctatagg  11220
tagtttgaca caagaattag aatatagagg tgaaagtcta ttatgcagtt taatatttag  11280
aaatgtatgg ttatataatc agattgctct acaattaaaa aatcatgcat tatgtaacaa  11340
taaactatat ttggacatat taaaggttct gaaacactta aaaacctttt ttaatcttga  11400
taatattgat acagcattaa cattgtatat gaatttacct atgttatttg gtggtggtga  11460
tcccaacttg ttatatcgaa gtttctatag aagaaccccc gacttcctca cagaggctat  11520
agttcactct gtgttcatac ttagttatta tacaaaccat gacttaaaag ataaacttca  11580
agatctgtca gatgatagat tgaataagtt cttaacatgc ataatcacgt ttgacaaaaa  11640
ccctaacgct gaattcgtaa cattgatgag agatcctcaa gctttagggt ctgagagaca  11700
agctaaaatt actagcgaaa tcaataggct ggcagttaca gaggttttga gtacagctcc  11760
aaacaaaata ttctccaaaa gtgcacaaca ttataccact acagagatag atctaaatga  11820
tattatgcaa aatatagaac ctacatatcc tcatgggcta agagttgttt atgaaagttt  11880
acccttttat aaagcagaga aaatagtaaa tcttatatca ggtacaaaat ctataactaa  11940
catactggaa aaaacttctg ccatagactt aacagatatt gatagagcca ctgagatgat  12000
gaggaaaaac ataactttgc ttataaggat acttccattg gattgtaaca gagataaaag  12060
```

```
agagatattg agtatggaaa acctaagtat tactgaatta agcaaatatg ttagggaaag  12120
atcttggtct ttattcaata tagttggtgt tacatcaccc agtatcatgt atacaatgga  12180
catcaaatat actacaagca ctatagctag tggcataatt atagagaaat ataatgttaa  12240
cagtttaaca cgtggtgaga gaggacccac taaaccatgg gttggttcat ctacacaaga  12300
gaaaaaaaca atgccagttt ataatagaca agtcttaacc aaaaaacaga gagatcaaat  12360
agatctatta gcaaaattgg attgggtgta tgcatctata gataacaagg atgaattcat  12420
ggaagaactc agcataggaa cccttgggtt aacatatgaa aaagccaaga aattatttcc  12480
acaatattta agtgtcaact atttgcatcg acttacagtc agtagtagac catgtgaatt  12540
ccctgcatca ataccagctt atagaacaac aaattatcac tttgacacta gccctattaa  12600
tcgcatatta acagaaaagt atggtgatga agatattgac atagtattcc aaaactgtat  12660
aagctttggc cttagcttaa tgtcagtagt agaacaattt actaatgtat gtcctaacag  12720
aattattctc atacctaagc ttaatgagat acatttgatg aaacctccca tattcacagg  12780
tgatgttgat attcacaagt taaaacaagt gatacaaaaa cagcatatgt tttaccaga   12840
caaaataagt ttgactcaat atgtagaatt attcttaagt aataaaacac tcaaatctgg  12900
atctcatgtt aattctaatt taatattggc acataaaata tctgactatt ttcataatac  12960
ttacatttta agtactaatt tagctggaca ttggattctg attatacaac ttatgaaaga  13020
ttctaagggt atttttgaaa aagattgggg agagggatat ataactgatc atatgtttat  13080
taatttgaaa gttttcttca atgcctataa gacctatctc ttgtgttttc ataaaggtta  13140
tggcaaagca aagctggagt gtgatatgaa cacctcagat ctcctatgtg tattggaatt  13200
aatagacagt agttattgga aatctatgtc taaggtattt ttagaacaaa aagttatcaa  13260
atacattctt agccaagatg caagtttaca tagagtaaaa ggatgtcata gcttcaaatt  13320
atggtttctt aaacgtctta atgtagcaga attcacagtt tgcccttggg ttgttaacat  13380
agattatcat ccaacacata tgaaagcaat attaacttat atagatcttg ttagaatggg  13440
attgataaat atagatagaa tacacattaa aaataaacac aaattcaatg atgaatttta  13500
tacttctaat ctcttctaca ttaattataa cttctcagat aatactcatc tattaactaa  13560
acatataagg attgctaatt ctgaattaga aaataattac aacaaattat atcatcctac  13620
accagaaacc ctagagaata tactagccaa tccgattaaa agtaatgaca aaaagacact  13680
gaatgaatat tgtataggta aaaatgttga ctcaataatg ttaccattgt tatctaataa  13740
gaagcttatt aaatcgtctg caatgattag aaccaattac agcaaacaag atttgtataa  13800
tttattccct atggttgtga ttgatagaat tatagatcat tcaggcaata cagccaaatc  13860
caaccaactt tacactacta cttcccacca aatatcttta gtgcacaata gcacatcact  13920
ttactgcatg cttccttggc atcatattaa tagattcaat tttgtattta gttctacagg  13980
ttgtaaaatt agtatagagt atattttaaa agatcttaaa attaaagatc ccaattgtat  14040
agcattcata ggtgaaggag cagggaattt attattgcgt acagtagtgg aacttcatcc  14100
tgacataaga tatatttaca gaagtctgaa agattgcaat gatcatagtt tacctattga  14160
gtttttaagg ctgtacaatg gacatatcaa cattgattat ggtgaaaatt tgaccattcc  14220
tgctacagat gcaaccaaca acattcattg gtcttattta catataaagt ttgctgaacc  14280
tatcagtctt tttgtctgtg atgctgaatt gcctgtaaca gtcaattgga gtaaaattat  14340
aatagaatgg agcaagcatg taagaaagtg caagtactgt tcctcagtta ataaatgtat  14400
```

```
gttaatagta aaatatcatg ctcaagatga tattgatttc aaattagaca atataactat  14460

attaaaaact tatgtatgct taggcagtaa gttaaaggga tcggaggttt acttagtcat  14520

cacaataggt cctgcaaata tattcccagc atttaatgta gtacaaaatg ctaaattgat  14580

actatcaaga accaaaaatt tcatcatgcc taagaaagct gataaagagt ctattgatgc  14640

aaatattaaa agtttgatac cctttctttg ttaccctata acaaaaaaag gaattaatac  14700

tgcattgtca aaactaaaga gtgttgttag tggagatata ctatcatatt ctatagctgg  14760

acgtaatgaa gttttcagca ataaacttat aaatcataaa catatgaaca tcttaaaatg  14820

gttcaatcat gttttaaatt tcagatcaac agaattaaac tataaccatt tatatatggt  14880

agaatctaca tatccttacc taagtgaatt gttaaacagc ttgacaacca atgaacttaa  14940

aaaactgatt aaaatcacag gtagtctgtt atacaacttt cataatgaat aatgaataaa  15000

gatcttataa taaagattcc catagctata cactaccatt gtattaaatt atagttatta  15060

aaaattaaaa atcatataat tttttaaata acttttagtg aactaatcct aaagttatca  15120

ttttgatcta ggaggaataa atttaaatcc taatctaatt ggtttatatg tgtattaact  15180

aaactacgag atattagttt ttgac                                        15205
```

<210> SEQ ID NO 26
<211> LENGTH: 15205
<212> TYPE: DNA
<213> ORGANISM: Respiratory syncytial virus, Merck strain p17
<220> FEATURE:
<221> NAME/KEY: variation
<222> LOCATION: (6538)...(6538)
<223> OTHER INFORMATION: n = g or a
<221> NAME/KEY: variation
<222> LOCATION: (7115)...(7115)
<223> OTHER INFORMATION: n = g or a
<221> NAME/KEY: variation
<222> LOCATION: (8937)...(8937)
<223> OTHER INFORMATION: n = a or c
<221> NAME/KEY: variation
<222> LOCATION: (14656)...(14656)
<223> OTHER INFORMATION: n = g or t

<400> SEQUENCE: 26

```
acgggaaaaa atgcgtacaa caaacttgcg taaaccaaaa aaatggggca aataagagtt     60

tgataagtac cacttaaatt taactccctt agttagagat gggcagcaat tcattgagta    120

tgataaaagt tagattacaa aatttgtttg acaatgatga agtagcattg ttaaaaataa    180

catgctatac tgataaatta atacatttaa ctaatgcttt ggctaaggca gtgatacata    240

caataaaatt gaatggcatt gtgtttgtgc atgttattac aagtagtgat atttgcccta    300

ataataatat tgtagtaaaa tccaatttca caacaatgcc agtactacaa aatggaggct    360

atatatggga aatgatggaa ttaacacatt gctctcaacc taatggtcta ctagatgaca    420

attgtgaaat taaattctcc aaaaaactaa gtgattcaac aatgaccaat tatatgaatc    480

aattatctga attgcttgga tttgatctta atccataaat tataattaat atcaactagc    540

taatcaatgt cactaacacc attagttaat ataaaactta acagaagaca aaaatggggc    600

aaataaatca attcagccaa cccaaccatg gacacgactc acaatgatac cacaccacaa    660

agactgatga tcacagatat gagaccattg tcacttgaga ccataataac atcactaacc    720

agagacatca taacacacaa atttatatac ttgataaatc atgaatgcat agtgagaaaa    780

cttgatgaaa gacaagccac atttacattc ctggtcaact atgaaatgaa actattgcac    840

aaagtaggaa gcactaaata taaaaaatat actgaataca acacaaaata tggcactttc    900
```

```
cctatgccga tattcatcaa tcatgatggg ttcttagaat gcattggcat taaacctaca    960
aagcatactc ccataatata caagtatgat ctcaatccat aaacttcaac acaatattca   1020
cacaatctaa aacaacaact ctatgcatga ctacactcca tagtccaaat ggagcctgaa   1080
aattatagta atttaaaatt aaggagagat ataagataga agatggggca aatacaaaga   1140
tggctcttag caaagtcaag ttgaatgata cactcaacaa agatcaactt ctgtcatcta   1200
gcaaatacac catccaacgg agcacaggag atagtattga tactcctaat tatgatgtgc   1260
agaaacacat caataagtta tgtggcatgt tattaatcac agaagatgct aatcataaat   1320
tcactgggtt aataggtatg ttatatgcga tgtctaggtt aggaagagaa gacaccataa   1380
aaatactcag agatgcggga tatcatgtaa aagcaaatgg agtagatgta acaacacatc   1440
gtcaagacat taatgggaaa gaaatgaaat ttgaagtgtt aacattggca agcttaacaa   1500
ctgaaattca aatcaacatt gaaatagaat ctagaaaatc ctacaaaaaa atgctaaaag   1560
aaatgggaga ggtagctcca gaatacaggc atgactctcc tgattgtggg atgataatat   1620
tatgtatagc agcattagta ataaccaaat tggcagcagg ggatagatct ggtcttacag   1680
ctgtgattag gagagctaat aatgtcttaa aaaatgaaat gaaacgttat aaaggcttac   1740
tacccaagga catagccaac agcttctatg aggtgtttga aaaacatccc cactttatag   1800
atgtttttgt tcattttggt atagcacaat cttctaccag aggtggcagt agagtcgaag   1860
ggatttttgc aggattgttt atgaatgcct atggtgcagg gcaagtgatg ttacggtggg   1920
gagtcttagc aaaatcagtt aaaaatatta tgttaggaca tgctagtgtg caagcagaaa   1980
tggaacaagt tgttgaggtt tatgaatatg cccaaaaatt gggtggtgaa gcaggattct   2040
accatatatt gaacaaccca aaagcttcat tattatcctt gactcaattt cctcacttct   2100
ccagtgtagt attaggcaat gctgctggcc taggcataat gggagagtac agaggtacac   2160
cgaggaatca agatctatat gatgcagcaa aggcatatgc tgaacaactc aaagaaaatg   2220
gtgtgattaa ctacagtgta ctagacttga cagcagaaga actagaggct atcaaacatc   2280
agcttaatcc aaaagataat gatgtagagc tttgagttaa taaaaaaatg ggcaaataa    2340
atcatcatgg aaaagtttgc tcctgaattc catggagaag atgcaaacaa cagggctact   2400
aaatttctag agtcaataaa gggcaaattc gcatcaccta aagatcccaa gaaaaaagat   2460
agtatcatat ctgtcaactc aatagatata gaagtaacca aagaaagccc tataacatca   2520
aattcaacta ttatcaaccc aacaaatgag acagatgata ctgcagggaa caagcccaat   2580
tatcaaagaa aacctctagt aagtttcaaa gaagacccca caccaagtga taatcccttt   2640
tctaaactat acaaagaaac catagaaaca tttgataaca atgaagaaga atccagctat   2700
tcatatgagg aaataaatga tcagacaaac gacaatataa cggcaagatt agataggatt   2760
gatgaaaagt taagtgaaat actaggaatg cttcacacat tagtggtggc aagtgcagga   2820
cctacatctg ctcgggatgg tataagagat gccatggttg gtttaagaga agaaatgata   2880
gaaaaaatca gaactgaagc attaatgacc aatgacagat tagaagctat ggcaagactc   2940
aggaatgagg aaagtgaaaa gatggcaaaa gacacatcag atgaagtatc tctaaatcca   3000
acatcagaga aattgaacaa cctgttggaa gggaatgata gtgacaatga tctatcactt   3060
gaagatttct gattagttac caatcttaac atcaaaacac aacaccaaca gaagaccaac   3120
aaactaacca acccaatcat ccaaccaaac atccatctgc caatcagcta agcagccaac   3180
aaaacaacca gccaatccaa aactagccac ccggaaaaaa tcgacaatat agttacaaaa   3240
aaagaaaggg tggggcaaat atggaaacat acgtgaacaa gcttcacgaa ggctccacat   3300
```

-continued

```
acacagctgc tgttcaatac aatgtcctag aaaaagacga tgaccctgca tcacttacaa   3360
tatgggtgcc catgttccaa tcatctatgc cagcagattt actcataaaa gaactagcta   3420
atgtcaacat actagtgaaa caaatatcca cacccaaggg accttcacta agagtcatga   3480
taaactcaag aagtgcagtg ctagcacaaa tgcccagcaa atttaccata agcgctaatg   3540
tgtccttaga tgaaagaagc aaactagcat atgatgtaac cacaccctgt gaaatcaagg   3600
catgcagtct aacatgccta aaatcaaaaa atatgttaac tacagttaaa gatctcacta   3660
tgaagacact caaccctaca catgatatta ttgctttatg tgaatttgaa aacatagtaa   3720
catcaaaaaa agtcataata ccaacatacc taagatccat cagtgtcaga aataaggatc   3780
tgaacacact tgaaaatata acaaccactg aattcaaaaa tgctatcaca aatgcaaaaa   3840
tcatccctta ctcaggatta ctattagtca tcacagtgac tgacaacaaa ggagcattca   3900
aatacataaa gccacaaagt caattcatag tagatcttgg agcttaccta gaaaaagaaa   3960
gtatatatta tgtcaccaca aattggaagc acacagctac aagatttgca atcaaaccta   4020
tggaagatta accttcttca actacatcag tgtgttaatt catacaaact ttctacctac   4080
attcttcact tcaccatcac aatcacaaac acttcgtggt tcaaccaatc aaacaaaact   4140
tatctaaagt cccagatcat cccaagtcat tgtttatcag atctagtact caaataagtt   4200
aataaaaaca tacacatggg gcaaataatc atcggagaaa atccaactaa tcacaatatc   4260
tgttaacata gacaagtcaa cacaccatac agaatcaacc gatggaaaat acatccataa   4320
caatagaatt ctcaagcaaa ttctggccct actttacact aatacacatg atcacaacaa   4380
taatctcttt actaatcata atctccatca tgattgcaat actaaacaaa ctttgtgaat   4440
ataacgtatt ccataacaaa acctttgagt taccaagagc tcgagtcaac acatagcatt   4500
catcaatcca acagctcaaa acagtaacct tgtatttaaa agtgaacaac ccctgcctct   4560
ttacaacacc ttatcaacgt cccaccatgc aaaccaccat ccatactata tagtagttaa   4620
ttaaaatagt cataacaatg aactaggata tcaagactaa caataacatt ggggcaaatg   4680
caaacatgtc caaaaacaaa gaccaacgca ctgctaagac actagaaagg acctgggaca   4740
ctctcaatca tttattattc atatcatcgt gcttatataa gttaaatctt aaatctgtag   4800
cacaaatcac attatccatt ttggcaatga taatctcaac ttcacttata attgcagcca   4860
tcatattcat tgcctcggca aaccacaaag tcacatcaac aactacaatc atacaagatg   4920
caacaagcca gatcaagaac acaaccccaa catacctcac ccagagtcct cagcttggaa   4980
tcagtccctc taatccgtct gaaattacat cacaaatcac caccatacta gcttcaacaa   5040
caccaggagt caagtcaacc ctgcaatcca caacagtcgg gaccaagaat acaacacaa   5100
ctcaagcaca acccagcaag cccaccacaa aacaacgcca aaacaaacca ccaagcaaac   5160
ccaacaatga ttttcacttt gaagtgttca actttgtacc ctgcagcata tgcagcaaca   5220
atccaacctg ctgggccatc tgcaaaagaa tacccaacaa aaaaccagga aagaaaacca   5280
ccaccaagcc cacagaagaa ccaaccttca agacggccaa agaggatccc aaacctcaga   5340
ccactggatc gggggaggtg cccaccacca agcccacagg ggagccaact atcaacacca   5400
ccaaaacaaa catcacaact acactactca cctccaacac cacgagaaat ccagaactca   5460
caagtcaaat ggaaaccttc cactcaactt cctccgaagg taatccaagc ccttctcaag   5520
tctccataac atccgagtac ctatcacaac cttcatctcc acccaacaca ccacgctagt   5580
agttattaaa aaacatatta tcacagaaag ccatgaccaa ctcaaacaga atcaaaataa   5640
```

```
actctggggc aaataacaat ggagttgcca atcctcaaag cgaatgcaat taccacaatc   5700
ctcactgcag tcacattttg ttttgcttct agtcaaaaca tcactgaaga attttatcaa   5760
tcaacatgca gtgcagttag caaaggctat cttagtgctc taagaactgg ttggtatacc   5820
agtgttataa ctatagaatt aagtaatatc aaggaaaata agtgtaatgg aacagatgct   5880
aaggtaaaat tgataaaaca agaattagat aaatataaaa atgctgtaac agaattgcag   5940
ttgctaatgc aaagcacacc agcagcaaac aatcgagcca gaagagaact accaaggttt   6000
atgaattata cactcaacaa tgccaaaaaa accaatgtaa cattaagcaa aaaaaggaaa   6060
agaagatttc ttggtttttt gttaggagtt ggatctgcaa tcgccagtgg cattgctgta   6120
tctaaggtcc tacacctaga aggggaagtg aacaagatca aaagtgctct actatccaca   6180
aacaaggctg tagtcagctt atcaaatgga gttagtgtct taaccagcaa agtgttagac   6240
ctcaaaaatt atatagataa acaattgtta cctattgtga acaagcaaag ctgcagcata   6300
tcaaatatag aaactgtgat agagttccaa caaaagaaca acagactact agagattacc   6360
agggaattta gtgttaatgc aggtgtaact acacctgtaa gcacttacat gttgactaat   6420
agtgaattat tgtcattaat caatgatatg cctataacaa atgatcagaa gaagttaatg   6480
tccaacaatg ttcaaatagt tagacagcaa agttactcta tcatgtccat aataaaanag   6540
gaagtcttag catatgtagt acaattacca ctatatggtg ttatagatac accttgttgg   6600
aaattacaca catcccctct atgtacaacc aacacaaaag aagggtccaa catctgttta   6660
acaagaactg acagaggatg gtactgtgac aatgcaggat cagtctcttt cttcccacaa   6720
gctgaaacat gtaaagttca atcgaatcga gtattttgtg acacaatgaa cagtttaaca   6780
ttaccaagtg aagtaaatct ctgcaatgtt gacatattca atcccaaata tgattgtaaa   6840
attatgactt caaaaacaga tgtaagcagc tctgttatca catctctagg agccattgtg   6900
tcatgctatg gcaaaactaa atgtacagca tccaataaaa atcgtggaat cataaagaca   6960
ttttctaacg ggtgcgatta tgtatcaaat aaaggggtgg acactgtgtc tgtaggcaac   7020
acattatatt atgtaaataa gcaagaaggc aaaagtctct atgtaaaagg tgaaccaata   7080
ataaatttct atgacccatt agtattcccc tctgntgaat ttgatgcatc aatatctcaa   7140
gtcaacgaga agattaacca gagcctggca tttattcgta aatccgatga attattacat   7200
aatgtaaatg ctggtaaatc caccacaaac atcatgataa ctgctataat tatagtgatt   7260
gtagtaatat tattatcatt aattgctgta ggactgctcc tatactgtaa ggccagaagc   7320
acaccagtca cactaagcaa agatcaactg agtggtataa ataatattgc atttagtaac   7380
taaataaaat agcatctaat catgttctta cgatggttta ctatctactc atagacagcc   7440
catctgtcat tggattttcc taaaatctga acttcatcga aactctcatc tataaaccat   7500
ctcacttaca ctatttaagt agattcctag ttcatagtta tataaaacat aattgaatgc   7560
cagattaact tactatctga aaaaatgaaa actggggcaa atatgtcacg aaggaatcct   7620
tgcaaatttg aaattcgagg tcattgctta aatggtaaga ggtgtcattt tagtcataat   7680
tattttgaat ggccaccccca tgcactgctt gtaagacaaa actttatgtt aaacagaata   7740
cttaagtcta tggataaaag tatagatacc ttatcagaaa taagtggagc tgcagagttg   7800
gacagaacag aagagtatgc tcttggtgta gttggagtgc tagagagtta tataggatca   7860
ataaacaata taactaaaca atcagcatgt gttgccatga gcaaactcct cactgaactc   7920
aatagtgatg atatcaaaaa gctgagggac aatgaagagc taaattcacc caagataaga   7980
gtgtacaata ctgtcatatc atatattgaa agcaacagga aaaacaataa acaaactatc   8040
```

```
catctgttaa aaagattgcc agcagacgtg ttgaagaaaa ccatcaaaaa cacattggat   8100
atccataaga gcataaccat caacaaccca aaagaattaa ctgttagtga tacaaatgac   8160
catgccaaaa ataatgatac tacctgacaa atatccttgt agtataactt ccatactaat   8220
tacaagtaga tgtagagtta ctatgtataa tcaaaagaac acactatatt tcaatcaaaa   8280
caatccaaat aaccatatgt actcactaaa tcaaacattc aatgaaatcc attggacctc   8340
tcaagatttg attgacacaa ttcaaaattt tctacaacat ctaggtatta ctgaggatat   8400
atatacaata tatatattag tgtcataaca ctcaattcta acacttacaa catcgttaca   8460
ttattaaatc aaacaattca agttgtggga caaaatggat cccattatta atggaaattc   8520
tgctaatgtt tatctaaccg atagttattt aaaaggtgtt atctctttct cagagtgtaa   8580
tgctttagga agctacatat tcaatggtcc ttatctcaaa aatgattata ccaacttaat   8640
tagtagacaa aatccattaa tagaacacat gaatctaaag aaactaaata taacacagtc   8700
cttaatatct aagtatcata aaggtgaaat aaaattagaa gaaccgactt attttcagtc   8760
attacttatg acatacaaga gtatgacctc gtcagaacag attgctacca ctaatttact   8820
taaaaagata ataagaagag ctatagaaat aagtgatgtc aaagtctatg ctatattgaa   8880
taaactaggg cttaaagaaa aggacaagat taaatccaac aatggacaag atgaagncaa   8940
ttcagttatt acgaccataa tcaaagatga tatactttca gctgttaaag ataatcaatc   9000
tcatcttaaa gcaggcaaaa atcactctac aaaacaaaaa gacacaatca aaacaacact   9060
cctgaagaaa ttgatgtgtt caatgcaaca tcctccatca tggttaatac attggtttaa   9120
cttatacaca aaattaaaca acatattaac acagtatcga tcaaatgagg taaaaaacca   9180
tgggtttaca ttgatagata atcaaactct tagtggattt caatttattt tgaaccaata   9240
tggttgtata gtttataata aggaactcaa aagaattact gtgacaacct ataatcaatt   9300
cttgacatgg aaagatatta gccttagtag attaaatgtt tgtttaatta catggattag   9360
taactgcttg aacacattaa ataaaagctt aggcttaaga tgcggattca ataatgttat   9420
cttaacacaa ctattccttt atggagattg tatactaaaa ctatttcaca atgaggggtt   9480
ctacataata aaagaggtag agggatttat tatgtctcta attttaaata taacagaaga   9540
agatcaattc agaaaacgat tttataatag tatgctcaac aacatcacag atgctgctaa   9600
taaagctcag aaaaatctgc tatcaagagt atgtcataca ttattagata agacagtatc   9660
cgataatata ataaatggca gatggataat tctattaagt aagttcctta aattaattaa   9720
gcttgcgggt gacaataacc ttaacaatct gagtgaacta tattttttgt tcagaatatt   9780
tggacaccca atggtagatg aaagacaagc catggatgct gttaaaatta attgcaatga   9840
gaccaaattt tacttgctaa gcagtctaag tatgttaaga ggtgccttta tatatagaat   9900
tataaaaggg tttgtaaata attacaacag atggcctact ttaagaaatg ctattgtttt   9960
acccttaaga tggttaactt actataaact aaacacttat ccttctttgt tggaacttac  10020
agaaagagat ttgattgtgt tatcaggact acgtttctat cgtgagtttc ggttgcctaa  10080
aaaagtggat cttgaaatga ttataaatga taaagctata tcacctccta aaaatttgat  10140
atggactagt ttccctagaa attacatgcc atcacacata caaaactata tagaacatga  10200
aaaattaaaa ttttccgaga gtgataaatc aagaagagta ttagagtatt atttaagaga  10260
taacaagttc aatgaatgtg atttatacaa ctgtgtagtt gatcaaagtt atctaaacaa  10320
ccctaatcat gtggtatcat tgacaggcaa agaaagagaa ctcagtgtag gtagaatgtt  10380
```

```
tgcaatgcaa ccgggaatgt tcagacaggt tcaaatatta gcagagaaaa tgatagctga  10440
aaacatttta caattctttc ctgaaagtct tacaagatat ggtgatctag aactacaaaa  10500
aatattagaa ttgaaagcag gaataagtaa caaatcaaat cgctacaatg acaattacaa  10560
caattacatt agtaagtgct ctatcatcac agatctcagc aaattcaatc aagcatttcg  10620
atatgaaacg tcatgtattt gtagtgatgt gcttgatgaa ctgcatggtg tacaatctct  10680
attttcctgg ttacatttaa ctattcctca tgttacaata atatgtacat ataggcatgc  10740
acccccctat ataggagatc atattgtaga tcttaacaat gtagatgaac aaagtggatt  10800
atatagatat cacatgggtg gcatcgaagg gtggtgtcaa aaactatgga ccatagaagc  10860
tatatcacta ttggatctaa tatctctcaa agggaaattc tcaattactg ctttaattaa  10920
tggtgacaat caatcaatag atataagcaa accaattaga ctcatggaag gtcaaactca  10980
tgctcaagca gattatttgc tagcattaaa tagccttaaa ttactgtata aagagtatgc  11040
aggcataggc cacaaattaa aaggaactga gacttatata tcacgagata tgcaatttat  11100
gagtaaaaca attcaacata acggtgtgta ttacccagct agtataaaga aagtcctaag  11160
agtgggaccg tggataaaca ctatacttga tgatttcaaa gtgagtttag aatctatagg  11220
tagtttgaca caagaattag aatatagagg tgaaagtcta ttatgcagtt taatatttag  11280
aaatgtatgg ttatataatc agattgctct acaattaaaa aatcatgcat tatgtaacaa  11340
taaactatat ttggacatat taaaggttct gaaacactta aaaacctttt ttaatcttga  11400
taatattgat acagcattaa cattgtatat gaatttacct atgttatttg gtggtggtga  11460
tcccaacttg ttatatcgaa gtttctatag aagaaccccc gacttcctca cagaggctat  11520
agttcactct gtgttcatac ttagttatta tacaaaccat gacttaaaag ataaacttca  11580
agatctgtca gatgatagat tgaataagtt cttaacatgc ataatcacgt ttgacaaaaa  11640
ccctaacgct gaattcgtaa cattgatgag agatcctcaa gctttagggt ctgagagaca  11700
agctaaaatt actagcgaaa tcaataggct ggcagttaca gaggttttga gtacagctcc  11760
aaacaaaata ttctccaaaa gtgcacaaca ttataccact acagagatag atctaaatga  11820
tattatgcaa aatatagaac ctacatatcc tcatgggcta agagttgttt atgaaagttt  11880
accctttttat aaagcagaga aaatagtaaa tcttatatca ggtacaaaat ctataactaa  11940
catactggaa aaaacttctg ccatagactt aacagatatt gatagagcca ctgagatgat  12000
gaggaaaaac ataactttgc ttataaggat acttccattg gattgtaaca gagataaaag  12060
agagatattg agtatggaaa acctaagtat tactgaatta agcaaatatg ttagggaaag  12120
atcttggtct ttattcaata tagttggtgt tacatcaccc agtatcatgt atacaatgga  12180
catcaaatat actacaagca ctatagctag tggcataatt atagagaaat ataatgttaa  12240
cagtttaaca cgtggtgaga gaggacccac taaaccatgg gttggttcat ctacacaaga  12300
gaaaaaaaca atgccagttt ataatagaca agtcttaacc aaaaaacaga gagatcaaat  12360
agatctatta gcaaaattgg attgggtgta tgcatctata gataacaagg atgaattcat  12420
ggaagaactc agcataggaa ccccttgggtt aacatatgaa aaagccaaga aattatttcc  12480
acaatattta agtgtcaact atttgcatcg acttacagtc agtagtagac catgtgaatt  12540
ccctgcatca ataccagctt atagaacaac aaattatcac tttgacacta gccctattaa  12600
tcgcatatta acagaaaagt atggtgatga agatattgac atagtattcc aaaactgtat  12660
aagctttggc cttagcttaa tgtcagtagt agaacaattt actaatgtat gtcctaacag  12720
aattattctc atacctaagc ttaatgagat acatttgatg aaacctccca tattcacagg  12780
```

tgatgttgat attcacaagt taaaacaagt gatacaaaaa cagcatatgt ttttaccaga 12840
caaaataagt ttgactcaat atgtagaatt attcttaagt aataaaacac tcaaatctgg 12900
atctcatgtt aattctaatt taatattggc acataaaata tctgactatt ttcataatac 12960
ttacatttta agtactaatt tagctggaca ttggattctg attatacaac ttatgaaaga 13020
ttctaagggt atttttgaaa aagattgggg agagggatat ataactgatc atatgtttat 13080
taatttgaaa gttttcttca atgcctataa gacctatctc ttgtgttttc ataaaggtta 13140
tggcaaagca aagctggagt gtgatatgaa cacctcagat ctcctatgtg tattggaatt 13200
aatagacagt agttattgga aatctatgtc taaggtattt ttagaacaaa aagttatcaa 13260
atacattctt agccaagatg caagtttaca tagagtaaaa ggatgtcata gcttcaaatt 13320
atggtttctt aaacgtctta atgtagcaga attcacagtt tgcccttggg ttgttaacat 13380
agattatcat ccaacacata tgaaagcaat attaacttat atagatcttg ttagaatggg 13440
attgataaat atagatagaa tacacattaa aaataaacac aaattcaatg atgaattttta 13500
tacttctaat ctcttctaca ttaattataa cttctcagat aatactcatc tattaactaa 13560
acatataagg attgctaatt ctgaattaga aaataattac aacaaattat atcatcctac 13620
accagaaacc ctagagaata tactagccaa tccgattaaa agtaatgaca aaaagacact 13680
gaatgaatat tgtataggta aaaatgttga ctcaataatg ttaccattgt tatctaataa 13740
gaagcttatt aaatcgtctg caatgattag aaccaattac agcaaacaag atttgtataa 13800
tttattccct atggttgtga ttgatagaat tatagatcat tcaggcaata cagccaaatc 13860
caaccaactt tacactacta cttcccacca aatatcttta gtgcacaata gcacatcact 13920
ttactgcatg cttccttggc atcatattaa tagattcaat tttgtattta gttctacagg 13980
ttgtaaaatt agtatagagt atattttaaa agatcttaaa attaaagatc ccaattgtat 14040
agcattcata ggtgaaggag cagggaattt attattgcgt acagtagtgg aacttcatcc 14100
tgacataaga tatatttaca gaagtctgaa agattgcaat gatcatagtt tacctattga 14160
gtttttaagg ctgtacaatg gacatatcaa cattgattat ggtgaaaatt tgaccattcc 14220
tgctacagat gcaaccaaca acattcattg gtcttattta catataaagt ttgctgaacc 14280
tatcagtctt tttgtctgtg atgctgaatt gcctgtaaca gtcaattgga gtaaaattat 14340
aatagaatgg agcaagcatg taagaaagtg caagtactgt tcctcagtta ataaatgtat 14400
gttaatagta aaatatcatg ctcaagatga tattgatttc aaattagaca atataactat 14460
attaaaaact tatgtatgct taggcagtaa gttaaaggga tcggaggttt acttagtcat 14520
cacaataggt cctgcaaata tattcccagc atttaatgta gtacaaaatg ctaaattgat 14580
actatcaaga accaaaaatt tcatcatgcc taagaaagct gataaagagt ctattgatgc 14640
aaatattaaa agtttnatac cctttctttg ttaccctata acaaaaaaag gaattaatac 14700
tgcattgtca aaactaaaga gtgttgttag tggagatata ctatcatatt ctatagctgg 14760
acgtaatgaa gttttcagca ataaacttat aaatcataaa catatgaaca tcttaaaatg 14820
gttcaatcat gttttaaatt tcagatcaac agaattaaac tataaccatt tatatatggt 14880
agaatctaca tatccttacc taagtgaatt gttaaacagc ttgacaacca atgaacttaa 14940
aaaactgatt aaaatcacag gtagtctgtt atacaacttt cataatgaat aatgaataaa 15000
gatcttataa taaagattcc catagctata cactaccatt gtattcaatt atagttatta 15060
aaaattaaaa atcatataat tttttaaata acttttagtg aactaatcct aaagttatca 15120

```
ttttgatcta ggaggaataa atttaaatcc taatctaatt ggtttatatg tgtattaact  15180

aaactacgag atattagttt ttgac                                        15205


<210> SEQ ID NO 27
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 27

acgggaaaaa atgcgtacaa caaac                                           25


<210> SEQ ID NO 28
<211> LENGTH: 40
<212> TYPE: DNA
<213> ORGANISM: Artificial Sequence
<220> FEATURE:
<223> OTHER INFORMATION: oligonucleotide primer

<400> SEQUENCE: 28

gtgtagtcat gcatagagtt gttgttttag attgtgtgaa                           40


<210> SEQ ID NO 29
<211> LENGTH: 31
<212> TYPE: DNA
<213> ORGANISM: Artificial Sequence
<220> FEATURE:
<223> OTHER INFORMATION: oligonucleotide primer

<400> SEQUENCE: 29

tatcaactag ctaatcaatg tcactaacac c                                    31


<210> SEQ ID NO 30
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 30

cctctcccat ttcttttagc atttt                                           25


<210> SEQ ID NO 31
<211> LENGTH: 40
<212> TYPE: DNA
<213> ORGANISM: Artificial Sequence
<220> FEATURE:
<223> OTHER INFORMATION: oligonucleotide primer

<400> SEQUENCE: 31

ttcacacaat ctaaaacaac aactctatgc atgactacac                           40


<210> SEQ ID NO 32
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 32

tttgggcata ttcataaacc tcaac                                           25


<210> SEQ ID NO 33
<211> LENGTH: 40
```

<212> TYPE: DNA
<213> ORGANISM: Artificial Sequence
<220> FEATURE:
<223> OTHER INFORMATION: oligonucleotide primer

<400> SEQUENCE: 33
aatcccacaa aaaaatgcta aaagaaatgg gagaggtagc 40

<210> SEQ ID NO 34
<211> LENGTH: 31
<212> TYPE: DNA
<213> ORGANISM: Artificial Sequence
<220> FEATURE:
<223> OTHER INFORMATION: oligonucleotide primer

<400> SEQUENCE: 34
ctgtctcatt tgttgggttg ataatagttg a 31

<210> SEQ ID NO 35
<211> LENGTH: 33
<212> TYPE: DNA
<213> ORGANISM: Artificial Sequence
<220> FEATURE:
<223> OTHER INFORMATION: oligonucleotide primer

<400> SEQUENCE: 35
tatgaatatg cccaaaaatt gggtggtgaa gca 33

<210> SEQ ID NO 36
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 36
tggctggttg ttttgttggc tgctt 25

<210> SEQ ID NO 37
<211> LENGTH: 34
<212> TYPE: DNA
<213> ORGANISM: Artificial Sequence
<220> FEATURE:
<223> OTHER INFORMATION: oligonucleotide primer

<400> SEQUENCE: 37
gccctataac atcaaattca actattatca accc 34

<210> SEQ ID NO 38
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 38
cgcttatggt aaatttgctg ggcat 25

<210> SEQ ID NO 39
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 39
acatcagaga aattgaacaa cctgt 25

<210> SEQ ID NO 40
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 40
ttgtagctgt gtgcttccaa tttgt 25

<210> SEQ ID NO 41
<211> LENGTH: 34
<212> TYPE: DNA
<213> ORGANISM: Artificial Sequence
<220> FEATURE:
<223> OTHER INFORMATION: oligonucleotide primer

<400> SEQUENCE: 41
ctagcacaaa tgcccagcaa atttaccata agcg 34

<210> SEQ ID NO 42
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 42
gtggtttgca tggtgggacg ttgat 25

<210> SEQ ID NO 43
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 43
agatttgcaa tcaaacctat ggaag 25

<210> SEQ ID NO 44
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 44
ttcagacgga ttagagggac tgatt 25

<210> SEQ ID NO 45
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 45
catcaatcca acagctcaaa acagt 25

<210> SEQ ID NO 46
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 46
taccttcgga ggaagttgag tggaa 25

<210> SEQ ID NO 47
<211> LENGTH: 26
<212> TYPE: DNA
<213> ORGANISM: Artificial Sequence
<220> FEATURE:
<223> OTHER INFORMATION: oligonucleotide primer

<400> SEQUENCE: 47
gaaattacat caacaaatca ccacca 26

<210> SEQ ID NO 48
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 48
aaaccttggt agttctcttc tggct 25

<210> SEQ ID NO 49
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 49
taatccaagc ccttctcaag tctcc 25

<210> SEQ ID NO 50
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 50
gatgtgtgta atttccaaca aggtg 25

<210> SEQ ID NO 51
<211> LENGTH: 31
<212> TYPE: DNA
<213> ORGANISM: Artificial Sequence
<220> FEATURE:
<223> OTHER INFORMATION: oligonucleotide primer

<400> SEQUENCE: 51
cactcaacaa tgccaaaaaa accaatgtaa c 31

<210> SEQ ID NO 52
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 52
gcatcaaatt caccagaggg gaata 25

<210> SEQ ID NO 53
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 53
tagacagcaa agttactcta tcatg 25

<210> SEQ ID NO 54
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 54
gatggtttat agatgagagt ttcga 25

<210> SEQ ID NO 55
<211> LENGTH: 33
<212> TYPE: DNA
<213> ORGANISM: Artificial Sequence
<220> FEATURE:
<223> OTHER INFORMATION: oligonucleotide primer

<400> SEQUENCE: 55
acactgtgtc tgtaggcaac acattatatt atg 33

<210> SEQ ID NO 56
<211> LENGTH: 40
<212> TYPE: DNA
<213> ORGANISM: Artificial Sequence
<220> FEATURE:
<223> OTHER INFORMATION: oligonucleotide primer

<400> SEQUENCE: 56
gtctgctggc aatcttttta acagatggat agtttgttta 40

<210> SEQ ID NO 57
<211> LENGTH: 39
<212> TYPE: DNA
<213> ORGANISM: Artificial Sequence
<220> FEATURE:
<223> OTHER INFORMATION: oligonucleotide primer

<400> SEQUENCE: 57
tgccagatta acttactatc tgaaaaatga aaactgggg 39

<210> SEQ ID NO 58
<211> LENGTH: 40
<212> TYPE: DNA
<213> ORGANISM: Artificial Sequence
<220> FEATURE:
<223> OTHER INFORMATION: oligonucleotide primer

<400> SEQUENCE: 58
cactctgaga aagagataac accttttaaa taactatcgg 40

<210> SEQ ID NO 59
<211> LENGTH: 40
<212> TYPE: DNA
<213> ORGANISM: Artificial Sequence
<220> FEATURE:
<223> OTHER INFORMATION: oligonucleotide primer

<400> SEQUENCE: 59
taaacaaact atccatctgt taaaaagatt gccagcagac 40

<210> SEQ ID NO 60
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 60
gagtgatttt tgcctgcttt aagat 25

<210> SEQ ID NO 61
<211> LENGTH: 28
<212> TYPE: DNA
<213> ORGANISM: Artificial Sequence
<220> FEATURE:
<223> OTHER INFORMATION: oligonucleotide primer

<400> SEQUENCE: 61
ggaaattctg ctaatgttta tctaaccg 28

<210> SEQ ID NO 62
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 62
cgttttctga attgatcttc ttctg 25

<210> SEQ ID NO 63
<211> LENGTH: 31
<212> TYPE: DNA
<213> ORGANISM: Artificial Sequence
<220> FEATURE:
<223> OTHER INFORMATION: oligonucleotide primer

<400> SEQUENCE: 63
tcatcttaaa gcaggcaaaa atcactctac a 31

<210> SEQ ID NO 64
<211> LENGTH: 40
<212> TYPE: DNA
<213> ORGANISM: Artificial Sequence
<220> FEATURE:
<223> OTHER INFORMATION: oligonucleotide primer

<400> SEQUENCE: 64
cgtagtcctg ataacacaat caaatctctt tctgtaagtt 40

<210> SEQ ID NO 65
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 65
cagaagaaga tcaattcaga aaacg 25

<210> SEQ ID NO 66

<211> LENGTH: 27
<212> TYPE: DNA
<213> ORGANISM: Artificial Sequence
<220> FEATURE:
<223> OTHER INFORMATION: oligonucleotide primer

<400> SEQUENCE: 66
gcgatttgat ttgttactta ttcctgc 27

<210> SEQ ID NO 67
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 67
ccttctttgt tggaacttac agaaa 25

<210> SEQ ID NO 68
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 68
gcaaataatc tgcttgagca tgagt 25

<210> SEQ ID NO 69
<211> LENGTH: 31
<212> TYPE: DNA
<213> ORGANISM: Artificial Sequence
<220> FEATURE:
<223> OTHER INFORMATION: oligonucleotide primer

<400> SEQUENCE: 69
gaaagcagga ataagtaaca aatcaaatcg c 31

<210> SEQ ID NO 70
<211> LENGTH: 40
<212> TYPE: DNA
<213> ORGANISM: Artificial Sequence
<220> FEATURE:
<223> OTHER INFORMATION: oligonucleotide primer

<400> SEQUENCE: 70
cgttagggtt tttgtcaaac gtgattatgc atgttaagaa 40

<210> SEQ ID NO 71
<211> LENGTH: 40
<212> TYPE: DNA
<213> ORGANISM: Artificial Sequence
<220> FEATURE:
<223> OTHER INFORMATION: oligonucleotide primer

<400> SEQUENCE: 71
atagccttaa attactgtat aaagagtatg caggcatagg 40

<210> SEQ ID NO 72
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 72
tttttcctca tcatctcagt ggctc 25

<210> SEQ ID NO 73
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 73
gacttcctca cagaggctat agttc 25

<210> SEQ ID NO 74
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 74
gtaagtcgat gcaaatagtt gacac 25

<210> SEQ ID NO 75
<211> LENGTH: 28
<212> TYPE: DNA
<213> ORGANISM: Artificial Sequence
<220> FEATURE:
<223> OTHER INFORMATION: oligonucleotide primer

<400> SEQUENCE: 75
actttgctta taaggatact tccattgg 28

<210> SEQ ID NO 76
<211> LENGTH: 40
<212> TYPE: DNA
<213> ORGANISM: Artificial Sequence
<220> FEATURE:
<223> OTHER INFORMATION: oligonucleotide primer

<400> SEQUENCE: 76
ctctccccaa tctttttcaa aaataccctt agaatctttc 40

<210> SEQ ID NO 77
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 77
atttgcatcg acttacagtc agtag 25

<210> SEQ ID NO 78
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 78
gggtttctgg tgtaggatga tataatt 27

<210> SEQ ID NO 79
<211> LENGTH: 40
<212> TYPE: DNA

<213> ORGANISM: Artificial Sequence
<220> FEATURE:
<223> OTHER INFORMATION: oligonucleotide primer

<400> SEQUENCE: 79
gaaagattct aagggtattt ttgaaaaaga ttggggagag 40

<210> SEQ ID NO 80
<211> LENGTH: 36
<212> TYPE: DNA
<213> ORGANISM: Artificial Sequence
<220> FEATURE:
<223> OTHER INFORMATION: oligonucleotide primer

<400> SEQUENCE: 80
ccttcaccta tgaatgcata acaattggga tcttta 36

<210> SEQ ID NO 81
<211> LENGTH: 40
<212> TYPE: DNA
<213> ORGANISM: Artificial Sequence
<220> FEATURE:
<223> OTHER INFORMATION: oligonucleotide primer

<400> SEQUENCE: 81
ttacaacaaa ttatatcatc ctacaccaga aaccctagag 40

<210> SEQ ID NO 82
<211> LENGTH: 40
<212> TYPE: DNA
<213> ORGANISM: Artificial Sequence
<220> FEATURE:
<223> OTHER INFORMATION: oligonucleotide primer

<400> SEQUENCE: 82
cagctttctt aggcatgatg aaatttttgg ttcttgatag 40

<210> SEQ ID NO 83
<211> LENGTH: 40
<212> TYPE: DNA
<213> ORGANISM: Artificial Sequence
<220> FEATURE:
<223> OTHER INFORMATION: oligonucleotide primer

<400> SEQUENCE: 83
attaaagatc ccaattgtat agcattcata ggtgaaggag 40

<210> SEQ ID NO 84
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 84
ggttgtcaag ctgtttaaca attca 25

<210> SEQ ID NO 85
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 85
tcggaggttt acttagtcat cacaa 25

<210> SEQ ID NO 86
<211> LENGTH: 28
<212> TYPE: DNA
<213> ORGANISM: Artificial Sequence
<220> FEATURE:
<223> OTHER INFORMATION: oligonucleotide primer

<400> SEQUENCE: 86
ggtagtgtat agctatggga atctttat 28

<210> SEQ ID NO 87
<211> LENGTH: 420
<212> TYPE: DNA
<213> ORGANISM: Respiratory syncytial virus, S2

<400> SEQUENCE: 87
atgggcagca attcattgag tatgataaaa gttagattac aaaatttgtt tgacaatgat 60
gaagtagcat tgttaaaaat aacatgctat actgacaaat taatacattt aactaatgct 120
ttggctaagg cagtgataca tacaatcaaa ttgaatggca ttgtgtttgt gcatgttatt 180
acaagtagtg atatttgccc taacaataat attgtagtaa aatccaattt cacaacaatg 240
ccagtactac aaaatggagg ttatatatgg gaaatgatgg aattaacaca ttgctctcaa 300
cctaatggtc tactagatga caattgtgaa attaaattct ccaaaaaact aagtgattca 360
acaatgacca attatatgaa tcaattatct gaattacttg gatttgatct taatccataa 420

<210> SEQ ID NO 88
<211> LENGTH: 139
<212> TYPE: PRT
<213> ORGANISM: Respiratory syncytial virus

<400> SEQUENCE: 88

Met Gly Ser Asn Ser Leu Ser Met Ile Lys Val Arg Leu Gln Asn Leu
1 5 10 15

Phe Asp Asn Asp Glu Val Ala Leu Leu Lys Ile Thr Cys Tyr Thr Asp
20 25 30

Lys Leu Ile His Leu Thr Asn Ala Leu Ala Lys Ala Val Ile His Thr
35 40 45

Ile Lys Leu Asn Gly Ile Val Phe Val His Val Ile Thr Ser Ser Asp
50 55 60

Ile Cys Pro Asn Asn Asn Ile Val Val Lys Ser Asn Phe Thr Thr Met
65 70 75 80

Pro Val Leu Gln Asn Gly Gly Tyr Ile Trp Glu Met Met Glu Leu Thr
85 90 95

His Cys Ser Gln Pro Asn Gly Leu Leu Asp Asp Asn Cys Glu Ile Lys
100 105 110

Phe Ser Lys Lys Leu Ser Asp Ser Thr Met Thr Asn Tyr Met Asn Gln
115 120 125

Leu Ser Glu Leu Leu Gly Phe Asp Leu Asn Pro
130 135

<210> SEQ ID NO 89
<211> LENGTH: 420
<212> TYPE: DNA
<213> ORGANISM: Respiratory syncytial virus, strain 287 and p17

<400> SEQUENCE: 89
atgggcagca attcattgag tatgataaaa gttagattac aaaatttgtt tgacaatgat 60

```
gaagtagcat tgttaaaaat aacatgctat actgataaat taatacattt aactaatgct    120

ttggctaagg cagtgataca tacaataaaa ttgaatggca ttgtgtttgt gcatgttatt    180

acaagtagtg atatttgccc taataataat attgtagtaa aatccaattt cacaacaatg    240

ccagtactac aaaatggagg ctatatatgg gaaatgatgg aattaacaca ttgctctcaa    300

cctaatggtc tactagatga caattgtgaa attaaattct ccaaaaaact aagtgattca    360

acaatgacca attatatgaa tcaattatct gaattgcttg gatttgatct taatccataa    420
```

<210> SEQ ID NO 90
<211> LENGTH: 420
<212> TYPE: DNA
<213> ORGANISM: Respiratory syncytial virus, Merck strain p17_pp

<400> SEQUENCE: 90

```
atgggcagca attcattgag tatgataaaa gttagattac aaaatttgtt tgacaatgat     60

gaagtagcat tgttaaaaat aacatgctat actgataaat taatacattt aactaatgct    120

ttggctaagg cagtgataca tacaataaaa ttgaatggca tagtgtttgt gcatgttatt    180

acaagtagtg atatttgccc taataataat attgtagtaa aatccaattt cacaacaatg    240

ccagtactac aaaatggagg ctatatatgg gaaatgatgg aattaacaca ttgctctcaa    300

cctaatggtc tactagatga caattgtgaa attaaattct ccaaaaaact aagtgattca    360

acaatgacca attatatgaa tcaattatct gaattgcttg gatttgatct taatccataa    420
```

<210> SEQ ID NO 91
<211> LENGTH: 15205
<212> TYPE: DNA
<213> ORGANISM: Respiratory syncytial virus, Merck strain p17_pp

<400> SEQUENCE: 91

```
acgggaaaaa atgcgtacaa caaacttgcg taaaccaaaa aaatggggca aataagagtt     60

tgataagtac cacttaaatt taactccctt agttagagat gggcagcaat tcattgagta    120

tgataaaagt tagattacaa aatttgtttg acaatgatga agtagcattg ttaaaaataa    180

catgctatac tgataaatta atacatttaa ctaatgcttt ggctaaggca gtgatacata    240

caataaaatt gaatggcata gtgtttgtgc atgttattac aagtagtgat atttgcccta    300

ataataatat tgtagtaaaa tccaatttca caacaatgcc agtactacaa aatggaggct    360

atatatggga aatgatggaa ttaacacatt gctctcaacc taatggtcta ctagatgaca    420

attgtgaaat taaattctcc aaaaaactaa gtgattcaac aatgaccaat tatatgaatc    480

aattatctga attgcttgga tttgatctta atccataaat tataattaat atcaactagc    540

taatcaatgt cactaacacc attagttaat ataaaactta acagaagaca aaaatggggc    600

aaataaatca attcagccaa cccaaccatg gacacgactc acaatgatac cacaccacaa    660

agactgatga tcacagatat gagaccattg tcacttgaga ccataataac atcactaacc    720

agagacatca taacacacaa atttatatac ttgataaatc atgaatgcat agtgagaaaa    780

cttgatgaaa gacaagccac atttacattc ctggtcaact atgaaatgaa actattgcac    840

aaagtaggaa gcactaaata taaaaaatat actgaataca acacaaaata tggcactttc    900

cctatgccga tattcatcaa tcatgatggg ttcttagaat gcattggcat taaacctaca    960

aagcatactc ccataatata caagtatgat ctcaatccat aaacttcaac acaatattca   1020

cacaatctaa aacaacaact ctatgcatga ctacactcca tagtccaaat ggagcctgaa   1080
```

```
aattatagta atttaaaatt aaggagagat ataagataga agatggggca aatacaaaga   1140
tggctcttag caaagtcaag ttgaatgata cactcaacaa agatcaactt ctgtcatcta   1200
gcaaatacac catccaacgg agcacaggag atagtattga tactcctaat tatgatgtgc   1260
agaaacacat caataagtta tgtggcatgt tattaatcac agaagatgct aatcataaat   1320
tcactgggtt aataggtatg ttatatgcga tgtctaggtt aggaagagaa gacaccataa   1380
aaatactcag agatgcggga tatcatgtaa aagcaaatgg agtagatgta acaacacatc   1440
gtcaagacat taatgggaaa gaaatgaaat ttgaagtgtt aacattggca agcttaacaa   1500
ctgaaattca aatcaacatt gaaatagaat ctagaaaatc ctacaaaaaa atgctaaaag   1560
aaatgggaga ggtagctcca gaatacaggc atgactctcc tgattgtggg atgataatat   1620
tatgtatagc agcattagta ataaccaaat tggcagcagg ggatagatct ggtcttacag   1680
ctgtgattag gagagctaat aatgtcttaa aaaatgaaat gaaacgttat aaaggcttac   1740
tacccaagga catagccaac agcttctatg aggtgtttga aaaacatccc cactttatag   1800
atgtttttgt tcattttggt atagcacaat cttctaccag aggtggcagt agagtcgaag   1860
ggatttttgc aggattgttt atgaatgcct atggtgcagg gcaagtgatg ttacggtggg   1920
gagtcttagc aaaatcagtt aaaaatatta tgttaggaca tgctagtgtg caagcagaaa   1980
tggaacaagt tgttgaggtt tatgaatatg cccaaaaatt gggtggtgaa gcaggattct   2040
accatatatt gaacaaccca aaagcttcat tattatcctt gactcaattt cctcacttct   2100
ccagtgtagt attaggcaat gctgctggcc taggcataat gggagagtac agaggtacac   2160
cgaggaatca agatctatat gatgcagcaa aggcatatgc tgaacaactc aaagaaaatg   2220
gtgtgattaa ctacagtgta ctagacttga cagcagaaga actagaggct atcaaacatc   2280
agcttaatcc aaaagataat gatgtagagc tttgagttaa taaaaaaatg gggcaaataa   2340
atcatcatgg aaaagtttgc tcctgaattc catggagaag atgcaaacaa cagggctact   2400
aaatttctag agtcaataaa gggcaaattc gcatcaccta aagatcccaa gaaaaaagat   2460
agtatcatat ctgtcaactc aatagatata gaagtaacca aagaaagccc tataacatca   2520
aattcaacta ttatcaaccc aacaaatgag acagatgata ctgcagggaa caagcccaat   2580
tatcaaagaa aacctctagt aagtttcaaa gaagacccca caccaagtga taatcccttt   2640
tctaaactat acaaagaaac catagaaaca tttgataaca atgaagaaga atccagctat   2700
tcatatgagg aaataaatga tcagacaaac gacaatataa cggcaagatt agataggatt   2760
gatgaaaagt taagtgaaat actaggaatg cttcacacat tagtggtggc aagtgcagga   2820
cctacatctg ctcgggatgg tataagagat gccatggttg gtttaagaga agaaatgata   2880
gaaaaaatca gaactgaagc attaatgacc aatgacagat tagaagctat ggcaagactc   2940
aggaatgagg aaagtgaaaa gatggcaaaa gacacatcag atgaagtatc tctaaatcca   3000
acatcagaga aattgaacaa cctgttggaa gggaatgata gtgacaatga tctatcactt   3060
gaagatttct gattagttac caatcttaac atcaaaacac aacaccaaca gaagaccaac   3120
aaactaacca acccaatcat ccaaccaaac atccatctgc caatcagcta agcagccaac   3180
aaaacaacca gccaatccaa aactagccac ccggaaaaaa tcgacaatat agttacaaaa   3240
aaagaaaggg tggggcaaat atggaaacat acgtgaacaa gcttcacgaa ggctccacat   3300
acacagctgc tgttcaatac aatgtcctag aaaaagacga tgaccctgca tcacttacaa   3360
tatgggtgcc catgttccaa tcatctatgc cagcagattt actcataaaa gaactagcta   3420
atgtcaacat actagtgaaa caaatatcca cacccaaggg accttcacta agagtcatga   3480
```

```
taaactcaag aagtgcagtg ctagcacaaa tgcccagcaa atttaccata agcgctaatg   3540
tgtccttaga tgaaagaagc aaactagcat atgatgtaac cacaccctgt gaaatcaagg   3600
catgcagtct aacatgccta aaatcaaaaa atatgttaac tacagttaaa gatctcacta   3660
tgaagacact caaccctaca catgatatta ttgctttatg tgaatttgaa aacatagtaa   3720
catcaaaaaa agtcataata ccaacatacc taagatccat cagtgtcaga aataaggatc   3780
tgaacacact tgaaaatata acaaccactg aattcaaaaa tgctatcaca aatgcaaaaa   3840
tcatccctta ctcaggatta ctattagtca tcacagtgac tgacaacaaa ggagcattca   3900
aatacataaa gccacaaagt caattcatag tagatcttgg agcttaccta gaaaaagaaa   3960
gtatatatta tgtcaccaca aattggaagc acacagctac aagatttgca atcaaaccta   4020
tggaagatta accttcttca actacatcag tgtgttaatt catacaaact ttctacctac   4080
attcttcact tcaccatcac aatcacaaac acttcgtggt tcaaccaatc aaacaaaact   4140
tatctaaagt cccagatcat cccaagtcat tgtttatcag atctagtact caaataagtt   4200
aataaaaaca tacacatggg gcaaataatc atcggagaaa atccaactaa tcacaatatc   4260
tgttaacata gacaagtcaa cacaccatac agaatcaacc gatggaaaat acatccataa   4320
caatagaatt ctcaagcaaa ttctggccct actttacact aatacacatg atcacaacaa   4380
taatctcttt actaatcata atctccatca tgattgcaat actaaacaaa ctttgtgaat   4440
ataacgtatt ccataacaaa acctttgagt taccaagagc tcgagtcaac acatagcatt   4500
catcaatcca acagctcaaa acagtaacct tgtatttaaa agtgaacaac ccctgcctct   4560
ttacaacacc ttatcaacgt cccaccatgc aaaccaccat ccatactata tagtagttaa   4620
ttaaaatagt cataacaatg aactaggata tcaagactaa caataacatt ggggcaaatg   4680
caaacatgtc caaaaacaaa gaccaacgca ctgctaagac actagaaagg acctgggaca   4740
ctctcaatca tttattattc atatcatcgt gcttatataa gttaaatctt aaatctgtag   4800
cacaaatcac attatccatt ttggcaatga taatctcaac ttcacttata attgcagcca   4860
tcatattcat tgcctcggca aaccacaaag tcacatcaac aactacaatc atacaagatg   4920
caacaagcca gatcaagaac acaaccccaa catacctcac ccagagtcct cagcttggaa   4980
tcagtccctc taatccgtct gaaattacat cacaaatcac caccatacta gcttcaacaa   5040
caccaggagt caagtcaacc ctgcaatcca caacagtcgg gaccaagaat acaacaacaa   5100
ctcaagcaca acccagcaag cccaccacaa aacaacgcca aaacaaacca ccaagcaaac   5160
ccaacaatga ttttcacttt gaagtgttca actttgtacc ctgcagcata tgcagcaaca   5220
atccaacctg ctgggccatc tgcaaaagaa tacccaacaa aaaaccagga aagaaaacca   5280
ccaccaagcc cacagaagaa ccaaccttca agacggccaa agaggatccc aaacctcaga   5340
ccactggatc gggggaggtg cccaccacca agcccacagg ggagccaact atcaacacca   5400
ccaaaacaaa catcacaact acactactca cctccaacac cacgagaaat ccagaactca   5460
caagtcaaat ggaaaccttc cactcaactt cctccgaagg taatccaagc ccttctcaag   5520
tctccataac atccgagtac ctatcacaac cttcatctcc acccaacaca ccacgctagt   5580
agttattaaa aacatattta tcacagaaag ccatgaccaa ctcaaacaga atcaaaataa   5640
actctggggc aaataacaat ggagttgcca atcctcaaag cgaatgcaat taccacaatc   5700
ctcactgcag tcacattttg ttttgcttct agtcaaaaca tcactgaaga attttatcaa   5760
tcaacatgca gtgcagttag caaaggctat cttagtgctc taagaactgg ttggtatacc   5820
```

```
agtgttataa ctatagaatt aagtaatatc aaggaaaata agtgtaatgg aacagatgct   5880
aaggtaaaat tgataaaaca agaattagat aaatataaaa atgctgtaac agaattgcag   5940
ttgctaatgc aaagcacacc agcagcaaac aatcgagcca gaagagaact accaaggttt   6000
atgaattata cactcaacaa tgccaaaaaa accaatgtaa cattaagcaa aaaaaggaaa   6060
agaagatttc ttggtttttt gttaggagtt ggatctgcaa tcgccagtgg cattgctgta   6120
tctaaggtcc tacacctaga aggggaagtg aacaagatca aaagtgctct actatccaca   6180
aacaaggctg tagtcagctt atcaaatgga gttagtgtct taaccagcaa agtgttagac   6240
ctcaaaaatt atatagataa acaattgtta cctattgtga acaagcaaag ctgcagcata   6300
tcaaatatag aaactgtgat agagttccaa caaaagaaca acagactact agagattacc   6360
agggaattta gtgttaatgc aggtgtaact acacctgtaa gcacttacat gttgactaat   6420
agtgaattat tgtcattaat caatgatatg cctataacaa atgatcagaa gaagttaatg   6480
tccaacaatg ttcaaatagt tagacagcaa agttactcta tcatgtccat aataaaaaag   6540
gaagtcttag catatgtagt acaattacca ctatatggtg ttatagatac accttgttgg   6600
aaattacaca catcccctct atgtacaacc aacacaaaag aagggtccaa catctgttta   6660
acaagaactg acagaggatg gtactgtgac aatgcaggat cagtctcttt cttcccacaa   6720
gctgaaacat gtaaagttca atcgaatcga gtattttgtg acacaatgaa cagtttaaca   6780
ttaccaagtg aagtaaatct ctgcaatgtt gacatattca atcccaaata tgattgtaaa   6840
attatgactt caaaaacaga tgtaagcagc tctgttatca catctctagg agccattgtg   6900
tcatgctatg gcaaaactaa atgtacagca tccaataaaa atcgtggaat cataaagaca   6960
ttttctaacg ggtgcgatta tgtatcaaat aaaggggtgg acactgtgtc tgtaggcaac   7020
acattatatt atgtaaataa gcaagaaggc aaaagtctct atgtaaaagg tgaaccaata   7080
ataaatttct atgacccatt agtattcccc tctggtgaat ttgatgcatc aatatctcaa   7140
gtcaacgaga agattaacca gagcctggca tttattcgta aatccgatga attattacat   7200
aatgtaaatg ctggtaaatc caccacaaac atcatgataa ctgctataat tatagtgatt   7260
gtagtaatat tattatcatt aattgctgta ggactgctcc tatactgtaa ggccagaagc   7320
acaccagtca cactaagcaa agatcaactg agtggtataa ataatattgc atttagtaac   7380
taaataaaat agcatctaat catgttctta cgatggttta ctatctactc atagacagcc   7440
catctgtcat tggattttcc taaaatctga acttcatcga aactctcatc tataaaccat   7500
ctcacttaca ctatttaagt agattcctag ttcatagtta tataaaacat aattgaatgc   7560
cagattaact tactatctga aaaaatgaaa actggggcaa atatgtcacg aaggaatcct   7620
tgcaaatttg aaattcgagg tcattgctta aatggtaaga ggtgtcattt tagtcataat   7680
tattttgaat ggccacccca tgcactgctt gtaagacaaa actttatgtt aaacagaata   7740
cttaagtcta tggataaaag tatagatacc ttatcagaaa taagtggagc tgcagagttg   7800
gacagaacag aagagtatgc tcttggtgta gttggagtgc tagagagtta tataggatca   7860
ataaacaata taactaaaca atcagcatgt gttgccatga gcaaactcct cactgaactc   7920
aatagtgatg atatcaaaaa gctgagggac aatgaagagc taaattcacc caagataaga   7980
gtgtacaata ctgtcatatc atatattgaa agcaacagga aaaacaataa acaaactatc   8040
catctgttaa aaagattgcc agcagacgtg ttgaagaaaa ccatcaaaaa cacattggat   8100
atccataaga gcataaccat caacaaccca aaagaattaa ctgttagtga tacaaatgac   8160
catgccaaaa ataatgatac tacctgacaa atatccttgt agtataactt ccatactaat   8220
```

```
tacaagtaga tgtagagtta ctatgtataa tcaaaagaac acactatatt tcaatcaaaa   8280
caatccaaat aaccatatgt actcactaaa tcaaacattc aatgaaatcc attggacctc   8340
tcaagatttg attgacacaa ttcaaaattt tctacaacat ctaggtatta ctgaggatat   8400
atatacaata tatatattag tgtcataaca ctcaattcta acacttacaa catcgttaca   8460
ttattaaatc aaacaattca agttgtggga caaaatggat cccattatta atggaaattc   8520
tgctaatgtt tatctaaccg atagttattt aaaaggtgtt atctctttct cagagtgtaa   8580
tgctttagga agctacatat tcaatggtcc ttatctcaaa aatgattata ccaacttaat   8640
tagtagacaa aatccattaa tagaacacat gaatctaaag aaactaaata taacacagtc   8700
cttaatatct aagtatcata aaggtgaaat aaaattagaa gaaccgactt attttcagtc   8760
attacttatg acatacaaga gtatgacctc gtcagaacag attgctacca ctaatttact   8820
taaaaagata ataagaagag ctatagaaat aagtgatgtc aaagtctatg ctatattgaa   8880
taaactaggg cttaaagaaa aggacaagat taaatccaac aatggacaag atgaagccaa   8940
ttcagttatt acgaccataa tcaaagatga tatactttca gctgttaaag ataatcaatc   9000
tcatcttaaa gcaggcaaaa atcactctac aaaacaaaaa gacacaatca aaacaacact   9060
cctgaagaaa ttgatgtgtt caatgcaaca tcctccatca tggttaatac attggtttaa   9120
cttatacaca aaattaaaca acatattaac acagtatcga tcaaatgagg taaaaaacca   9180
tgggtttaca ttgatagata atcaaactct tagtggattt caatttattt tgaaccaata   9240
tggttgtata gtttataata aggaactcaa aagaattact gtgacaacct ataatcaatt   9300
cttgacatgg aaagatatta gccttagtag attaaatgtt tgtttaatta catggattag   9360
taactgcttg aacacattaa ataaaagctt aggcttaaga tgcggattca ataatgttat   9420
cttaacacaa ctattccttt atggagattg tatactaaaa ctatttcaca atgaggggtt   9480
ctacataata aaagaggtag agggatttat tatgtctcta attttaaata taacagaaga   9540
agatcaattc agaaaacgat tttataatag tatgctcaac aacatcacag atgctgctaa   9600
taaagctcag aaaaatctgc tatcaagagt atgtcataca ttattagata agacagtatc   9660
cgataatata ataaatggca gatggataat tctattaagt aagttcctta aattaattaa   9720
gcttgcgggt gacaataacc ttaacaatct gagtgaacta tattttttgt tcagaatatt   9780
tggacaccca atggtagatg aaagacaagc catggatgct gttaaaatta attgcaatga   9840
gaccaaattt tacttgctaa gcagtctaag tatgttaaga ggtgccttta tatatagaat   9900
tataaaaggg tttgtaaata attacaacag atggcctact ttaagaaatg ctattgtttt   9960
acccttaaga tggttaactt actataaact aaacacttat ccttctttgt tggaacttac  10020
agaaagagat ttgattgtgt tatcaggact acgtttctat cgtgagtttc ggttgcctaa  10080
aaaagtggat cttgaaatga ttataaatga taaagctata tcacctccta aaaatttgat  10140
atggactagt ttccctagaa attacatgcc atcacacata caaaactata tagaacatga  10200
aaaattaaaa ttttccgaga gtgataaatc aagaagagta ttagagtatt atttaagaga  10260
taacaagttc aatgaatgtg atttatacaa ctgtgtagtt gatcaaagtt atctaaacaa  10320
ccctaatcat gtggtatcat tgacaggcaa agaaagagaa ctcagtgtag gtagaatgtt  10380
tgcaatgcaa ccgggaatgt tcagacaggt tcaaatatta gcagagaaaa tgatagctga  10440
aaacatttta caattctttc ctgaaagtct tacaagatat ggtgatctag aactacaaaa  10500
aatattagaa ttgaaagcag gaataagtaa caaatcaaat cgctacaatg acaattacaa  10560
```

```
caattacatt agtaagtgct ctatcatcac agatctcagc aaattcaatc aagcatttcg 10620
atatgaaacg tcatgtattt gtagtgatgt gcttgatgaa ctgcatggtg tacaatctct 10680
attttcctgg ttacatttaa ctattcctca tgttacaata atatgtacat ataggcatgc 10740
acccccctat ataggagatc atattgtaga tcttaacaat gtagatgaac aaagtggatt 10800
atatagatat cacatgggtg gcatcgaagg gtggtgtcaa aaactatgga ccatagaagc 10860
tatatcacta ttggatctaa tatctctcaa agggaaattc tcaattactg ctttaattaa 10920
tggtgacaat caatcaatag atataagcaa accaattaga ctcatggaag gtcaaactca 10980
tgctcaagca gattatttgc tagcattaaa tagccttaaa ttactgtata aagagtatgc 11040
aggcataggc cacaaattaa aaggaactga gacttatata tcacgagata tgcaatttat 11100
gagtaaaaca attcaacata acggtgtgta ttacccagct agtataaaga aagtcctaag 11160
agtgggaccg tggataaaca ctatacttga tgatttcaaa gtgagtttag aatctatagg 11220
tagtttgaca caagaattag aatatagagg tgaaagtcta ttatgcagtt taatatttag 11280
aaatgtatgg ttatataatc agattgctct acaattaaaa aatcatgcat tatgtaacaa 11340
taaactatat ttggacatat taaaggttct gaaacactta aaaacctttt ttaatcttga 11400
taatattgat acagcattaa cattgtatat gaatttacct atgttatttg gtggtggtga 11460
tcccaacttg ttatatcgaa gtttctatag aagaaccccc gacttcctca cagaggctat 11520
agttcactct gtgttcatac ttagttatta tacaaaccat gacttaaaag ataaacttca 11580
agatctgtca gatgatagat tgaataagtt cttaacatgc ataatcacgt ttgacaaaaa 11640
ccctaacgct gaattcgtaa cattgatgag agatcctcaa gctttagggt ctgagagaca 11700
agctaaaatt actagcgaaa tcaataggct ggcagttaca gaggttttga gtacagctcc 11760
aaacaaaata ttctccaaaa gtgcacaaca ttataccact acagagatag atctaaatga 11820
tattatgcaa aatatagaac ctacatatcc tcatgggcta agagttgttt atgaaagttt 11880
acccttttat aaagcagaga aaatagtaaa tcttatatca ggtacaaaat ctataactaa 11940
catactggaa aaaacttctg ccatagactt aacagatatt gatagagcca ctgagatgat 12000
gaggaaaaac ataactttgc ttataaggat acttccattg gattgtaaca gagataaaag 12060
agagatattg agtatggaaa acctaagtat tactgaatta agcaaatatg ttagggaaag 12120
atcttggtct ttattcaata tagttggtgt tacatcaccc agtatcatgt atacaatgga 12180
catcaaatat actacaagca ctatagctag tggcataatt atagagaaat ataatgttaa 12240
cagtttaaca cgtggtgaga gaggacccac taaaccatgg gttggttcat ctacacaaga 12300
gaaaaaaaca atgccagttt ataatagaca agtcttaacc aaaaaacaga gagatcaaat 12360
agatctatta gcaaaattgg attgggtgta tgcatctata gataacaagg atgaattcat 12420
ggaagaactc agcataggaa cccttgggtt aacatatgaa aaagccaaga aattatttcc 12480
acaatattta agtgtcaact atttgcatcg acttacagtc agtagtagac catgtgaatt 12540
ccctgcatca ataccagctt atagaacaac aaattatcac tttgacacta gccctattaa 12600
tcgcatatta acagaaaagt atggtgatga agatattgac atagtattcc aaaactgtat 12660
aagctttggc cttagcttaa tgtcagtagt agaacaattt actaatgtat gtcctaacag 12720
aattattctc atacctaagc ttaatgagat acatttgatg aaacctccca tattcacagg 12780
tgatgttgat attcacaagt taaaacaagt gatacaaaaa cagcatatgt tttaccaga 12840
caaaataagt ttgactcaat atgtagaatt attcttaagt aataaaacac tcaaatctgg 12900
atctcatgtt aattctaatt taatattggc acataaaata tctgactatt ttcataatac 12960
```

```
ttacatttta agtactaatt tagctggaca ttggattctg attatacaac ttatgaaaga  13020
ttctaagggt atttttgaaa aagattgggg agagggatat ataactgatc atatgtttat  13080
taatttgaaa gttttcttca atgcctataa gacctatctc ttgtgttttc ataaaggtta  13140
tggcaaagca aagctggagt gtgatatgaa cacctcagat ctcctatgtg tattggaatt  13200
aatagacagt agttattgga aatctatgtc taaggtattt ttagaacaaa aagttatcaa  13260
atacattctt agccaagatg caagtttaca tagagtaaaa ggatgtcata gcttcaaatt  13320
atggtttctt aaacgtctta atgtagcaga attcacagtt tgcccttggg ttgttaacat  13380
agattatcat ccaacacata tgaaagcaat attaacttat atagatcttg ttagaatggg  13440
attgataaat atagatagaa tacacattaa aaataaacac aaattcaatg atgaatttta  13500
tacttctaat ctcttctaca ttaattataa cttctcagat aatactcatc tattaactaa  13560
acatataagg attgctaatt ctgaattaga aaataattac aacaaattat atcatcctac  13620
accagaaacc ctagagaata tactagccaa tccgattaaa agtaatgaca aaaagacact  13680
gaatgaatat tgtataggta aaaatgttga ctcaataatg ttaccattgt tatctaataa  13740
gaagcttatt aaatcgtctg caatgattag aaccaattac agcaaacaag atttgtataa  13800
tttattccct atggttgtga ttgatagaat tatagatcat tcaggcaata cagccaaatc  13860
caaccaactt tacactacta cttcccacca aatatcttta gtgcacaata gcacatcact  13920
ttactgcatg cttccttggc atcatattaa tagattcaat tttgtattta gttctacagg  13980
ttgtaaaatt agtatagagt atattttaaa agatcttaaa attaaagatc ccaattgtat  14040
agcattcata ggtgaaggag cagggaattt attattgcgt acagtagtgg aacttcatcc  14100
tgacataaga tatatttaca gaagtctgaa agattgcaat gatcatagtt tacctattga  14160
gtttttaagg ctgtacaatg gacatatcaa cattgattat ggtgaaaatt tgaccattcc  14220
tgctacagat gcaaccaaca acattcattg gtcttattta catataaagt ttgctgaacc  14280
tatcagtctt tttgtctgtg atgctgaatt gcctgtaaca gtcaattgga gtaaaattat  14340
aatagaatgg agcaagcatg taagaaagtg caagtactgt tcctcagtta ataaatgtat  14400
gttaatagta aaatatcatg ctcaagatga tattgatttc aaattagaca atataactat  14460
attaaaaact tatgtatgct taggcagtaa gttaaaggga tcggaggttt acttagtcat  14520
cacaataggt cctgcaaata tattcccagc atttaatgta gtacaaaatg ctaaattgat  14580
actatcaaga accaaaaatt tcatcatgcc taagaaagct gataaagagt ctattgatgc  14640
aaatattaaa agttttatac cctttctttg ttaccctata acaaaaaaag gaattaatac  14700
tgcattgtca aaactaaaga gtgttgttag tggagatata ctatcatatt ctatagctgg  14760
acgtaatgaa gttttcagca ataaacttat aaatcataaa catatgaaca tcttaaaatg  14820
gttcaatcat gttttaaatt tcagatcaac agaattaaac tataaccatt tatatatggt  14880
agaatctaca tatccttacc taagtgaatt gttaaacagc ttgacaacca atgaacttaa  14940
aaaactgatt aaaatcacag gtagtctgtt atacaacttt cataatgaat aatgaataaa  15000
gatcttataa taaagattcc catagctata cactaccatt gtattcaatt atagttatta  15060
aaaattaaaa atcatataat tttttaaata acttttagtg aactaatcct aaagttatca  15120
ttttgatcta ggaggaataa atttaaatcc taatctaatt ggtttatatg tgtattaact  15180
aaactacgag atattagttt ttgac                                         15205
```

<210> SEQ ID NO 92

<211> LENGTH: 1725
<212> TYPE: DNA
<213> ORGANISM: Respiratory syncytial virus, Merck strain p17_pp

<400> SEQUENCE: 92

```
atggagttgc caatcctcaa agcgaatgca attaccacaa tcctcactgc agtcacattt     60

tgttttgctt ctagtcaaaa catcactgaa gaattttatc aatcaacatg cagtgcagtt    120

agcaaaggct atcttagtgc tctaagaact ggttggtata ccagtgttat aactatagaa    180

ttaagtaata tcaaggaaaa taagtgtaat ggaacagatg ctaaggtaaa attgataaaa    240

caagaattag ataaatataa aaatgctgta acagaattgc agttgctaat gcaaagcaca    300

ccagcagcaa acaatcgagc cagaagagaa ctaccaaggt ttatgaatta tacactcaac    360

aatgccaaaa aaaccaatgt aacattaagc aaaaaaagga aaagaagatt tcttggtttt    420

ttgttaggag ttggatctgc aatcgccagt ggcattgctg tatctaaggt cctacaccta    480

gaaggggaag tgaacaagat caaaagtgct ctactatcca caaacaaggc tgtagtcagc    540

ttatcaaatg gagttagtgt cttaaccagc aaagtgttag acctcaaaaa ttatatagat    600

aaacaattgt tacctattgt gaacaagcaa agctgcagca tatcaaatat agaaactgtg    660

atagagttcc aacaaaagaa caacagacta ctagagatta ccagggaatt tagtgttaat    720

gcaggtgtaa ctacacctgt aagcacttac atgttgacta atagtgaatt attgtcatta    780

atcaatgata tgcctataac aaatgatcag aagaagttaa tgtccaacaa tgttcaaata    840

gttagacagc aaagttactc tatcatgtcc ataataaaaa aggaagtctt agcatatgta    900

gtacaattac cactatatgg tgttatagat acaccttgtt ggaaattaca cacatcccct    960

ctatgtacaa ccaacacaaa agaagggtcc aacatctgtt taacaagaac tgacagagga   1020

tggtactgtg acaatgcagg atcagtctct ttcttcccac aagctgaaac atgtaaagtt   1080

caatcgaatc gagtattttg tgacacaatg aacagtttaa cattaccaag tgaagtaaat   1140

ctctgcaatg ttgacatatt caatcccaaa tatgattgta aaattatgac ttcaaaaaca   1200

gatgtaagca gctctgttat cacatctcta ggagccattg tgtcatgcta tggcaaaact   1260

aaatgtacag catccaataa aaatcgtgga atcataaaga cattttctaa cgggtgcgat   1320

tatgtatcaa ataaaggggt ggacactgtg tctgtaggca acacattata ttatgtaaat   1380

aagcaagaag gcaaaagtct ctatgtaaaa ggtgaaccaa taataaattt ctatgaccca   1440

ttagtattcc cctctggtga atttgatgca tcaatatctc aagtcaacga gaagattaac   1500

cagagcctgg catttattcg taaatccgat gaattattac ataatgtaaa tgctggtaaa   1560

tccaccacaa acatcatgat aactgctata attatagtga ttgtagtaat attattatca   1620

ttaattgctg taggactgct cctatactgt aaggccagaa gcacaccagt cacactaagc   1680

aaagatcaac tgagtggtat aaataatatt gcatttagta actaa                   1725
```

<210> SEQ ID NO 93
<211> LENGTH: 574
<212> TYPE: PRT
<213> ORGANISM: Respiratory syncytial virus, Merck strain p17_pp

<400> SEQUENCE: 93

```
Met Glu Leu Pro Ile Leu Lys Ala Asn Ala Ile Thr Thr Ile Leu Thr
1               5                   10                  15

Ala Val Thr Phe Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
```

```
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Ala Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Lys Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460
```

```
Lys Ser Leu Tyr Val Lys Gly Glu Pro Ile Ile Asn Phe Tyr Asp Pro
465                 470                 475                 480

Leu Val Phe Pro Ser Gly Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Ala Ile Ile Ile Val Ile Val Val Ile Leu Leu Ser Leu Ile Ala Val
    530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570


<210> SEQ ID NO 94
<211> LENGTH: 6505
<212> TYPE: DNA
<213> ORGANISM: Respiratory syncytial virus, Merck strain p17_pp

<400> SEQUENCE: 94

atggatccca ttattaatgg aaattctgct aatgtttatc taaccgatag ttatttaaaa     60

ggtgttatct ctttctcaga gtgtaatgct ttaggaagct acatattcaa tggtccttat    120

ctcaaaaatg attataccaa cttaattagt agacaaaatc cattaataga acacatgaat    180

ctaaagaaac taaatataac acagtcctta atatctaagt atcataaagg tgaaataaaa    240

ttagaagaac cgacttattt tcagtcatta cttatgacat acaagagtat gacctcgtca    300

gaacagattg ctaccactaa tttacttaaa aagataataa gaagagctat agaaataagt    360

gatgtcaaag tctatgctat attgaataaa ctagggctta aagaaaagga caagattaaa    420

tccaacaatg gacaagatga agccaattca gttattacga ccataatcaa agatgatata    480

ctttcagctg ttaaagataa tcaatctcat cttaaagcag gcaaaaatca ctctacaaaa    540

caaaaagaca caatcaaaac aacactcctg aagaaattga tgtgttcaat gcaacatcct    600

ccatcatggt taatacattg gtttaactta tacacaaaat taaacaacat attaacacag    660

tatcgatcaa atgaggtaaa aaaccatggg tttacattga tagataatca aactcttagt    720

ggatttcaat ttattttgaa ccaatatggt tgtatagttt ataataagga actcaaaaga    780

attactgtga caacctataa tcaattcttg acatggaaag atattagcct tagtagatta    840

aatgtttgtt taattacatg gattagtaac tgcttgaaca cattaaataa aagcttaggc    900

ttaagatgcg gattcaataa tgttatctta acacaactat tcctttatgg agattgtata    960

ctaaaactat ttcacaatga ggggttctac ataataaaag aggtagaggg atttattatg   1020

tctctaattt taaatataac agaagaagat caattcagaa aacgatttta taatagtatg   1080

ctcaacaaca tcacagatgc tgctaataaa gctcagaaaa atctgctatc aagagtatgt   1140

catacattat tagataagac agtatccgat aatataataa atggcagatg gataattcta   1200

ttaagtaagt tccttaaatt aattaagctt gcgggtgaca ataaccttaa caatctgagt   1260

gaactatatt ttttgttcag aatatttgga cacccaatgg tagatgaaag acaagccatg   1320

gatgctgtta aaattaattg caatgagacc aaattttact tgctaagcag tctaagtatg   1380

ttaagaggtg cctttatata tagaattata aaagggtttg taaataatta caacagatgg   1440

cctactttaa gaaatgctat tgttttaccc ttaagatggt taacttacta taaactaaac   1500
```

```
acttatcctt ctttgttgga acttacagaa agagatttga ttgtgttatc aggactacgt   1560
ttctatcgtg agtttcggtt gcctaaaaaa gtggatcttg aaatgattat aaatgataaa   1620
gctatatcac ctcctaaaaa tttgatatgg actagtttcc ctagaaatta catgccatca   1680
cacatacaaa actatataga acatgaaaaa ttaaaatttt ccgagagtga taaatcaaga   1740
agagtattag agtattattt aagagataac aagttcaatg aatgtgattt atacaactgt   1800
gtagttgatc aaagttatct aaacaaccct aatcatgtgg tatcattgac aggcaaagaa   1860
agagaactca gtgtaggtag aatgtttgca atgcaaccgg gaatgttcag acaggttcaa   1920
atattagcag agaaaatgat agctgaaaac attttacaat tctttcctga aagtcttaca   1980
agatatggtg atctagaact acaaaaaata ttagaattga aagcaggaat aagtaacaaa   2040
tcaaatcgct acaatgacaa ttacaacaat tacattagta agtgctctat catcacagat   2100
ctcagcaaat tcaatcaagc atttcgatat gaaacgtcat gtatttgtag tgatgtgctt   2160
gatgaactgc atggtgtaca atctctattt tcctggttac atttaactat tcctcatgtt   2220
acaataatat gtacatatag gcatgcaccc ccctatatag gagatcatat tgtagatctt   2280
aacaatgtag atgaacaaag tggattatat agatatcaca tgggtggcat cgaagggtgg   2340
tgtcaaaaac tatggaccat agaagctata tcactattgg atctaatatc tctcaaaggg   2400
aaattctcaa ttactgcttt aattaatggt gacaatcaat caatagatat aagcaaacca   2460
attagactca tggaaggtca aactcatgct caagcagatt atttgctagc attaaatagc   2520
cttaaattac tgtataaaga gtatgcaggc ataggccaca aattaaaagg aactgagact   2580
tatatatcac gagatatgca atttatgagt aaaacaattc aacataacgg tgtgtattac   2640
ccagctagta taaagaaagt cctaagagtg ggaccgtgga taaacactat acttgatgat   2700
ttcaaagtga gtttagaatc tataggtagt ttgacacaag aattagaata tagaggtgaa   2760
agtctattat gcagtttaat atttagaaat gtatggttat ataatcagat tgctctacaa   2820
ttaaaaaatc atgcattatg taacaataaa ctatatttgg acatattaaa ggttctgaaa   2880
cacttaaaaa cctttttaa tcttgataat attgatacag cattaacatt gtatatgaat   2940
ttacctatgt tatttggtgg tggtgatccc aacttgttat atcgaagttt ctatagaaga   3000
acccccgact tcctcacaga ggctatagtt cactctgtgt tcatacttag ttattataca   3060
aaccatgact taaaagataa acttcaagat ctgtcagatg atagattgaa taagttctta   3120
acatgcataa tcacgtttga caaaaaccct aacgctgaat tcgtaacatt gatgagagat   3180
cctcaagctt tagggtctga gagacaagct aaaattacta gcgaaatcaa taggctggca   3240
gttacagagg ttttgagtac agctccaaac aaaatattct ccaaaagtgc acaacattat   3300
accactacag agatagatct aaatgatatt atgcaaaata tagaacctac atatcctcat   3360
gggctaagag ttgtttatga aagtttaccc ttttataaag cagagaaaat agtaaatctt   3420
atatcaggta caaaatctat aactaacata ctggaaaaaa cttctgccat agacttaaca   3480
gatattgata gagccactga gatgatgagg aaaaacataa ctttgcttat aaggatactt   3540
ccattggatt gtaacagaga taaaagagag atattgagta tggaaaacct aagtattact   3600
gaattaagca aatatgttag ggaaagatct tggtctttat tcaatatagt tggtgttaca   3660
tcacccagta tcatgtatac aatggacatc aaatatacta caagcactat agctagtggc   3720
ataattatag agaaatataa tgttaacagt ttaacacgtg gtgagagagg acccactaaa   3780
ccatgggttg gttcatctac acaagagaaa aaaacaatgc cagtttataa tagacaagtc   3840
```

```
ttaaccaaaa aacagagaga tcaaatagat ctattagcaa aattggattg ggtgtatgca   3900
tctatagata acaaggatga attcatggaa gaactcagca taggaaccct tgggttaaca   3960
tatgaaaaag ccaagaaatt atttccacaa tatttaagtg tcaactattt gcatcgactt   4020
acagtcagta gtagaccatg tgaattccct gcatcaatac cagcttatag aacaacaaat   4080
tatcactttg acactagccc tattaatcgc atattaacag aaaagtatgg tgatgaagat   4140
attgacatag tattccaaaa ctgtataagc tttggcctta gcttaatgtc agtagtagaa   4200
caatttacta atgtatgtcc taacagaatt attctcatac ctaagcttaa tgagatacat   4260
ttgatgaaac ctcccatatt cacaggtgat gttgatattc acaagttaaa acaagtgata   4320
caaaaacagc atatgttttt accagacaaa ataagtttga ctcaatatgt agaattattc   4380
ttaagtaata aaacactcaa atctggatct catgttaatt ctaatttaat attggcacat   4440
aaaatatctg actattttca taatacttac attttaagta ctaatttagc tggacattgg   4500
attctgatta tacaacttat gaaagattct aagggtattt ttgaaaaaga ttggggagag   4560
ggatatataa ctgatcatat gtttattaat ttgaaagttt tcttcaatgc ctataagacc   4620
tatctcttgt gttttcataa aggttatggc aaagcaaagc tggagtgtga tatgaacacc   4680
tcagatctcc tatgtgtatt ggaattaata gacagtagtt attggaaatc tatgtctaag   4740
gtatttttag aacaaaaagt tatcaaatac attcttagcc aagatgcaag tttacataga   4800
gtaaaaggat gtcatagctt caaattatgg tttcttaaac gtcttaatgt agcagaattc   4860
acagtttgcc cttgggttgt taacatagat tatcatccaa cacatatgaa agcaatatta   4920
acttatatag atcttgttag aatgggattg ataaatatag atagaataca cattaaaaat   4980
aaacacaaat tcaatgatga attttatact tctaatctct tctacattaa ttataacttc   5040
tcagataata ctcatctatt aactaaacat ataaggattg ctaattctga attagaaaat   5100
aattacaaca aattatatca tcctacacca gaaaccctag agaatatact agccaatccg   5160
attaaaagta atgacaaaaa gacactgaat gaatattgta taggtaaaaa tgttgactca   5220
ataatgttac cattgttatc taataagaag cttattaaat cgtctgcaat gattagaacc   5280
aattacagca aacaagattt gtataattta ttccctatgg ttgtgattga tagaattata   5340
gatcattcag gcaatacagc caaatccaac caactttaca ctactacttc ccaccaaata   5400
tctttagtgc acaatagcac atcactttac tgcatgcttc cttggcatca tattaataga   5460
ttcaattttg tatttagttc tacaggttgt aaaattagta tagagtatat tttaaaagat   5520
cttaaaatta aagatcccaa ttgtatagca ttcataggtg aaggagcagg gaatttatta   5580
ttgcgtacag tagtggaact tcatcctgac ataagatata tttacagaag tctgaaagat   5640
tgcaatgatc atagtttacc tattgagttt ttaaggctgt acaatggaca tatcaacatt   5700
gattatggtg aaaatttgac cattcctgct acagatgcaa ccaacaacat tcattggtct   5760
tatttacata taaagtttgc tgaacctatc agtctttttg tctgtgatgc tgaattgcct   5820
gtaacagtca attggagtaa aattataata gaatggagca agcatgtaag aaagtgcaag   5880
tactgttcct cagttaataa atgtatgtta atagtaaaat atcatgctca agatgatatt   5940
gatttcaaat tagacaatat aactatatta aaaacttatg tatgcttagg cagtaagtta   6000
aagggatcgg aggtttactt agtcatcaca ataggtcctg caaatatatt cccagcattt   6060
aatgtagtac aaaatgctaa attgatacta tcaagaacca aaaatttcat catgcctaag   6120
aaagctgata aagagtctat tgatgcaaat attaaaagtt ttataccctt tctttgttac   6180
cctataacaa aaaaaggaat taatactgca ttgtcaaaac taaagagtgt tgttagtgga   6240
```

```
gatatactat catattctat agctggacgt aatgaagttt tcagcaataa acttataaat   6300

cataaacata tgaacatctt aaaatggttc aatcatgttt taaatttcag atcaacagaa   6360

ttaaactata accatttata tatggtagaa tctacatatc cttacctaag tgaattgtta   6420

aacagcttga caaccaatga acttaaaaaa ctgattaaaa tcacaggtag tctgttatac   6480

aactttcata atgaataatg aataa                                         6505


<210> SEQ ID NO 95
<211> LENGTH: 2166
<212> TYPE: PRT
<213> ORGANISM: Respiratory syncytial virus, Merck strain p17_pp

<400> SEQUENCE: 95

Met Asp Pro Ile Ile Asn Gly Asn Ser Ala Asn Val Tyr Leu Thr Asp
 1               5                  10                  15

Ser Tyr Leu Lys Gly Val Ile Ser Phe Ser Glu Cys Asn Ala Leu Gly
            20                  25                  30

Ser Tyr Ile Phe Asn Gly Pro Tyr Leu Lys Asn Asp Tyr Thr Asn Leu
        35                  40                  45

Ile Ser Arg Gln Asn Pro Leu Ile Glu His Met Asn Leu Lys Lys Leu
    50                  55                  60

Asn Ile Thr Gln Ser Leu Ile Ser Lys Tyr His Lys Gly Glu Ile Lys
65                  70                  75                  80

Leu Glu Glu Pro Thr Tyr Phe Gln Ser Leu Leu Met Thr Tyr Lys Ser
                85                  90                  95

Met Thr Ser Ser Glu Gln Ile Ala Thr Thr Asn Leu Leu Lys Lys Ile
            100                 105                 110

Ile Arg Arg Ala Ile Glu Ile Ser Asp Val Lys Val Tyr Ala Ile Leu
        115                 120                 125

Asn Lys Leu Gly Leu Lys Glu Lys Asp Lys Ile Lys Ser Asn Asn Gly
    130                 135                 140

Gln Asp Glu Ala Asn Ser Val Ile Thr Thr Ile Ile Lys Asp Asp Ile
145                 150                 155                 160

Leu Ser Ala Val Lys Asp Asn Gln Ser His Leu Lys Ala Gly Lys Asn
                165                 170                 175

His Ser Thr Lys Gln Lys Asp Thr Ile Lys Thr Thr Leu Leu Lys Lys
            180                 185                 190

Leu Met Cys Ser Met Gln His Pro Pro Ser Trp Leu Ile His Trp Phe
        195                 200                 205

Asn Leu Tyr Thr Lys Leu Asn Asn Ile Leu Thr Gln Tyr Arg Ser Asn
    210                 215                 220

Glu Val Lys Asn His Gly Phe Thr Leu Ile Asp Asn Gln Thr Leu Ser
225                 230                 235                 240

Gly Phe Gln Phe Ile Leu Asn Gln Tyr Gly Cys Ile Val Tyr Asn Lys
                245                 250                 255

Glu Leu Lys Arg Ile Thr Val Thr Thr Tyr Asn Gln Phe Leu Thr Trp
            260                 265                 270

Lys Asp Ile Ser Leu Ser Arg Leu Asn Val Cys Leu Ile Thr Trp Ile
        275                 280                 285

Ser Asn Cys Leu Asn Thr Leu Asn Lys Ser Leu Gly Leu Arg Cys Gly
    290                 295                 300

Phe Asn Asn Val Ile Leu Thr Gln Leu Phe Leu Tyr Gly Asp Cys Ile
305                 310                 315                 320
```

-continued

```
Leu Lys Leu Phe His Asn Glu Gly Phe Tyr Ile Ile Lys Glu Val Glu
                325                 330                 335

Gly Phe Ile Met Ser Leu Ile Leu Asn Ile Thr Glu Glu Asp Gln Phe
            340                 345                 350

Arg Lys Arg Phe Tyr Asn Ser Met Leu Asn Asn Ile Thr Asp Ala Ala
        355                 360                 365

Asn Lys Ala Gln Lys Asn Leu Leu Ser Arg Val Cys His Thr Leu Leu
    370                 375                 380

Asp Lys Thr Val Ser Asp Asn Ile Ile Asn Gly Arg Trp Ile Ile Leu
385                 390                 395                 400

Leu Ser Lys Phe Leu Lys Leu Ile Lys Leu Ala Gly Asp Asn Asn Leu
                405                 410                 415

Asn Asn Leu Ser Glu Leu Tyr Phe Leu Phe Arg Ile Phe Gly His Pro
            420                 425                 430

Met Val Asp Glu Arg Gln Ala Met Asp Ala Val Lys Ile Asn Cys Asn
        435                 440                 445

Glu Thr Lys Phe Tyr Leu Leu Ser Ser Leu Ser Met Leu Arg Gly Ala
    450                 455                 460

Phe Ile Tyr Arg Ile Ile Lys Gly Phe Val Asn Asn Tyr Asn Arg Trp
465                 470                 475                 480

Pro Thr Leu Arg Asn Ala Ile Val Leu Pro Leu Arg Trp Leu Thr Tyr
                485                 490                 495

Tyr Lys Leu Asn Thr Tyr Pro Ser Leu Leu Glu Leu Thr Glu Arg Asp
            500                 505                 510

Leu Ile Val Leu Ser Gly Leu Arg Phe Tyr Arg Glu Phe Arg Leu Pro
        515                 520                 525

Lys Lys Val Asp Leu Glu Met Ile Ile Asn Asp Lys Ala Ile Ser Pro
    530                 535                 540

Pro Lys Asn Leu Ile Trp Thr Ser Phe Pro Arg Asn Tyr Met Pro Ser
545                 550                 555                 560

His Ile Gln Asn Tyr Ile Glu His Glu Lys Leu Lys Phe Ser Glu Ser
                565                 570                 575

Asp Lys Ser Arg Arg Val Leu Glu Tyr Tyr Leu Arg Asp Asn Lys Phe
            580                 585                 590

Asn Glu Cys Asp Leu Tyr Asn Cys Val Val Asp Gln Ser Tyr Leu Asn
        595                 600                 605

Asn Pro Asn His Val Val Ser Leu Thr Gly Lys Glu Arg Glu Leu Ser
    610                 615                 620

Val Gly Arg Met Phe Ala Met Gln Pro Gly Met Phe Arg Gln Val Gln
625                 630                 635                 640

Ile Leu Ala Glu Lys Met Ile Ala Glu Asn Ile Leu Gln Phe Phe Pro
                645                 650                 655

Glu Ser Leu Thr Arg Tyr Gly Asp Leu Glu Leu Gln Lys Ile Leu Glu
            660                 665                 670

Leu Lys Ala Gly Ile Ser Asn Lys Ser Asn Arg Tyr Asn Asp Asn Tyr
        675                 680                 685

Asn Asn Tyr Ile Ser Lys Cys Ser Ile Ile Thr Asp Leu Ser Lys Phe
    690                 695                 700

Asn Gln Ala Phe Arg Tyr Glu Thr Ser Cys Ile Cys Ser Asp Val Leu
705                 710                 715                 720

Asp Glu Leu His Gly Val Gln Ser Leu Phe Ser Trp Leu His Leu Thr
                725                 730                 735

Ile Pro His Val Thr Ile Ile Cys Thr Tyr Arg His Ala Pro Pro Tyr
```

```
            740                 745                 750

Ile Gly Asp His Ile Val Asp Leu Asn Asn Val Asp Glu Gln Ser Gly
        755                 760                 765

Leu Tyr Arg Tyr His Met Gly Gly Ile Glu Gly Trp Cys Gln Lys Leu
    770                 775                 780

Trp Thr Ile Glu Ala Ile Ser Leu Leu Asp Leu Ile Ser Leu Lys Gly
785                 790                 795                 800

Lys Phe Ser Ile Thr Ala Leu Ile Asn Gly Asp Asn Gln Ser Ile Asp
                805                 810                 815

Ile Ser Lys Pro Ile Arg Leu Met Glu Gly Gln Thr His Ala Gln Ala
            820                 825                 830

Asp Tyr Leu Leu Ala Leu Asn Ser Leu Lys Leu Leu Tyr Lys Glu Tyr
        835                 840                 845

Ala Gly Ile Gly His Lys Leu Lys Gly Thr Glu Thr Tyr Ile Ser Arg
    850                 855                 860

Asp Met Gln Phe Met Ser Lys Thr Ile Gln His Asn Gly Val Tyr Tyr
865                 870                 875                 880

Pro Ala Ser Ile Lys Lys Val Leu Arg Val Gly Pro Trp Ile Asn Thr
                885                 890                 895

Ile Leu Asp Asp Phe Lys Val Ser Leu Glu Ser Ile Gly Ser Leu Thr
            900                 905                 910

Gln Glu Leu Glu Tyr Arg Gly Glu Ser Leu Leu Cys Ser Leu Ile Phe
        915                 920                 925

Arg Asn Val Trp Leu Tyr Asn Gln Ile Ala Leu Gln Leu Lys Asn His
    930                 935                 940

Ala Leu Cys Asn Asn Lys Leu Tyr Leu Asp Ile Leu Lys Val Leu Lys
945                 950                 955                 960

His Leu Lys Thr Phe Phe Asn Leu Asp Asn Ile Asp Thr Ala Leu Thr
                965                 970                 975

Leu Tyr Met Asn Leu Pro Met Leu Phe Gly Gly Gly Asp Pro Asn Leu
            980                 985                 990

Leu Tyr Arg Ser Phe Tyr Arg Arg Thr Pro Asp Phe Leu Thr Glu Ala
        995                 1000                1005

Ile Val His Ser Val Phe Ile Leu Ser Tyr Tyr Thr Asn His Asp Leu
    1010                1015                1020

Lys Asp Lys Leu Gln Asp Leu Ser Asp Asp Arg Leu Asn Lys Phe Leu
1025                1030                1035                1040

Thr Cys Ile Ile Thr Phe Asp Lys Asn Pro Asn Ala Glu Phe Val Thr
                1045                1050                1055

Leu Met Arg Asp Pro Gln Ala Leu Gly Ser Glu Arg Gln Ala Lys Ile
            1060                1065                1070

Thr Ser Glu Ile Asn Arg Leu Ala Val Thr Glu Val Leu Ser Thr Ala
        1075                1080                1085

Pro Asn Lys Ile Phe Ser Lys Ser Ala Gln His Tyr Thr Thr Thr Glu
    1090                1095                1100

Ile Asp Leu Asn Asp Ile Met Gln Asn Ile Glu Pro Thr Tyr Pro His
1105                1110                1115                1120

Gly Leu Arg Val Val Tyr Glu Ser Leu Pro Phe Tyr Lys Ala Glu Lys
                1125                1130                1135

Ile Val Asn Leu Ile Ser Gly Thr Lys Ser Ile Thr Asn Ile Leu Glu
            1140                1145                1150

Lys Thr Ser Ala Ile Asp Leu Thr Asp Ile Asp Arg Ala Thr Glu Met
        1155                1160                1165
```

```
Met Arg Lys Asn Ile Thr Leu Leu Ile Arg Ile Leu Pro Leu Asp Cys
    1170                1175                1180

Asn Arg Asp Lys Arg Glu Ile Leu Ser Met Glu Asn Leu Ser Ile Thr
1185                1190                1195                1200

Glu Leu Ser Lys Tyr Val Arg Glu Arg Ser Trp Ser Leu Phe Asn Ile
                1205                1210                1215

Val Gly Val Thr Ser Pro Ser Ile Met Tyr Thr Met Asp Ile Lys Tyr
            1220                1225                1230

Thr Thr Ser Thr Ile Ala Ser Gly Ile Ile Ile Glu Lys Tyr Asn Val
        1235                1240                1245

Asn Ser Leu Thr Arg Gly Glu Arg Gly Pro Thr Lys Pro Trp Val Gly
    1250                1255                1260

Ser Ser Thr Gln Glu Lys Lys Thr Met Pro Val Tyr Asn Arg Gln Val
1265                1270                1275                1280

Leu Thr Lys Lys Gln Arg Asp Gln Ile Asp Leu Leu Ala Lys Leu Asp
                1285                1290                1295

Trp Val Tyr Ala Ser Ile Asp Asn Lys Asp Glu Phe Met Glu Glu Leu
            1300                1305                1310

Ser Ile Gly Thr Leu Gly Leu Thr Tyr Glu Lys Ala Lys Lys Leu Phe
        1315                1320                1325

Pro Gln Tyr Leu Ser Val Asn Tyr Leu His Arg Leu Thr Val Ser Ser
    1330                1335                1340

Arg Pro Cys Glu Phe Pro Ala Ser Ile Pro Ala Tyr Arg Thr Thr Asn
1345                1350                1355                1360

Tyr His Phe Asp Thr Ser Pro Ile Asn Arg Ile Leu Thr Glu Lys Tyr
                1365                1370                1375

Gly Asp Glu Asp Ile Asp Ile Val Phe Gln Asn Cys Ile Ser Phe Gly
            1380                1385                1390

Leu Ser Leu Met Ser Val Val Glu Gln Phe Thr Asn Val Cys Pro Asn
        1395                1400                1405

Arg Ile Ile Leu Ile Pro Lys Leu Asn Glu Ile His Leu Met Lys Pro
    1410                1415                1420

Pro Ile Phe Thr Gly Asp Val Asp Ile His Lys Leu Lys Gln Val Ile
1425                1430                1435                1440

Gln Lys Gln His Met Phe Leu Pro Asp Lys Ile Ser Leu Thr Gln Tyr
                1445                1450                1455

Val Glu Leu Phe Leu Ser Asn Lys Thr Leu Lys Ser Gly Ser His Val
            1460                1465                1470

Asn Ser Asn Leu Ile Leu Ala His Lys Ile Ser Asp Tyr Phe His Asn
        1475                1480                1485

Thr Tyr Ile Leu Ser Thr Asn Leu Ala Gly His Trp Ile Leu Ile Ile
    1490                1495                1500

Gln Leu Met Lys Asp Ser Lys Gly Ile Phe Glu Lys Asp Trp Gly Glu
1505                1510                1515                1520

Gly Tyr Ile Thr Asp His Met Phe Ile Asn Leu Lys Val Phe Phe Asn
                1525                1530                1535

Ala Tyr Lys Thr Tyr Leu Leu Cys Phe His Lys Gly Tyr Gly Lys Ala
            1540                1545                1550

Lys Leu Glu Cys Asp Met Asn Thr Ser Asp Leu Leu Cys Val Leu Glu
        1555                1560                1565

Leu Ile Asp Ser Ser Tyr Trp Lys Ser Met Ser Lys Val Phe Leu Glu
    1570                1575                1580
```

```
Gln Lys Val Ile Lys Tyr Ile Leu Ser Gln Asp Ala Ser Leu His Arg
1585                1590                1595                1600

Val Lys Gly Cys His Ser Phe Lys Leu Trp Phe Leu Lys Arg Leu Asn
                1605                1610                1615

Val Ala Glu Phe Thr Val Cys Pro Trp Val Val Asn Ile Asp Tyr His
            1620                1625                1630

Pro Thr His Met Lys Ala Ile Leu Thr Tyr Ile Asp Leu Val Arg Met
        1635                1640                1645

Gly Leu Ile Asn Ile Asp Arg Ile His Ile Lys Asn Lys His Lys Phe
    1650                1655                1660

Asn Asp Glu Phe Tyr Thr Ser Asn Leu Phe Tyr Ile Asn Tyr Asn Phe
1665                1670                1675                1680

Ser Asp Asn Thr His Leu Leu Thr Lys His Ile Arg Ile Ala Asn Ser
                1685                1690                1695

Glu Leu Glu Asn Asn Tyr Asn Lys Leu Tyr His Pro Thr Pro Glu Thr
            1700                1705                1710

Leu Glu Asn Ile Leu Ala Asn Pro Ile Lys Ser Asn Asp Lys Lys Thr
        1715                1720                1725

Leu Asn Glu Tyr Cys Ile Gly Lys Asn Val Asp Ser Ile Met Leu Pro
    1730                1735                1740

Leu Leu Ser Asn Lys Lys Leu Ile Lys Ser Ser Ala Met Ile Arg Thr
1745                1750                1755                1760

Asn Tyr Ser Lys Gln Asp Leu Tyr Asn Leu Phe Pro Met Val Val Ile
                1765                1770                1775

Asp Arg Ile Ile Asp His Ser Gly Asn Thr Ala Lys Ser Asn Gln Leu
            1780                1785                1790

Tyr Thr Thr Thr Ser His Gln Ile Ser Leu Val His Asn Ser Thr Ser
        1795                1800                1805

Leu Tyr Cys Met Leu Pro Trp His His Ile Asn Arg Phe Asn Phe Val
    1810                1815                1820

Phe Ser Ser Thr Gly Cys Lys Ile Ser Ile Glu Tyr Ile Leu Lys Asp
1825                1830                1835                1840

Leu Lys Ile Lys Asp Pro Asn Cys Ile Ala Phe Ile Gly Glu Gly Ala
                1845                1850                1855

Gly Asn Leu Leu Leu Arg Thr Val Val Glu Leu His Pro Asp Ile Arg
            1860                1865                1870

Tyr Ile Tyr Arg Ser Leu Lys Asp Cys Asn Asp His Ser Leu Pro Ile
        1875                1880                1885

Glu Phe Leu Arg Leu Tyr Asn Gly His Ile Asn Ile Asp Tyr Gly Glu
    1890                1895                1900

Asn Leu Thr Ile Pro Ala Thr Asp Ala Thr Asn Asn Ile His Trp Ser
1905                1910                1915                1920

Tyr Leu His Ile Lys Phe Ala Glu Pro Ile Ser Leu Phe Val Cys Asp
                1925                1930                1935

Ala Glu Leu Pro Val Thr Val Asn Trp Ser Lys Ile Ile Ile Glu Trp
            1940                1945                1950

Ser Lys His Val Arg Lys Cys Lys Tyr Cys Ser Ser Val Asn Lys Cys
        1955                1960                1965

Met Leu Ile Val Lys Tyr His Ala Gln Asp Asp Ile Asp Phe Lys Leu
    1970                1975                1980

Asp Asn Ile Thr Ile Leu Lys Thr Tyr Val Cys Leu Gly Ser Lys Leu
1985                1990                1995                2000

Lys Gly Ser Glu Val Tyr Leu Val Ile Thr Ile Gly Pro Ala Asn Ile
```

-continued

```
                2005                2010                2015

Phe Pro Ala Phe Asn Val Val Gln Asn Ala Lys Leu Ile Leu Ser Arg
            2020                2025                2030

Thr Lys Asn Phe Ile Met Pro Lys Lys Ala Asp Lys Glu Ser Ile Asp
        2035                2040                2045

Ala Asn Ile Lys Ser Phe Ile Pro Phe Leu Cys Tyr Pro Ile Thr Lys
    2050                2055                2060

Lys Gly Ile Asn Thr Ala Leu Ser Lys Leu Lys Ser Val Val Ser Gly
2065                2070                2075                2080

Asp Ile Leu Ser Tyr Ser Ile Ala Gly Arg Asn Glu Val Phe Ser Asn
                2085                2090                2095

Lys Leu Ile Asn His Lys His Met Asn Ile Leu Lys Trp Phe Asn His
            2100                2105                2110

Val Leu Asn Phe Arg Ser Thr Glu Leu Asn Tyr Asn His Leu Tyr Met
        2115                2120                2125

Val Glu Ser Thr Tyr Pro Tyr Leu Ser Glu Leu Leu Asn Ser Leu Thr
    2130                2135                2140

Thr Asn Glu Leu Lys Lys Leu Ile Lys Ile Thr Gly Ser Leu Leu Tyr
2145                2150                2155                2160

Asn Phe His Asn Glu Ile
                2165
```